United States Patent
Chen et al.

(10) Patent No.: US 11,525,020 B2
(45) Date of Patent: *Dec. 13, 2022

(54) PROCESSES TO PRODUCE POLY ALPHA-OLEFIN TRIMERS

(71) Applicant: ExxonMobil Chemical Patents Inc., Baytown, TX (US)

(72) Inventors: Patrick C. Chen, Houston, TX (US); Mark H. Li, Sugar Land, TX (US); Jennifer L. Rapp, Houston, TX (US); Monica D. Lotz, Houston, TX (US); Babak LotfizadehDehkordi, Houston, TX (US); Craig J. Emett, Houston, TX (US); Najeeb M. Kuzhiyil, League City, TX (US); Jian Yang, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 17 days.

This patent is subject to a terminal disclaimer.

(21) Appl. No.: 17/360,275

(22) Filed: Jun. 28, 2021

(65) Prior Publication Data

US 2022/0127392 A1 Apr. 28, 2022

Related U.S. Application Data

(60) Division of application No. 16/537,349, filed on Aug. 9, 2019, now Pat. No. 11,078,308, which is a continuation-in-part of application No. 16/270,085, filed on Feb. 7, 2019, now Pat. No. 11,084,894.

(60) Provisional application No. 62/732,311, filed on Sep. 17, 2018, provisional application No. 62/629,200, filed on Feb. 12, 2018.

(51) Int. Cl.
*C07C 2/30* (2006.01)
*C07C 2/32* (2006.01)
*C08F 4/6592* (2006.01)
*C08F 10/14* (2006.01)
*C08F 4/659* (2006.01)

(52) U.S. Cl.
CPC ............... *C08F 10/14* (2013.01); *C07C 2/30* (2013.01); *C07C 2/32* (2013.01); *C08F 4/65908* (2013.01); *C08F 4/65925* (2013.01)

(58) Field of Classification Search
CPC . C07C 2/30; C07C 2/32; C08F 4/6592; C08F 4/65925
See application file for complete search history.

(56) References Cited

U.S. PATENT DOCUMENTS

| 5,284,988 | A | * | 2/1994 | Schaerl, Jr | C10G 50/02 585/16 |
| 2008/0146469 | A1 | * | 6/2008 | Sato | F16C 33/109 384/100 |
| 2013/0090273 | A1 | * | 4/2013 | Martin | C10M 105/04 508/389 |

* cited by examiner

*Primary Examiner* — Caixia Lu
(74) *Attorney, Agent, or Firm* — Exxonmobil Chemical Patents Inc.

(57) ABSTRACT

The present disclosure generally relates to processes to produce alpha-olefin oligomers and poly alpha-olefins. In an embodiment, a process to produce a poly alpha-olefin (PAO) includes introducing a first alpha-olefin and a first catalyst system comprising a metallocene compound into a continuous stirred tank reactor or a continuous tubular reactor under first reactor conditions to form a first reactor effluent. The alpha-olefin is introduced to the reactor at a flow rate of about 100 g/hr or more. The first reactor effluent includes PAO dimer comprising at least 96 mol % of vinylidene and 4 mol % or less of trisubstituted vinylene and disubstituted vinylene, based on total moles of vinylidene, trisubstituted vinylene, and disubstituted vinylene. The method includes introducing the first reactor effluent, a second alpha-olefin and a second catalyst composition comprising an acid catalyst into a second reactor under second reactor conditions to form a second reactor effluent comprising PAO trimer.

1 Claim, 8 Drawing Sheets

(CONVENTIONAL APPARATUS)

PROCESSES TO PRODUCE POLY ALPHA-OLEFIN TRIMERS

CROSS-REFERENCE TO RELATED APPLICATIONS

This application is a divisional application of U.S. application Ser. No. 16/537,349 filed Aug. 9, 2019, which is a continuation-in-part of U.S. Ser. No. 16/270,085, filed Feb. 7, 2019, which claims priority to and benefit of U.S. Ser. No. 62/629,200, filed Feb. 12, 2018, and U.S. Ser. No. 62/732,311, filed Sep. 17, 2018.

This application is related to the U.S. patent application Ser. No. 16/537,364, (2019EM302) entitled "Metallocene Dimer Selective Catalysts and Processes to Produce Poly Alpha-Olefin Dimers," and U.S. patent application Ser. No. 16/537,381, (2019EM304) entitled "Processes to Produce Poly Alpha-Olefin Trimers and Apparatus Therefor;" having common inventors and assignee and filed on the same date herewith, the disclosures of which are incorporated by reference herein in their entireties.

FIELD

The present disclosure generally relates to processes to produce alpha-olefin oligomers and poly alpha-olefins.

BACKGROUND

As society looks to curb carbon emission, equipment builders have accelerated design changes to improve energy efficiency. For example, passenger vehicles have drastically modified the design of their internal combustion engines, trending toward smaller engines that operate at higher (and more efficient) temperatures. There has also been a significant rise in the design of electrified vehicles, and in some designs, equipment builders have eliminated the internal combustion engine in favor of electric vehicles. Similar trends can be observed in industrial equipment design.

Alpha-olefins and poly alpha-olefins (PAOs), such as vinylidene-terminated PAOs, are used as intermediates in the manufacture of many commercial products such as lubricant base oil components, basestocks, and surfactants.

As a result of the equipment changes mentioned above, lubricant requirements have generally become more stringent. For example, there have been multiple engine oil viscosity grades added to development over the past decade (e.g. 0W-8, 0W-12, 0W-16). These engine oils require extremely low viscosity base oils without significantly increasing volatility of the lubricant. These lubricants are also required to deliver outstanding oxidative stability. Additionally electric vehicles have brought new and diverse challenges for driveline fluids and cooling systems, which require tailored lubricant design.

While mineral-oil base stocks are widely available, they generally lack tailored performance to meet specific lubricant needs. When analyzing available Group HT base stocks, for example, nearly all suppliers offer three or four grades ranging from 3 cSt to 8 cSt. For very low viscosity engine oils (e.g. 0W-8), for example, these base stocks are often insufficient to meet both volatility and viscometric targets.

While polyalphaolefins (PAOs) have a wide availability of viscosity grades, the vast majority of commercial low viscosity PAOs (below 10 cSt KV100) are produced from $BF_3$ catalysts, which are difficult to tailor to specific product performance.

Catalyst systems to selectively produce solely or predominantly alpha-olefin dimers (e.g., >80%) at high yields and with high vinylidene unsaturation would allow for better tailoring of PAO molecules (through two-step processing or further functionalization), but such catalyst systems remain elusive. For example, conventional metallocene catalyst systems, such as supported dimethylsilyl bis(2-methyl-4-phenyl-indenyl) zirconium dimethyl, typically produce about 50% vinyl and about 50% vinylidene terminal unsaturations (of the termini that are unsaturated). Conventional metallocene catalyst systems to construct high vinylidene dimerized olefins require the use of an alumoxane, aluminum alkyl, or ionic activator, and in some cases the presence of hydrogen. Certain conventional processes to produce alpha-olefin dimers utilize bridged metallocenes, such as bis(cyclopentadienyl)zirconium dichloride, in the presence of methyl alumoxane (MAO), trialkylaluminum, or higher alkyl alumoxane and an activator such as trimethyl aluminum. Such processes can produce predominantly vinylidene dimer olefins at high yields, but lack in catalyst efficiency, kinetics, and/or high product yield.

An exemplary PAO molecule is a "hybrid trimer" which is a reaction product of a metallocene dimer, such as a PAO dimer, with linear alpha-olefin (LAO) using an acid catalyst system, e.g., $BF_3$-alcohol promoter catalyst system. For example, a hybrid $C_{30}$ trimer is a reaction product of a $C_{20}$ metallocene PAO dimer and $C_{10}$ LAO. Conventional methods of forming hybrid trimers involve reaction of a PAO dimer feedstock that contains a significant amount of disubstituted vinylene. The disubstituted vinylene, however, is not highly reactive when added to a $BF_3$ catalyzed conventional reactor, and the reaction kinetics are very slow. In addition, the unreacted dimer in the stream going into the $BF_3$ catalyzed conventional reactor contaminates the stream produced from the $BF_3$ process and reduces the value of that reactor effluent.

Furthermore, conventional plants for the production of PAO molecules, such as hybrid trimers, can generate a PAO dimer from a first oligomerization reactor. The PAO dimer product from the first oligomerization reactor is of such poor quality (e.g., there are timers, tetramers, and higher oligomers) that it is enriched via a separation stage prior to being fed into a second oligomerization reactor. This process involves a separation stage, e.g., a distillation operation, prior to a second oligomerization reactor because feeding the trimer and higher (tetramer+) oligomers to the second oligomerization reactor produces an undesired heavier product from the second oligomerization reaction. The additional equipment, operators, and downtime involved for the separation stage, for example, can be a burden in terms of cost and efficiencies.

Therefore, there is a need for processes to selectively produce PAO dimers, with high vinylidene and very low vinylene content, at high catalyst efficiency, good kinetics, and high conversion. There is also a need for improved processes and apparatus for producing PAOs, such as low viscosity PAOs including hybrid trimers, from feedstocks containing the PAO dimers.

References for citing in an Information Disclosure Statement (37 C.F.R. 1.97(h)): U.S. application Ser. No. 12/642, 453 filed Dec. 18, 2009; Ser. No. 12/533,465 filed Jul. 31, 2009; 61/136,172 filed Aug. 15, 2008; 62/477,683 filed Mar. 28, 2017; 62/477,706 filed Mar. 28, 2017; PCT Publication Nos. WO 1995/027717; WO 2009/155471; WO 2009/155472; WO 2009/155510; WO 2009/155517; WO 2012/134720; WO 2012/133717; WO 2017/188602; WO 2017/155149; WO 2018/094088; WO 2018/182982; U.S. Pat.

Nos. 9,796,645; 9,688,792; 9,365,788; 7,129,197; 6,548,724; 6,548,723; 6,479,722; 5,625,105; 5,087,788; 4,973,788; 4,658,078; 3,367,987; 7,214,745; 8,816,027; 8,748,361; 8,318,998; 8,669,326; 8,940,839; 8,754,170; 8,426,659; 8,841,397; 8,501,894; 8,669,330; 8,835,563; 8,841,394; 8,399,724; 8,623,974; 8,981,029; 6,403,732; 6,818,585; 7,199,072; US Patent Application Publication Nos. 2018/0094088; 2017/0233516; 2015/0344598; 2013/0303818; 2013/0023633; 2009/0318644; 2005/0159299; 2004/0102590; Japanese Publication No. JP 2005-336092; JP 2011-037164A; Chinese Publication No. CN 105622807; EP Publication Nos. EP 0659756; EP 0610851; EP 0283739; Korean Publication No. KR 17250040000; Rulhoff, S. et al. (2006) "Synthesis and Characterization of Defined Branched Poly(propylene)s with Different Microstructures by Copolymerization of Propylene and Linear Ethylene Oligomers ($C_n$=26-28) with Metallocenes/MAO Catalysts," *Macromolecules*, v. 207, pp. 1450-1460; Kaneyoshi, Hiromu et al. (2005) "Synthesis of Block and Graft Copolymers with Linear Polyethylene Segments by Combination of Degenerative Transfer Coordination Polymerization and Atom Transfer Radical Polymerization," *Macromolecules*, v. 38(13), pp. 5425-5435; Teuben, J. et al. (1990) *J. Mol. Catal.*, v. 62(3), pp. 277-287); Yang, X. et al, (1992) *Angew. Chem., Int'l. Edn.*, Engl., v. 31, pp. 1375-1377); Small and Brookhart (*Macromol.*, v. 32, 1999, pp. 2120-2130); Weng et al. (*Macromol Rapid Comm.*, 2000, v. 21, pp. 1103-1107); *Macromolecules*, v. 33, 2000, pp. 8541-8548; Moscardi et al. (*Organomet.*, v. 20, 2001, pp. 1918); Zhu et al. (*Macromol.*, 2002, v. 35, pp. 10062-10070 and *Macromol. Rap. Commun.*, 2003, v. 24, pp, 311-315); Coates et al (*Macromol.*, 2005, v. 38, pp, 6259-6268); Rose et al. (*Macromolecules*, 2008. v. 41, pp. 559-567); Janiak, C. et al. (2006) *Macromol. Symp.*, v. 236, pp. 14-22), U.S. Pat. Nos. 9,409,834; 6,548,724; 4,658,078; Organometallics 2017, v. 36, pp. 2934-2939; Organometallics, 1997, v. 16, pp. 2492-2494, and U.S. Pat. No. 9,399,746.

SUMMARY

The present disclosure generally relates to processes to produce alpha-olefin oligomers and poly alpha-olefins.

In at least one embodiment, a process to produce a poly alpha-olefin (PAO) includes introducing a first alpha-olefin and a first catalyst system comprising a metallocene compound into a continuous stirred tank reactor or a continuous tubular reactor under first reactor conditions to form a first reactor effluent. The alpha-olefin is introduced to the reactor at a flow rate of about 100 g/hr. The first reactor diluent includes PAO dimer comprising at least 96 mol % of vinylidene and 4 mol % or less of trisubstituted vinylene and disubstituted vinylene, based on total moles of vinylidene, trisubstituted vinylene, and disubstituted vinylene. The method includes introducing the first reactor effluent, a second alpha-olefin and a second catalyst composition comprising an acid catalyst into a second reactor under second reactor conditions to form a second reactor effluent comprising PAO trimer.

In at least one embodiment, a blend includes a PAO product of the present disclosure.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

So that the manner in which the above-recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

To facilitate understanding, identical reference numerals have been used, where possible, to designate identical elements that are common to the figures. It is contemplated that elements and features of one example may be beneficially incorporated in other examples without further recitation.

DETAILED DESCRIPTION

Figure 1:
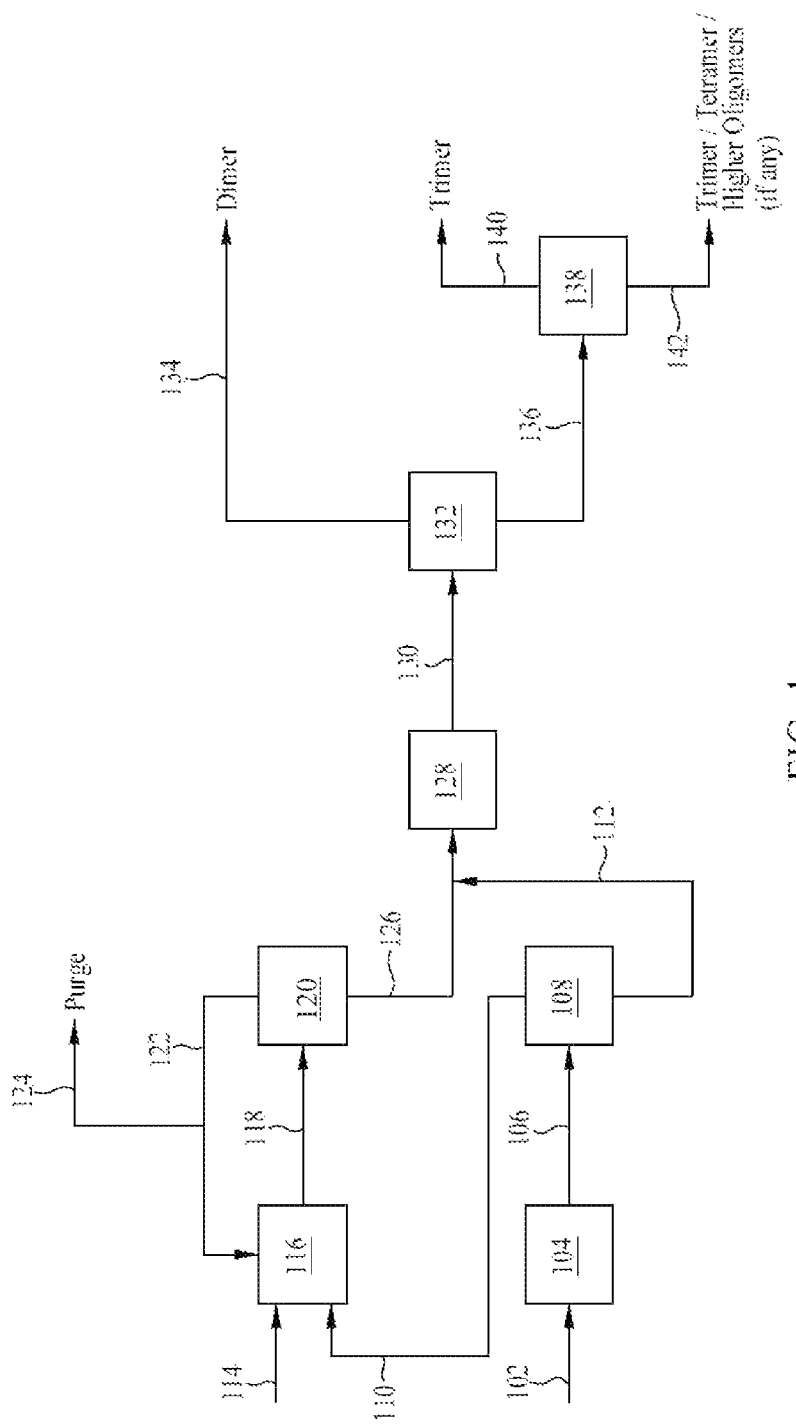
FIG. 1 shows a conventional apparatus for alpha-olefin processing.

The present disclosure provides processes for producing poly alpha-olefins using metallocene catalyst compounds having asymmetric unbridged metallocenes. In some examples, these metallocenes contain indacenyl-type ligands. Catalyst systems comprising such compounds can be used. The catalyst systems and processes incorporating such catalyst systems rival and/or surpass conventional catalyst systems in producing alpha-olefin oligomers and polymers.

Relative to conventional catalysts and catalyst systems, the catalysts and catalyst systems described herein can selectively produce alpha-olefin dimers at high product yield (high linear alpha-olefin conversion) and with very high vinylidene unsaturation with very high catalyst efficiency (low catalyst loading), high conversion, and good kinetics. In at least one example, the inventors have found that the catalyst systems disclosed herein can produce dimer selective olefins (greater than 90%), with >95 wt % vinylidene and 0 wt % vinylene content.

The present disclosure also provides processes and apparatus for producing alpha-olefin oligomers from feedstocks containing predominantly PAO dimers. In an example, the inventors have found that a so-called "hybrid trimer", which can be formed from a reaction of a PAO dimer with an alpha-olefin monomer, can be produced in high yields. The inventors have found that a higher purity PAO dimer feedstock, having low amounts of trimer, tetramer, and higher oligomers, can form higher amounts of the hybrid trimer relative to conventional processes. In addition, the inventors have found that reducing (or eliminating) the amount of disubstituted vinylene in the PAO dimer feedstock produces a PAO hybrid trimer at higher yields and higher purity relative to conventional processes.

The present disclosure also provides processes and apparatus for producing alpha-olefin oligomers. In an example, the process eliminates the need for a separation stage between a first oligomerization operation and a second oligomerization operation. The inventors have found that PAO trimer produced from a process, which includes a first and second oligomerization, meets and/or exceeds conventional process yields of PAO trimer, even while removing the separation operation between the two oligomerizations. This can reduce cost and increase the efficiencies of production relative to conventional processes and apparatus.

Processes and apparatus of the present disclosure can provide one or more the following:
a. No alumina specie present in the PAO product (able to not have to remove Al as it can be considered an impurity for final product; preferable to not have to reduce LAO isomerization which leads to yield loss)
  i. >60% dimer selectivity at a catalyst productivity of >10,000 g PAO/g cat without the use of alumoxane
  ii. >60% dimer selectivity at a catalyst productivity of >10,000 g PAO/g cat without the use of alumoxane nor alkyl alumina
  iii. >60% dimer selectivity at a catalyst productivity of >10,000 g PAO/g cat with <500 ppm of an alkyl alumina
  iv. >60% dimer selectivity at a catalyst productivity of >10,000 g PAO/g cat with <20 ppm of an alkyl alumina
  v. >60% dimer selectivity at a catalyst productivity of >10,000 g PAO/g cat with <2% LAO isomerization
b. Activity with selectivity (e.g., more efficient production of high dimer)
  i. >60% dimer selectivity with catalyst productivity of >10,000 g PAO/g cat
  ii. >60% dimer selectivity with catalyst activity >2,000 g PAO/mol cat sec
  iii. >90% dimer selectivity with catalyst productivity >60,000 g PAO/g cat
c. Low residence times (which is another indicator of higher efficiency)
  i. <24 hours; preferably <10 hours; preferably <5 hours
d. Vinylidene purity (useful for functionalization by alkylation, further oligomerization)
  i. >90%; preferably >95%
e. Catalyst family
  i. New type of catalyst specifically suitable for highly efficient production of high vinylidene dimers.

Processes and apparatus of the present disclosure can provide one or more the following:
continuous processes,
PAO products having an Mn below 300,
Processes at activity above 2,000 gPAOls·mol with low Mn,
Processes at conversion above 80% with low Mn,
Processes at conversion above 80% with high vinylidene,
Processes can operate at higher temperature of, for example, 120-148.5° C.,
Processes with reduced LAO isomerization without alkyl alumina,
Processes can use $C_6$-$C_{20}$ LAOs,
Processes can optionally be MAO-free,
Processes can be optionally alkyl-alumina free.

For the purposes of this present disclosure, and unless otherwise specified, the term "alkyl" or "alkyl group" interchangeably refers to a saturated hydrocarbyl group consisting of carbon and hydrogen atoms. An alkyl group can be substituted or unsubstituted and can be linear, branched, or cyclic.

For the purposes of this present disclosure, and unless otherwise specified, the term "cycloalkyl" or "cycloalkyl group" interchangeably refers to a saturated hydrocarbyl group wherein the carbon atoms form one or more ring structures.

For the purposes of this present disclosure, and unless otherwise specified, the term "alkenyl" or "alkenyl group" interchangeably refers to a linear unsaturated hydrocarbyl group comprising a C=C bond therein.

For the purposes of this present disclosure, and unless otherwise specified, the term "cycloalkenyl" or "cycloalkenyl group" interchangeably refers to cyclic hydrocarbyl group comprising a C=C bond in the ring.

For the purposes of this present disclosure, and unless otherwise specified, the term "aryl" or "aryl group" interchangeably refers to a hydrocarbyl group comprising an aromatic ring structure therein.

The term "branched (such as branched linear)" is defined to mean a branched group that is not dendritic (i.e., branch on branch) or crosslinked, typically a branched (such as branched linear) group is a linear group that has one or more branches.

For the purposes of this present disclosure, and unless otherwise specified, a substituted group refers to a group in which at least one atom is replaced by a different atom or a group. Thus, a substituted alkyl group is an alkyl group in which at least one hydrogen atom is replaced by a hydrocarbyl group, a halogen, any other non-hydrogen group, and/or at least one carbon atom and hydrogen atoms bonded thereto is replaced by a different group. As a non-limiting example, a substituted group is a radical in which at least one hydrogen atom has been substituted with a heteroatom or heteroatom containing group, such as with at least one functional group, such as halogen (Cl, Br, I, F), $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$, and the like or where at least one heteroatom has been inserted within the hydrocarbyl radical, such as halogen (Cl, Br, I, F), O, S, Se, Te, $NR^*$, $PR^*$, $AsR^*$, $SbR^*$, $BR^*$, $SiR^*_2$, $GeR^*_2$, $SnR^*_2$, $PbR^*_2$, and the like, where $R^*$ is, independently, hydrogen or a hydrocarbyl.

For the purposes of this present disclosure, and unless otherwise specified, the terms "hydrocarbyl radical," "hydrocarbyl group," or "hydrocarbyl" interchangeably refer to a group consisting of hydrogen and carbon atoms only. A hydrocarbyl group can be saturated or unsaturated, linear or branched, cyclic or acyclic, aromatic, or non-aromatic.

For the purposes of this present disclosure, and unless otherwise specified, substituted hydrocarbyl radicals are radicals in which at least one hydrogen atom has been substituted with a heteroatom or heteroatom containing group, such as with at least one functional group, such as halogen (Cl, Br, I, F), NR*$_2$, OR*, SeR*, TeR*, PR*$_2$, AsR*$_2$, SbR*$_2$, SR*, BR*$_2$, SiR*$_3$, GeR*$_3$, SnR*$_3$, PbR*$_3$, and the like or where at least one heteroatom has been inserted within the hydrocarbyl radical, such as halogen (Cl, Br, I, F), O, S, Se, Te, NR*, PR*, AsR*, SbR*, BR*, SiR*$_2$, GeR*$_2$, SnR*$_2$, PbR*$_2$, and the like, where R* is, independently, hydrogen or a hydrocarbyl.

In some embodiments, the hydrocarbyl radical is independently selected from methyl, ethyl, ethenyl and isomers of propyl, butyl, pentyl, hexyl, heptyl, octyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl. Also included are isomers of saturated, partially unsaturated and aromatic cyclic structures wherein the radical may additionally be subjected to the types of substitutions described above. Examples include phenyl, methylphenyl, benzyl, methylbenzyl, naphthyl, cyclohexyl, cyclohexenyl, methylcyclohexyl, and the like. For this present disclosure, when a radical is listed, it indicates that radical type and all other radicals formed when that radical type is subjected to the substitutions defined above. Alkyl, alkenyl, and alkynyl radicals listed include all isomers including where appropriate cyclic isomers, for example, butyl includes n-butyl, 2-methylpropyl, 1-methylpropyl, tert-butyl, and cyclobutyl (and analogous substituted cyclopropyls); pentyl includes n-pentyl, cyclopentyl, 1-methylbutyl, 2-methylbutyl, 3-methylbutyl, 1-ethylpropyl, and neopentyl (and analogous substituted cyclobutyls and cyclopropyls); butenyl includes E and Z forms of 1-butenyl, 2-butenyl, 3-butenyl, 1-methyl-1-propenyl, 1-methyl-2-propenyl, 2-methyl-1-propenyl, and 2-methyl-2-propenyl (and cyclobutenyls and cyclopropenyls). Cyclic compound having substitutions include all isomer forms, for example, methylphenyl would include ortho-methylphenyl, meta-methylphenyl and para-methylphenyl; dimethylphenyl would include 2,3-dimethylphenyl, 2,4-dimethylphenyl, 2,5-dimethylphenyl, 2,6-diphenylmethyl, 3,4-dimethylphenyl, and 3,5-dimethylphenyl.

For the purposes of this present disclosure, and unless otherwise specified, silylcarbyl radicals (also referred to as silylcarbyls, silylcarbyl groups or silylcarbyl substituents) are radicals in which one or more hydrocarbyl hydrogen atoms have been substituted with at least one SiR*$_3$ containing group or where at least one —Si(R*)$_2$— has been inserted within the hydrocarbyl radical where R* is independently a hydrocarbyl or halocarbyl radical, and two or more R* may join together to form a substituted or unsubstituted saturated, partially unsaturated or aromatic cyclic or polycyclic ring structure. Silylcarbyl radicals can be bonded via a silicon atom or a carbon atom.

For the purposes of this present disclosure, and unless otherwise specified, substituted silylcarbyl radicals are silylcarbyl radicals in which at least one hydrogen atom has been substituted with at least one functional group such as NR*$_2$, OR*, SeR*, TeR*, PR*$_2$, AsR*$_2$, SbR*$_2$, SR*, BR*$_2$, GeR*$_3$, SnR*$_3$, PbR$_3$ and the like or where at least one non-hydrocarbon atom or group has been inserted within the silylcarbyl radical, such as —O—, —S—, —Se—, —Te—, —N(R*)—, =N—, —P(R*)—, =P—, —As(R*)—, —Sb(R*)—, =Sb—, —B(R*)—, —B—, —Ge(R*)$_2$—, —Sn(R*)$_2$—, —Pb(R*)$_2$— and the like, where R* is independently a hydrocarbyl or halocarbyl radical, and two or more R* may join together to form a substituted or unsubstituted saturated, partially unsaturated or aromatic cyclic or polycyclic ring structure.

For the purposes of this present disclosure, and unless otherwise specified, halocarbyl radicals are radicals in which one or more hydrocarbyl hydrogen atoms have been substituted with at least one halogen (e.g, F, Cl, Br, I) or halogen-containing group (e.g., CF$_3$).

For the purposes of this present disclosure, and unless otherwise specified, substituted halocarbyl radicals are radicals in which at least one halocarbyl hydrogen or halogen atom has been substituted with at least one functional group such as NR*$_2$, OR*, SeR*, TeR*, PR*$_2$, AsR*$_2$, SbR*$_2$, SR*, BR*$_2$, SiR*$_3$, GeR*$_3$, SnR*$_3$, PbR*$_3$, and the like or where at least one non-carbon atom or group has been inserted within the halocarbyl radical such as —O—, —S—, —Se—, —Te—, —N(R*)—, =N—, —P(R*)—, =P—, —As(R*)—, =As—, —Sb(R*)—, =Sb—, —B(R*)—, =B—, —Si(R*)$_2$—, —Ge(R*)$_2$—, —Sn(R*)$_2$—, —Pb(R*)$_2$— and the like, where R* is independently a hydrocarbyl or halocarbyl radical provided that at least one halogen atom remains on the original halocarbyl radical. Additionally, two or more R* may join together to form a substituted or unsubstituted saturated, partially unsaturated or aromatic cyclic or polycyclic ring structure.

For the purposes of this present disclosure, and unless otherwise specified, germanyl radicals (also referred to as germanyls, germanyl groups or germanyl substituents) are radicals in which one or more hydrocarbyl hydrogen atoms have been substituted with at least one GeR*$_3$ containing group or where at least one —Ge(R*)2— has been inserted within the hydrocarbyl radical where R* is independently a hydrocarbyl or halocarbyl radical, and two or more R* may join together to form a substituted or unsubstituted saturated, partially unsaturated or aromatic cyclic or polycyclic ring structure. Germanyl radicals can be bonded via a silicon atom or a carbon atom.

For the purposes of this present disclosure, and unless otherwise specified, substituted germanyl radicals are germanyl radicals in which at least one hydrogen atom has been substituted with at least one functional group such as NR*$_2$, OR*, SeR*, TeR*, PR*$_2$, AsR*$_2$, SbR*$_2$, SR*, BR*$_2$, SiR*$_3$, SnR*$_3$, PbR$_3$ and the like or where at least one non-hydrocarbon atom or group has been inserted within the germanyl radical, such as —O—, —S—, —Se—, —Te—, —N(R*)—, =N—, —P(R*)—, =P—, —As(R*)—, =As—, —Sb(R*)—, =Sb—, —B(R*)—, αB—, —Si(R*)$_2$—, —Sn(R*)$_2$—, —Pb(R*)$_2$— and the like, where R* is independently a hydrocarbyl or halocarbyl radical, and two or more R* may join together to form a substituted or unsubstituted saturated, partially unsaturated or aromatic cyclic or polycyclic ring structure.

For the purposes of this present disclosure, and unless otherwise specified, the term "Cn" group or compound refers to a group or a compound comprising carbon atoms at total number thereof of n. Thus, a "Cm-Cn" group or compound refers to a group or compound comprising carbon atoms at a total number thereof in the range from m to n.

Thus, a $C_1$-$C_{50}$ alkyl group refers to an alkyl group comprising carbon atoms at a total number thereof in the range from 1 to 50.

For the purposes of this present disclosure, and unless otherwise specified, the term "olefin," alternatively termed "alkene," refers to an unsaturated hydrocarbon compound having a hydrocarbon chain containing at least one carbon-to-carbon double bond in the structure thereof, wherein the carbon-to-carbon double bond does not constitute a part of an aromatic ring. The olefin may be linear, branched, or cyclic. For purposes of this specification and the claims appended thereto, when a polymer or copolymer is referred to as comprising an olefin, including, but not limited to ethylene, propylene, and butene, the olefin present in such polymer or copolymer is the polymerized form of the olefin. For example, when a copolymer is said to have an "ethylene" content of 35 wt % to 55 wt %, it is understood that the mer unit in the copolymer is derived from ethylene in the polymerization reaction and said derived units are present at 35 wt % to 55 wt %, based upon the weight of the copolymer. A "polymer" has two or more of the same or different mer units. A "homopolymer" is a polymer having mer units that are the same. A "copolymer" is a polymer having two or more mer units that are different from each other. A "terpolymer" is a polymer having three trier units that are different from each other. "Different" as used to refer to mer units indicates that the mer units differ from each other by at least one atom or are different isomerically. Thus, an "olefin" is intended to embrace all structural isomeric forms of olefins, unless it is specified to mean a single isomer or the context clearly indicates otherwise. An oligomer is a polymer having a low molecular weight, such as an Mn of 21,000 g/mol or less (such as 10,000 g/mol or less), and/or a low number of mer units, such as 100 mer units or less (such as 75 mer units or less).

For the purposes of this present disclosure, and unless otherwise specified, the term "alpha-olefin" refers to an olefin having a terminal carbon-to-carbon double bond in the structure thereof ((R'R")—C═$CH_2$, where R' and R" is independently hydrogen or any hydrocarbyl group; such as R' is hydrogen and R" is an alkyl group). A "linear alpha-olefin" is an alpha-olefin defined in this paragraph wherein R' is hydrogen, and R" is hydrogen or a linear alkyl group. Non-limiting examples of α-olefins include ethylene, 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-eicosene, 1-heneicosene, 1-docosene, 1-tricosene, 1-tetracosene, 1-pentacosene, 1-hexacosene, 1-heptacosene, 1-octacosene, 1-nonacosene, 1-triacontene, 4-methyl-1-pentene, 3-methyl-1-pentene, 5-methyl-1-nonene, 3,5,5-trimethyl-1-hexene, vinylcyclohexane, and vinylnorbornane. Non-limiting examples of cyclic olefins and diolefins include cyclobutene, cyclopentene, cyclohexene, cycloheptene, cyclooctene, cyclononene, cyclodecene, norbornene, 4-methylnorbornene, 2-methylcyclopentene, 4-methylcyclopentene, vinylcyclohexane, norbornadiene, dicyclopentadiene, 5-ethylidene-2-norbornene, vinylcyclohexene, 5-vinyl-2-norbornene, 1,3-divinylcyclopentane, 1,2-divinylcyclohexane, 1,3-divinylcyclohexane, 1,4-divinylcyclohexane, 1,5-divinylcyclooctane, 1-allyl-4-vinylcyclohexane, 1,4-diallylcyclohexane, 1-allyl-5-vinylcyclooctane, and 1,5-diallylcyclooctane.

The term "vinyl" refers to an olefin having the following formula:

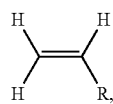

wherein R is a hydrocarbyl group, such as a saturated hydrocarbyl group, such as an alkyl group.

The term "vinylidene" refers to an olefin having the following formula:

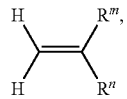

wherein $R^m$ and $R^n$ are each independently a hydrocarbyl group, such as a saturated hydrocarbyl group, such as alkyl group. Vinylidenes are 1,1-disubstituted vinylene groups.

The term "disubstituted vinylene" refers to:

(i) an olefin having the following formula:

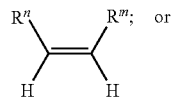

(ii) an olefin having the following formula:

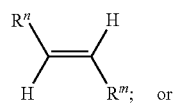

(iii) a mixture of (i) and (ii) at any proportion thereof, wherein $R^m$ and $R^n$, the same or different at each occurrence, are each independently a hydrocarbyl group, such as saturated hydrocarbyl group such as alkyl group. Disubstituted vinylenes represent only 1,2-disubstituted vinylene groups and do not include vinylidenes, or 1,1-disubstituted vinylenes. The term "vinylene," as used herein, is an alternative term for "disubstituted vinylene" only and not as a generic class of multiple vinylene species.

The term "trisubstituted vinylene" means an olefin having the following formula:

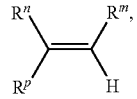

wherein $R^m$, $R^n$, and $R^p$ are each independently a hydrocarbyl group, such as a saturated hydrocarbyl group, such as alkyl group, or alternatively $R^m$ and $R^n$ can together form a non-aryl ring structure with $R^p$ being a pendant hydrocarbyl group.

For the purposes of this present disclosure, and unless otherwise specified, "poly alpha-olefin(s)" (PAO(s)) are polymers of one or more alpha-olefin monomers, such as an oligomer of one or more alpha-olefins. PAOs are polymeric, typically oligomeric, molecules produced from the polymerization/oligomerization reactions of alpha-olefin monomer molecules in the presence of a catalyst system. Thus, the PAO can be a dimer (resulting from two terminal olefin molecules), a trimer (resulting from three terminal olefin molecules), a tetramer (resulting from four terminal olefin molecules), or any other oligomer or polymer comprising two or more structure units derived from one or more terminal olefin monomer(s). The PAOs formed in the present disclosure have a kinematic viscosity (at 100° C.) of 3,000 cSt or less as determined by ASTM D445, or have an Mn of 20,000 g/mol or less as determined by GC (as described herein), or have a combination thereof.

The PAO molecule can be highly regio-regular, such that the bulk material may exhibit an isotacticity, or a syndiotacticity when measured by $^{13}$C NMR. The PAO molecule can be highly regio-irregular, such that the bulk material can be substantially atactic when measured by $^{13}$C NMR. A PAO material made by using a metallocene-based catalyst system is typically called a metallocene-PAO, and a PAO material made by using traditional non-metallocene-based catalysts (e.g., Lewis acids, supported chromium oxide, and the like) is typically called a conventional PAO.

For the purposes of this present disclosure, and unless otherwise specified, the term "carbon backbone" refers to the longest straight carbon chain in the molecule of the compound or the group in question. "Branches" or "pendant groups" interchangeably refer to any non-hydrogen group connected to the carbon backbone other than those attached to the carbon atoms at the very ends of the carbon backbone. As used herein, the term "length" of a pendant group is defined as the total number of carbon atoms in the longest carbon chain in the pendant group, counting from the first carbon atom attached to the carbon backbone and ending with the final carbon atom therein, without taking into consideration any substituents or pendant groups on the chain. In some embodiments, the pendant group is free of substituents comprising more than 2 carbon atoms (or more than 1 carbon atom), or is free of any substituent. A pendant group may contain a cyclic group or a portion thereof in the longest carbon chain, in which case half of the carbon atoms in the cyclic group are counted toward the length of the pendant group. Thus, by way of examples, a linear $C_8$ pendant group has a length of 8; each of the pendant groups PG-1 (cyclohexylmethylene) and PG-2 (phenylmethylene) has a length of 4; and each of the pendant groups PG-3 (o-heptyl-phenylmethylene) and PG-4 (p-heptylphenylmethylene) has a length of 11. Where a PAO molecule contains multiple pendant groups, the arithmetic average of the lengths of all such pendant groups is calculated as the average length of all pendant groups in the PAO molecule.

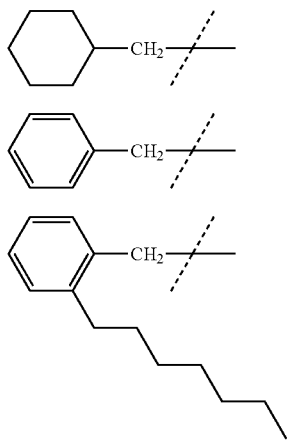

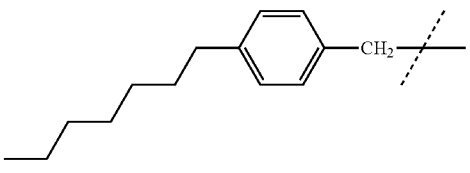

In the present disclosure, any metallocene compound may have one or more optical isomers. All metallocene compounds identified herein by name or structure shall include all possible optical isomers thereof and mixtures of any such optical isomers. For example, metallocene compound Me$_2$Si(Me$_4$Cp)(3-PrInd)ZrMe$_2$ shall include the following two optical isomers and mixtures thereof, even if only one structure is given when it is described:

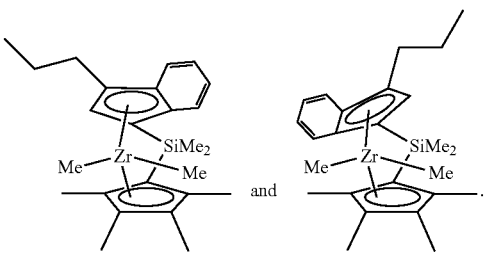

For the purposes of this present disclosure, and unless otherwise specified, the term "substantially all" with respect to PAO molecules means at least 90 mol % (such as at least 95 mol %, at least 98 mol %, at least 99 mol %, or even 100 mol %).

For the purposes of this present disclosure, and unless otherwise specified, the term "substantially free of" with respect to a particular component means the concentration of that component in the relevant composition is no greater than 10 mol % (such as no greater than 5 mol %, no greater than 3 mol %, no greater than 1 mol %, or about 0%, within the bounds of the relevant measurement framework), based on the total quantity of components of the relevant composition.

For the purposes of this present disclosure, and unless otherwise specified, a "reactor" refers to one or more vessels configured to perform oligomerization processes.

For the purposes of this present disclosure, and unless otherwise specified, a "metallocene" catalyst compound is a transition metal catalyst compound having one, two or three, typically one or two, substituted or unsubstituted cyclopentadienyl ligands bound to the transition metal, typically a metallocene catalyst is an organometallic compound containing at least one π-bound cyclopentadienyl moiety (or substituted cyclopentadienyl moiety). Substituted or unsubstituted cyclopentadienyl ligands include substituted or unsubstituted indenyl, fluroenyl, indacenyl, benzindenyl, and the like.

For the purposes of this present disclosure, and unless otherwise specified, the terms "catalyst" and "catalyst compound" are defined to mean a compound capable of initiating catalysis and/or of facilitating a chemical reaction with little or no poisoning/consumption. In the description herein, the catalyst may be described as a catalyst precursor, a pre-catalyst compound, or a transition metal compound, and these terms are used interchangeably. A catalyst compound may be used by itself to initiate catalysis or may be used in combination with an activator to initiate catalysis. When the catalyst compound is combined with an activator to initiate catalysis, the catalyst compound is often referred to as a pre-catalyst or catalyst precursor.

A "catalyst system" is a combination of at least one catalyst compound, at least one activator, and optional co-activator, where the system can polymerize/oligomerize monomers to form polymer/oligomer.

For the purposes of this present disclosure, and unless otherwise specified, a scavenger is a compound typically added to facilitate oligomerization/polymerization by scavenging impurities. Some scavengers may also act as activators and may be referred to as co-activators. A co-activator, that is not a scavenger, may be used in conjunction with an activator in order to form an active catalyst. In some embodiments, a co-activator can be pre-mixed with the catalyst compound to form an alkylated catalyst compound.

For the purposes of this present disclosure, and unless otherwise specified, all kinematic viscosity values in the present disclosure are as determined according to ASTM D445. Kinematic viscosity at 100° C. is reported herein as KV100, and kinematic viscosity at 40° C. is reported herein as KV40. Unit of all KV100 and KV40 values herein is cSt, unless otherwise specified.

For the purposes of this present disclosure, and unless otherwise specified, all viscosity index (VI) values in the present disclosure are as determined according to ASTM D2270.

For the purposes of this present disclosure, and unless otherwise specified, all Noack volatility (NV) values in the present disclosure are as determined according to ASTM D5800 and units of all NV values are wt %.

For the purposes of this present disclosure, and unless otherwise specified, bromine number values in the present disclosure are determined according to ASTM D 1159.

For the purposes of this present disclosure, and unless otherwise specified, rotating pressure vessel oxidation test (RPVOT) values in the present disclosure are determined according to ASTM D2272.

For the purposes of this present disclosure, and unless otherwise specified, all numerical values within the detailed description and the claims herein are modified by "about" or "approximately" the indicated value, and consider experimental error and variations that would be expected by a person having ordinary skill in the art.

For the purposes of this present disclosure, and unless otherwise specified, all percentages of pendant groups, terminal carbon chains, and side chain groups are by mole, unless specified otherwise. Percent by mole is expressed as "mol %," and percent by weight is expressed as "wt %."

For the purposes of this present disclosure, and unless otherwise specified, all molecular weight data are in the unit of g·mol$^{-1}$.

The following abbreviations may be used through this specification: Cp is cyclopentadiene or cyclopentadienyl; Me is methyl, Ph is phenyl, Et is ethyl, Pr is propyl, iPr is isopropyl, n-Pr is normal propyl, Bu is butyl, iBu is isobutyl, tBu is tertiary butyl, p-tBu is para-tertiary butyl, nBu is normal butyl, TMS is trimethylsilyl, TIBAL is triisobutylaluminum, TNOAL or TNOA is trin-octylaluminum, MAO is methylalumoxane, pMe is para-methyl, Ar* is 2,6-diisopropylaryl, Bz or Bn are interchangeably benzyl, THF is tetrahydrofuran, RT is room temperature (i.e., approximately 23° C.), and tol is toluene.

I. METALLOCENE DIMER SELECTIVE PROCESS

The present disclosure includes catalyst compounds that can dimerize alpha-olefins, e.g., linear alpha-olefins, in the presence of metallocene catalysts to produce PAO dimers with high selectivity and high yields, with very low amounts of trimers, tetramers, and higher oligomers (if any), where the higher oligomers are oligomers that have degree of polymerization of 5 or more. As used herein, "degree of polymerization" refers to the number of monomeric units of an oligomer. For example, an oligomer having a degree of polymerization of 3 is an oligomer that is the reaction product of 3 monomers. A "dimer" has a degree of polymerization of 2, and a "turner" has a degree of polymerization of 3.

In addition, the catalyst compounds can produce, based on the amount of PAO dimers produced, very low disubstituted and trisubstituted vinylene content (e.g., about 0 mol %), very low trisubstituted unsaturation (e.g., about 5 mol % or lower), and very high vinylidene content (e.g., about 95 mol % or higher). The metallocene catalysts, catalyst systems incorporating such, and processes using such, can produce this distribution of dimers with high catalyst efficiency, high product yield, good kinetics as compared to conventional catalysts for dimerizing alpha-olefins.

The metallocene dimer selective reaction is referred to interchangeably as "first oligomerization" or "first oligomerization process."

In some embodiments, the metallocene compound useful in the first oligomerization process for making PAOs can have a structure represented by formula (MC-I):

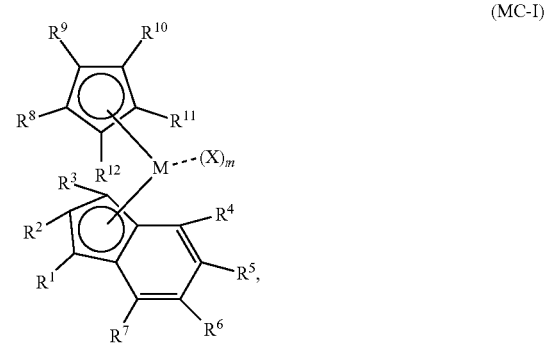

(MC-I)

wherein:

each of $R^1$, $R^2$, and $R^3$ is independently hydrogen, a substituted or unsubstituted linear, branched, or cyclic $C_1$-$C_{30}$ (such as $C_1$-$C_{20}$, e.g., a $C_1$-$C_8$) hydrocarbyl group;

each of $R^4$, $R^5$, $R^6$, and $R^7$ is independently hydrogen, a substituted or unsubstituted linear, branched, or cyclic $C_1$-$C_{30}$ (such as a $C_1$-$C_{20}$, e.g., a $C_1$-$C_8$) hydrocarbyl group, or one or more of $R^4$ and $R^5$, $R^5$ and $R^6$, or $R^5$ and $R^7$, taken together with the carbon atoms in the indenyl ring to which they are directly connected, collectively form one or more substituted or unsubstituted rings fused to the indenyl ring;

each of $R^8$, $R^9$, $R^{10}$, $R^{11}$, and $R^{12}$ is independently a substituted or unsubstituted linear, branched, or cyclic $C_1$-$C_{30}$ (such as $C_1$-$C_{20}$, a $C_3$-$C_8$) hydrocarbyl, silylcarbyl, or germanyl group;

M is a transition metal, such as a group 3, 4, or 5 transition metal, such as a group 4 transition metal, such as Hf, Ti, or Zr;

each X is independently a halogen, a hydride, an amide, an alkoxide, a sulfide, a phosphide, a diene, an amine, a phosphine, an ether, or a $C_1$-$C_{20}$ (e.g., a $C_1$-$C_8$) substituted or unsubstituted linear, branched, or cyclic hydrocarbyl group, or optionally two or more X moieties may together form a fused ring or ring system; and m is an integer equal to 1, 2 or 3, such as 2.

In at least one metallocene compound formula herein, each of $R^1$, $R^2$, and $R^3$ can be independently hydrogen or a substituted or unsubstituted linear, branched, or cyclic $C_1$-$C_6$ hydrocarbyl group (e.g., a methyl, an ethyl, a propyl, a butyl, a cyclohexyl, or a phenyl).

In at least one metallocene compound formula herein, each of $R^1$, $R^2$, and $R^3$ can be subject to the proviso that at least one of $R^1$, $R^2$, and $R^3$ is a substituted or unsubstituted linear, branched, or cyclic $C_1$-$C_{20}$), such as $C_1$-$C_8$ hydrocarbyl group, such as $C_1$-$C_6$ hydrocarbyl group (e.g., a methyl, an ethyl, a propyl, a butyl, a cyclohexyl, or a phenyl), and two of $R^1$, $R^2$, and $R^3$ are each hydrogen. In some embodiments, a first one of $R^1$, $R^2$, and $R^3$ is a substituted or unsubstituted linear, branched, or cyclic $C_1$-$C_{20}$ (such as a $C_1$-$C_8$, such as $C_1$-$C_6$ hydrocarbyl group, e.g., a methyl, an ethyl, a propyl, a butyl, a cyclohexyl, or a phenyl) hydrocarbyl group; a second one of $R^1$, $R^2$, and $R^3$ is hydrogen; and a third one of $R^1$, $R^2$, and $R^3$ is hydrogen, a substituted or unsubstituted linear, branched, or cyclic $C_1$-$C_{20}$ (such as a $C_1$-$C_8$, such as $C_1$-$C_6$ hydrocarbyl group, e.g., a methyl, an ethyl, a propyl, a butyl, a cyclohexyl, or a phenyl) hydrocarbyl group.

In at least one metallocene compound formula herein, each of $R^1$ and $R^3$ can be independently a substituted or unsubstituted linear, branched, or cyclic $C_2$-$C_6$ hydrocarbyl group (e.g., an ethyl, a propyl, a butyl, a cyclohexyl, or a phenyl), and $R^2$ can be a hydrogen. In at least one embodiment, each of $R^1$ and $R^3$ can be independently each a methyl group and $R^2$ can be a hydrogen.

In at least one metallocene compound formula herein, one or both of $R^1$ and $R^3$ can be a tertiary or quaternary beta branched ligand in which the alpha and beta atoms are a Group 14 atom, e.g., carbon, silicon, germanium, and two or more, such as three, substituted or unsubstituted linear, branched, or cyclic $C_1$-$C_{18}$, such as $C_1$-$C_8$, hydrocarbyl groups attached to the beta atom. Examples include neopentyl, beta trialkylsilyl-methyl, and beta-trialkylgermanyl-methyl moieties.

In at least one metallocene compound formula herein, examples of $C_1$-$C_{20}$ and/or $C_1$-$C_{30}$ substituted or unsubstituted linear, branched, or cyclic hydrocarbyl groups can include: methyl, ethyl, n-propyl, isopropyl, n-butyl, 1-methylpropyl, 1-ethylethyl, n-pentyl, neopentyl (2,2-methylpropyl), 1-methylpentyl, 1-ethylpropyl, 1-hexyl, 1-methylpentyl, 1-ethylbutyl, 1-propylpropyl, optionally substituted cyclohexyl, optionally substituted phenyl, optionally substituted benzyl, and the like, and any ethylenically unsaturated group that can be derived from them by eliminating one available hydrogen group from each of two adjacent carbon atoms therein.

In at least one metallocene compound formula herein, M can comprise, can consist essentially of, or can be Ti, Zr, and/or Hf. In at least one embodiment, M can comprise, can consist essentially of, or can be Zr and/or Hf, such as Hf. In some embodiments, m can be an integer equal to 1, 2 or 3, such as 2.

In at least one metallocene compound formula herein, each X can be independently a halogen or a substituted or unsubstituted linear, branched, or cyclic $C_1$-$C_6$ hydrocarbyl group, e.g., a methyl, an ethyl, a propyl, a butyl, a phenyl, a benzyl, a chloride, a bromide, or an iodide, such as methyl.

In at least one metallocene compound formula herein, at least three of $R^8$, $R^9$, $R^{10}$, $R^{11}$, and $R^{12}$ are not hydrogen. In some embodiments, at least four of $R^8$, $R^9$, $R^{10}$, $R^{11}$, and $R^{12}$ are each independently a substituted or unsubstituted linear, branched, or cyclic $C_1$-$C_8$ hydrocarbyl group, such as methyl or ethyl.

In at least one metallocene compound formula herein, $R^{12}$ is a substituted or unsubstituted linear, branched, or cyclic $C_1$-$C_8$ hydrocarbyl group, such as methyl or ethyl. In some embodiments, i) at least three of $R^8$, $R^9$, $R^{10}$, $R^{11}$, and $R^{12}$ if present are not hydrogen; ii) two or more of $R^8$, $R^9$, $R^{10}$, $R^{11}$, and $R^{12}$ if present together form a fused ring or ring system; iii) at least two of $R^4$, $R^5$, $R^6$, and $R^7$ are hydrogen; iv) each X is independently a halogen or a substituted or unsubstituted linear, branched, or cyclic $C_1$-$C_6$ hydrocarbyl group; v) M comprises Zr or Hf; or a combination thereof.

In at least one metallocene compound formula herein, $R^8$, $R^9$, $R^{10}$, $R^{11}$, and $R^{12}$ are each independently a substituted or unsubstituted linear, branched, or cyclic $C_1$-$C_8$ hydrocarbyl group, such as methyl or ethyl.

In at least one metallocene compound formula herein, the metallocene compound useful in the first oligomerization process for making PAOs can have a structure represented by formula (MC-II):

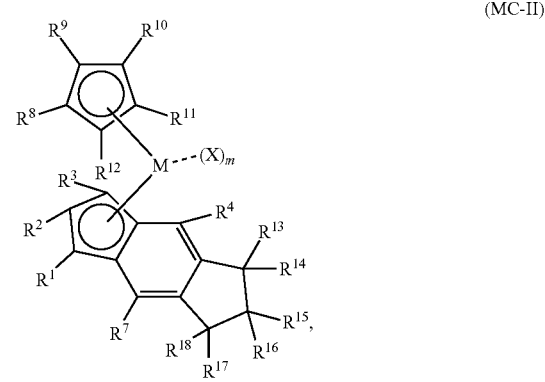

(MC-II)

wherein:

each of $R^{13}$, $R^{14}$, $R^{15}$, $R^{16}$, $R^{17}$, and $R^{18}$ can be independently hydrogen or a substituted or unsubstituted linear, branched, or cyclic $C_1$-$C_{30}$ (such as $C_1$-$C_{20}$, e.g., a $C_1$-$C_8$) hydrocarbyl, silylcarbyl, or germanyl group; and each of $R^1$, $R^2$, $R^3$, $R^4$, $R^7$, $R^8$, $R^9$, $R^{10}$, $R^{11}$, $R^{12}$, M, X, m, $C_1$-$C_{30}$, and $C_1$-$C_{20}$ can be as described above.

In some embodiments, a catalyst compound useful for the first oligomerization process can include catalyst I.A, catalyst I.B, catalyst I.C, or a combination thereof:

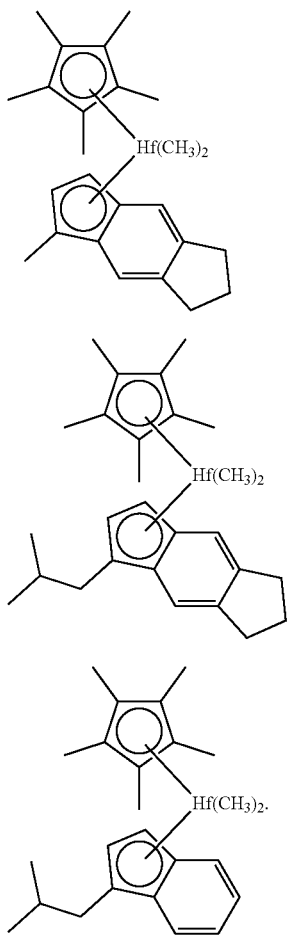

In some embodiments, a catalyst compound useful for the first oligomerization process can include those suitable oligomerization catalysts described herein.

In at least one embodiment, the catalyst compound can be part of a catalyst system, and such catalyst systems for the first oligomerization can include those suitable oligomerization catalysts described herein.

In at least one embodiment, a process to produce a poly alpha-olefin (PAO) includes introducing a $C_4$-$C_{32}$ alpha-olefin (e.g., a $C_6$-$C_{32}$ alpha-olefin) and a catalyst system comprising an activator and a metallocene compound into a reactor under reactor conditions and obtaining a product comprising PAO dimer, optional higher oligomers of alpha-olefin, or a combination thereof, the PAO dimer comprising 96 mol % or more of vinylidene based on total moles of vinylidene, disubstituted vinylene, and trisubstituted vinylene in the product, the metallocene compound is represented by formula (MC-I) and/or formula (MC-II).

In at least one embodiment, a first oligomerization process for making a poly alpha-olefin (e.g., a dimer of an alpha-olefin) can include introducing an alpha-olefin and a catalyst system into a reactor, e.g., a polymerization or oligomerization reactor, under reactor conditions to form a product comprising PAO dimer.

In at least one embodiment, the product produced from the first oligomerization process can include one or more PAO dimer, such as disubstituted vinylene, trisubstituted vinylene, vinylidene, or a combination thereof. In some embodiments, the product produced from the first oligomerization process can include PAO dimers (e.g., vinylidene, disubstituted vinylene, trisubstituted vinylene), trimer of alpha-olefins (PAO trimer), tetramer of alpha-olefins (PAO tetramer), higher oligomers of alpha-olefins (if any), vinyls, or a combination thereof.

In at least one embodiment, the first oligomerization process can have a selectivity towards vinylidenes at about 80 mol % or more, such as about 85 mol % or more, such as about 88 mol % or more, such as about 90 mol % or more, such as from about 91 mol % to about 100 mol %, such as from about 92 mol % to about 99 mol %, such as from about 93 mol % to about 98 mol %, such as about 94 mol %, about 95 mol %, about 96 mol %, or about 97 mol %, based on a total moles of a product produced.

In at least one embodiment, the first oligomerization process can have a selectivity towards products other than vinylidene (e.g., trisubstituted vinylene, disubstituted vinylene, vinyls, PAO trimer, PAO tetramer, higher oligomers, or a combination thereof) of about 20 mol % or less, such as about 15 mol % or less, such as about 12 mol % or less, such as about 10 mol % or less, such as from about 0 mol % to about 9 mol %, such as from about 1 mol % to about 8 mol %, such as from about 2 mol % to about 7 mol %, such as about 3 mol %, about 4 mol %, about 5 mol %, or about 6 mol %, based on the total moles of product produced.

In at least one embodiment, the first oligomerization process can have a selectivity towards a PAO trimer of about 20 wt % or less, such as about 15 wt % or less, such as about 12 wt % or less, such as about 10 wt % or less, such as from about 0 wt % to about 9 wt %, such as from about 1 wt % to about 8 wt %, such as from about 2 wt % to about 7 wt %, such as about 3 wt %, about 4 wt %, about 5 wt %, or about 6 wt %, based on the total moles of product produced.

In at least one embodiment, the first oligomerization process can have a selectivity towards a PAO tetramer and/or higher oligomers of alpha-olefins of about 20 wt % or less, such as about 15 wt % or less, such as about 12 wt % or less, such as about 10 wt % or less, such as from about 0 wt % to about 9 wt %, such as from about 1 wt % to about 8 wt %, such as from about 2 wt % to about 7 wt %, such as about 3 wt %, about 4 mol %, about 5 wt %, or about 6 wt %, based on the total moles of product produced.

In at least one embodiment, the first oligomerization process can form an amount (in weight percent, wt %) of PAO dimer of about 40 wt % or more, such as from about 45 wt % to about 100 wt %, such as from about 50 wt % to about 99 wt %, such as from about 55 wt % to about 98 wt %, such as from about 60 wt % to about 95 wt %, such as from about 65 wt % to about 90 wt %, such as from about 70 wt % to about 85 wt %, such as from about 75 wt % to about 85 wt %, based on a total amount of product produced. In some embodiments, the first oligomerization process can form an amount of PAO dimer of about 80 wt % or more, such as about 81 wt % or more, about 82 wt % or more, about 83 wt % or more, about 84 wt % or more, about 85 wt % or more, about 86 wt % or more, about 87 wt % or more, about 88 wt % or more, about 89 wt % or more, about 90 wt % or more, about 91 wt % or more, about 92 wt % or more, about 93 wt % or more, about 94 wt % or more, about 95 wt % or more, about 96 wt % or more, about 97 wt % or more, about 98 wt % or more, about 99 wt % or more, or about 100 wt %, based on the total amount of product produced.

In at least one embodiment, the first oligomerization process can form an amount of PAO trimer, PAO tetramer, higher oligomers of alpha-olefin, or a combination thereof of about 60 wt % or less, such as from about 0 wt % to about 55 wt %, such as from about 1 wt % to about 50 wt %, such as from about 2 wt % to about 49 wt %, such as from about 5 wt % to about 40 wt %, such as from about 10 wt % to about 35 wt %, such as from about 15 wt % to about 30 wt %, such as from about 20 wt % to about 25 wt %, based on a total amount of product produced. In some embodiments, the first oligomerization process can form an amount of PAO trimer, PAO tetramer, higher oligomers of alpha-olefin, or a combination thereof of about 20 wt % or less, such as about 0 wt %, about 1 wt % or less, about 2 wt % or less, about 3 wt % or less, about 4 wt % or less, about 5 wt % or less, about 6 wt % or less, about 7 wt % or less, about 8 wt % or less, about 9 wt % or less, about 10 wt % or less, about 11 wt % or less, about 12 wt % or less, about 13 wt % or less, about 14 wt % or less, about 15 wt % or less, about 16 wt % or less, about 17 wt % or less, about 18 wt % or less, or about 19 wt % or less, based on the total amount of product produced.

In at least one embodiment, the first oligomerization process can form an amount of vinylidene, based on the total moles of PAO dimer produced, of about 50 mol % or more, such as from about 55 mol % to about 100 mol %, such as from about 60 mol % to about 95 mol %, such as from about 65 mol % to about 90 mol %, such as from about 70 mol % to about 85 mol %, such as from about 75 mol % to about 80 mol %, where PAO dimer includes vinylidenes, disubstituted vinylene, and trisubstituted vinylene. In some embodiments, the first oligomerization process can form an amount of vinylidene, based on the total moles of PAO dimer produced, of about 80 mol % or more, such as about 81 mol % or more, about 82 mol % or more, about 83 mol % or more, about 84 mol % or more, about 85 mol % or more, about 86 mol % or more, about 87 mol % or more, about 88 mol % or more, about 89 mol % or more, about 90 mol % or more, about 91 mol % or more, about 92 mol % or more, about 93 mol % or more, about 94 mol % or more, about 95 mol % or more, about 96 mol % or more, about 97 mol % or more, about 98 mol % or more, about 99 mol % or more, or about 100 mol %, where PAO dimer includes vinylidenes, disubstituted vinylene, and trisubstituted vinylene.

In at least one embodiment, the first oligomerization process can form an amount of disubstituted vinylene, trisubstituted vinylene, or a combination thereof, based on the total moles of PAO dimer produced, of about 50 mol % or less, such as about 0% to about 45%, such as from about 5% to about 40%, such as from about 10% to about 35%, such as from about 15% to about 30%, such as from about 20% to about 25%, where PAO dimer includes vinylidenes, disubstituted vinylene, and trisubstituted vinylene. In some embodiments, the first oligomerization process can form an amount of disubstituted vinylene, trisubstituted vinylene, or a combination thereof, based on the total moles of PAO dimer produced, of about 20 mol % or less, such as about 0 mol %, about 1 mol % or less, about 2 mol % or less, about 3 mol % or less, about 4 mol % or less, about 5 mol % or less, about 6 mol % or less, about 7 mol % or less, about 8 mol % or less, about 9 mol % or less, about 10 mol % or less, about 11 mol % or less, about 12 mol % or less, about 13 mol % or less, about 14 mol % or less, about 15 mol % or less, about 16 mol % or less, about 17 mol % or less, about 18 mol % or less, or about 19 mol % or less, based on the total moles of PAO dimer produced.

In at least one embodiment, the amount of PAO (e.g., dimer, timer, tetramer, higher oligomers of an alpha olefin, or a combination thereof) produced per gram of catalyst (gPAO/gCat) in the first oligomerization process can be from about 1,000 gPAO/gCat to about to 150,000 gPAO/gCat, such as from about 10,000 gPAO/gCat to about 100,000 gPAO/gCat, such as from about 30,000 gPAO/gCat to about 75,000 gPAO/gCat. In at least one embodiment, the amount of PAO (e.g., dimer, trimer, tetramer, higher oligomers of an alpha olefin, or a combination thereof) produced per gram of catalyst (gPAO/gCat) in the first oligomerization process can be from about 30,000 gPAO/gCat or more, such as from about 35,000 gPAO/gCat to about 80,000 gPAO/gCat, such as from about 40,000 gPAO/gCat to about 75,000 gPAO/gCat, such as from about 45,000 gPAO/gCat to about 70,000 gPAO/gCat, such as from about 50,000 gPAO/gCat to about 65,000 gPAO/gCat, such as from about 55,000 gPAO/gCat to about 60,000 gPAO/gCat.

In at least one embodiment, the amount of conversion in the first oligomerization of LAO to PAO dimer (e.g., vinylidenes, disubstituted vinylene, and trisubstituted vinylene, or a combination thereof), PAO trimer, higher oligomers of alpha-olefin, or a combination thereof can be greater than about 25%, such as greater than about 75%, such as greater than about 80%, such as greater than about 85%, such as greater than about 90%, such as greater than about 95%, such as greater than about 99%.

In at least one embodiment, the LAO can isomerize to branched and/or internal olefin during the first oligomerization. The amount of such isomerization can be less than about 5 wt %, such as less than about 3 wt %, such as less than about 2 wt %, such as less than about 1.9 wt %, such as less than about 1.5 wt %, such as less than about 1 wt %, such as less than about 0.9 wt %, such as less than about 0.5 wt %.

In some embodiments, the reactor conditions for the first oligomerization process can include a mol ratio of catalyst (e.g., metallocene compound) to activator, an amount of scavenger in the catalyst batch, an amount of scavenger in LAO, an amount of solvent, reactor temperature, reactor pressure, residence time, and catalyst loading.

In at least one embodiment, the reactor conditions for the first oligomerization process can include a mol ratio of catalyst to activator of from about 0.1:1 to 10:1, such as from about 0.5:1 to about 5:1, such as from about 0.75:1 to about 3:1, such as from about 1:1.2 to about 1:1, such as about 1:1.05, about 1:1.10, or about 1:1.15.

In at least one embodiment, the reactor conditions for the first oligomerization process can include an amount of scavenger in LAO of about 0 ppm or greater, such as about 4 ppm or greater, such as from about 5 ppm to about 200 ppm, such as from about 10 ppm to about 190 ppm, such as from about 30 ppm to about 170, such as from about 50 ppm to about 150 ppm, such as from about 75 ppm to about 125 ppm. In at least one embodiment, the reactor conditions for the first oligomerization process can include an amount of scavenger in LAO of about 0 to about 500 ppm; such as from about 0.1 to about 100 ppm, such as from about 1 to about 20 ppm.

In at least on embodiment, the amount of scavenger in the catalyst batch for the first oligomerization process can be about 0 wt % or more, such as from about 0.001 wt % to about 5 wt %, such as from about 0.01 wt % to about 2 wt %, such as from about 0.1 wt % to about 0.5 wt %.

In at least one embodiment, the reactor conditions for the first oligomerization process can include a reactor temperature of from about 0° C. to about 300° C., such as from about 10° C. to about 230° C., such as from about 25° C. to about 200° C., such as from about 100° C. to about 160° C. such as from about 110° C. to about 155° C., such as from about 130° C. to about 148° C., such as from about 135° C. to about 145° C. In some embodiments, the reactor conditions for the first oligomerization process can include a reactor temperature of about 130° C., about 131° C., about 132° C., about 1.33° C., about 134° C., about 135° C., about 136° C., about 137° C., about 138° C., about 139° C., about 140° C., about 141° C., about 142° C., about 143° C., about 144° C., about 145° C., about 146° C., about 147° C., or about 148° C. In at least one embodiment, the reactor conditions for the first oligomerization process can include a reactor temperature of about 120° C. or more, such as from about 130° C. to about 180° C.

In at least one embodiment, the reactor conditions for the first oligomerization process can include a reactor pressure of from about 1.5 psia to about 1,500 psia, such as from about 7 psia to about 1,200 psia, such as from about 15 psia to about 750 psia, such as from about 30 psia to about 100 psia.

In at least one embodiment, the reactor conditions for the first oligomerization process can include a residence time such as less than about 72 hours, such as from about 1 minute to about 20 hours, such as from about 5 minutes to about 10 hours, such as from about 30 minutes to about 9 hours, such as from about 1 hour to about 5 hours, such as from about 3 hours to about 4 hours. In at least one embodiment, the reactor conditions for the first oligomerization process can include a residence time of about 24 hours or less, such as about 10 hours or less, such as about 5 hours or less, such as about 3 hours or less.

In at least one embodiment, the reactor conditions for the first oligomerization process can include a catalyst loading of from about 20,000 grams linear alpha-olefin (gLAO) per 1 g Cat (gCat) (gLAO/gCat) to about 150,000 gLAO/gCat, such as 1,000 gLAO/gCat or more, 5,000 gLAO/gCat or more, 10,000 gLOA/gCat or more, 20,000 gLAO/gCat or more, such as from about 25,000 gLAO/gCat to about 80,000 gLAO/gCat, such as from about 30,000 gLAO/gCat to about 80,000 gLAO/gCat, such as from about 35,000 gLAO/gCat to about 75,000 gLAO/gCat, such as from about 40,000 gLAO/gCat to about 65,000 gLAO/gCat, such as from about 45,000 gLAO/gCat to about 60,000 gLAO/gCat, such as from about 50,000 gLAO/gCat to about 55,000 gLAO/gCat. In at least one embodiment, the reactor conditions for the first oligomerization process can include a catalyst loading of from about 40,000 g gLAO/gCat to 80,000 gLAO/gCat, such as from about 50,000 gLAO/gCat to about 75,000 gLAO/gCat.

In at least one embodiment, the reactor conditions for the first oligomerization process can include a flow rate of the catalyst system of greater than about 5 gCat/hr, such as from about 6 gCat/hr to about 70 kgCat/hr, such as about 6 gCat/hr to about 10 kgCat/hr, such as about 6 gCat/hr to about 1 kgCat/hr, such as about 6 gCat/hr to 50 gCat/hr, such as 6 gCat/hr to 25 gCat/hr, such as from about 7 gCat/hr to about 24 gCat/hr, such as from about 8 gCat/hr to about 23 gCat/hr, such as about 9 gCat/hr, about 10 gCat/hr, about 11 gCat/hr, about 12 gCat/hr, about 13 gCat/hr, about 14 gCat/hr, about 15 gCat/hr, about 16 gCat/hr, about 17 gCat/hr, about 18 gCat/hr, about 19 gCat/hr, about 20 gCat/hr, about 21 gCat/hr, or about 22 gCat/hr.

In at least one embodiment, the reactor conditions for the first oligomerization process can include a flow rate of the alpha-olefin of greater than about 100 g/hr, such as from about 200 g/hr to 45,000 kg/hr, such as from about 1,000 g/hr to 15,000 kg/hr, such as from about 1,500 g/hr to 1,000,000 g/hr, such as from about 1,800 g/hr to 10,000 g/hr, such as about 1,900 g/hr, such as about 2,080 g/hr.

In at least one embodiment, the reactor conditions for the first oligomerization process can include a flow rate of the alpha-olefin of about 100 grams alpha-olefin per hour (ghr) or more, such as from about 150 g/hr to about 7,500 g/hr, such as from about 300 g/hr to about 3,000 g/hr, such as from about 500 g/hr to about 2,000 g/hr, such as from about 750 g/hr to about 1,500 g/hr.

In at least one embodiment, the reactor conditions for the first oligomerization process can include a flow rate of the alpha-olefin of about 100 grams alpha-olefin per hour (ghr also written as g/hr) or more, such as 1,000 g/hr or more, such as 10,000 g/hr or more, such as 100,000 g/hr or more, such as 200,000 g/hr or more, such as 300,000 g/hr or more, such as 400,000 g/hr or more.

In at least one embodiment, the first oligomerization process can include a PAO dimer selectivity (in weight ratio) of about 60% or more with at least one of the following conditions: (i) at a catalyst productivity of about 10,000 gPAO/gCat or more (such as about 10,000 to about 100,000 gPAO/gCat) without the use of alumoxane; (ii) at a catalyst productivity of about 10,000 gPAO/gCat or more (such as about 10,000 to about 100,000 gPAO/gCat) without the use of alumoxane nor aluminum alkyl; (iii) at a catalyst productivity of about 10,000 gPAO/gCat or more (such as about 10,000 to about 100,000 gPAO/gCat) with about 500 ppm or less of an aluminum alkyl; (iv) at a catalyst productivity of about 10,000 gPAO/gCat or more (such as about 10,000 to about 100,000 gPAO/gCat) with about 20 ppm or less of an aluminum alkyl; (v) at a catalyst productivity of about 10,000 gPAO/gCat or more (such as about 10,000 to about 100,000 gPAO/gCat) with a residence time of about 24 hours or less; (vi) at a catalyst productivity of about 10,000 gPAO/gCat or more (such as about 10,000 to about 100,000 gPAO/gCat) with a residence time of about 10 hours or less; or (vii) at a catalyst productivity of about 30,000 gPAO/gCat or more (such as about 30,000 to about 100,000 gPAO/gCat) with a residence time of about 10 hours or less. The PAO dimer selectivity is based on a weight ratio of PAO dimer/(PAO dimer+PAO trimer+PAO tetramer+heavier oligomers of LAO).

In at least one embodiment, the first oligomerization process can include a PAO dimer selectivity (in weight ratio) of about 85% or more with at least one of the following conditions: (i) at a catalyst productivity of about 30,000 gPAO/gCat or more (such as about 30,000 to about 100,000 gPAO/gCat) with a residence time of about 10 hours or less; (ii) at a catalyst productivity of about 30,000 gPAO/gCat or more (such as about 30,000 to about 100,000 gPAO/gCat) with a residence time of about 5 hours or less; or (iii) at a catalyst productivity of about 50,000 gPAO/gCat or more (such as about 50,000 to about 100,000 gPAO/gCat) with a residence time of about 5 hours or less. The PAO dimer selectivity is based on a weight ratio of PAO dimer/(PAO dimer+PAO trimer+PAO tetramer+heavier oligomers of LAO).

In at least one embodiment, the first oligomerization process can include a PAO dimer selectivity (in weight ratio) of about 90% or more with at least one of the following conditions: (i) at a catalyst productivity of about 50,000 gPAO/gCat or more (such as about 50,000 to about 100,000 gPAO/gCat) with a residence time of about 10 hours or less; (ii) at a catalyst productivity of about 50,000 gPAO/gCat or more (such as about 50,000 to about 100,000 gPAO/gCat) with a residence time of about 5 hours or less; (iii) at a catalyst productivity of about 60,000 gPAO/gCat or more (such as about 60,000 to about 100,000 gPAO/gCat) with a residence time of about 5 hours or less; (iv) at a catalyst productivity of about 60,000 gPAO/gCat or more (such as about 60,000 to about 100,000 gPAO/gCat) with a residence time of about 3 hours or less; or (v) at a catalyst productivity of about 65,000 gPAO/gCat or more (such as about 65,000 to about 100,000 gPAO/gCat) with a residence time of about 3 hours or less. The PAO dimer selectivity is based on a weight ratio of PAO dimer/(PAO dimer+PAO trimer+PAO tetramer+heavier oligomers of LAO).

In at least one embodiment, the reactor conditions for the first oligomerization process can include one or more of the following conditions: a mol ratio of catalyst:activator of about 1:1.05 in about 390 g toluene with about 10 ppm to about 12 ppm TNOA; the activator is N,N-dimethylanilinium tetrakis (pentafluorophenyl)borate; an alpha-olefin (LAO) flow rate of about 2080 g/hr; a catalyst loading of about 65,000 gLAO/gCat; a catalyst system flow rate of about 0.24 mL/min (12.7 g/hr); an amount of TNOA as scavenger in LAO of about 55 ppm; a temperature of from about 130° C. to about 148° C.; and a residence time of about 3 hours.

In at least one embodiment, the alpha-olefin in the feed for the first oligomerization process can be one or more $C_2$-$C_{32}$ alpha-olefins, such as $C_4$-$C_{32}$ alpha-olefins, such as $C_6$-$C_{30}$ alpha-olefins, such as $C_6$-$C_{24}$ alpha-olefins, such as $C_6$-$C_{18}$ alpha-olefins, $C_8$-$C_{18}$ alpha-olefins, $C_6$ to $C_{16}$ alpha-olefins, $C_6$-$C_{12}$ alpha-olefins, or a combination thereof. Non-limiting examples of alpha-olefins include 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, and a combination thereof. Various suitable alpha-olefins (e.g., linear alpha-olefins) and their characteristics that can be used for the first oligomerization process are discussed below in suitable sections of Section IV.

In at least one embodiment, hydrogen is optionally added to the reactor at a concentration of 0 to 100 psi; such as from 0 to 50 psi, such as from 5-10 psi.

In at least one embodiment, the heavy oligomers (degree of oligomerization of at least 3) are hydrogenated to create a finished PAO lubricant. In at least one embodiment, the kinematic viscosity at 100° C. of at least a portion of the hydrogenated first reactor effluent the trimer) can be less than 5 cSt, such as less than 3.5 cSt.

In at least one embodiment, the Noack volatility of at least a portion of the hydrogenated first reactor effluent (e.g., the trimer) can be less than 15 wt %, such as less than 13 wt %.

In at least one embodiment, the rotating pressure vessel oxidation test (RPVOT) of at least a portion of the hydrogenated first reactor effluent (e.g., the trimer) can be greater than 40 minutes, such as greater than 60 minutes, such as greater than 75 minutes.

Embodiments for feed purification, the first oligomerization reaction, and the catalyst system for the first oligomerization reaction may be found in suitable sections of Section IV. Other parameters for the selectivity and yield of products produced from the first oligomerization reaction may be found in suitable sections of Section IV.

II. PROCESS FOR PRODUCING PAO TRIMERS FROM PAO DIMERS

The present disclosure also includes processes using metallocene catalysts to improve yields for producing PM) trimer, such as a low viscosity PAO trimer. Conventional methods of forming PAO trimers involve a reaction of a PAO dimer feedstock made from an oligomerization process that contains a significant amount of disubstituted vinylene as well as PAO trimer, PAO tetramer, and higher oligomers of alpha-olefin. The disubstituted vinylene, however, is not highly reactive when added to a second oligomerization process (e.g., a $BF_3$ catalyzed process), and the reaction kinetics are very slow. In addition, the unreacted dimer in the stream going into the $BF_3$ catalyzed conventional reactor contaminates the stream produced out of the $BF_3$ process and reduces the value of that by-product.

The inventors have found that reducing (or eliminating) the amount of disubstituted vinylene in the PAO dimer feedstock from the first oligomerization process can provide production of a PAO trimer product at higher yields and higher purity than conventional processes. In addition, the higher purity intermediate PAO (e.g., the PAO dimer feedstock) produced from the first oligomerization process (having lower amounts of PAO trimer, lower amounts of PAO tetramer, and lower amounts of higher oligomers of alpha-olefin relative to conventional PAO dimer feedstocks) provides the production of high amounts of PAO trimer from the second oligomerization process.

The PAO produced from the first oligomerization process described above in Section I can include dimer (such as vinylidene dimers), trimer, optionally tetramer and higher oligomers of the respective alpha-olefin feedstocks, or a combination thereof. This PAO produced from the first oligomerization process described above is referred to interchangeably as "intermediate PAO" and "first reactor effluent." The oligomerization process described in Section I above can be performed in a first reactor, e.g., a metallocene reactor. The PAO produced from the second oligomerization process is referred to interchangeably as "hybrid trimer," "hybrid dimer" and "second reactor effluent." The second oligomerization may be performed in a second reactor, and the second reactor may include one or more sub-reactors.

The hybrid process is referred to interchangeably as "second oligomerization process" or "second oligomerization."

The intermediate PAO (e.g., the PAO dimer feedstock) may be used as the sole olefin feedstock to the second oligomerization process or may be used together with an alpha-olefin feedstock of the type used as the olefin starting material for the first oligomerization process. Other portions of the effluent from the first oligomerization process may also be used as a feedstock to the second oligomerization process, including unreacted LAO. Alpha-olefins with the same attributes as those used for the first oligomerization process may be used for the second oligomerization. Typical ratios for the PAO dimer portion of the intermediate PAO to the alpha-olefins fraction of the intermediate PAO can be from about 90:10 to about 10:90, such as from about 80:20 to about 20:80 by weight. In at least one embodiment, the PAO dimer of the intermediate PAO can make up about 50 mol % of the olefinic feed material since the properties and distribution of the final product, dependent in part upon the starting material, can be favorably affected by feeding the intermediate PAO at an equimolar ratio with the alpha-olefins.

In at least one embodiment, the feed for second oligomerization process can have a distribution of PAO dimer, PAO trimer, PAO tetramer, higher oligomers of alpha-olefin, or a combination thereof, can have the same distribution of effluent produced in the metallocene dimer selective process described in Section I. In at least one embodiment, the feed for the second oligomerization reactor is a product from the metallocene dimer selective process described in Section I.

The PAO dimer of the intermediate PAO can possess at least one carbon-carbon unsaturated double bond. Portions of the PAO dimer can include vinylidene dimers, disubstituted vinylenes, trisubstituted vinylenes, and a combination thereof. The distribution of vinylidene dimers, disubstituted vinylenes, trisubstituted vinylenes, and a combination thereof in the PAO dimer can be the distribution as described above.

The structure of the intermediate PAO can be such that, when reacted in a second oligomerization, the intermediate PAO can react with the optional LAO to form a "hybrid trimer" at high yields. This allows for high conversion and yield rates of the PAO products. In at least one embodiment, the PAO product from the second oligomerization comprises primarily a hybrid trimer formed from the dimer and the respective LAO feedstock.

Any suitable oligomerization process and acid catalyst composition may be used for the second oligomerization process. A catalyst for the second oligomerization can be a non-transition metal catalyst. A catalyst can be a Lewis acid catalyst. U.S. Patent Publication Nos. 2009/0156874 and 2009/0240012 describe a process that can be used for the second oligomerization, to which reference is made for details of feedstocks, compositions, catalysts and co-catalysts, and process conditions. The Lewis acid catalysts of US 2009/0156874 and US 2009/0240012 include the metal and metalloid halides conventionally used as Friedel-Crafts catalysts, and examples include $AlCl_3$, $BF_3$, $AlBr_3$, $TiCl_3$, and $TiCl_4$ either alone or with a protic promoter/activator. Boron trifluoride is commonly used but not particularly suitable unless it is used with a protic promoter. Useful co-catalysts are well known and described in detail in US 2009/0156874 and US 2009/0240012. Solid Lewis acid catalysts, such as synthetic or natural zeolites, acid clays, polymeric acidic resins, amorphous solid catalysts such as silica-alumina, and heteropoly acids such as the tungsten zirconates, tungsten molybdates, tungsten vanadates, phosphotungstates and molybdotungstovanadogermanates (e.g., $WO_x/ZrO_2$, $WO_x/MoO_3$) may also be used although these are not generally as favored economically. Additional process conditions and other details are described in detail in US 2009/0156874 and US 2009/0240012, and incorporated herein by reference.

In at least one embodiment, the second oligomerization can be performed in the presence of $BF_3$ and at least one activator such as an alcohol, or the second oligomerization can be performed in the presence of $BF_3$ and at least two different activators selected from alcohols and alkyl acetates. The alcohols can be $C_1$ to $C_{10}$ alcohols and the alkyl acetates are $C_1$ to $C_{10}$ alkyl acetates. For example, both co-activators are $C_1$ to $C_6$ based compounds. Two example combinations of co-activators can be i) ethanol and ethyl acetate and ii) n-butanol and n-butyl acetate. The ratio of alcohol to alkyl acetate can be from about 0.2 to about 15, such as about 0.5 to about 7.

Temperatures for the second oligomerization in the second reactor can be from about 0° C. to about 60° C., such as from about 10° C. to about 55° C., such as from about 20° C. to about 40° C., from about 10° C. to about 40° C., or from about 15° C. to about 25° C. In at least one embodiment, the temperatures for the second oligomerization in the second reactor can be less than about 32° C., such as from about 15° C. to about 30° C. such as from about 20° C. to about 25° C.

In at least one embodiment, the acid catalyst composition loading for the second oligomerization can be from about 0.5 mmol per 100 g LAO (mmolCat/100 gLAO) to about 30 mmolCat/100 gLAO, such as from about 5 mmolCat/100 gLAO to about 15 mmolCat/100 gLAO, such as from about 6 mmolCat/100 gLAO to about 14 mmolCat/100 gLAO, such as about 8 mmolCat/100 gLAO, about 10 mmolCat/100 gLAO, or about 12 mmolCat/1.00 gLAO.

In at least one embodiment, the LAO feedstock for the second oligomerization (as well as the first oligomerization) can be one or more $C_2$-$C_{32}$ alpha-olefins, such as a $C_4$-$C_{32}$ alpha-olefin, $C_6$-$C_{30}$ alpha-olefin, such as a $C_6$-$C_{24}$ alpha-olefin, such as a $C_6$-$C_{18}$ alpha-olefin, a $C_8$-$C_{18}$ alpha-olefin, a $C_6$ to $C_{16}$ alpha-olefin, or a $C_6$-$C_{12}$ alpha-olefin, or a combination thereof. Non-limiting examples of LAOs can be 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-octadecene, 1-icocene, $C_{22}$, $C_{24}$, $C_{26}$, $C_{28}$, $C_{30}$, and $C_{32}$ LAOs, and a combination thereof. Other suitable alpha-olefin monomers for the second oligomerization can be found in Section IV.

In at least one embodiment, a molar ratio of the PAO dimer of the intermediate PAO to LAO for the second oligomerization process can be about 1:1 or greater, such as from about 1.5 to about 10:1, such as from about 2:1 to about 5:1, such as from about 3:1 to about 4:1. In at least one embodiment, a molar ratio of the PAO dimer of the intermediate PAO to LAO for the second oligomerization process can be from about 0.1:1 to about 10:1, such as from about 0.5 to about 5:1, such as from about 0.5:1 to about 3:1, such as from about 0.8:1 to about 1.2:1, such as from about 0.9:1 to about 1.1:1.

In at least one embodiment, the reactor conditions for the second oligomerization can include a reactor pressure of from about 10 psia to about 35 psia, such as from about 15 psia to about 25 psia, such as from about 19 psia to about 21 psia.

In at least one embodiment, the second oligomerization can be carried out in two reactors in series, such as two continuous stirred tank reactors (CSTRs) in series. In some embodiments, the residence time in the first reactor of the second oligomerization can be from about 0.25 hour to about 5 hours, such as from about 0.5 hour to about 3 hours, and the residence time in the second reactor of the second oligomerization can be from about 0.25 hour to about 5 hours, such as from about 0.5 hour to about 3 hours.

In at least one embodiment, the second oligomerization can be carried out in one reactor such as a CSTR, in some embodiments, the residence time in the reactor for the second oligomerization can be from about 1 minutes to 10 hour, such as from about 1 hour to about 7 hours, such as from about 1 hour to about 2 hours.

Table 1 shows non-limiting types of the PAO product (the hybrid trimer) that can be produced from the second oligomerization process of a PAO dimer with the LAO monomer.

TABLE 1

|  | C6 | C8 | C9 | C10 | C12 | C14 | C16 |
| --- | --- | --- | --- | --- | --- | --- | --- |
| C6 dimer | C18 | C20 | C21 | C22 | C24 | C26 | C28 |
| C8 dimer | C22 | C24 | C25 | C26 | C28 | C30 | C32 |
| C9 dimer | C24 | C26 | C27 | C28 | C30 | C32 | C34 |
| C10 dimer | C26 | C28 | C29 | C30 | C32 | C34 | C36 |
| C12 dimer | C30 | C32 | C33 | C34 | C36 | C38 | C40 |
| C14 dimer | C34 | C36 | C37 | C38 | C40 | C42 | C44 |
| C16 dimer | C38 | C40 | C41 | C42 | C44 | C46 | C48 |

In at least one embodiment, where the LAO feedstock for the first oligomerization and the second oligomerization processes is the same, the incorporation of PAO dimer of the intermediate PAO into hybrid trimer, tetramer, higher oligomers, or a combination thereof can be about 75% or more, such as about 80% or more, such as about 85% or more, such as about 90% or more, such as about 95% or more, such as about 99% or more; the conversion of the LAO can be about 75% or more, such as about 80% or more, such as about 85% or more, such as about 90% or more, such as about 95% or more, such as about 99% or more; and/or the yield % of about 75% or more, such as about 80% or more, such as about 85% or more, such as about 90% or more, such as about 95% or more, such as about 99% or more.

In at least one embodiment, where the LAO feedstock for the first oligomerization and the second oligomerization processes is different, the incorporation of PAO dimer of the intermediate PAO into hybrid trimer, tetramer, higher oligomers, or a combination thereof can be about 75% or more, such as about 80% or more, such as about 85% or more, such as about 90% or more, such as about 95% or more, such as about 99% or more; the conversion of the LAO can be about 75% or more, such as about 80% or more, such as about 85% or more, such as about 90% or more, such as about 95% or more, such as about 99% or more; and/or the yield % of about 75% or more, such as about 80% or more, such as about 85% or more, such as about 90% or more, such as about 95% or more, such as about 99% or more.

In at least one embodiment, the yield % of PAO trimer in the second reactor effluent is about 60 wt % or more, such as about 70 wt % or more, such as about such as about 75 wt % or more, such as about 76 wt % or more, such as about 77 wt % or more, such as about 78 wt % or more, 79 wt % or more, such as about 80 wt % or more, such as about 81 wt % or more, such as about 82 wt % or more, such as about 83 wt % or more, such as about 84 wt % or more, such as about 85 wt % or more, such as about 86 wt % or more, such as about 87 wt % or more, such as about 88 wt % or more, such as about 89 wt % or more, such as about 90 wt % or more, such as about 91 wt % or more, such as about 92 wt % or more, such as about 93 wt % or more, such as about 94 wt % or more, such as about 95 wt % or more, such as about 96 wt % or more, such as about 97 wt % or more, such as about 98 wt % or more, such as about 99 wt % or more, such as about 100 wt %, based on a total moles of PAO dimer, PAO trimer, PAO tetramer, and higher oligomers of alpha-olefin in the second reactor effluent.

In at least one embodiment, the second oligomerization process can have a selectivity towards hybrid trimer of about 60 wt % or more, such as about 70 wt % or more, such as about 75 wt % or more, such as about 76 wt % or more, such as about 77 wt % or more, such as about 78 wt % or more, 79 wt % or more, such as about 80 wt % or more, such as about 81 wt % or more, such as about 82 wt % or more, such as about 83 wt % or more, such as about 84 wt % or more, such as about 85 wt % or more, such as about 86 wt % or more, such as about 87 wt % or more, such as about 88 wt % or more, such as about 89 wt % or more, such as about 90 wt % or more, such as about 91 wt % or more, such as about 92 wt % or more, such as about 93 wt % or more, such as about 94 wt % or more, such as about 95 wt % or more, such as about 96 wt % or more, such as about 97 wt % or more, such as about 98 wt % or more, such as about 99 wt % or more, such as about 100 wt %, based on a total moles of PAO dimer, PAO trimer, PAO tetramer, and higher oligomers of alpha-olefin in the second reactor effluent.

In at least one embodiment, the yield % of PAO dimer, PAO tetramer, higher oligomers of alpha-olefin, or a combination thereof, in the second reactor effluent can be about 40 wt % or less, such as about 30 wt % or less, such as about 25 wt % or less, such as about 24 wt % or less, such as about 23 wt % or less, such as about 22 wt % or less, such as about 21 wt % or less, such as about 20 wt % or less, such as about 19 wt % or less, such as about 18 wt % or less, such as about 17 wt % or less, such as about 16 wt % or less, such as about 15 wt % or less, such as about 14 wt % or less, such as about 13 wt % or less, such as about 12 wt % or less, such as about 11 wt % or less, such as about 10 wt % or less, such as about 9 wt % or less, such as about 8 wt % or less, such as about 7 wt % or less, such as about 6 wt % or less, such as about 5 wt % or less, such as about 4 wt % or less, such as about 3 wt % or less, such as about 2 wt % or less, such as about 1 wt % or less, such as about 0 wt %, based on a total weight of PAO dimer, PAO trimer, PAO tetramer, and higher oligomers of alpha-olefin in the second reactor effluent.

In at least one embodiment, the second oligomerization process can have a selectivity towards PAO dimer, PAO tetramer, higher oligomers of alpha-olefin, or a combination thereof, of about 40 mol % or less, such as about 30 mol % or less, such as about 25 mol % or less, such as about 24 mol % or less, such as about 23 mol % or less, such as about 22 mol % or less, such as about 21 mol % or less, such as about 20 mol % or less, such as about 19 mol % or less, such as about 18 mol % or less, such as about 17 mol % or less, such as about 16 mol % or less, such as about 15 mol % or less, such as about 14 mol % or less, such as about 13 mol % or less, such as about 12 mol % or less, such as about 11 mol % or less, such as about 10 mol % or less, such as about 9 mol % or less, such as about 8 mol % or less, such as about 7 mol % or less, such as about 6 mol % or less, such as about 5 mol % or less, such as about 4 mol % or less, such as about 3 mol % or less, such as about 2 mol % or less, such as about 1 mol % or less, such as about 0 mol $\%_2$ based on a total moles of PAO dimer, PAO trimer, PAO tetramer, and higher oligomers of alpha-olefin in the second reactor effluent.

In at least one embodiment, the trimer has an A-A-B structure, where A and B are different alpha-olefins.

In at least one embodiment, the monomer can be optional as a feedstock in the second reactor (e.g., an oligomerization reactor). In some embodiments, the first reactor effluent comprises unreacted monomer, and the unreacted monomer can be ted to the second reactor. In some embodiments, monomer can be fed into the second reactor, and the monomer can be an LAO selected from the group including 1-hexene, 1-octene, 1-nonene, 1-decene, 1-dodecene, 1-tetradecene, 1-hexadecene. In some embodiments, the PAO produced in the second oligomerization can be derived from the PAO dimer portion of the intermediate PAO plus only one monomer to form one or more trimers. In some embodiments, the PAO produced in the second oligomerization can be derived from the PAO dimer of the intermediate PAO plus two or more monomers, or three or more monomers, or four or more monomers, or even five or more monomers. For example, the PAO dimer plus a $C_8$, $C_{10}$, $C_{12}$-LAO mixture, or a $C_6$, $C_7$, $C_8$, $C_9$, $C_{10}$, $C_{11}$, $C_{12}$, $C_{13}$, $C_{14}$-LAO mixture, or a $C_4$, $C_6$, $C_8$, $C_{10}$, $C_{12}$, $C_{14}$, $C_{16}$, $C_{18}$-LAO mixture can be used as a feed to form trimers.

In at least one embodiment, the second reactor effluent may contain trace amounts of transition metal compound if the catalyst in the first or subsequent oligomerization is a metallocene catalyst. A trace amount of transition metal compound may be any amount of transition metal compound or Group 4 metal present in the PAO. Presence of Group 4 metal may be detected at the ppm or ppb level by ASTM 5185.

In at least one embodiment, the second reactor effluent or a portion of the second reactor effluent is hydrogenated to a Bromine number less than 2.

In at least one embodiment, the kinematic viscosity at 100° C. of the second reactor effluent or a portion of the second reactor effluent (e.g., the hybrid trimer) can be less than about 10 cSt, such as less than about 6 cSt, such as less than about 4.5 cSt, such as less than about 3.2 cSt, such as from about 2.8 cSt to about 4.5 cSt. In some embodiments, the second reactor effluent or a portion of the second reactor effluent is hydrogenated to form a hydrogenated second reactor effluent having a kinematic viscosity at 100° C. less than about 10 cSt, such as less than about 6 cSt, such as less than about 4,5 cSt, such as less than about 3.2 cSt, such as from about 2.8 cSt to about 4.5 cSt.

In at least one embodiment, the kinematic viscosity at 40° C. of the second reactor effluent or a portion of the second reactor effluent can be less than about 25 cSt, such as less than about 15 cSt. In some embodiments, the second reactor effluent or a portion of the second reactor effluent is hydrogenated to form a hydrogenated second reactor effluent having a kinematic viscosity at 40° C. of the second reactor effluent or a portion of the second reactor effluent can be less than about 25 cSt, such as less than about 15 cSt.

In at least one embodiment, the pour point of the second reactor effluent or a portion of the second reactor effluent can be below about −30° C., such as below about −40° C., such as below about −50° C., such as below about −60° C., such as below about −70° C., such as below about −80° C. In some embodiments, the second reactor effluent or a portion of the second reactor effluent is hydrogenated to form a hydrogenated second reactor effluent having a pour point of the second reactor effluent or a portion of the second reactor effluent can be below about −30° C., such as below about −40° C., such as below about −50° C., such as below about −60° C., such as below about −70° C., such as below about −80° C.

In at least one embodiment, the Noack volatility of the second reactor effluent or a portion of the second reactor effluent can be less than about 19 wt %, such as less than about 14 wt %, such as less than about 12 wt %, such as less than about 10 wt %, such as less than about 9.0 wt %, such as less than about 8.5 wt %, such as less than about 8.0 wt %, such as less than about 7.5 wt %. In some embodiments, the second reactor effluent or a portion of the second reactor effluent is hydrogenated to form a hydrogenated second reactor effluent having a Noack volatility of the second reactor effluent or a portion of the second reactor effluent can be less than about 19 wt %, such as less than about 14 wt %, such as less than about 12 wt %, such as less than about 10 wt %, such as less than about 9.0 wt %, such as less than about 8.5 wt %, such as less than about 8.0 wt %, such as less than about 7.5 wt %.

In at least one embodiment, the viscosity index of the second reactor effluent or a portion of the second reactor effluent can be more than about 120, such as more than about 121, such as more than about 125, such as more than about 130, such as more than about 135, such as more than about 136. In some embodiments, the second reactor effluent or a portion of the second reactor effluent is hydrogenated to form a hydrogenated second reactor effluent having a viscosity index of the second reactor effluent or a portion of the second reactor effluent can be more than about 120, such as more than about 121, such as more than about 125, such as more than about 130, such as more than about 135, such as more than about 136.

In at least one embodiment, the cold crank simulator value (CCS) at −3555° C. of the second reactor effluent or a portion of the second reactor effluent may be not more than about 1200 cP, such as not more than about 1000 cP, such as not more than about 900 cP. In some embodiments, the second reactor effluent or a portion of the second reactor effluent is hydrogenated to form a hydrogenated second reactor effluent having a cold crank simulator value (CCS) at −35° C. of the second reactor effluent or a portion of the second reactor effluent may be not more than about 1200 cP, such as not more than about 1000 cP, such as not more than about 900 cP.

In at least one embodiment, the second reactor effluent or a portion of the second reactor effluent can have a Brookfield viscosity at 40° C. of less than about 3000 cP, such as less than about 2000 cP, such as less than about 1500 cP. In some embodiments, the second reactor effluent or a portion of the second reactor effluent is hydrogenated to form a hydrogenated second reactor effluent having a Brookfield viscosity at 40° C. of less than about 3000 cP, such as less than about 2000 cP, such as less than about 1500 cP.

In at least one embodiment, the second reactor effluent or a portion of the second reactor effluent can have a rotating pressure vessel oxidation test (RPVOT) of about 70 minutes or more, such as about 80 minutes or more, such as about 90 minutes or more, such as about 100 minutes or more. In some embodiments, the second reactor effluent or a portion of the second reactor effluent is hydrogenated to form a hydrogenated second reactor effluent having a rotating pressure vessel oxidation test (RPVOT) of about 70 minutes or more, such as about 80 minutes or more, such as about 90 minutes or more, such as about 100 minutes or more.

In at least one embodiment, the second reactor effluent or a portion of the second reactor effluent can have a kinematic viscosity at 100° C. of not more than about 3.2 cSt and a Noack volatility of not more than about 19 wt %. In at least one embodiment, the second reactor effluent or a portion of the second reactor effluent can have a kinematic viscosity at 100° C. of not more than about 3.6 cSt and a Noack volatility of not more than about 13.0 wt %. In some embodiments, the second reactor effluent or a portion of the second reactor effluent is hydrogenated to form a hydrogenated second reactor effluent having a kinematic viscosity at 100° C. of not more than about 3.2 cSt and a Noack volatility of not more than about 19 wt %. In at least one embodiment, the second reactor effluent or a portion of the second reactor effluent is hydrogenated to form a hydrogenated second reactor effluent having a kinematic viscosity at 100° C. of not more than about 3.6 cSt and a Noack volatility of not more than about 13.0 wt %.

Functionalized PAOs and Uses of Functionalized PAOs

PAO products (e.g., unhydrogenated LAO dimers and trimers) of the present disclosure can be functionalized with one or more reactants (and can be optionally hydrogenated) through various chemical reactions to produce a functionalized PAO product. For example, PAOs of the present disclosure that have been functionalized (and optionally hydrogenated) may be used in gear oils, industrial oils, hydraulic oils, compressor oils, or in a driveline or electric vehicle fluid.

PAOs prepared herein may be functionalized by reacting a heteroatom containing group with the PAO with or without a catalyst. Examples include catalytic hydrosilylation, ozonolysis, hydroformylation, or hydroamination, sulfonation, halogenation, hydrohalogenation, hydroboration, epoxidation, or Diels-Alder reactions with polar dienes. Friedel-Crafts reactions with polar aromatics, maleation with activators such as free radical generators (e.g. peroxides). The functionalized PAO's can be used in oil additives, as anti-fogging or wetting additives, surfactants for soaps, detergents, fabric softeners, antistatics, and many other applications. Preferred uses include additives for lubricants and or fuels, preferably where the heteroatom containing group includes one or more of amines, aldehydes, alcohols, acids, anhydrides, sulphonates, particularly succinic acid, maleic acid and maleic anhydride.

In some embodiments the PAO's produced herein are functionalized as described in U.S. Pat. No. 6,022,929; A. Toyota, T. Tsutsui, and N. Kashiwa, *Polymer Bulletin*, v. 48, pp. 213-219, 2002; and *J. An. Chem. Soc.,* 1990, v. 112, pp. 7433-7434. In some embodiments the functionalized PAO's produced herein are further functionalized (derivatized), such as described in U.S. Pat. No. 6,022,929; A. Toyota, T. Tsutsui, and N. Kashiwa, *Polymer Bulletin, v.* 48, pp. 213-219, 2002; *J. Am. Chem. Soc.,* 1990, v. 112, pp. 7433-7434; and WO 2009/155472.

In preferred embodiments, the PAO's of the present disclosure can be functionalized (e.g. chemically modified with one or more functional groups (also referred to as a heteroatom containing group) typically containing heteroatoms such as P, O, S, N, Br, Cl, F, I and or Br (preferably N, O, Cl and or Br, preferably N and or O). Preferred functional groups are selected from the group consisting of acids, esters, anhydrides, acid-esters, oxycarbonyls, carbonyls, formyls, formylcarbonyls, hydroxyls, and acetyl halides. Particularly preferred functional groups include those represented by the formula: —C(O)—X, where the O is double bonded to the C and the X is hydrogen, nitrogen, hydroxy, oxyhydrocarbyl (e.g. ester), oxygen, the salt moiety —OM wherein M is a metal, e.g. alkali, alkaline earth, transition metal, copper, zinc and the like, oxyhetero, e.g. —O—Z wherein Z represents a heteroatom such as phosphorus boron, sulfur, which heteroatom may be substituted with hydrocarbyl or oxyhydrocarbyl groups, or two acyl groups may be joined through (X).

Preferred heteroatom containing groups include acyl groups derived from monounsaturated mono-or dicarboxylic acids and their derivatives, e.g. esters and salts.

More specifically, PAO's functionalized with mono-or dicarboxylic acid material, i.e., acid, anhydride, salt or acid ester are preferred, including the reaction product of the PAO with a monounsaturated carboxylic reactant comprising at least one member selected from the group consisting of (i) monounsaturated $C_4$ to $C_{10}$ dicarboxylic acid (preferably wherein (a) the carboxyl groups are vicinyl, (i.e. located on adjacent carbon atoms) and (b) at least one, preferably both, of said adjacent carbon atoms are part of said mono-unsaturation); (ii) derivatives of (i) such as anhydrides or $C_4$ to $C_5$ alcohol derived mono-or diesters of (i); (iii) monounsaturated $C_3$ to $C_{10}$ monocarboxylic acid wherein the carbon-carbon double bond is conjugated to the carboxyl group, i.e., of the structure —C≡C—C(O)— (where O is double bonded to C), and (iv) derivatives of (iii) such as $C_1$ to $C_5$ alcohol derived monoesters of (iii). Upon reaction with the PAO, the double bond of the monounsaturated carboxylic reactant becomes saturated. Thus, for example, maleic anhydride reacted with the PAO becomes succinic anhydride, and acrylic acid becomes a propionic acid.

Suitable unsaturated acid materials thereof which are useful functional compounds, include acrylic acid, crotonic acid, methacrylic acid, maleic acid, maleic anhydride, fumaric acid, itaconic acid, itaconic anhydride, citraconic acid, citraconic anhydride, mesaconic acid, glutaconic acid, chloromaleic acid, aconitic acid, crotonic acid, methylcrotonic acid, sorbic acid, 3-hexenoic acid, 10-decenoic acid, 2-pentene-1,3,5-tricarboxylic acid, cinnamic acid, and lower alkyl (e.g. $C_1$ to $C_4$ alkyl) acid esters of the foregoing, e.g. methyl maleate, ethyl fumarate, methyl fumarate, etc. Particularly preferred are the unsaturated dicarboxylic acids and their derivatives, especially maleic acid, fumaric acid and maleic anhydride.

Typically, from about 0.7 to about 4.0 (e.g., 0.8 to 2.6), preferably from about 1.0 to about 2.0, and most preferably from about 1.1 to about 1.7 moles of said monounsaturated carboxylic reactant are charged to the reactor per mole of PAO charged.

Functionalization can be achieved by any suitable method. Useful methods include the reaction of an olefinic bond of the PAO with an unsaturated, preferably a mono-unsaturated, carboxylic reactant. Alternatively, the oligomer can be halogenated using chlorine or bromine-containing compounds. The halogenated PAO can then be reacted with the monounsaturated carboxylic acid. The PAO and the monounsaturated carboxylic reactant can also be contacted at elevated temperatures to cause a thermal "ene" reaction to take place. Alternatively, the monounsaturated carboxylic acid can be reacted with the PAO by free radical induced grafting. The PAO of the present disclosure can be functionalized by contact with a hydroxy aromatic compound in the presence of a catalytically effective amount of at least one acidic alkylation catalyst. The alkylated hydroxy aromatic compound can then be further reacted to form a derivative by Mannich Base condensation with an aldehyde and an amine reagent to yield a Mannich Base condensate. In yet another means to functionalize the PAO, the PAO may be contacted with carbon monoxide in the presence of an acid catalyst under Koch reaction conditions to yield the PAO substituted with carboxylic acid groups. In addition to the above methods of functionalization, the PAO of the present disclosure can be functionalized by methods of air oxidation, ozonolysis, hydroformylation, epoxidation and chloroamination. (For more information please see U.S. Pat. No. 6,022,929 Column 21, line 16 to column 33, line 27.)

The polyalpha-olefins produced herein contain one or more unsaturated double bonds, rich in vinylidene content with some 1,2-disubstituted olefins. These unsaturated polymers are particularly suitable for further functionalization reactions. Examples of such functionalization reactants includes alkylation with aromatic compounds, such as benzene, toluene, xylene, naphthalene, anisole, phenol or alkylphenols. The PAO's can also react with maleic anhydride to give PAO-succinic anhydride, which can be further converted with amines or alcohols to corresponding succinimide or succinate esters. These imides and esters are superior dispersants.

The functionalized PAO can in turn be derivatized with a derivatizing compound. (For purposes of this disclosure and the claims thereto the term functionalized PAO encompasses derivatized PAO.) The derivatizing compound can react with the functional groups of the functionalized PAO by means such as nucleophilic substitution, Mannich Base condensation, and the like. The derivatizing compound can be polar and/or contain reactive derivative groups. Preferred derivatizing compounds are selected from hydroxy containing compounds, amines, metal salts, anhydride containing compounds and acetyl halide containing compounds. The derivatizing compounds can comprise at least one nucleophilic group and preferably at least two nucleophilic groups. A typical derivatized PAO is made by contacting a functionalized PAO, i.e., substituted with a carboxylic acid/anhydride or ester, with a nucleophilic reagent, e.g., amine, alcohol, including polyols, amino alcohols, reactive metal compounds and the like. (For more information please see U.S. Pat. No. 6,022,929 column 33, line 27 to column 74, line 63.) Alternatively a derivatized PAO may be made by contacting a functionalized PAO, substituted with a carboxylic acid/anhydride or ester, with a nucleophilic reagent, e.g., amine, to make a quaternary; ammonium compound or amine oxide.

The functionalized PAO's and/or derivatized PAO's have uses as lubricating additives which can act as dispersants, viscosity index improvers, or multifunctional viscosity index improvers. Additionally they may be used as disinfectants (functionalized amines) and or wetting agents.

The functionalized PAO prepared herein may be used in oil additivation, lubricants, fuels and many other applications. Preferred uses include additives for lubricants and or fuels.

In particular embodiments herein, the PAO's disclosed herein, or functionalized/derivatized analogs thereof, are useful as additives and/or base stocks, preferably in a lubricant.

The functionalized PAO's and/or derivatized PAO's produced herein have uses as lubricating additives which can act as dispersants, viscosity index improvers, or multifunctional viscosity index improvers. Additionally they may be used as disinfectants (functionalized amines) and or wetting agents.

Functionalized PAOs and/or derivatized PAOs having uses as dispersants typically have an Mn of less than 1,000 g/mol, preferably less than 500 g/mol, preferably less than 300 g/mol, and typically can range from 100 g/mol to 500 g/mol, preferably from 200 g/mol to 400 g/mol, preferably from 200 g/mol to 300 g/mol.

The functionalized PAOs and/or derivatized PAOs described herein having Mn's (g/mol) of greater than 100 g/mol, preferably 200 to 400 g/mol (preferably 200 to 300 g/mol) are useful for viscosity index improvers for lubricating oil compositions, adhesive additives, antifogging and wetting agents, ink and paint adhesion promoters, coatings, tackifiers and sealants, and the like. In addition, such PAOs may be functionalized and derivatized to make multifunctional viscosity index improvers which also possess dispersant properties. (For more information please see U.S. Pat. No. 6,022,929.)

The functionalized PAOs and/or derivatized PAOs described herein may be combined with other additives (such as viscosity index improvers, corrosion inhibitor, oxidation inhibitor, dispersant, lube oil flow improver, detergents, demulsifiers, rust inhibitors, pour point depressant, anti-foaming agents, antiwear agents, seal swellant, friction modifiers, and the like (described for example in U.S. Pat. No. 6,022,929 at columns 60, line 42-column 78, line 54 and the references cited therein) to form compositions for many applications, including but not limited to lube oil additive packages, lube oils, and the like.

Compositions containing these additives are typically blended into a base oil in amounts which are effective to provide their normal attendant function. Representative effective amounts of such additives are illustrated as follows:

| Compositions | (Typical) wt %* | (Preferred) wt %* |
|---|---|---|
| Viscosity Index Improver | 1-12 | 1-4 |
| Corrosion Inhibitor | 0.01-3 | 0.01-1.5 |
| Oxidation Inhibitor | 0.01-5 | 0.01-1.5 |
| Dispersant | 0.1-10 | 0.1-5 |
| Lube Oil Flow Improver | 0.01-2 | 0.01-1.5 |
| Detergents and Rust inhibitors | 0.01-6 | 0.01-3 |
| Pour Point Depressant | 0.01-1.5 | 0.01-1.5 |

-continued

| Compositions | (Typical) wt %* | (Preferred) wt %* |
|---|---|---|
| Anti-Foaming Agents | 0.001-0.1 | 0.001-0.01 |
| Antiwear Agents | 0.001-5 | 0.001-1.5 |
| Seal Swellant | 0.1-8 | 0.1-4 |
| Friction Modifiers | 0.01-3 | 0.01-1.5 |
| Lubricating Base Oil | Balance | Balance |

*Wt %'s are based on active ingredient content of the additive, and/or upon the total weight of any additive-package, or formulation which will be the sum of the A.I. weight of each additive plus the weight of total oil or diluent.

When other additives are employed, it may be desirable, although not necessary, to prepare additive concentrates comprising concentrated solutions or dispersions of the subject additives of this disclosure (in concentrate amounts hereinabove described), together with one or more of said other additives (said concentrate when constituting an additive mixture being referred to herein as an additive-package) whereby several additives can be added simultaneously to the base oil to form the lubricating oil composition. Dissolution of the additive concentrate into the lubricating oil may be facilitated by solvents and by mixing accompanied with mild heating, but this is not essential. The subject functionalized or derivatized PAOs of the present disclosure can be added to small amounts of base oil or other compatible solvents along with other desirable additives to form additive-packages containing active ingredients in collective amounts of typically from about 2.5 to about 90%, and preferably from about 15 to about 75%, and most preferably from about 25 to about 60% by weight additives in the appropriate proportions with the remainder being base oil.

The final formulations may employ typically about 10 wt % of the additive-package with the remainder being base oil.

In another embodiment, the PAO's described herein can be use in any process, blend or product disclosed in WO 2009/155472 or U.S. Pat. No. 6,022,929, which are incorporated by reference herein.

In a preferred embodiment, this disclosure relates to a fuel comprising any PAO produced herein. In a preferred embodiment, this disclosure relates to a lubricant comprising any PAO produced herein.

Hydrogenation

Any of polyalphaolefins produced herein can be hydrogenated. In particular the polyalpha-olefin is preferably treated to reduce heteroatom containing compounds to less than 600 ppm, and then contacted with hydrogen and a hydrogenation catalyst to produce a polyalpha-olefin having a bromine number less than 1.8. In a preferred embodiment, the treated polyalpha-olefin comprises 100 ppm of heteroatom containing compounds or less, preferably 10 ppm of heteroatom containing compounds or less. (A heteroatom containing compound is a compound containing at least one atom other than carbon and hydrogen.) Preferably the hydrogenation catalyst is selected from the group consisting of supported Group 7, 8, 9, and 10 metals, preferably the hydrogenation catalyst selected from the group consisting of one or more of Ni, Pd, Pt, Co, Rh, Fe, Ru, Os, Cr, Mo, and W, supported on silica, alumina, clay, titania, zirconia, or mixed metal oxide supports. A preferred hydrogenation catalyst is nickel supported on keiselguhr, or platinum or palladium supported on alumina, or cobalt-molybdenum supported on alumina. Usually, a high nickel content catalyst, such as 60% Ni on keiselguhr catalyst is used, or a supported catalyst with high amount of Co—Mo loading. Alternately, the hydrogenation catalyst is nickel supported on keiselguhr, silica, alumina, clay or silica-alumina.

A polyalpha-olefin is contacted with hydrogen and a hydrogenation catalyst at a temperature from 25 to 350° C., preferably 100 to 300° C. In another preferred embodiment the polyalpha-olefin is contacted with hydrogen and a hydrogenation catalyst for a time period from 5 minutes to 100 hours, preferably from 5 minutes to 24 hours. In another preferred embodiment the polyalpha-olefin is contacted with hydrogen and a hydrogenation catalyst at a hydrogen pressure of from 25 psi to 2500 psi, preferably from 100 to 2000 psi. For further information on hydrogenation of PAO's please see U.S. Pat. No. 5,573,657 and "Lubricant Base Oil Hydrogen Refining Processes" (page 119 to 152 of *Lubricant Base Oil and Wax Processing*, by Avilino Sequeira, Jr., Marcel Dekker, Inc., NY, 1994.

This hydrogenation process can be accomplished in a slurry reactor in a batch operation or in a continuous stirred tank reactor (CSTR), where the catalyst in 0,001 wt % to 20 wt % of the PAO feed or preferably 0.01 to 10 wt %, hydrogen and the polyalpha-olefins are continuously added to the reactor to allow for certain residence time, usually 5 minutes to 10 hours to allow complete hydrogenation of the unsaturated olefins and to allow proper conversion of the mm diads. The amount of catalyst added is usually very small just to compensate for the catalyst deactivation. The catalyst and hydrogenated PAO are continuously withdrawn from the reactor. The product mixture was then filtered, centrifuged or settled to remove the solid hydrogenation catalyst. The catalyst can be regenerated and reused. The hydrogenated PAO can be used as is or further distilled or fractionated to the right component if necessary. In some cases, when the hydrogenation catalyst show no catalyst deactivation over long term operation, the stir tank hydrogenation process can be carried out in a manner where a fixed amount of catalyst is maintained in the reactor, usually 0.1 wt % to 10% of the total reactant, and only hydrogen and PAO feed are continuously added at certain feed rate and only hydrogenated PAO was withdrawn from the reactor.

The hydrogenation process can also be accomplished by a fixed bed process, in which the solid catalyst is packed inside a tubular reactor and heated to reactor temperature. Hydrogen and PAO feed can be fed through the reactor simultaneously from the top or bottom or counter-currently to maximize the contact between hydrogen, PAO and catalyst and to allow best heat management. The feed rate of the PAO and hydrogen are adjusted to give proper residence to allow complete hydrogenation of the unsaturated olefins in the feed and to allow desirable conversion of mm triads in the process. The hydrogenated PAO fluid can be used as is or further distilled or fractionated to give the right component, if necessary. Usually, the finished hydrocarbon PAO fluids have bromine number less than 2 and have reduced amount of mm triads than the unhydrogenated PAO.

III. APPARATUS FOR PRODUCING PAOS

The present disclosure also includes apparatus for producing a hybrid trimer from a PAO dimer. In conventional processes and apparatus to produce hybrid trimers, and after generation of the PAO dimer in a first oligomerization reactor, the PAO dimer starting material can be enriched by removing impurities for feed into a second oligomerization reactor. This process, however, involves an additional separation operation because feeding the trimer and higher (tetramer+) oligomers to the second oligomerization reactor produces an undesired heavier product from the second oligomerization reaction. Being able to eliminate the separation equipment between these two reactors can dramatically reduce capital spending and simplify plant design and operation.

In an example, the process eliminates the need for a separation stage between a first oligomerization operation and a second oligomerization operation. The inventors have found that the desired hybrid trimer produced from the process, which includes a first and second oligomerization, meets and/or exceeds conventional process yields of hybrid trimer, even while removing the separation operation between the two oligomerizations. The inventors have found that by using the metallocene dimer selective catalyst, the olefin distribution produced in the first oligomerization reactor (e.g., the metallocene reactor) contains significant amounts of dimer and very small amounts of trimer and higher oligomers (tetramer+). With that distribution, the inventors have also found that an apparatus for producing hybrid trimers can be designed without separation equipment disposed between the first oligomerization reactor and the second oligomerization reactor (e.g., separation equipment is merely optional) because there is no longer a requirement to separate out the higher molecules. Therefore, the processes and configurations described herein can greatly simplify PAO processing while maintaining high yields of desired PAO products, such as low viscosity PAO trimers or "hybrid trimers".

Conventional apparatus and processes for the production of low viscosity PAO using conventional metallocene technology is shown in FIG. 1. As shown in FIG. 1, the conventional apparatus and processes requires a monomer/dimer separation operation after forming the PAO dimer in the first oligomerization reactor.

With reference to FIG. 1, the conventional apparatus includes a feed line 102 (LAO feed 1) for directing alpha-olefin monomer into a first oligomerization reactor 104 to form a first oligomerization reactor effluent. The first oligomerization reactor effluent of line 106 is transferred to a separation stage 108 (e.g., a first distillation unit) to remove PAO trimers, tetramers, and higher oligomers (tetramer+) from the first oligomerization reactor effluent. Separation stage 108 can include a pre-heater, distillation column, vacuum system, overhead condenser, overhead accumulator, reflux pump, reboiler, and/or bottoms pump. The monomer/dimer is removed as a first tops fraction via a line 110 and is then transferred to a second oligomerization reactor 116 where it can combine with another alpha-olefin monomer of line 114 (LAO feed 2) and form a second oligomerization reactor effluent. A first bottoms fraction of line 112 can also be separated. The second oligomerization reactor effluent flows to a second distillation unit 120 via line 118 where byproducts and/or contaminants can be separated from the second reactor effluent. The byproducts and/or contaminants may be removed as a second tops fraction via a line 122 and recycled back to second reactor 116 or purged from the process via line 124. The second bottoms fraction, including PAO dimer, trimer, tetramer, and higher oligomers, is then transferred to a hydrogenation unit 128 via line 126. The first bottoms fraction in line 112 (containing, e.g., PAO trimer, tetramer and heavier oligomers) can also combine with second bottoms fraction and flow into the hydrogenation unit 128. The hydrogenation effluent can be transferred, via line 130, to the third distillation unit 132 where PAO dimer is separated from the other components of the hydrogenation effluent such as trimers, tetramers, and higher oligomers. The dimers are removed as a third tops fraction from the third reactor effluent via a line 134. The bottoms fraction from the third distillation unit 132 is transferred to a fourth distillation unit 138 via a line 136, where PAO trimer is partially separated from other components of the third distillation effluent. The PAO trimer can be removed as a third tops fraction from the fourth distillation unit 138 via line 140, and a fourth distillation effluent that includes trimers, tetramers, and higher oligomers can be removed from the fourth distillation unit 138 via line 142.

The conventional metallocene technology used in the conventional apparatus involves a separation stage between the first oligomerization and second oligomerization. As discussed below, the separation stage can be eliminated without reducing the yield of desired PAO trimer, as compared to conventional apparatus.

Figure 2:
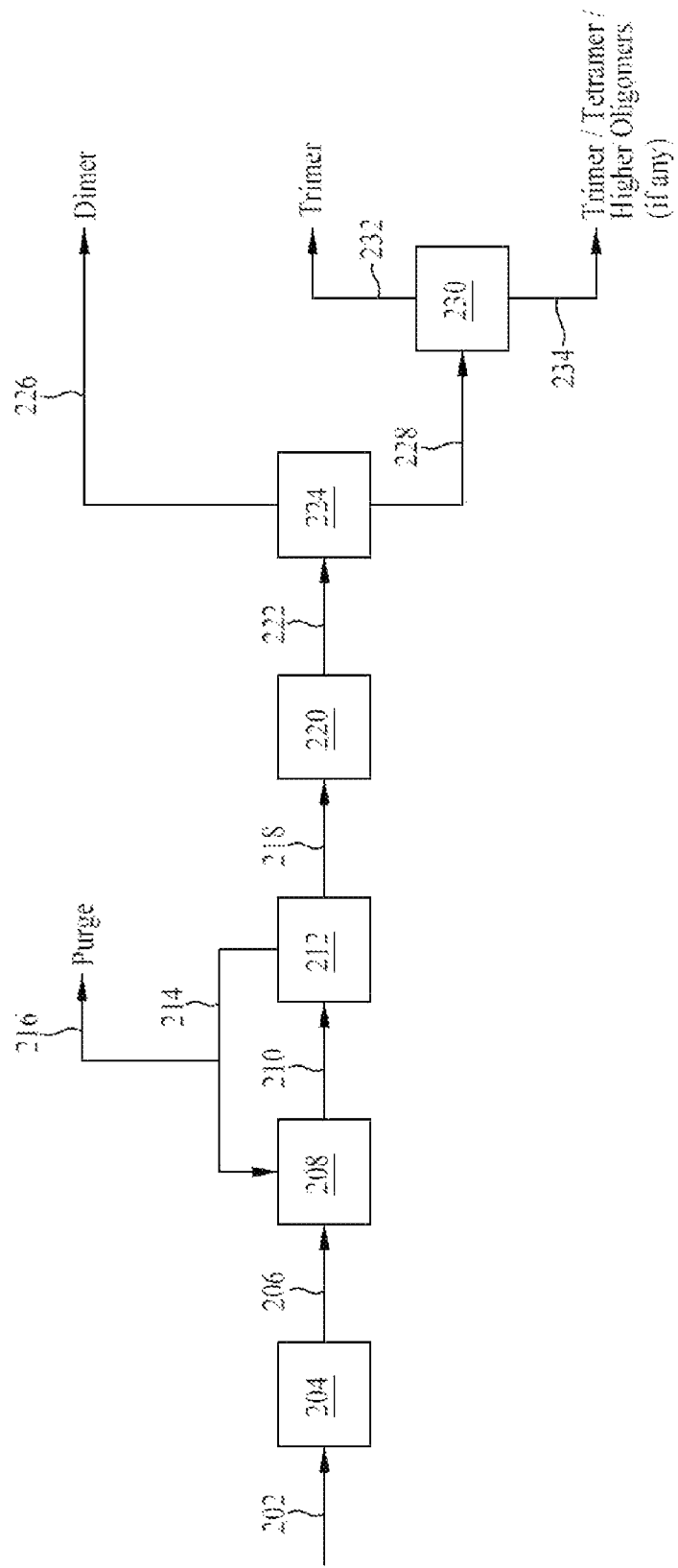
FIG. 2 is an example apparatus for forming poly alpha-olefins according to at least one embodiment.

FIG. 2 is a diagram illustrating an apparatus for carrying out certain aspects of the present disclosure according to at least one embodiment. More generally, a configuration shown in FIG. 2 or similar to FIG. 2 can be used for forming poly alpha-olefins of the present disclosure. FIG. 2 is a non-limiting example of a configuration.

As shown in FIG. 2, an apparatus can include a feed line 202 (LAO feed 1) coupled with a first reactor 204 (e.g., an oligomerization reactor). During use, a feed of the feed line 202 can include an alpha-olefin. The first reactor 204 can be coupled (e.g., directly) with a second reactor 208 (e.g., an oligomerization reactor) via a line 206. A first reactor effluent (e.g., intermediate PAO) of the line 206 can be transferred to the second reactor 208 where the first reactor effluent can undergo a second oligomerization, by, e.g., a $BF_3$-mediated process, to form a second reactor effluent. The second reactor 208 can be coupled to a first distillation unit 212 via a line 210. The second reactor effluent (including the hybrid trimer) can be transferred to the first distillation unit 212 where byproducts and/or contaminants, such as monomer and catalyst components can be separated from the second reactor effluent. The byproducts and/or contaminants may be removed as a first tops fraction via a line 214 and recycled back to second reactor 208 or purged from the process via line 216. The first distillation unit 212 can be further coupled to a third reactor (e.g., a hydrogenation unit) 220. The first distillation effluent (including PAO trimer) of a line 218 can be transferred to the hydrogenation unit 220. The first distillation effluent may further include dimers, tetramers and higher oligomers (if any). The hydrogenation unit 220 can be coupled to a second distillation unit 224 via a line 222. The hydrogenation effluent can be transferred to the second distillation unit 224 where PAO dimer can be separated from the other components of the hydrogenation effluent such as turners, tetramers, and higher oligomers (if any). The dimers may be removed as a second tops fraction from the hydrogenation effluent via a line 226. Optionally, the second distillation unit 224 can be further coupled to a third distillation unit 230 via a line 228. A second distillation effluent that includes trimers, tetramer, and higher oligomers (if any) can be transferred to the third distillation unit 230 where PAO trimer can be partially separated from other components of the second distillation effluent. The PAO trimer can be removed as a third tops fraction from the third distillation unit 230 via line 232, and a third distillation effluent (e.g., a low viscosity PAO effluent) that includes trimers, tetramers, and higher oligomers (if any) can be removed from the third distillation unit 230 via line 234.

In at least one embodiment, the line 206 can be free of a separation stage, e.g., any suitable separation device such as one that separates a lighter component from a heavier component, such as a flash drum(s), multiple flash stages in series, atmospheric distillation column(s), vacuum distillation column(s), stripper(s), steam stripper(s), nitrogen stripper(s), membrane separation(s), chromatography column(s), and/or crystallization(s).

In some embodiments, one or more additional apparatus components are disposed between the first reactor and the second reactor. For example, one or more heat exchangers or mixers is disposed between the first reactor and the second reactor.

In at least one embodiment, the third tops fraction or a portion of the third tops fraction can have a KV (100° C.) of 4 cSt or less, such as less than about 3.6 cSt.

In at least one embodiment, the third tops fraction or a portion of the third tops fraction has a KV (1.00° C.) between 3.4 and 4.0 and a Noack volatility (y) that does not exceed the value defined by the following equation, where x is the kinematic viscosity at 100° C.:

$$y=-21.0x^2+148.7x-248.9$$

In at least one embodiment, the third distillation effluent or a portion of the third distillation effluent can have a KV (100° C.) of from about 4 cSt to about 10 cSt, such as from about 5 cSt to about 7 cSt.

In at least one embodiment, the third distillation is performed such that at the bottoms stream consists of at least 5 wt % trimer, such as from 5 wt % trimer to 40 wt % trimer, such as from 10 wt % trimer to 30 wt % trimer, such as from 15 wt % trimer to 25 wt % trimer.

In at least one embodiment, the first oligomerization can utilize the metallocene dimer catalysts and the metallocene dimer selective processes discussed in Section I, and the first oligomerization can form the products discussed in Section I. In at least one embodiment, the second oligomerization can utilize the catalysts and processes for producing PAO trimers (hybrid timers) discussed in Section If, and can form the products discussed in Section II.

IV. THE FIRST OLIGOMERIZATION REACTION

In some embodiments according to the present disclosure, a process for making a poly alpha-olefin can include contacting a feed containing a $C_6$-$C_{32}$ alpha-olefin and optional ethylene with a catalyst system comprising a metallocene compound in a polymerization reactor under polymerization conditions to effect a polymerization reaction to obtain a product, wherein the metallocene compound is represented by formula (MC-I), wherein each of $R^1$, $R^2$, $R^3$, $R^4$, $R^5$, $R^6$, $R^7$, $R^8$, $R^9$, $R^{10}$, $R^{11}$, $R^{12}$, M, X, and m can be as described above.

In some embodiments, the metallocene compound is represented by formula (MC-II), wherein each of $R^1$, $R^2$, $R^3$, $R^4$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, M, X, m, can be as described above.

In some embodiments of the process, the polymerization reaction exhibits a selectivity toward a combination of greater than or equal to about 96.5 mol % vinylidenes, from 0.5 mol % to 3.5 mol % trisubstituted vinylenes, less than or equal to about 1.5 mol % disubstituted vinylenes, and less than or equal to about 1.5 mol % vinyls, based on total moles of vinyls, vinylidenes, disubstituted vinylenes, and trisubstituted vinylenes in the first reactor effluent.

In some embodiments of the process, the polymerization reaction exhibits a selectivity toward a combination of vinylidenes of equal to or greater than 97.0 mol %, such as equal to or greater than 97.9 mol %; trisubstituted vinylenes of less than 2.1 mol %; disubstituted vinylenes of 0.5 mol % or less; and vinyls of 1.0 mol % or less, based on total moles of vinyls, vinylidenes, disubstituted vinylenes, and trisubstituted vinylenes in the first reactor effluent. In some embodiments of the process, the polymerization reaction exhibits a selectivity towards a combination of vinylidenes and trisubstituted vinylenes of collectively greater than 98.0 mol %, such as greater than 98.5 mol %, and a combination of disubstituted vinylenes and vinyls of collectively less than 2.0 mol %, such as less than 1.5 mol %, based on total moles of vinyls, vinylidenes, disubstituted vinylenes, and trisubstituted vinylenes in the first reactor effluent.

In some embodiments of the process the polymerization reaction results in the first reactor effluent having a number average molecular weight (Mn) of 1500 g/mol or less, such as from 300 to 800 g/mol, as measured by $^1$H NMR. In some embodiments, the catalyst system further comprises a non-coordinating anion type activator, such as wherein the non-coordinating anion type activator comprises: dimethylanilinium tetrakisperfluorophenylborate, dimethylanilinium tetrakisperfluoronaphthylborate, triphenylcarbonium tetrakisperfluorophenylborate, triphenylcarbonium tetrakisperfluoronaphthylborate, dimethylanilinium tetrakisperfluorophenylaluminate, dimethylanilinium tetrakisperfluoronaphthylaluminate, or a combination thereof.

In some embodiments of the process, the polymerization conditions comprise a reaction temperature from 40° C. to 150° C.; an average activity level of at least 1200 g/s·mol; the product exhibits an oligomer yield of at least 10%; or a combination thereof.

In some embodiments of the process, the feed comprises $C_6$-$C_{24}$ alpha-olefin; and any combination of $C_2$-$C_5$ alpha-olefins are collectively present in the alpha-olefin feed at no higher than 25 mol %, based on the total moles of the alpha-olefins supplied to the polymerization reactor, such as wherein the alpha-olefin feed is substantially free of ethylene, propylene, $C_4$ alpha-olefins, and $C_5$ alpha-olefins; or a combination thereof. In some embodiments, the alpha-olefin feed is substantially free (or absent, 0 mol %) of propylene, $C_4$ alpha-olefins, and $C_5$ alpha-olefins; or a combination thereof and optionally comprises less than 25 mol % ethylene, such as less than 15 mol %, such as less than 5 mol %.

In embodiments of the present disclosure, an unsaturated poly alpha-olefin product comprises greater than or equal to about 80 mol % vinylidenes, such as 90 mol % vinylidenes, such as 96.5 mol % vinylidenes, based on total moles of vinyls, vinylidenes, disubstituted vinylenes, and trisubstituted vinylenes contained therein. In some embodiments, the unsaturated poly alpha-olefin product comprises 96.5 mol % to 99.9 mol % of vinylidenes; 0.1 mol % to 3.5 mol % of trisubstituted vinylenes; 3.0 mol % or less of disubstituted vinylenes; 3.0 mol % or less of vinyl groups; based on total moles of vinylidenes, trisubstituted vinylenes, disubstituted vinylenes, and vinylidenes contained therein; and a number average molecular weight (Mn) of 1500 g/mol or less as measured by $^1$H NMR.

In some embodiments, the unsaturated poly alpha-olefin product comprises less than or equal to about 1.0 mol % disubstituted vinylenes, when present; less than or equal to about 1.0 mol % vinyl groups when present; and a number average molecular weight (Mn) of 1000 g/mol or less as measured by $^1$H NMR.

In some embodiments, the unsaturated poly alpha-olefin product comprises from 98 mol % to 99.5 mol % of a combination of vinylidenes and trisubstituted vinylenes; 0.5 mol % to 2 mol % of a combination of disubstituted vinylenes and vinyl groups, and a number average molecular weight (Mn) of 800 g/mol or less as measured by $^1$H NMR.

In embodiments of the present disclosure, a catalyst compound suitable to produce a first reactor effluent from $C_6$-$C_{32}$ alpha-olefin under polymerization conditions comprises a polymerization selectivity suitable to form a first reactor effluent comprising greater than or equal to about 80 mol % vinylidenes, such as 90 mol % vinylidenes, such as 96.5 mol % vinylidenes, based on total moles of vinyls, vinylidenes, disubstituted vinylenes, and trisubstituted vinylenes in the first reactor effluent.

In some embodiments, the catalyst compound comprises a polymerization selectivity suitable to form a first reactor effluent comprising 96.5 mol % to 99.9 mol % of vinylidenes; 0.1 mol % to 3.5 mol % of trisubstituted vinylenes; 2.0 mol % or less of disubstituted vinylenes; 2.0 mol % or less of vinyl groups; based on total moles of vinyls, vinylidenes, disubstituted vinylenes, and trisubstituted vinylenes in the first reactor effluent; and a number average molecular weight (Mn) of 1500 g/mol or less as measured by $^1$H NMR.

In some embodiments, the catalyst compound comprises a polymerization selectivity suitable to form a first reactor effluent comprising: greater than or equal to about 96.5 mol % vinylidenes; less than or equal to about 3.5 mol % trisubstituted vinylenes; less than or equal to about 1.0 mol % disubstituted vinylenes, when present; less than or equal to about 1.0 mol % vinyl groups when present; based on total moles of vinyls, vinylidenes, disubstituted vinylenes, and trisubstituted vinylenes in the first reactor effluent; and a number average molecular weight (Mn) of 1500 g/mol or less as measured by $^1$H NMR.

IV. A First Reactor Effluent

The first reactor effluent includes PAOs. PAOs are polymeric, typically oligomeric, molecules produced from the polymerization reactions of alpha-olefin monomer molecules in the presence of a catalyst system. An unsaturated poly alpha-olefin molecule in the material of the present disclosure contains a C=C bond therein. Each PAO molecule of the first reactor effluent has a carbon chain with the largest number of carbon atoms, which is designated the carbon backbone of the molecule. Any non-hydrogen group attached to the carbon backbone other than to the carbon atoms at the very ends thereof is defined as a pendant group. The number of carbon atoms in the longest carbon chain in each pendant group is defined as the length of the pendant group. The backbone typically comprises the carbon atoms derived from the C=C bonds in the monomer molecules participating in the polymerization reactions, and additional carbon atoms from monomer molecules and/or molecules in the catalyst system that form the two ends of the backbone. A typical PAO molecule of the first reactor effluent can be represented by the following formula (F-1):

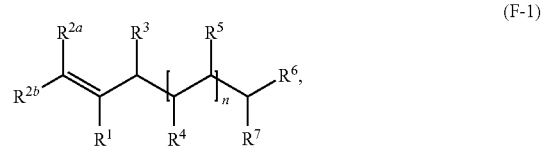

(F-1)

where $R^1$, $R^{2a}$, $R^{2b}$, $R^3$, each of $R^4$ and $R^5$, $R^6$, and $R^7$, the same or different at each occurrence, independently represents a hydrogen or a substituted or unsubstituted hydrocarbyl (such as an alkyl) group, and n is a non-negative integer corresponding to the degree of polymerization. Where $R^1$, $R^{2a}$ and $R^{2b}$ are all hydrogen, (F-1) represents a vinyl PAO; where $R^1$ is not hydrogen, and both $R^{2a}$ and $R^{2b}$ are hydrogen, (F-1) represents a vinylidene PAO; where $R^1$ is hydrogen, and only one of $R^{2a}$ and $R^{2b}$ is hydrogen, (F-1) represents a disubstituted vinylene PAO; and where $R^1$ is not hydrogen, and only one of $R^{2a}$ and $R^{2b}$ is hydrogen, then (F-1) represents a trisubstituted vinylene PAO.

Where n=0, (F-1) represents a PAO dimer produced from the reaction of two monomer molecules after a single addition reaction between two C=C bonds.

Where n=m, m being a positive integer, (F-1) represents a molecule produced from the reactions of m+2 monomer molecules after m+1 steps of linear addition reactions between two C=C bonds.

Thus, where n=1, (F-1) represents a trimer produced from the reactions of three monomer molecules after two steps of linear addition reactions between two C=C bonds.

Assuming a carbon chain starting from $R^1$ and ending with $R^7$ has the largest number of carbon atoms among all straight carbon chains existing in (F-1), that carbon chain starting from $R^1$ and ending with $R^7$ having the largest number of carbon atoms constitutes the carbon backbone of the first reactor effluent molecule (F-1). $R^2$, $R^3$, each of $R^4$ and $R^5$, and $R^6$, which can be substituted or unsubstituted hydrocarbyl (such as alkyl) groups, are pendant groups (if not hydrogen).

If only alpha-olefin monomers are used in the polymerization process, and no isomerization of the monomers and oligomers ever occurs in the reaction system during polymerization, about half, typically at least one more than half, of $R^1$, $R^{2a}$, $R^{2b}$, $R^3$, all $R^4$ and $R^5$, $R^6$, and $R^7$ would be hydrogen, and one of $R^1$, $R^{2a}$, $R^{2b}$, $R^6$, and $R^7$ would be a hydrocarbyl, such as methyl, and about half, typically less than half, of groups $R^1$, $R^{2a}$, $R^{2b}$, $R^3$, all $R^4$ and $R^5$, $R^6$, and $R^7$ would be hydrocarbyl groups introduced from the alpha-olefin monomer molecules. in a specific example of such case, assuming $R^{2a}$ and $R^{2b}$ are hydrogen, $R^3$, all $R^5$, and $R^6$ are hydrogen, and $R^1$, all $R^4$, and $R^7$ have 8 carbon atoms in the longest carbon chains contained therein, and n=8, then the carbon backbone of the (F-1) PAO molecule would comprise 35 carbon atoms, and the average pendant group length of the pendant groups (the initial=$CR^{2a}R^{2b}$ group, and all of $R^4$) would be 7.22 (i.e., (1+8*8)/9). Such an PAO molecule, which may be produced by polymerizing 1-decene using certain metallocene catalyst systems, such as described in greater detail below, can be represented by formula (F-2) below:

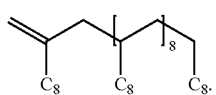

(F-2)

In such a molecule, the longest 5%, 10%, 20%, 40%, 50%, and 100% of the pendant groups have average pendant group length of Lpg(5%) of 8, Lpg(10%) of 8, Lpg(20%) of 8, Lpg(50%) of 8, and Lpg(100%) of 7.22, respectively.

Depending on the polymerization catalyst system used, however, different degrees of isomerization of the monomers and/or oligomers can occur in the reaction system during the polymerization process, resulting in different degrees of substitution on the carbon backbone. In a specific example of such case, assuming $R^{2a}$ and $R^{2b}$ are both hydrogen, $R^3$ and all $R^5$ are methyl, $R^6$ is hydrogen, $R^1$ has 8 carbon atoms in the longest carbon chain contained therein, all $R^4$ and $R^7$ have 7 carbon atoms in the longest carbon chain contained therein, and n=8, then the carbon backbone of the (F-1) PAO molecule would comprise 34 carbon atoms, and the average pendant group length of the pendant groups (the initial=$CR^{2a}R^{2b}$ group, all $R^4$, and $R^5$) would be ~3.7 (i.e., (1+1+7*8+8*1)/18). Such a PAO molecule, which may be produced by polymerizing either 1-decene, with a given level and pattern of isomerization, or by polymerizing a combination of 1-decene and 2-decene, using certain non-metallocene catalyst systems, such as described in greater detail below, can be represented by the following formula (F-3):

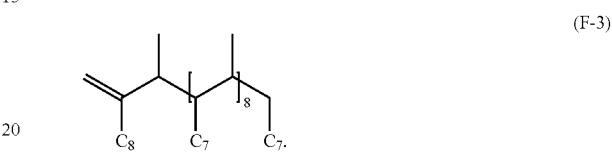

(F-3)

In this molecule, the longest 5%, 10%, 20%, 40%, 50%, and 100% of the pendant groups have average pendant group lengths of Lpg(5%) of 7, Lpg(10%) of 7, Lpg(20%) of 7, Lpg(50%) of 6.3, and Lpg(100%) of 3.7, respectively.

One skilled in the art, with knowledge of the molecular structure or the monomer(s) used in the polymerization step for making the first reactor effluent, the process conditions (catalyst used, reaction conditions, etc.), and the polymerization reaction mechanism, inter can approximate the molecular structure of the PAO molecules, thus the pendant groups attached to the carbon backbone, and hence approximate values of Lpg(5%), Lpg(10%), Lpg(20%), Lpg(50%) of 6.3, and Lpg(100%), respectively.

One skilled in the art can determine the Lpg(5%). Lpg (10%), Lpg(20%), Lpg(50%), and Lpg(100%) values of a given first reactor effluent by using separation and characterization techniques available to polymer chemists. For example, gas chromatography/mass spectroscopy machines equipped with boiling point column separator can be used to separate and identify individual chemical species and fractions; and standard characterization methods such as NMR, IR, and IJV spectroscopy can be used to further confirm the structures.

The first reactor effluent of the present disclosure may be a homopolymer made from a single alpha-olefin monomer or a copolymer made from a combination of two or more alpha-olefin monomers. In some embodiments, the alpha-olefin monomers) can include, consist essentially of, or be 1-hexene, 1-octene, 1-decene, 1-dodecene, or a combination thereof, such as 1-octene, 1-decene, and 1-dodecene.

The first reactor effluent of the present disclosure may be produced by using a catalyst system comprising a specific type of metallocene compound, such as described in detail below. The first reactor effluent can be substantially free of the alpha-olefin monomer(s), and may advantageously contain vinylidenes at a high concentration, such as in the range from c1 to c2 mol % in total, where c1 and c2 can be, independently, about 80, about 85, about 90, about 91, about 92, about 93, about 941, about 95, about 96, about 96.5, about 97, about 98, about 99, about 99.5, or about 99.9, based on the total moles of vinyls, vinylidenes, disubstituted vinylenes, and trisubstituted vinylenes, as long as c1<c2. In some embodiments, c1=90 and c2=99; c1=91 and c2=99; c1=92 and c2=98; c1=93 and c2=97; c1=96.5 and c2=99.9; or c1=98 and c2=99.5. Without intending to be bound by a particular theory, it is believed that the high concentrations of vinylidenes can be achieved partly by the unique structure of the metallocene compound used in the catalyst system.

Between the vinylidenes and trisubstituted vinylenes in the first reactor effluent of the present disclosure, trisubstituted vinylenes tend to have a considerably lower concentration than the vinylidenes. In some embodiments, the first reactor effluent of the present disclosure can contain a concentration of trisubstituted vinylenes in the range from c3 to c4 mol %, based on the total moles of the vinyls, vinylidenes, disubstituted vinylenes, and trisubstituted vinylenes, where c3 and c4 can be, independently, about 0, about 0.1, about 0.5, about 1.0, about 1.5, about 2.0, about 2.5, about 3.0, about 3.5, about 4.0, about 4.5, about 5.0, about 5.5 or about 6.0, as long as c3<c4. In some embodiments, c3=0.5 and c4=5.5; c3=1.0 and c4=5.0; c3=0.5 and c4=4.0 c3=0 and c4=4.0, c3=0.1 and c4=3.5; or c3=0.5 and c4=2.

In some embodiments, the first reactor effluent of the present disclosure can contain a high combined concentration of vinylidenes and trisubstituted vinylenes, the combined concentration being in the range from c5 to c6 mol %, based on the total moles of the vinyls, vinylidenes, disubstituted vinylenes, and trisubstituted vinylenes, where c5 and c6 can be, independently, about 85, about 90, about 91, about 92, about 93. about 94, about 95, about 96, about 97, about 98, about 99, or about 99.5, based on the total moles of vinyls, vinylidenes, disubstituted vinylenes, and trisubstituted vinylenes, as long as c5<c6. In some embodiments, c5=90 and c6=99.5; c5=92 and c6=99.5; c5=94 and c6=99; c5=95 and c6=99; or c5=98 and c6=99.5.

The first reactor effluent of the present disclosure can contain disubstituted vinylenes at a low concentration in the range from c7 to c8 mol %, based on the total moles of vinyls, vinylidenes, disubstituted vinylenes, and trisubstituted vinylenes, where c7 and c8 can be about 0, about 0.1, about 0.2, about 0.3, about 0.4, about 0.5, about 0.6, about 0.7, about 0.8, about 1.0, about 1.2, about 1.4, about 1.6, about 1.8, about 2.0, about 2.5, about 3.0, about 3.5, about 4.0, about 4.5, or about 5.0, as long as c7<c8. In some embodiments, c7=0 and c8=4.0; c7=0 and c8=3.0; c7=0 and c8=2.0; c7=0 and c8=1; c7=0 and c8=1.2; or c7=0.1 and c8=2.5. Without intending to be bound by a particular theory, it is believed that such low concentrations of disubstituted vinylenes in the first reactor effluent are achieved by the low selectivity toward these olefins in the polymerization reactions, which can be provided at least partially by the unique structure of the metallocene compound in the catalyst system used in the polymerization reaction.

Depending on the metallocene compound used in the catalyst system, the first reactor effluent of the present disclosure can contain vinyls at a low concentration, e.g., from c9 to c10 mol %, based on the total moles of vinyls, vinylidenes, disubstituted vinylenes, and trisubstituted vinylenes, where c9 and c10 can be about 0, about 0.1, about 0.2, about 0.3, about 0.4, about 0.5, about 0.6, about 0.7, about 0.8, about 1.0, about 1.2, about 1.4, about 1.6, about 1.8, about 2.0, about 2.5, about 3.0, about 3.5, about 4.0, about 4.5, or about 5,0, as long as c9<c10. In some embodiments, c9=0 and c10=4.0; c9=0 and c10=3.0; c9=0 and c10=2; c9=0 and c10=1.6; c9=0 and c10=1.0; or c9=0.1 and c10=1.2. Without intending to be bound by a particular theory, it is believed that such low concentration of vinyls in the first reactor effluent are achieved by the low selectivity toward vinyls in the polymerization reactions, which can be provided by choosing the molecular structure of the metallocene compound in the catalyst system used in the polymerization reaction.

In some embodiments, the first reactor effluent of the present disclosure can contain a low combined concentration of vinyls and disubstituted vinylenes, the combined concentration being in the range from c11 to c12 mol %, based on the total moles of the vinyls, vinylidenes, disubstituted vinylenes, and trisubstituted vinylenes, where c11 and c12 can be, independently, about 0, about 0.1, about 0.2, about 0.3, about 0.4, about 0.5, about 0.6, about 0.7, about 0.8, about 1.0, about 1.2, about 1.4, about 1.6, about 1.8, about 2.0, about 2.5, about 3.0, about 3.5, about 4.0, about 4.5, about 5.0, about 5.5, or 6.0, as long as c11<c12. In some embodiments, c11=0 and c12=5.0; c11=0 and c12=4.0; c11=0.5 and c12=2; c11=0.5 and c12=4.5; or c11=0.8 and c12=5.0.

Thus, the first reactor effluent of the present disclosure can typically comprise a plurality of PAO molecules, which may be the same or different. Each PAO molecule of the first reactor effluent can comprise a plurality of pendant groups, which may be the same or different, and the longest about 5%, about 10%, about 20%, about 40%, about 50%, and about 100% of the pendant groups of all of the olefin molecules of the first reactor effluent have an average pendent group length of Lpg(5%), Lpg(10%), Lpg(20%), Lpg(40%), Lpg(50%), and Lpg(100%), respectively. In some embodiments, at least one of the following conditions are met:
(i) a1≤Lpg(5%)≤a2, where a1 and a2 can be, independently, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0 15.5, or 16.0, as long as a1<a2;
(ii) b1≤Lpg(1.0%)≤b2, where b1 and b2 can be, independently, 4.0, 4.5, 5.0, 5.5, 6,0, 6.5, 7,0, 7.5, 8.0, 8.5, 9.0, 9.5, 10.0, 10.5, 11.0, 11.5, 12.0, 12.5, 13.0, 13.5, 14.0, 14.5, or 15.0, as long as b1<b2;
(iii) c1≤Lpg(20%)≤c2, where c1 and c2 can be, independently, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, or 15.0, as long as c1<c2;
(iv) d1≤Lpg(40%)≤d2; where d1 and d2 can be, independently, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, or 15.0, as long as d1<d2;
(v) e1≤Lpg (50%)≤e2; where e1 and e2 can be, independently, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, or 14.0, as long as e1<e2; and
(vi) f1≤Lpg(100%)≤f2, where f1 and f2 can be, independently, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, or 13.0, as long as f1<f2.

In some embodiments, at least about 60% of the pendent groups on olefin molecules in the first reactor effluent are straight chain alkyls having at least 4 (e.g., at least 6, at least 8, or at least 10) carbon atoms. In some embodiments, at least 90% of the pendent groups on the olefin molecules in the first reactor effluent are straight chain alkyls having at least 4 (e.g., at least 6, at least 8, or at least 10) carbon atoms.

The first reactor effluent of the present disclosure may have various levels of regio-regularity. For example, each PAO molecule of the first reactor effluent may be substantially atactic, isotactic, or syndiotactic. A category of metallocene compounds can lack $C_1$, $C_2$, and $C_s$ symmetry. Without intending to be bound by a particular theory, it is believed that PAO materials made by using such asymmetrical metallocene-based catalyst system can tend to be atactic.

The first reactor effluent of the present disclosure can have viscosity varying in a broad range. For example, the first reactor effluent may have a KV100 in a range from about 1 to about 5000 cSt, such as about 1 to about 3000 cSt, about 2 to about 2000 cSt, about 2 to about 1000 cSt, about 2 to about 800 cSt, about 2 to about 600 cSt, about 2 to about 500 cSt, about 2 to about 400 cSt, about 2 to about 300 cSt, about 2 to about 200 cSt, or about 5 to about 100 cSt. The exact viscosity of the first reactor effluent can be controlled by, e.g., monomer used, polymerization temperature, polymerization reactor residence time, catalyst used, concentration of catalyst used, distillation and separation conditions, and mixing multiple first reactor effluent with different viscosity.

In addition, the first reactor effluent of the present disclosure advantageously have a low polydispersity index (PDI) in the range from about 1.0 to about 5,0 (e.g., from about 1.2 to about 4.0, from about 1.3 to about 3.0, from about 1.4 to about 2.5, from about 1.5 to about 2.0, or from about 1.6 to about 1.8). A narrow molecular weight distribution of the PAO molecules of the first reactor effluent can be achieved by using metallocene-compound-based catalyst systems in the polymerization step under controlled polymerization conditions (temperature fluctuation, residence time, and the like). Such narrow PDI can be desirable in that it defines a material with a high degree of homogeneity in molecular weight, molecular size, rheology behavior, viscosity index, and degrading behavior (such as shear stability and oxidation stability).

In general, the product in the first reactor effluent of the present disclosure can have an average molecular weight that can vary widely (and correspondingly, a KV100 that can vary widely). In some embodiments, the product of the first reactor effluent can have a number average molecular weight of Mn, where Mn1≤Mn≤Mn2, where Mn1 and Mn2 can be, independently, about 150, about 200, about 300, about 400, about 500, about 600, about 700, about 800, about 900, about 1000, about 1100, about 1200, about 1300 about 1400, about 1500, about 1700, about 2000, about 2500, about 3000, about 3500, about 4000, about 4500, about 5000, about 6000, about 7000, about 8,000, about 9000, or about 10000 g/mol, as long as Mn1<Mn2. In some embodiments, the product of the first reactor effluent can have a number average molecular weight of about 3000 g/mol or less, e.g., about 2500 g/mol or less, about 2000 g/mol or less, about 1700 g/mol or less, about 1500 g/mol or less, about 1400 g/mol or less, about 1300 g/mol or less, about 1200 g/mol or less, about 1100 g/mol or less, about 1000 g/mol or less, about 900 g/mol or less, about 800 g/mol or less, about 700 g/mol or less, about 650 g/mol or less, about 620 g/mol or less, about 600 g/mol or less, about 520 g/mol or less, about 500 g/mol or less, about 400 g/mol or less, about 380 g/mol or less, about 370 g/mol or less, about 360 g/mol or less, about 350 g/mol or less, about 340 g/mol or less, about 330 g/mol or less, or about 320 g/mol or less; typically, as the product can exclude olefin monomers but may include dimers and higher mers, the number average molecular weight can optionally be at least about 100 g/mol, e.g., at least about 150 g/mol or at least about 200 g/mol, depending upon the molecular weight of a monomeric feed olefin component.

In general, it can be desired that the first reactor effluent of the present disclosure has a bromine number in a range from Nb(PAO)1 to Nb(PAO)2, where Nb(PAO)1 and Nb(PAO)2 can be, independently, 1.0. 1.5, 2.0, 2.5, 3.0, 3.5, 4.0, 4.5, 5.0, 6.0, 7.0, 8.0, 9.0, or even 10.0, 15.0, 10.0, as long as Nb(PAO)1<Nb(PAO)2. In some embodiments, a great majority, such as at least about 80, about 85, about 90, about 95, about 98, or even about 99 mol % of the molecules in the first reactor effluent of the present disclosure may be unsaturated.

Because of the presence of the C=C bonds in the PAO molecules in the first reactor effluent, when exposed to $O_2$ molecules (such as when exposed to air), the first reactor effluent can be oxidized if not protected by a more reactive material toward $O_2$. To that end, in the first reactor effluent, anti-oxidant materials may be added to prolong shelf life and facilitate handling, storage, and transportation thereof. Non-limiting examples of such anti-oxidants and the use quantity thereof are given in paragraphs [0101]-[0108], pages 9 and 10 of U.S. Patent Publication No. 2010/0087349, the content of which is hereby incorporated by reference in its entirety.

IV. B. The Catalyst System of the First Oligomerization

In embodiments, the catalyst system of the first oligomerization comprises a catalyst compound, such as a metallocene compound which is activated by one or more activators. The catalyst system may further include a solvent, a support, one or more scavengers, accelerators, and/or the like.

IV. B.1 The Metallocene Compound of the First Oligomerization

The initial part to a catalyst system of the first oligomerization described herein is a metallocene compound.

The metallocene compound used in the process of the present disclosure for making PAOs is generally represented by formula (Z) or (Z-1):

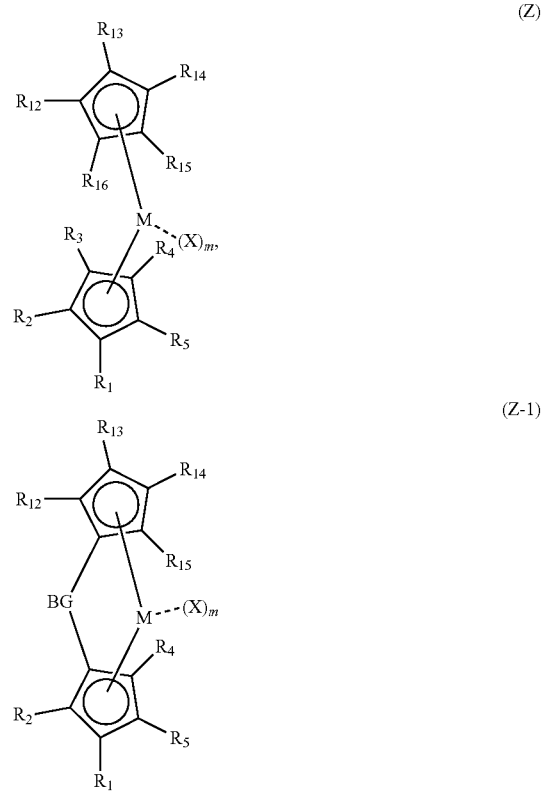

wherein:

each $R^1$, $R^2$, and $R^3$ is, independently, hydrogen or a substituted or unsubstituted linear, branched (such as branched linear), or cyclic $C_1$ to $C_{20}$, preferably $C_1$-$C_8$, hydrocarbyl group, wherein one of $R^1$, $R^2$, and $R^3$ is a substituted or unsubstituted linear, branched (such as branched linear), or cyclic $C_1$ to $C_{20}$, preferably $C_1$-$C_8$, hydrocarbyl group, and either (i) two of $R^1$, $R^2$, and $R^3$ are each a hydrogen, or (ii) one of $R^1$, $R^2$, and $R^3$ is a hydrogen or a substituted or unsubstituted linear, branched (such as branched linear), or cyclic $C_1$ to $C_{20}$, preferably $C_1$-$C_8$, hydrocarbyl group, and one of $R^1$, $R^2$, and $R^3$, taken together with $R^{16}$, is a bridging group connecting the first and second cyclopentadienyl rings;

$R^4$ and $R^5$ are each independently a substituted or unsubstituted linear, branched (such as branched linear), or cyclic $C_1$-$C_{30}$ hydrocarbyl group, or $R^4$ and $R^5$, taken together with the carbon atoms in the first cyclopentadienyl ring to which they are directly connected, collectively form one or more substituted or unsubstituted rings annelated to the first cyclopentadienyl ring;

$R^{12}$, $R^{13}$, $R^{14}$, and $R^{15}$ are each independently a hydrogen, or a substituted or unsubstituted linear, branched (such as branched linear), or cyclic $C_1$ to $C_{20}$, preferably $C_1$-$C_8$, hydrocarbyl group;

$R^{16}$ is a hydrogen, a substituted or unsubstituted linear, branched (such as branched linear), or cyclic $C_1$ to $C_{20}$, preferably $C_1$-$C_8$, hydrocarbyl group, a substituted silyl group, or a substituted germanyl group, or, taken together with one of $R^1$, $R^2$, and $R^3$, is a bridging group connecting the first and second cyclopentadienyl rings, preferably at least three (preferably at least four, preferably all five) of $R^{12}$, $R^{13}$, $R^{14}$, $R^{15}$, and $R^{16}$ are not hydrogen, optionally two or more of $R^{12}$, $R^{13}$, $R^{14}$, $R^{15}$ and $R^{16}$ moieties may together form a fused ring or ring system, provided that the fused ring or ring system is not unsaturated when $R^1$ is bridged to $R^{16}$, and provided that $R^2$ is not Me when $R^1$ or $R^3$ is bridged to $R^{16}$;

M is a transition metal (preferably a group 4 transition metal, preferably Hf, Ti, or Zr), having an integer valency of v, preferably v is 3, 4, or 5;

each X is independently a halogen, a hydride, an amide, an alkoxide, a sulfide, a phosphide, a diene, an amine, a phosphine, an ether, or a $C_1$-$C_{20}$ substituted or unsubstituted linear, branched, or cyclic hydrocarbyl group, or optionally two or more X moieties may together form a fused ring or ring system;

m is an integer equal to v-2 (preferably m is 1, 2 or 3, preferably 2), preferably M is Zr or Hf, v is 4 and m is 2; and bridging group (BG) is represented by the formula:

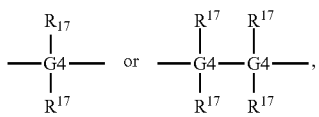

where each G4, the same or different at each occurrence, is independently carbon, silicon, or germanium, and $R^{17}$, the same or different at each occurrence, is each independently a $C_1$-$C_{20}$, preferably $C_1$-$C_8$, substituted or unsubstituted linear, branched, or cyclic hydrocarbyl group.

Optionally, at least four (alternately all five) of R12, R13, R14, R15, and R16 are each independently a substituted or unsubstituted linear, branched linear, or cyclic C1-C8 hydrocarbyl group, preferably methyl or ethyl.

Optionally, $R^4$ and $R^5$, taken together with the carbon atoms in the first cyclopentadienyl ring to which they are directly connected, collectively form a substituted or unsubstituted ring annelated to the first cyclopentadienyl ring, such that the metallocene compound is represented by the formula (Z-2):

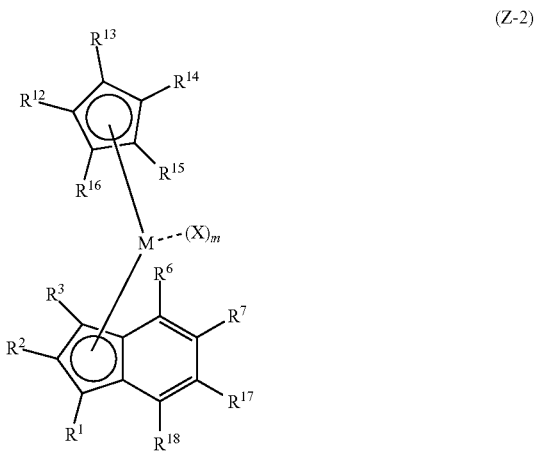

where, M, X, m, $R^1$, $R^2$, $R^3$, $R^{12}$, $R^{13}$, $R^{14}$, $R^{15}$, and $R^{16}$ are as defined for formula (Z), and $R^6$, $R^7$, $R^{17}$, and $R^{18}$ are each independently hydrogen; a substituted or unsubstituted linear, branched linear, or cyclic $C_1$-$C_{30}$ hydrocarbyl group; or $R^6$ and $R^7$, $R^7$ and $R^{17}$, or $R^{17}$ and $R^{18}$, taken together with the carbon atoms in the indenyl ring to which they are directly connected, collectively form one or more substituted or unsubstituted rings annelated to the indenyl ring.

[1] In formula (Z), (Z-1) or (Z-2):
  i) at least three of $R^{12}$, $R^{13}$, $R^{14}$, $R^{15}$, and $R^{16}$ if present are not hydrogen;
  ii) two or more of $R^{12}$, $R^{13}$, $R^{14}$, $R^{15}$ and $R^{16}$ if present together form a fused ring or ring system;
  iii) at least two of $R^6$, $R^7$, $R^{17}$, and $R^{18}$ are hydrogen;
  iv) each X is independently a halogen or a substituted or unsubstituted linear, branched linear, or cyclic $C_1$-$C_6$ hydrocarbyl group;
  v) M comprises Zr or Hf;
  or a combination thereof.

[2] Optionally, one of $R^1$, $R^2$, and $R^3$ is a substituted or unsubstituted linear, branched (such as branched linear), or cyclic $C_1$-$C_6$ hydrocarbyl group, and two of $R^1$, $R^2$, and $R^3$ are each a hydrogen. In other particular embodiments, one of $R^1$ and $R^3$ is a substituted or unsubstituted linear, branched (such as branched linear), or cyclic $C_1$-$C_6$ hydrocarbyl group, $R^2$ is a hydrogen, and one of $R^1$ and $R^3$ is a substituted or unsubstituted linear, branched (such as branched linear), or cyclic $C_1$-$C_6$ hydrocarbyl group, or, taken together with $R^{16}$, is a bridging group connecting the first and second cyclopentadienyl rings.

[3] Preferably, $R^2$ is hydrogen.

[4] Preferably, each $R^1$, $R^2$, and $R^3$ is, independently, hydrogen or a substituted or unsubstituted linear, branched (such as branched linear), or cyclic $C_1$-$C_6$ hydrocarbyl group (e.g., a methyl, an ethyl, a propyl, a butyl, a cyclohexyl, or a phenyl). When BG (formula Z-1) is present, $R^2$ is preferably hydrogen or a $C_2$ to $C_8$ hydrocarbyl group (e.g., an ethyl, a propyl, a butyl, a pentyl, a hexyl (such as cyclohexyl), a heptyl, an octyl, or a phenyl).

[5] In some embodiments, one of $R^1$, $R^2$, and $R^3$ is a substituted or unsubstituted linear, branched (such as branched linear), or cyclic $C_1$-$C_6$ hydrocarbyl group (e.g., a methyl, an ethyl, a propyl, a butyl, a cyclohexyl, or a phenyl, such as methyl), and (the other) two of $R^1$, $R^2$, and $R^3$ are each a hydrogen.

[6] In some embodiments, $R^1$ and $R^3$ are each individually a substituted or unsubstituted linear, branched (such as branched linear), or cyclic $C_2$-$C_6$ hydrocarbyl group (e.g., an ethyl, a propyl, a butyl, a cyclohexyl, or a phenyl), and $R^2$ is a hydrogen. In another embodiment, $R^1$ and $R^3$ are each a methyl group and $R^2$ is a hydrogen.

[7] In some embodiments, $R^4$ and $R^5$, taken together with the carbon atoms in the first cyclopentadienyl ring to which they are directly connected, collectively form a substituted or unsubstituted phenyl ring annelated to the first cyclopentadienyl ring. In such embodiments, the four phenyl ring carbons not connected to the first cyclopentadienyl ring are each independently bonded to a hydrogen or a substituted or unsubstituted linear, branched (such as branched linear), or cyclic $C_1$-$C_6$ hydrocarbyl group (e.g., a methyl, an ethyl, a propyl, a butyl, a cyclohexyl, or a phenyl). In some such embodiments, at least two (e.g., at least three or all four) of the four phenyl ring carbons not connected to the first cyclopentadienyl ring are connected to a hydrogen.

[8] In some embodiments, $R^4$ and $R^5$, taken together with the carbon atoms in the first cyclopentadienyl ring to which they are directly connected, collectively form a substituted or unsubstituted naphthenyl ring annelated to the first cyclopentadienyl ring.

[9] In any embodiment of any formula (Z), (Z-1), or (Z-2), BG is a bridging group represented by the formula: $R^*_2C$, $R^*_2Si$, $R^*_2Ge$, $R^*_2CCR^*_2$, $R^*_2CCR^*_2CR^*_2$, $R^*_2CCR^*_2CR^*_2CR^*_2$, $R^*C=CR^*$, $R^*C=CR^*CR^*_2$, $R^*_2CCR^*=CR^*CR^*_2$, $R^*C=CR^*CR^*=CR^*$, $R^*C=CR^*CR^*_2CR^*_2$, $R^*_2CSiR^*_2$, $R^*_2SiSiR^*_2$, $R^*_2SiOSiR^*_2$, $R^*_2CSiR^*_2CR^*_2$, $R^*_2SiCR^*_2SiR^*_2$, $R^*C=CR^*SiR^*_2$, $R^*_2CGeR^*_2$, $R^*_2GeGeR^*_2$, $R^*_2CGeR^*_2CR^*_2$, $R^*_2GeCR^*_2GeR^*_2$, $R^*_2SiGeR^*_2$, $R^*C=CR^*GeR^*_2$, where $R^*$ is hydrogen or a $C_1$-$C_{20}$ containing hydrocarbyl, substituted hydrocarbyl, halocarbyl, substituted halocarbyl, silylcarbyl or germylcarbyl substituent and optionally two or more adjacent $R^*$ may join to form a substituted or unsubstituted, saturated, partially unsaturated or aromatic, cyclic or polycyclic substituent. Preferred examples for the bridging group BG include $CH_2$, $CH_2CH_2$, $SiMe_2$, $SiPh_2$, $SiMePh$, $Si(CH_2)_3$, $Si(Ph\text{-}SiMe_3)_2$, and $Si(CH_2)_4$. In a preferred embodiment of the invention in any embodiment of any formula described herein, BG is represented by the formula $ER^d_2$ or $(ER^d_2)_2$, where E is C, Si, or Ge, and each $R^d$ is, independently, hydrogen, halogen, $C_1$ to $C_{20}$ hydrocarbyl (such as methyl, ethyl, propyl, butyl, pentyl, hexyl, heptyl, octyl, nonyl, decyl, undecyl, or dodecyl) or a $C_1$ to $C_{20}$ substituted hydrocarbyl, and two $R^d$ can form a cyclic structure including aromatic, partially saturated, or saturated cyclic or fused ring system. Preferably, BG is a bridging group comprising carbon or silica, such as dialkylsilyl, preferably BG is selected from $CH_2$, $CH_2CH_2$, $C(CH_3)_2$, $SiMe_2$, $Me_2Si\text{—}SiMe_2$, cyclotrimethylenesilylene ($Si(CH_2)_3$), cyclopentamethylenesilylene ($Si(CH_2)_5$) and cyclotetramethylenesilylene ($Si(CH_2)_4$).

[10] Optionally the metallocene compound is not represented by the formula

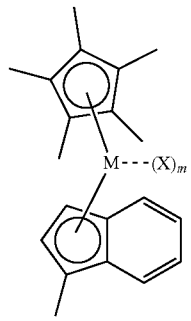

where M, X and m are as defined for formula (Z).

The metallocene compound used in processes of the present disclosure for making PAOs preferably has a structure represented by formula (MC-I) and/or formula (MC-II).

In at least one embodiment, the metallocene compound is preferably represented by formula (MC-III):

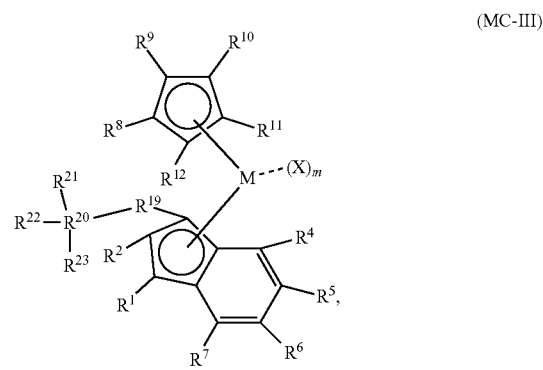

(MC-III)

wherein: each of $R^1$, $R^2$, $R^4$, $R^5$, $R^6$, $R^7$, $R^8$, $R^9$, $R^{10}$, $R^{11}$, $R^{12}$, M, X, and m can be as described above; $R^{19}$ and $R^{20}$ comprise Group 14 atoms, such as C, Ge, or Si (such as $R^{19}$ is C and $R^{20}$ is C or Si), and $R^{21}$, $R^{22}$, and $R^{23}$ are each independently hydrogen or a substituted or unsubstituted linear, branched, or cyclic $C_1$-$C_{20}$ hydrocarbyl group and at least two of $R^{21}$, $R^{22}$, and $R^{23}$ each independently a substituted or unsubstituted linear, branched, or cyclic $C_1$-$C_{20}$ hydrocarbyl group, wherein at least two of $R^{21}$, $R^{22}$, and $R^{23}$ are a substituted or unsubstituted linear, branched, or cyclic $C_1$-$C_{20}$ hydrocarbyl group, where examples of $C_1$-$C_{20}$ substituted or unsubstituted linear, branched, or cyclic hydrocarbyl groups can be as described above.

In some embodiments, the metallocene compound can be represented by formula (MC-1), (MC-2), (MC-3), (MC-4), (MC-5), (MC-6), (MC-7), (MC-8), (MC-9), (MC-10), (MC-11), (MC-12), or (MC-13):

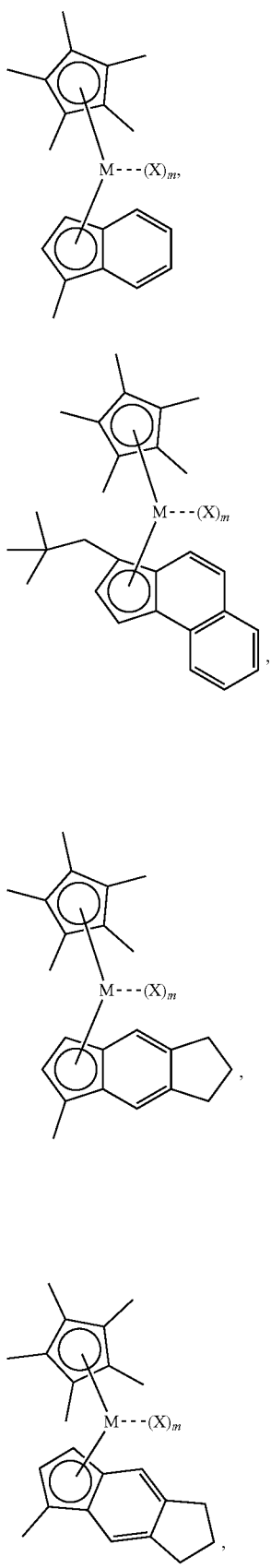
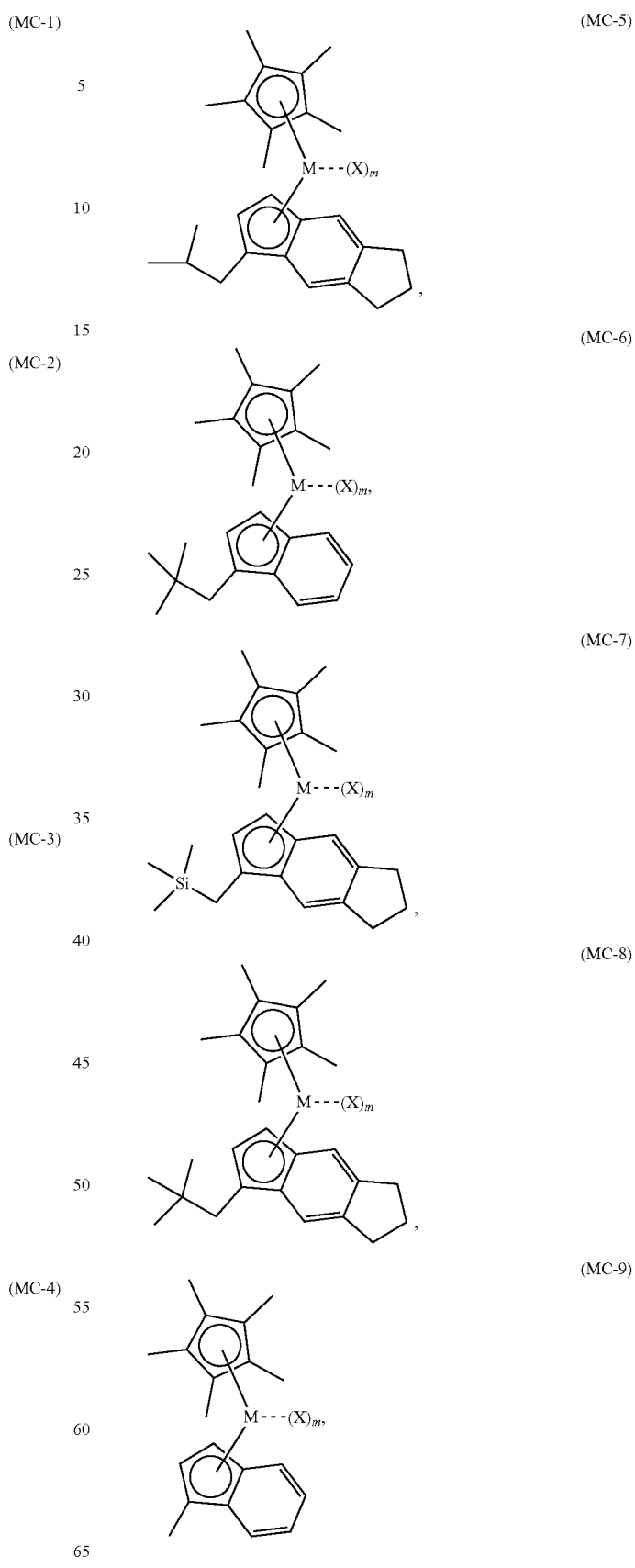

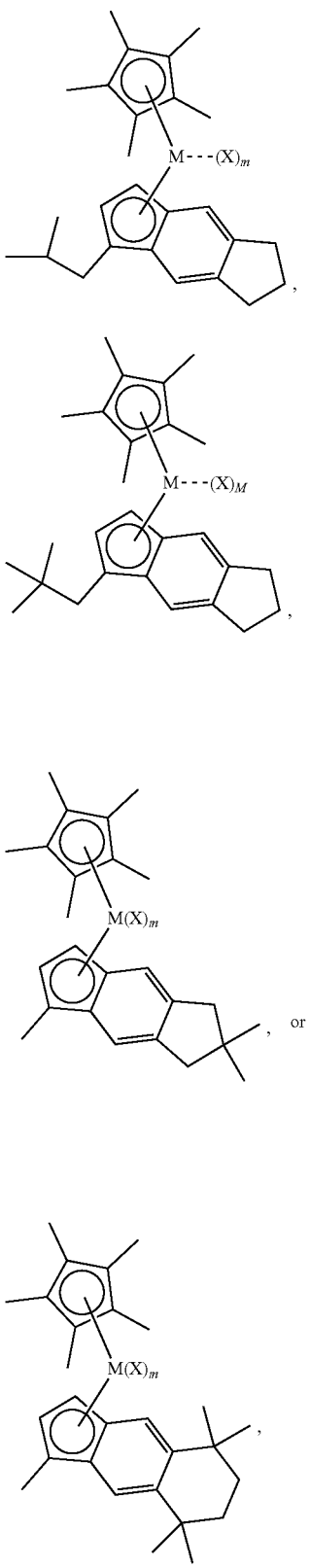

wherein: each of X, M and m can be as described above.

In some embodiments, the catalyst compound is represented by the formula (MC-IV):

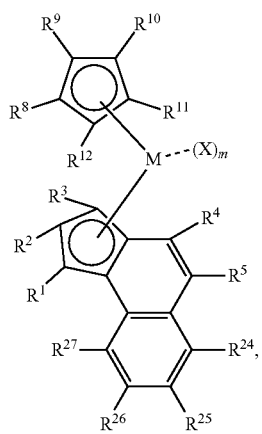

wherein: each of $R^1$, $R^2$, $R^4$, $R^5$, $R^8$, $R^9$, $R^{10}$, $R^1$, $R^{12}$, M, X, and m can be as described above; and $R^{24}$, $R^{25}$, $R^{26}$, and $R^{27}$ can be independently a hydrogen or a substituted or unsubstituted linear, branched, or cyclic $C_1$-$C_{20}$ hydrocarbyl group.

In at least one embodiment of formula (MC-IV), (i) one of and $R^1$, $R^2$, and $R^3$ is an alpha Group 14 atom directly attached to the indenyl ring, and a beta Group 14 atom attached to the alpha atom, and two or more, such as three, substituted or unsubstituted linear, branched, or cyclic $C_1$-$C_8$ hydrocarbyl groups attached to the beta atom, optionally two of $R^1$, $R^2$, and $R^3$ are each hydrogen; and/or (ii) each of $R^4$, $R^5$, $R^{24}$ $R^{25}$, $R^{26}$, and $R^{27}$ is independently a hydrogen or a substituted or unsubstituted linear, branched, or cyclic $C_1$-$C_{20}$ hydrocarbyl group; and/or (iii) $R^8$, $R^9$, $R^{10}$, and $R^{11}$ are each independently a hydrogen, or a substituted or unsubstituted linear, branched, or cyclic $C_1$-$C_{20}$ hydrocarbyl group; and/or $R^{12}$ is a hydrogen, a substituted or unsubstituted linear, branched, or cyclic $C_1$-$C_{20}$ hydrocarbyl group or silylcarbyl group; and/or (v) each X is independently a halogen, a hydride, an amide, an alkoxide, a sulfide, a phosphide, a diene, an amine, a phosphine, an ether, or a $C_1$-$C_{20}$ substituted or unsubstituted linear, branched, or cyclic hydrocarbyl group, or two or more X moieties together form a fused ring or ring system; and/or (vi) M is a transition metal, such as a group 3, 4, or 5 transition metal, such as a group 4 transition metal, such as Hf, Ti, or Zr; and/or (vii) m is an integer equal to 1, 2 or 3, such as 2.

In some embodiments of formula (MC-IV), $R^4$, $R^5$, $R^{24}$, $R^{25}$, $R^{26}$, and $R^{27}$ are each independently a hydrogen or a substituted or unsubstituted linear, branched, or cyclic $C_1$-$C_6$ hydrocarbyl group (e.g., a methyl, an ethyl, a propyl, a butyl, a cyclohexyl, or a phenyl), optionally $R^1$ and $R^{27}$ are not both hydrocarbyl groups.

In some embodiments of formula (MC-IV), at least two (e.g., at least three, at least four, at least five, or all six) of $R^4$, $R^5$, $R^{24}$, $R^{25}$, $R^{26}$, and $R^{27}$ are a hydrogen. Alternately, in some embodiments of formula (MC-IV), both $R^1$ and $R^{27}$ are hydrocarbyl, alternately $C_1$ to $C_{12}$ hydrocarbyl. Alternately, in some embodiments of formula (MC-IV), both $R^1$ and $R^{27}$ are not hydrocarbyl.

In some embodiments, the catalyst compound is represented by formula (MC-I), (MC-II) (MC-III), or (MC-IV), wherein:

i) according to formula (MC-I): a first one of $R^1$ and $R^3$ is a substituted or unsubstituted linear, branched, or cyclic $C_1$-$C_{20}$ hydrocarbyl group; a second one of $R^1$, $R^2$, and $R^3$ is a hydrogen; the third one of $R^1$, $R^2$, and $R^3$ is a hydrogen; $R^4$, $R^5$, $R^6$, and $R^7$ are each independently hydrogen, a substituted or unsubstituted linear, branched, or cyclic $C_1$-$C_{30}$ hydrocarbyl group; and $R^8$, $R^9$, $R^{10}$, $R^{11}$, and $R^{12}$ are each independently a substituted or unsubstituted linear, branched, or cyclic $C_1$-$C_{20}$ hydrocarbyl group or $R^{12}$ may be a substituted or unsubstituted linear, branched, or cyclic $C_1$-$C_{20}$, such as $C_1$-$C_8$, hydrocarbyl group or silylcarbyl group;

ii) according to formula (MC-II): one of $R^1$ and $R^3$ is a substituted or unsubstituted linear, branched, or cyclic $C_1$-$C_{20}$ hydrocarbyl group; two of $R^1$, $R^2$, and $R^3$ are each hydrogen; $R^4$, $R^7$, $R^{13}$, $R^{14}$, $R^{15}$, $R^{16}$, $R^{17}$, and $R^{18}$ are each independently hydrogen, a substituted or unsubstituted linear, branched, or cyclic $C_1$-$C_{30}$ hydrocarbyl group, or two of $R^4$, $R^7$, $R^{13}$, $R^{14}$, $R^{15}$, $R^{16}$, $R^{17}$, and $R^{18}$ taken together with the carbon atoms in the cyclopentan-indenyl ring to which they are directly connected, collectively form one or more substituted or unsubstituted rings fused to the cyclopentan-indenyl ring; and $R^8$, $R^9$, $R^{10}$, $R^{11}$, and $R^{12}$ are each independently a substituted or unsubstituted linear, branched, or cyclic $C_1$-$C_{20}$ hydrocarbyl group;

iii) according to formula (MC-III): $R^1$ and $R^2$ are hydrogen; $R^{19}$ and $R^{20}$ comprise Group 14 atoms, such as C, Ge, and Si; $R^{21}$, $R^{22}$, and $R^{23}$ are each independently hydrogen or a substituted or unsubstituted linear, branched, or cyclic $C_1$-$C_{20}$ hydrocarbyl group, wherein at least two of $R^{21}$, $R^{22}$, and $R^{23}$ are a substituted or unsubstituted linear, branched, or cyclic $C_1$-$C_{20}$ hydrocarbyl group; $R^4$, $R^5$, $R^6$, and $R^7$ are each independently hydrogen, a substituted or unsubstituted linear, branched, or cyclic $C_1$-$C_{30}$ hydrocarbyl group, or two of $R^4$, $R^5$, $R^6$, and $R^7$ taken together with the carbon atoms in the indenyl ring to which they are directly connected, collectively form one or more substituted or unsubstituted rings fused to the indenyl ring; and $R^8$, $R^9$, $R^{10}$, $R^{11}$, and $R^{12}$ are each independently a substituted or unsubstituted linear, branched, or cyclic $C_1$-$C_{20}$ hydrocarbyl group; or iv) according to formula (MC-IV): one of $R^1$ and $R^3$ is a substituted or unsubstituted linear, branched, or cyclic $C_1$-$C_{20}$ hydrocarbyl group; two of $R^1$, $R^2$, and $R^3$ are each hydrogen; $R^4$, $R^5$, $R^{24}$, $R^{25}$, $R^{26}$, and $R^{27}$ are each independently hydrogen, a substituted or unsubstituted linear, branched, or cyclic $C_1$-$C_{30}$ hydrocarbyl group, or two of $R^4$, $R^5$, $R^{24}$, $R^{25}$, $R^{16}$, and $R^{27}$ taken together with the carbon atoms in the benzindenyl ring to which they are directly connected, collectively form one or more substituted or unsubstituted rings fused to the benz-indenyl ring; and $R^8$, $R^9$, $R^{10}$, $R^{11}$, and $R^{12}$ are each independently a substituted or unsubstituted linear, branched, or cyclic $C_1$-$C_{20}$ hydrocarbyl group;

wherein in the formulae (MC-I), (MC-II), (MC-III), (MC-IV): each X is independently a halogen, a hydride, an amide, an alkoxide, a sulfide, a phosphide, a diene, an amine, a phosphine, an ether, a $C_1$-$C_{20}$ substituted or unsubstituted linear, branched, or cyclic hydrocarbyl group, or two or more X moieties together form a fused ring or ring system; M is a transition metal, such as a group 3, 4, or 5 transition metal, such as a group 4 transition metal, such as Hf Ti, or Zr; and m is an integer equal to 1, 2 or 3, such as 2.

In some embodiments, the catalyst compound is represented by formula (MC-2), (MC-3), (MC-4), (MC-5), (MC-6), (MC-7), (MC-8), (MC-9), (MC-10), (MC-11) (MC-12) or (MC-13), wherein: each X is independently a halogen, a hydride, an amide, an alkoxide, a sulfide, a phosphide, a diene, an amine, a phosphine, an ether, or a $C_1$-$C_{20}$ substituted or unsubstituted linear, branched, or cyclic hydrocarbyl group, or two or more X moieties may together form a fused ring or ring system; M is a transition metal, such as a group 3, 4, or 5 transition metal, such as a group 4 transition metal, such as Hf, Ti, or Zr; and m is an integer equal to 1, 2 or 3, such as 2.

The metallocene compound used in the process of the present disclosure for making PAOs generally can have a structure represented by formula (MC-V):

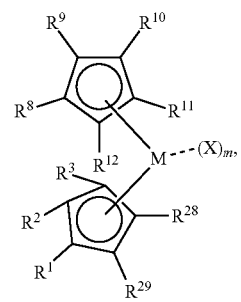

(MC-V)

wherein:

each of $R^1$, $R^2$, and $R^3$, $R^8$, $R^9$, $R^{10}$, $R^{11}$, and $R^{12}$, M, X, and m can be as described above; and $R^{28}$ and $R^{29}$ are each independently a substituted or unsubstituted linear, branched, or cyclic $C_1$-$C_{30}$ hydrocarbyl group, or $R^{28}$ and $R^{29}$, taken together with the carbon atoms in the first cyclopentadienyl ring to which they are directly connected, can collectively form one or more substituted or unsubstituted rings fused to the first cyclopentadienyl ring.

In at least one embodiment of formula (MC-V), $R^{28}$ and $R^{29}$, taken together with the carbon atoms in the first cyclopentadienyl ring to which they are directly connected, can collectively form a substituted or unsubstituted phenyl ring fused to the first cyclopentadienyl ring. In such embodiments, the four phenyl ring carbons not connected to the first cyclopentadienyl ring can each be independently bonded to a hydrogen or a substituted or unsubstituted linear, branched, or cyclic $C_1$-$C_6$ hydrocarbyl group (e.g., a methyl, an ethyl, a propyl, a butyl, a cyclohexyl, or a phenyl). In some such embodiments, at least two (e.g., at least three or all four) of the four phenyl ring carbons not connected to the first cyclopentadienyl ring can be connected to a hydrogen.

In at least one embodiment of formula (MC-V), $R^{28}$ and $R^{29}$, taken together with the carbon atoms in the first cyclopentadienyl ring to which they are directly connected, can collectively form a substituted or unsubstituted naphthenyl ring fused to the first cyclopentadienyl ring. In some embodiments, the fused ring or rings may comprise saturated ring carbons, unsaturated ring compounds, or a combination of saturated and unsaturated carbon atoms, for example, a non-aromatic ring or a combination of aromatic and non-aromatic rings.

In at least one metallocene compound formula herein, both the first and second Cp rings in the metallocene compound of the present disclosure can be substituted. In some embodiments, one, and not both, of the first and second Cp rings can be fused to one or more rings.

In at least one metallocene compound formula herein, one of $R^1$ and $R^3$ is a beta branched ligand in which a Group 14 atom, e.g., carbon, silicon, germanium, is attached directly to the cyclopentadienyl ring, this same atom further includes at least two non-hydrogen substituents according to the above listing. In other words, the Group 14 atom is tertiary or quaternarily substituted, which includes the bond between the cyclopentadienyl ring and the group 14 atom. Examples include isobutyl, neopentyl, trialkylsilyl, and trialkylgermanyl moieties according to formula (MC-III), wherein $R^{19}$ and $R^{20}$ comprise Group 14 atoms, such as carbon, silicon and/or germanium (such as $R^{19}$ is C and $R^{20}$ is C or Si), and at least two of $R^{21}$, $R^{22}$, and $R^{23}$ are each independently a substituted or unsubstituted linear, branched, or cyclic $C_1$-$C_{20}$, such as $C_1$-$C_8$, hydrocarbyl group.

In at least one metallocene compound formula herein, $R^4$, $R^5$, $R^6$, and $R^7$ are each independently hydrogen, a substituted or unsubstituted linear, branched, or cyclic $C_1$-$C_{30}$ hydrocarbyl group. In at least one metallocene compound formula herein, $R^4$, $R^5$, $R^6$, and $R^7$ are each independently hydrogen, a substituted or unsubstituted linear, branched, or cyclic $C_1$-$C_{30}$ hydrocarbyl group in which two of $R^4$, $R^5$, $R^6$, and $R^7$ taken together with the carbon atoms in the indenyl ring to which they are directly connected, collectively form one or more substituted or unsubstituted rings fused to the indenyl ring. The rings are indicated by the dotted lines between the respective R group substitutions with a ring between $R^4$ and $R^5$ indicated as Ring 4-5, a ring between $R^5$ and $R^6$ indicated as Ring 5-6 and a ring between $R^6$ and $R^7$ indicated as Ring 6-7 as shown in the general formula (MC-III-A) below:

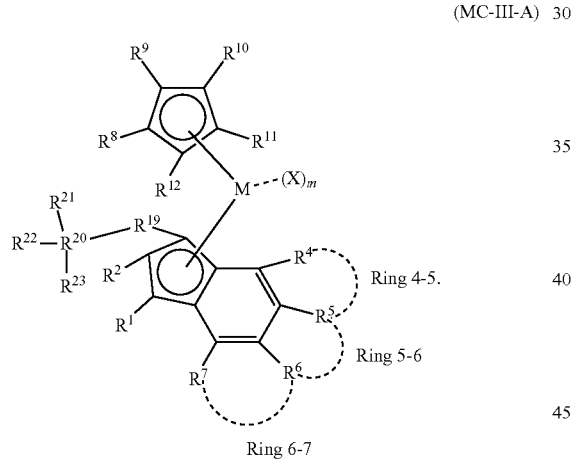

(MC-III-A)

In some embodiments, $R^5$ and $R^6$ taken together with the carbon atoms in the indenyl ring to which they are directly connected, collectively form Ring 4-5 comprising a $C_3$-$C_6$ ring, such as an alicyclic ring, such as a 5 membered ring including two the carbons of the indenyl ring. In such embodiments, the 3 alicyclic ring carbons not directly part of the indenyl ring are each independently bonded to a hydrogen or a substituted or unsubstituted linear, branched, or cyclic $C_1$-$C_6$ hydrocarbyl group (e.g., a methyl, an ethyl, a propyl, a butyl, a cyclohexyl, or a phenyl). In some embodiments, at least two or all three of the alicyclic ring carbons are connected to a hydrogen, one of $R^1$ is a substituted or unsubstituted linear, branched, or cyclic $C_1$-$C_6$ hydrocarbyl group (e.g., a methyl, an ethyl, a propyl, a butyl, a pentyl, an isoamyl, a neopentyl, a cyclohexyl, or a phenyl), and $R^2$ is hydrogen.

In some embodiments, at least one of $R^{21}$, $R^{22}$, or $R^{23}$ is $C_1$-$C_6$ hydrocarbyl group (e.g., a methyl, an ethyl, a propyl, a butyl, a pentyl, an isoamyl, a neopentyl, a cyclohexyl, or a phenyl), such that $R^3$ is a beta-branched moiety. In some embodiments, $R^{19}$ and $R^{19}$ are carbon, silicon or germanium, and $R^{21}$, $R^{22}$, and $R^{23}$ are each a $C_1$-$C_6$ hydrocarbyl group; such as $R^{19}$ is a methylene group (—$CH_2$—) and $R^{20}$, $R^{21}$, $R^{22}$ and $R^{23}$ form a trimethylsilyl, triethylsilyl, or terphenylsilyl moiety. As an example, and in any of the above embodiments, $R^8$, $R^9$, $R^{10}$, $R^{11}$, $R^{12}$, $R^6$, and $R^7$ are each independently a hydrogen, or a substituted or unsubstituted linear, or branched $C_1$-$C_6$, hydrocarbyl group. In some embodiments, $R^5$ and $R^6$ taken together with the carbon atoms in the indenyl ring to which they are directly connected, collectively form Ring 5-6 comprising three additional carbons to form a 5 membered alicyclic ring; $R^1$, $R^8$, $R^9$, $R^{10}$, $R^{11}$, and $R^{12}$ are methyl radicals, $R^2$, $R^3$, $R^4$, and $R^7$, are hydrogen. In such embodiments, the metallocene compound can have a structure represented by formula (MG-3) below:

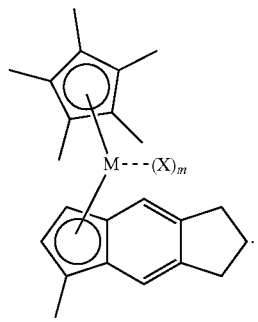

(MC-3)

In some embodiments $R^6$ and $R^7$ taken together with the carbon atoms in the indenyl ring to which they are directly connected, collectively form one or more substituted or unsubstituted $C_3$-$C_6$ rings fused to the indenyl ring; and $R^4$, $R^5$, $R^8$, $R^9$, $R^{10}$, $R^{11}$, and $R^{12}$ are each independently a hydrogen, or a substituted or unsubstituted linear, or branched $C_1$-$C_6$, hydrocarbyl group. In some embodiments, $R^6$ and $R^7$ taken together with the carbon atoms in the indenyl ring to which they are directly connected, collectively form a six membered phenyl ring, Ring 6-7 comprising four additional carbons. In such embodiments, the four phenyl ring carbons not directly part of the indenyl ring (the carbons attached to $R^{24}$, $R^{25}$, $R^{26}$, and $R^{27}$ in formula (MC-VI) below) are each independently bonded to a hydrogen or a substituted or unsubstituted linear, branched, or cyclic $C_1$-$C_6$ hydrocarbyl group (e.g., a methyl, an ethyl, a propyl, a butyl, a cyclohexyl, or a phenyl). In such embodiments, at least two of, or at least three of, or all four of $R^{24}$, $R^{25}$, $R^{26}$, and $R^{27}$ are hydrogen. Stated another way, $R^6$ and $R^7$ taken together with the carbon atoms in the first cyclopentadienyl ring to which they are directly connected, collectively form a substituted or unsubstituted naphthenyl ring fused to the first cyclopentadienyl ring. In such embodiments, the metallocene compound can have a structure represented by formula (MC-VI) below:

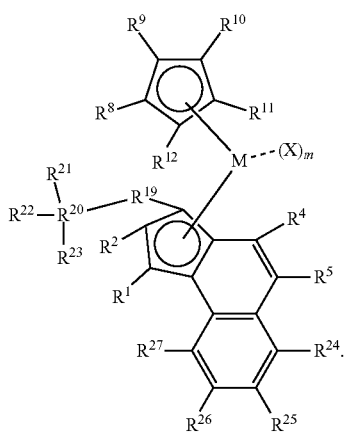

(MC-VI)

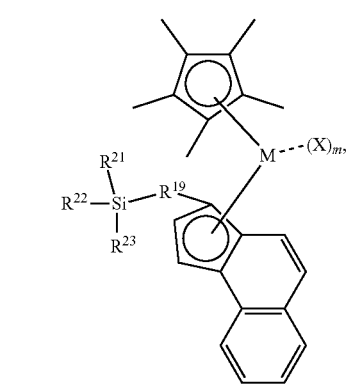

(MC-VI-SI)

In at least one embodiment, one of $R^1$ and $R^{19}$ are a substituted or unsubstituted linear, branched, or cyclic $C_1$-$C_6$ hydrocarbyl group (e.g., a methyl, an ethyl, a propyl, a butyl, a pentyl, an isoamyl, a neopentyl, a cyclohexyl, or a phenyl), $R^2$ and $R^1$ are hydrogen. In such an embodiment, $R^{19}$ and $R^{20}$-$R^{23}$ form a neopentyl (i.e., 2,2-dimethylpropyl), $R^1$, $R^2$, $R^4$, $R^5$, $R^{24}$, $R^{25}$, $R^{26}$, and $R^{27}$ are each hydrogen, and $R^8$, $R^9$, $R^{10}$, $R^{11}$, $R^{12}$ are methyl; the metallocene compound can have a structure represented by formula (III-B) below:

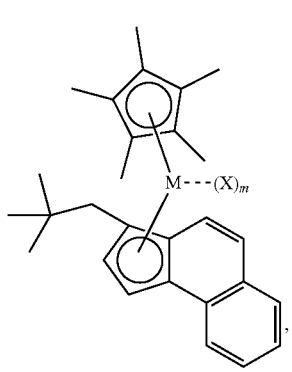

(III-B)

where M is Hf or Zr and M is 2.

In some embodiments, $R^{19}$ and $R^{20}$-$R^{23}$ form a methyl-trimethylsilyl, methyl-triethylsilyl, or methyl-triphenylsilyl moiety, $R^4$, $R^5$, $R^6$, and $R^7$, are each hydrogen, and or a substituted or unsubstituted linear, or branched $C_1$-$C_6$, hydrocarbyl group. In some embodiments, $R^4$, $R^5$, $R^6$, and $R^7$ are hydrogen, and $R^8$, $R^9$, $R^{10}$, $R^{11}$, $R^{12}$ are methyl; having a structure represented by formula (MC-VI-SI) below.

wherein $R^{19}$, $R^{21}$, $R^{22}$, and $R^{23}$ are substituted or unsubstituted linear, branched, or cyclic $C_1$-$C_6$ hydrocarbyl group, such as methyl, ethyl, or phenyl, such as each of $R^{19}$, $R^{21}$, $R^{22}$, and $R^{23}$ are methyl.

It is noted, in the embodiments listed above, $R^1$ and $R^3$ may be interchangeable. Reference to either of $R^1$ and $R^3$ are maintained for consistency and clarity herein. In any of the above embodiments, M comprises, consists essentially of, or is Zr and/or Hf; m is 2; and each X is independently a methyl, an ethyl, a propyl, a butyl, a hexyl, an octyl, a phenyl, a benzyl, a chloride, a bromide, or an iodide.

Example metallocene compounds useful for the process of the present disclosure include the following compounds and their optical isomers, if applicable (not shown):

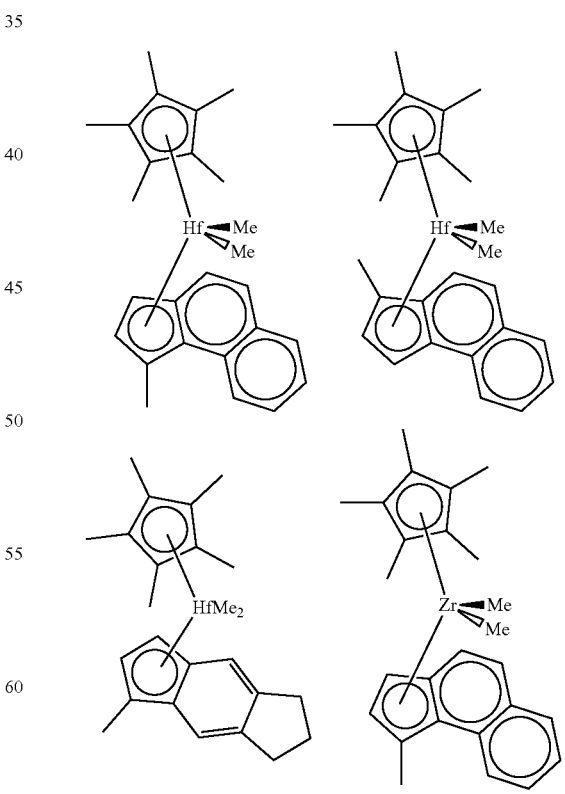

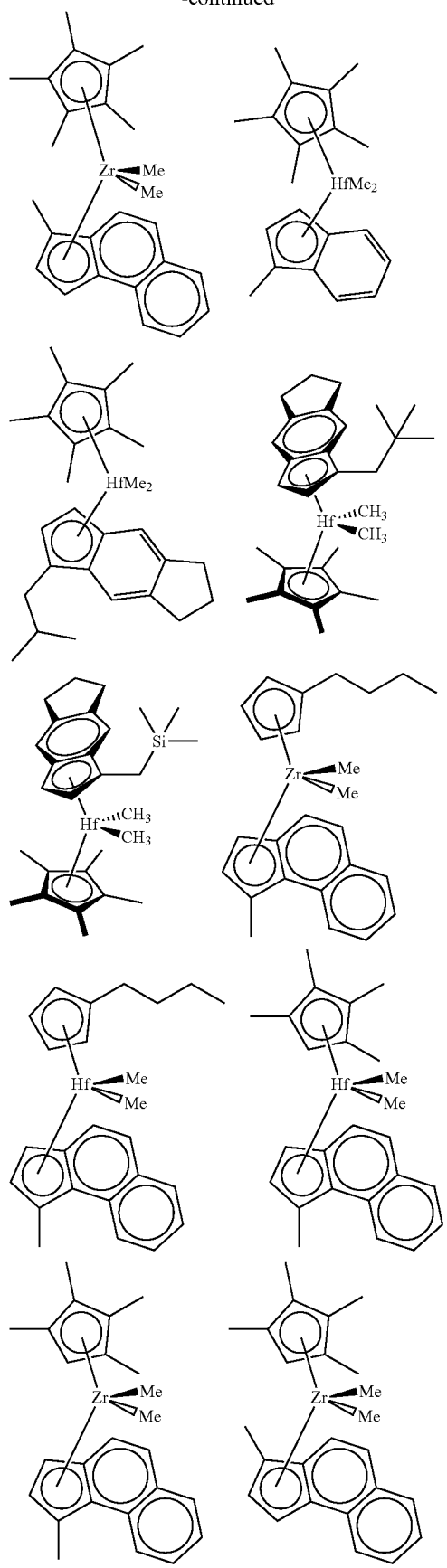
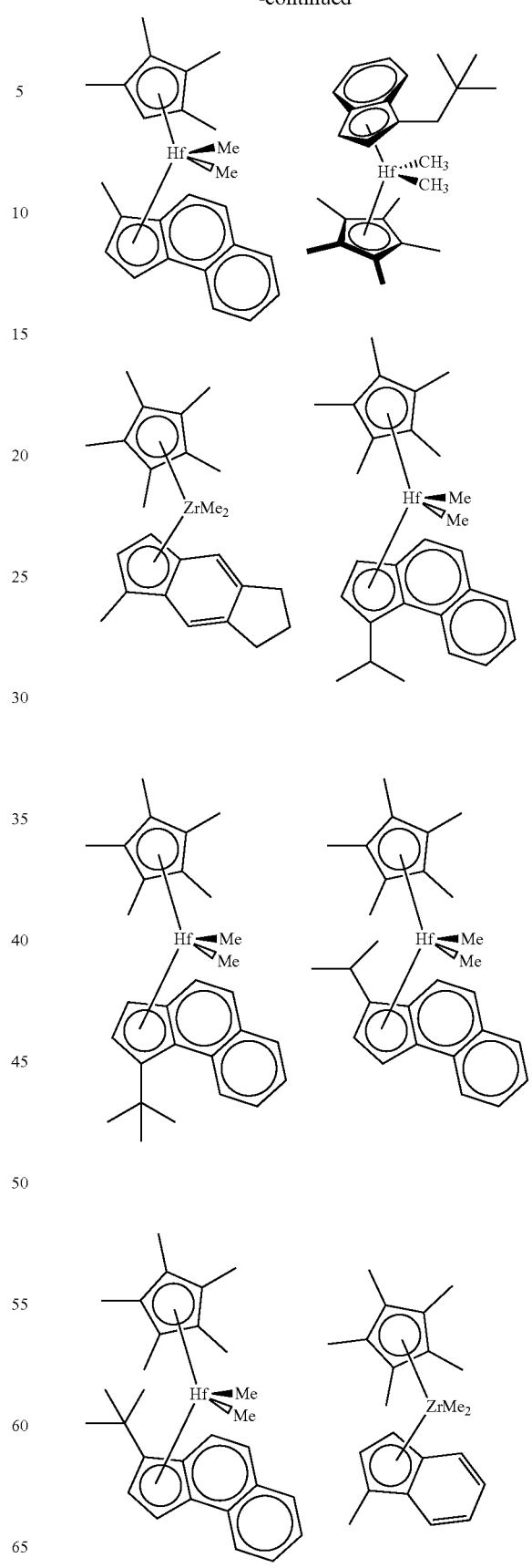

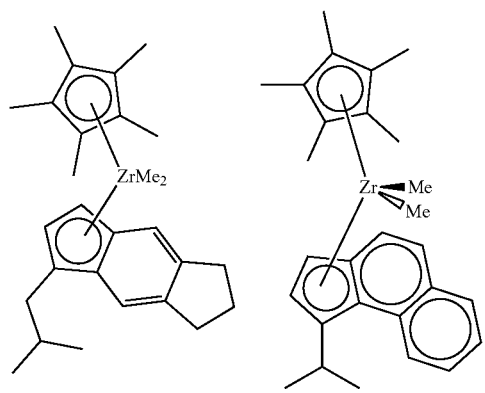
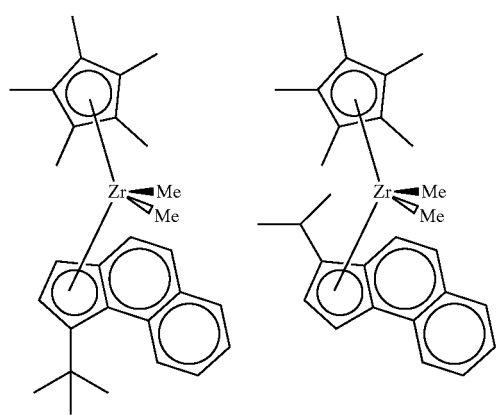
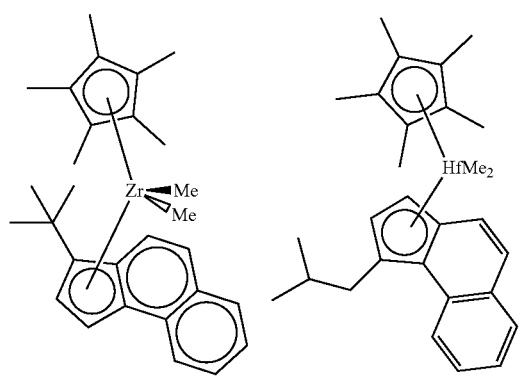
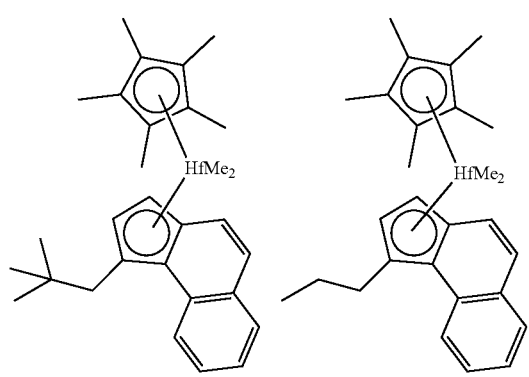
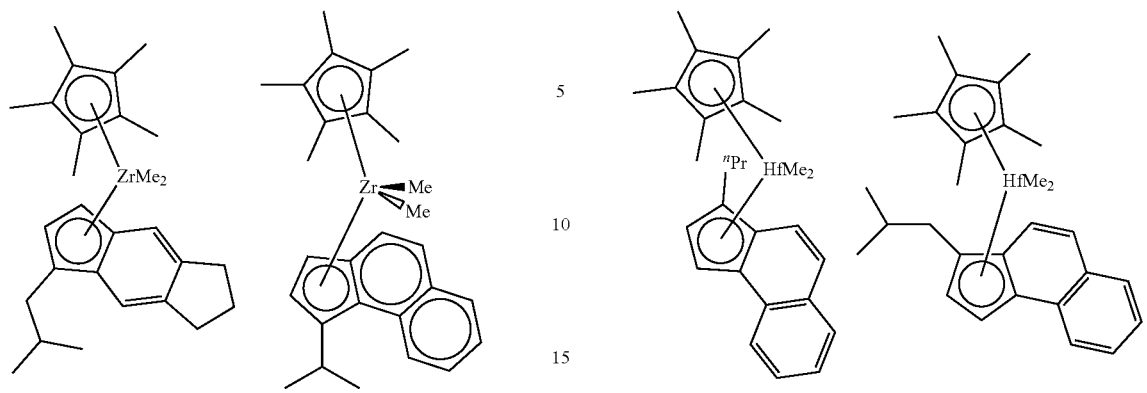
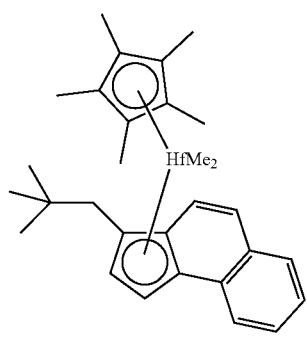
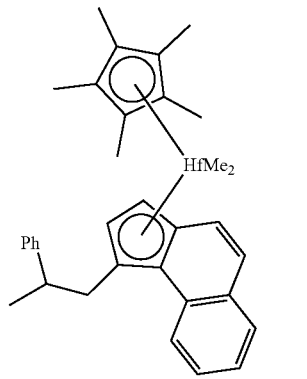
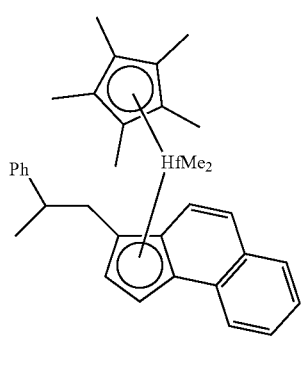

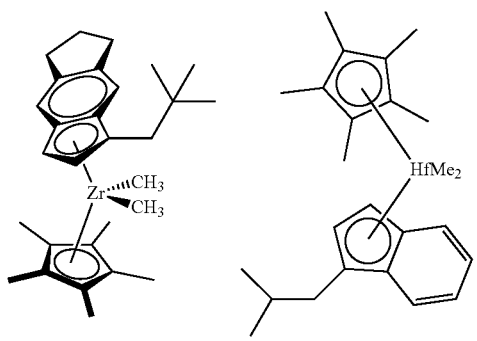
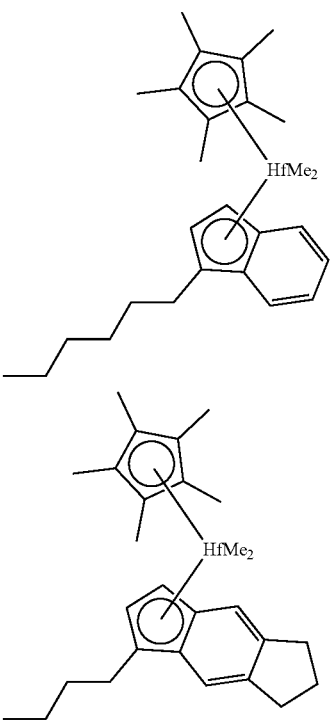
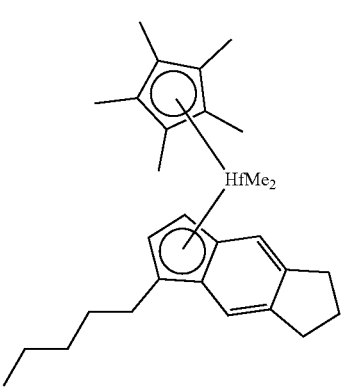
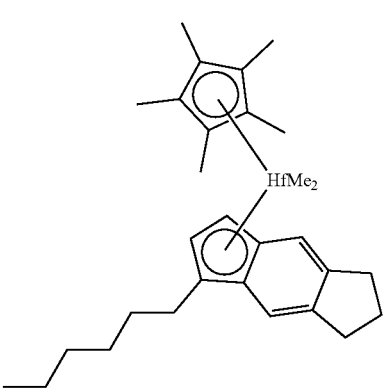

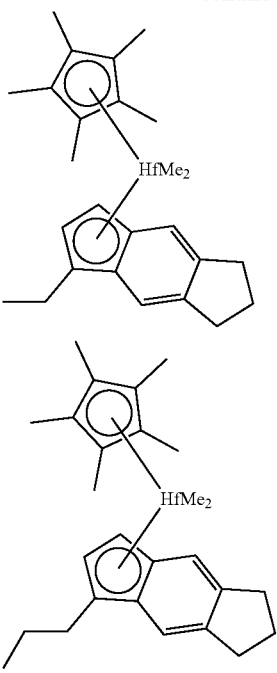

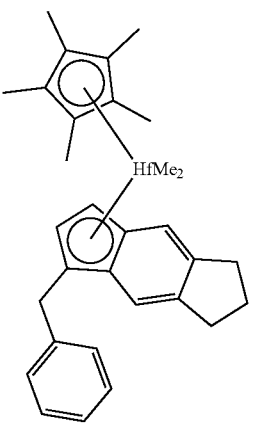

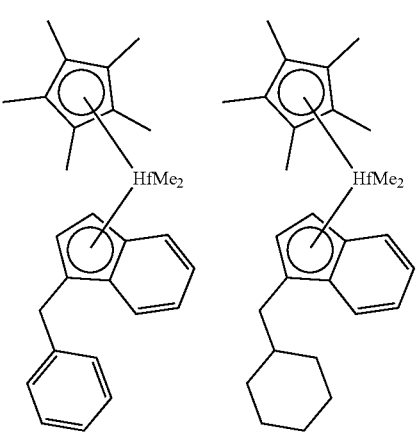

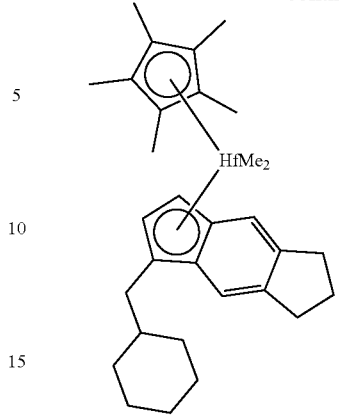

Metallocene compounds generally can be synthesized by using typical chemical reagents (e.g., halides of hafnium, zirconium, titanium) and intermediates (such as ligands containing one or two substituted or unsubstituted Cp rings, substituted or unsubstituted fused Cp ring such as indenyl rings or benzindenyl rings, and the like) that are commercially available, and following typical reaction schemes exemplified in various synthesis descriptions, e.g., as described in the example sections of U.S. Provisional Application Nos. 62/477,683 and 62/477,706, both filed Mar. 28, 2017, the contents of each of which are hereby incorporated by reference.

IV. B.2 Activators and Activation of the Metallocene Compound

The catalyst may be activated by any suitable activator such as a non-coordinating anion (NCA) activator. An NCA is an anion which either does not coordinate to the catalyst metal cation or that coordinates only weakly to the metal cation. An NCA coordinates weakly enough that a neutral Lewis base, such as an olefinically or acetylenically unsaturated monomer, can displace it from the catalyst center. Any metal or metalloid that can form a compatible, weakly coordinating complex with the catalyst metal cation may be used or contained in the NCA. Suitable metals include aluminum, gold, and platinum. Suitable metalloids include boron, aluminum, phosphorus, and silicon.

Lewis acid and ionic activators may also be used. Useful but non-limiting examples of Lewis acid activators include triphenylboron, tris-perfluorophenylboron, and tris-perfluorophenylaluminum. Useful but non-limiting examples of ionic activators include dimethylanilinium tetrakisperfluorophenylborate, triphenylcarbenium tetrakisperfluorophenylborate, and dimethylanilinium tetrakisperfluorophenylaluminate.

An additional subclass of useful NCAs comprises stoichiometric activators, which can be either neutral or ionic. Examples of neutral stoichiometric activators include trisubstituted boron, tellurium, aluminum, gallium and indium or mixtures thereof. The three substituent groups are each independently selected from alkyls, alkenyls, halogen, substituted alkyls, aryls, arylhalides, alkoxy, and halides. For example, the three groups can be independently selected from halogen, mono or multicyclic (including halosubstituted) aryls, alkyls, and alkenyl compounds and mixtures thereof, for example alkenyl groups having 1 to 20 carbon atoms, alkyl groups having 1 to 20 carbon atoms, alkoxy groups having 1 to 20 carbon atoms, and aryl groups having 3 to 20 carbon atoms (including substituted aryls). For example, the three groups can be alkyls having 1 to 4 carbon groups, phenyl, naphthyl, or mixtures thereof. For example, the three groups are halogenated, such as fluorinated, aryl groups. Ionic stoichiometric activator compounds may contain an active proton, or some other cation associated with, but not coordinated to, or only loosely coordinated to, the remaining ion of the ionizing compound.

Ionic catalysts can be prepared by reacting a transition metal compound with an activator, such as $B(C_6F_6)_3$, which upon reaction with the hydrolyzable ligand (X') of the transition metal compound forms an anion, such as ([B$(C_6F_5)_3(X')]^-$), which stabilizes the cationic transition metal species generated by the reaction. The catalysts can be prepared with activator components which are ionic compounds or compositions. Additionally or alternatively, activators can be prepared utilizing neutral compounds.

Compounds used as an activator component in the preparation of the ionic catalyst systems used in a process of the present disclosure can include a cation, which can be a Brønsted acid capable of donating a proton, and a compatible NCA which anion is relatively large (bulky), capable of stabilizing the active catalyst species which is formed when the two compounds are combined and said anion will be sufficiently labile to be displaced by olefinic, diolefinic, and acetylenically unsaturated substrates or other neutral Lewis bases such as ethers or nitriles.

In at least one embodiment, the ionic stoichiometric activators include a cation and an anion component, and may be represented by the following formula:

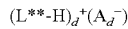

wherein:
L** is an neutral Lewis base;
H is hydrogen;
(L**-H)$^+$ is a Brønsted acid or a reducible Lewis acid; and
A$^{d-}$ is an NCA having the charge d-, and d is an integer from 1 to 3.

The cation component, (L**-H)$_d^+$ may include Brønsted acids such as protons or protonated Lewis bases or reducible Lewis acids capable of protonating or abstracting a moiety, such as an alkyl or aryl, from the catalyst after alkylation.

The activating cation (L-H)$_d^+$ may be a Brønsted acid, capable of donating a proton to the alkylated transition metal catalytic precursor resulting in a transition metal cation, including ammoniums, oxoniums, phosphoniums, silyliums, and mixtures thereof, such as ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxoniums from ethers such as dimethyl ether, diethyl ether, tetrahydrofuran and dioxane, sulfoniums from thioethers, such as diethyl thioethers and tetrahydrothiophene, and mixtures thereof. The activating cation (L-H)d$^+$ may also be a moiety such as silver, tropylium, carbeniums, ferroceniums and mixtures, such as carbeniums and ferroceniums; such as triphenyl carbenium. The anion component A$_d^-$ includes those having the formula [Mk+Qn]$_d^-$ wherein k is an integer from 1 to 3; n is an integer from 2-6; n-k=d; M is an element selected from Group 13 of the Periodic Table of the Elements, such as boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than one occurrence is Q a halide. For example, each Q is a fluorinated hydrocarbyl group having 1 to 20 carbon atoms, such as each Q is a fluorinated aryl group, such as each Q is a pentafluoryl aryl group. Examples of suitable A$_d^-$ also include diboron compounds as disclosed in U.S. Pat. No. 5,447,895, which is incorporated herein by reference.

Boron compounds which may be used as an NCA activator in combination with a co-activator are trisubstituted ammonium salts such as: trimethylammonium tetraphenylborate, triethylammonium tetraphenylborate, tripropylammonium tetraphenylborate, tri(n-butyl)ammonium tetraphenylborate, tri(tert-butyl)ammonium tetraphenylborate, N,N-dimethylanilinium tetraphenylborate, tetraphenylborate, N,N-dimethyl-(2,4,6-trimethylanilinium)tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium)tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(tert-butyl) ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium)tetrakis-(2,3,4,6-tetrafluorophenyl) borate, trimethylammonium tetrakis(perfluoronaphthyl) borate, triethylammonium tetrakis(perfluoronaphthyl) borate, tripropylammonium tetrakis(perfluoronaphthyl) borate, tri(n-butyl)ammonium tetrakis(perfluoronaphthyl) borate, tri(tert-butyl)ammonium tetrakis(perfluoronaphthyl) borate, N,N-dimethylanilinium tetrakis(perfluoronaphthyl) borate, N,N-diethylanilinium tetrakis(perfluoronaphthyl) borate, N,N-dimethyl-(2,4,6-trimethylanillinium)tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(tert-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium)tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(tert-butyl)ammonium tetrakis(3,5-bis(trifluoromethyl)phenyl) borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium)tetrakis(3,5-bis(trifluoromethyl)phenyl) borate, and dialkyl ammonium salts such as: di-(iso-propyl) ammonium tetrakis(pentafluorophenyl)borate, and dicyclohexylammonium tetrakis(pentafluorophenyl)borate; and other salts such as tri(o-tolyl)phosphonium tetrakis (pentafluorophenyl)borate, tri(2,6-dimethylphenyl)phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium)tetrakis(pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium)tetrakis-(2,3,4,6-tetrafluorophenyl)borate, tropillium tetrakis(perfluoronaphthyl)borate, triphenylcarbenium tetrakis(perfluoronaphthyl)borate, triphenyl phosphonium tetrakis(perfluoronaphthyl)borate, triethylsilylium tetrakis(perfluoronaphthyl)borate, benzene(diazonium)tetrakis (perfluoronaphthyl)borate, tropillium tetrakis (perfluorobiphenyl)borate, triphenylcarbenium tetrakis (perfluorobiphenyl)borate, triphenylphosphonium tetrakis (perfluorobiphenyl)borate, triethylsilylium tetrakis (perfluorobiphenyl)borate, benzene(diazonium)tetrakis (perfluorobiphenyl)borate, tropillium tetrakis(3,5-bis (trifluoromethyl)phenyl)borate, triphenylcarbenium tetrakis (3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl) phenyl)borate, and benzene(diazonium)tetrakis(3,5-bis(trifluoromethyl)phenyl)borate.

In at least one embodiment, the NCA activator, (L**-H)$_d^+$(A$_d^-$), is N,N-dimethylanilinium tetrakis(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis (trifluoromethyl)phenyl)borate, triphenylcarbenium tetrakis (perfluoronaphthyl)borate, triphenylcarbenium tetrakis (perfluorobiphenyl)borate, triphenylcarbenium tetrakis(3,5-bis(trifluoromethyl)phenyl)borate, or triphenylcarbenium tetra(perfluorophenyl)borate.

In at least one embodiment, the activator is selected from Lewis acid activators such as triphenylboron, tris-perfluorophenylboron, tris-perfluorophenylaluminum and the like and or ionic activators such as N,N-dimethylanilinium tetrakis(perfluorophenyl)borate, N,N-dimethylanilinium tetrakis(perfluoronaphthyl)borate, triphenylcarbonium tetrakis (perfluorophenyl)borate, triphenylcarbonium tetrakis (perfluoronaphthyl)borate, N,N-dimethylanilinium tetrakis (perfluorophenyl)aluminate, N,N-dimethylanilinium tetrakis(perfluoronaphthyl)aluminate, and the like.

Pehlert et al., U.S. Pat. No. 7,511,104 provides additional details on NCA activators that may be useful, and these details are hereby incorporated by reference.

Additional activators that may be used include alumoxanes or alumoxanes in combination with an NCA. In one embodiment, alumoxane activators are utilized as an activator. Alumoxanes are generally oligomeric compounds containing —Al(R$^1$)—O— sub-units, where R$^1$ is an alkyl group. Examples of alumoxanes include methylalumoxane (MAO), modified methylalumoxane (MMAO), ethylalumoxane and isobutylalumoxane. Alkylalumoxanes and modified alkylalumoxanes are suitable as catalyst activators, such as when the abstractable ligand is an alkyl, halide, alkoxide or amide. Mixtures of different alumoxanes and modified alumoxanes may also be used.

A catalyst co-activator is a compound capable of alkylating the catalyst, such that when used in combination with an activator, an active catalyst is formed. Co-activators may include alumoxanes such as methylalumoxane, modified alumoxanes such as modified methylalumoxane, and aluminum alkyls such trimethylaluminum, tri-isobutylaluminum, triethylaluminum, tri-isopropylaluminum, tri-n-hexylaluminum, tri-n-octylaluminum, tri-n-decylaluminum, and tri-n-dodecylaluminum. Co-activators are typically used in combination with Lewis acid activators and ionic activators when the catalyst is not a dihydrocarbyl or dihydride complex.

The co-activator may also be used as a scavenger to deactivate impurities in feed or reactors. A scavenger is a compound that is sufficiently Lewis acidic to coordinate with polar contaminates and impurities adventitiously occurring in the polymerization feedstocks or reaction medium. Such impurities can be inadvertently introduced with any of the reaction components, and adversely affect catalyst activity and stability. Scavenging compounds may be organometallic compounds such as triethyl aluminum, triethyl borane, tri-isobutyl aluminum, methylalumoxane, isobutyl aluminumoxane, tri-n-hexyl aluminum, tri-n-octyl aluminum, and those having bulky substituents covalently bound to the metal or metalloid center being exemplary to minimize adverse interaction with the active catalyst. Other useful scavenger compounds may include those mentioned in U.S. Pat. No. 5,241,025; EP-A 0426638; and WO 1997/022635, which are hereby incorporated by reference for such details.

U.S. Pat. No. 9,409,834 (e.g., at line 39, column 21 to line 44, column 26) provides a detailed description of the activators and coactivators that may be used with the metallocene compound in the catalyst system of the present disclosure. The relevant portions of this patent are incorporated herein by reference in their entirety. Additional information of activators and co-activators that may be used with the metallocene compounds in the catalyst system of the present disclosure can be found in US Patent Application Publication No. 2013/0023633 (ex., at paragraph [0178] page 16 to paragraph [0214], page 22). The relevant portions of this reference are incorporated herein by reference in their entirety.

The reaction time or reactor residence time can be dependent on the type of catalyst used, the amount of catalyst used, and the desired conversion level. Different transition metal compounds (also referred to as metallocene) have different activities. A high amount of catalyst loading tends to give high conversion at short reaction time. However, a high amount of catalyst usage can make the production process uneconomical and difficult to manage the reaction heat or to control the reaction temperature. Therefore, it is useful to choose a catalyst with maximum catalyst productivity to minimize the amount of metallocene and the amount of activators needed. For a catalyst system of metallocene plus a Lewis Acid or an ionic promoter with NCA component, the transition metal compound used may be from about 0.01 microgram to about 500 micrograms of metallocene component/gram of alpha-olefin feed, such as from about 0.1 microgram to about 100 microgram of metallocene component per gram of alpha-olefin feed. Furthermore, the molar ratio of the NCA activator to metallocene can be from about 0.1 to about 10, such as about 0.5 to about 5, such as about 0.5 to about 3. For the co-activators of alkylaluminums, the molar ratio of the co-activator to metallocene can be from about 1 to about 1,000, such as about 2 to about 500, such as about 4 to about 400.

In selecting oligomerization conditions, to obtain the desired first reactor effluent, the system uses the transition metal compound (also referred to as the catalyst), activator, and co-activator. US 2007/0043248 and US 2010/029242 provide additional details of metallocene catalysts, activators, co-activators, and appropriate ratios of such compounds in the feedstock that may be useful, and these additional details are hereby incorporated by reference.

IV. B.3 Scavengers for the First Oligomerization

A scavenger can be an additional component of a catalyst system described herein. A scavenger is a compound typically added to facilitate oligomerization or polymerization by scavenging impurities. Some scavengers may also act as activators and may be referred to as co-activators. A co-activator which is not a scavenger may also be used in conjunction with an activator in order to form an active catalyst with a transition metal compound. In some embodiments, a co-activator can be pre-mixed with the transition metal compound to form an alkylated transition metal compound, also referred to as an alkylated catalyst compound or alkylated metallocene. To the extent scavengers facilitate the metallocene compound in performing the intended catalytic function, scavengers, if used, are sometimes considered as a part of the catalyst system.

U.S. Pat. No. 9,409,834 (e.g., at line 37, column 33 to line 61, column 34) provides detailed description of scavengers useful in the process of the present disclosure for making PAO. The relevant portions in this patent on scavengers, their identities, quantity, and manner of use are incorporated herein in their entirety.

IV. C Process for Making PAO

IV. C.1 Monomer(s)

The alpha-olefin feed for making the PAO materials of the present disclosure may comprise one or more of $C_6$-$C_{32}$ alpha-olefins (such as $C_6$-$C_{24}$, such as $C_6$-$C_{18}$, $C_8$-$C_{18}$, or $C_6$-$C_{12}$). The alpha-olefin feed may comprise ethylene, propylene, $C_4$ alpha-olefins, and $C_5$ alpha-olefins. In certain embodiments, each of ethylene, propylene, $C_4$ alpha-olefins (1-butene and 2-methyl-1-propene), and $C_5$ alpha-olefins (1-pentene and various isomers of methyl-1-butene) is supplied to the polymerization reactor, each independently at no higher than c1 mol %, based on the total moles of the alpha-olefins supplied to the polymerization reactor, where c1 can be 25, 20, 10, 5, 4, 3, 2, 1, 0.5, 0.1, or 0.01, for each monomer additionally or alternatively, any combination of $C_2$-$C_5$ alpha-olefins (including two or more, three or more, or all four of ethylene, propylene, $C_4$ alpha-olefins, and $C_5$ alpha-olefins) are supplied to the polymerization reactor collectively at no higher than c1 mol %, based on the total moles of the alpha-olefins supplied to the polymerization reactor. In some embodiments, the alpha-olefin feed is substantially free of ethylene, propylene, $C_4$ alpha-olefins, and $C_5$ alpha-olefins (or completely free of intentionally added $C_2$-$C_5$ alpha-olefins, allowing for impurities present in other feed components). In some embodiments, substantially all alpha-olefins in the feed are $C_6$-$C_{30}$ (e.g., $C_6$-$C_{24}$, such as $C_6$-$C_{18}$, $C_8$-$C_{18}$, or $C_6$-$C_{12}$) alpha-olefins. "Substantially all" means at least 90 mol % (e.g., at least about 92 mol %, at least about 94 mol %, at least about 95 mol %, at least about 96 mol %, at least about 98 mol %, at least about 99%, at least about 99.5 mol %, or completely all, allowing for some impurities present in feed components), based on the total moles of the alpha-olefins present in the feed. In some embodiments, any combination of $C_2$-$C_5$ alpha-olefins are collectively present in the alpha-olefin feed at no higher than c1 mol %, (where c1 can be about 25, about 20, about 10, about 5, about 4, about 3, about 2, about 1, about 0.5, about 0.1, or about 0.01), based on the total moles of the alpha-olefins supplied to the polymerization reactor.

In some embodiments, at least a portion (e.g., at least about 80 mol %, at least about 85 mol %, at least about 90 mol %, at least about 95 mol %, at least about 96 mol %, at least about 98 mol %, at least about 99 mol %, at least about 99.5 mol %, or completely all, allowing for some impurities present in feed components) of the alpha-olefins present in the feed are linear alpha-olefins (LAOs), i.e., those without a branch attached to the carbon backbone thereof. Non-limiting examples of LAOs are 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-octadecene, 1-icocene, $C_{22}$, $C_{24}$, $C_{26}$, $C_{28}$, $C_{30}$ and $C_{32}$ LAOs, and a combination thereof. Without being bound by theory, PAO products made from such LAOs by using the process of the present disclosure can tend to have fewer branches and pendant groups, leading to generally more uniform PAO molecular structures.

Where a single alpha-olefin is fed to the polymerization reactor, the thus obtained PAO is a homopolymer. Homopolymers can have substantially uniform molecular structure, and accordingly desirable physical and rheological properties such as viscosity index. A homopolymer can tend to have pendant groups attached to the carbon backbone with highly uniform length.

In certain situations, a mixture of two, three, or even more alpha-olefins in the feed may be desired to produce a copolymer PAO product. To that end, alpha-olefins with the following combinations can be advantageous: $C_6/C_8$, $C_6/C_{10}$, $C_6/C_{12}$, $C_6/C_{14}$, $C_6/C_{16}$, $C_8/C_{10}$, $C_8/C_{12}$, $C_8/C_{14}$, $C_8/C_{16}$, $C_{10}/C_{12}$, $C_{10}/C_{14}$, $C_{10}/C_{16}$, $C_{10}/C_{18}$, $C_{12}/C_{14}$, $C_{12}/C_{16}$, $C_{12}/C_{18}$, $C_{12}/C_{20}$, $C_6/C_8/C_{10}$, $C_6/C_8/C_{12}$, $C_6/C_8/C_{14}$, $C_6/C_{10}/C_{12}$, $C_6/C_{10}/C_{14}$, $C_8/C_{10}/C_{12}$, $C_8/C_{10}/C_{14}$, $C_8/C_{12}/C_{14}$, $C_{10}/C_{12}/C_{16}$, $C_{10}/C_{12}/C_{18}$, $C_{10}/C_{14}/C_{16}$, $C_{10}/C_{14}/C_{18}$, and the like. In some embodiments, at least one of the alpha-olefins in the mixture feed can be an LAO. In some embodiments, substantially all of the alpha-olefins in the mixture feed can be LAOs.

In some embodiments, alpha-olefin monomers are mono-olefins containing one C=C bond per monomer molecule, though those olefins containing two or more C=C bonds per monomer molecule can be used as well.

In some embodiments, monomers useful herein include substituted or unsubstituted $C_6$ to $C_{32}$ alpha-olefins, or $C_6$ to $C_{20}$ alpha-olefins, or $C_6$ to $C_{14}$ alpha-olefins, or hexene, heptene, octene, nonene, decene, undecene, dodecene, tetradecene and isomers thereof. In some embodiments, the poly alpha-olefin prepared herein comprises about 50 mol % or more (such as about 60 mol % or more, such as about 70 mol % or more, such as about 80 mol % or more, such as about 90 mol % or more, such as about 99 mol % or more) of one or more $C_6$ to $C_{32}$ (such as $C_6$ to $C_{20}$, such as $C_8$ to $C_{18}$) alpha-olefin monomers.

Useful $C_6$ to $C_{32}$ alpha-olefin monomers include hexene, heptene, octene, nonene, decene, undecene, dodecene, tetradecene, substituted derivatives thereof, and isomers thereof.

In some embodiments, the monomers comprise $C_6$ to $C_{20}$ alpha-olefins, or $C_6$ to $C_{14}$ alpha-olefins, and/or $C_8$ to $C_{12}$ alpha-olefins.

In some embodiments, olefin monomers include one (alternately two, alternately three) or more of hexene, heptene, octene, nonene, decene, dodecene, and tetradecene.

In an embodiment the PAO is a homopolymer of any $C_8$ to $C_{12}$ alpha-olefin, i.e., the PAO is a homopolymer of 1-hexene, 1-heptene, 1-octene, 1-nonene, 1-decene, 1-undecene, 1-dodecene or 1-tetradecene. In some embodiments, the PAO is a homopolymer of decene. In at least one embodiment the PAO is a copolymer comprising decene and one or more of any of the monomers listed above.

In an embodiment, the PAO comprises two or more monomers, or three or more monomers, or four or more monomers, or five or more monomers. For example, a $C_8$, $C_{10}$, $C_{12}$-linear alpha-olefin mixture, or a $C_6$, $C_7$, $C_8$, $C_9$, $C_{10}$, $C_{11}$, $C_{12}$, $C_{13}$, $C_{14}$-linear alpha-olefin mixture, or a $C_6$, $C_8$, $C_{10}$, $C_{12}$, $C_{14}$, $C_{16}$, $C_{18}$-linear alpha-olefin mixture can be used as a feed.

In at least one embodiment, the PAO comprises less than about 50 mol % of $C_2$, $C_3$, and $C_4$ monomers, or less than about 40 mol %, or less than about 30 mol %, or less than about 20 mol %, or less than about 10 mol %, or less than about 5 mol %, or less than about 3 mol %, or about 0 mol %. Specifically, in at least one embodiment, the PAO comprises less than about 50 mol % of ethylene, propylene and butene, or less than about 40 mol %, or less than about 30 mol %, or less than about 20 mol %, or less than about 10 mol %, or less than about 5 mol %, or less than about 3 mol %, or about 0 mol %. In at least one embodiment, the PAO comprises less than about 40 mol %, or less than about 20 mol %, or less than about 10 mol %, or less than about 5 mol %, or less than about 3 mol %, or about 0 mol % of ethylene.

In at least one embodiment, the PAO comprises less than 25 mol % of $C_2$, $C_3$, and $C_4$ monomers, or less than about 20 mol %, or less than about 15 mol %, or less than about 10 mol %, or less than about 5 mol %, or less than about 1 mol %, or about 0 mol %. Specifically, in at least one embodiment, the PAO comprises less than about 25 mol % of ethylene, propylene and butene, or less than about 20 mol %, or less than about 15 mol %, or less than about 10 mol %, or less than about 5 mol %, or less than about 1 mol %, or about 0 mol %. In at least one embodiment, the PAO comprises less than about 25 mol %, or less than about 20 mol %, or less than about 10 mol %, or less than about 5 mol %, or less than about 1 mol %, or about 0 mol % of ethylene.

In at least one embodiment, the PAO comprises less than about 40 mol % of propylene. In at least one embodiment, the PAO comprises less than about 40 mol % of butene. In at least one embodiment, the PAO comprises less than about 10 mol % of ethylene. In at least one embodiment, the PAO comprises less than about 10 mol % of propylene. In at least one embodiment, the PAO comprises less than about 10 mol % of butene.

In at least one embodiment, the PAO comprises less than about 25 mol % of propylene. In at least one embodiment, the PAO comprises less than about 25 mol % of butene. In at least one embodiment, the PAO comprises less than about 5 mol % of ethylene. In at least one embodiment, the PAO comprises less than about 5 mol % of propylene. In at least one embodiment, the PAO comprises less than about 5 mol % of butene. In at least one embodiment, the PAO comprises less than about 1 mol % of ethylene. In at least one embodiment, the PAO comprises less than about 1 mol % of propylene. In at least one embodiment, the PAO comprises less than about 1 mol % of butene.

The alpha-olefins used herein can be produced directly from ethylene growth process as practiced by several commercial production processes, or they can be produced from Fischer-Tropsch hydrocarbon synthesis from $CO/H_2$ syngas, or from metathesis of internal olefins with ethylene, or from cracking of petroleum or Fischer-Tropsch synthetic wax at high temperature, or any other alpha-olefin synthesis routes. An exemplary feed for this disclosure can be at least 80 wt % alpha-olefin (such as linear alpha-olefin), such as at least 90 wt % alpha-olefin (such as linear alpha-olefin), or approximately 100% alpha-olefin (such as linear alpha-olefin). However, alpha-olefin mixtures can also be used as feeds in this disclosure, especially if the other components are internal-olefins, branched olefins, paraffins, cyclic paraffins, aromatics (such as toluene and or xylenes). These components may have diluent effects and are believed to not have a substantial detrimental effect on the polymerization of alpha-olefins. In other words, the process described herein can selectively convert alpha-olefins in a mixture and leave the other components largely, if not completely, unreacted. This can be useful when ethylene is not present in the mixture. This technology can be used to separate out alpha-olefins from a mixture by selectively reacting them with polymerization or oligomerization catalyst systems, effectively if not completely eliminating the need to separate alpha-olefins from the remainder of the components in a mixed feed stream. This can be economically advantageous, for example, in a process utilizing Fisher-Tropsch synthesis olefin product streams containing alpha-olefins, internal-olefins and branched olefins. Such a mixture can be fed to oligomerization technology as described herein and to selectively react away the alpha-olefin. No separate step to isolate the alpha-olefin may be needed. Another example of the utility of this process involves alpha-olefins produced by the metathesis of internal olefins with ethylene, which may contain some internal olefins. This mixed olefin base stock feed can be reacted as-is in the polymerization/oligomerization process of the present disclosure, which selectively converts the alpha-olefins into lube products. Thus, one can use the alpha-olefin for the base stock synthesis without having to separate the alpha-olefin from internal olefin. This can bring a significant improvement in process economics. The feed olefins can be the mixture of olefins produced from other linear alpha-olefin process containing $C_4$ to $C_{20}$ alpha-olefins as described in Chapter 3 "Routes to Alpha-Olefins" of the book *Alpha Olefins Applications Handbook*, Edited by G. R. Lappin and J. D. Sauer, published by Marcel Dekker, Inc. N.Y. 1989.

IV. C.2 Feed Purification

Olefin feed and or solvents may be treated to remove catalyst poisons, such as peroxides, oxygen, or nitrogen-containing organic compounds or acetylenic compounds before being supplied to the polymerization reactor. For example, the treatment of the linear alpha-olefin with an activated 13 Å molecular sieve and a de-oxygenate catalyst (i.e., a reduced copper catalyst) can increase catalyst productivity (expressed in terms of quantity of PAO produced per micromole of the metallocene compound used) more than 10-fold. Alternatively, the feed olefins and or solvents may be treated with an activated molecular sieve, such as 3 Å, 4 Å, 8 Å, or 13 Å molecular sieve, and/or in combination with an activated alumina or an activated de-oxygenate catalyst. Such treatment can increase catalyst productivity 2- to 10-fold or more.

IV. C.3 Polymerization Reaction

Many polymerization/oligomerization processes and reactor types used for metallocene-catalyzed polymerization or oligomerization such as solution, slurry, and bulk polymerization or oligomerization processed can be used in this present disclosure. If a solid or supported catalyst is used, a slurry or continuous fixed bed or plug flow process may be suitable. In some embodiments, the monomers are contacted with the metallocene compound and the activator in the solution phase, bulk phase, or slurry phase, for example in a continuous stirred tank reactor or a continuous tubular reactor, in some embodiments, the temperature in any reactor used herein can be from about −10° C. to about 250° C., e.g., from about 30° C. to about 220° C., such as from about 50° C. to about 180° C., from about 60° C. to about 170° C., or from about 70° C. to about 150° C. In some embodiments, the pressure in any reactor used herein can be from about 0.1 to about 100 atmospheres, e.g., from about 0.5 to about 75 atmospheres or from about 1 to about 50 atmospheres. Alternatively, the pressure in any reactor used herein can be from about 1 to about 50,000 atmospheres, e.g., from about 1 to about 25,000 atmospheres. Additionally or alternatively, the monomer(s), metallocene and activator can be contacted for a residence time of about 1 second to about 100 hours, e.g., about 30 seconds to about 50 hours, about 2 minutes to about 6 hours, or about 1 minute to about 4 hours. Additionally or alternatively, solvent or diluent may be present in the reactor and may include butanes, pentanes, hexanes, heptanes, octanes, nonanes, decanes, undecanes, dodecanes, tridecanes, tetradecanes, pentadecanes, hexadecanes, toluene, o-xylene, m-xylene, p-xylene, mixed xylenes, ethylbenzene, propylbenzenes such as isopropylbenzene, butylbenzenes such as n-butylbenzene or t-butylbenzene, cumene, or a combination thereof; solvents can include toluene, xylenes, ethylbenzene, normal paraffins (such as NORPAR® solvents available from ExxonMobil Chemical Company in Houston, Tex.), isoparaffin solvents (such as ISOPAR® solvents available from ExxonMobil Chemical Company in Houston, Tex.), or a combination thereof. These solvents or diluents may typically be pre-treated in same manners as the feed olefins.

Regardless of the type of reactor or process, it can be desired that the average activity level of the catalyst system be maintained at or above a sufficiently high level, so as to attain a minimum reasonable yield of oligomeric product, relative to monomeric reactant(s). For example, in some embodiments, the catalytic reaction can have an average activity level of at least about 800 g/s·mol, e.g., at least about 900 g/s·mol, at least about 1000 g/s·mol, at least about 1100 g/s·mol, at least about 1200 g/s·mol, at least about 1300 g/s·mol, at least about 1400 g/s·mol, at least about 1500 g/s·mol, at least about 1700 g/s·mol, at least about 1900 g/s·mol, at least about 2100 g/s·mol, at least about 2500 g/s·mol, or at least about 2800 g/s·mol; although average activity levels are not often characterized as being "too high," it is theoretically possible for the average activity level to be so high that control of the reaction product may be difficult to achieve in practice, such that the average catalytic reaction activity level can optionally be less than about 1000 kg/s·mol, e.g., less than about 500 kg/s·mol, in some embodiments. Additionally or alternatively, in some embodiments, the catalytic reaction can provide a minimum reasonable yield (grams of oligomer per grams of monomer feed) of at least about 18%, e.g., at least about 19%, at least about 20%, at least about 22%, at least about 24%, at least about 27%, at least about 30%, at least about 33%, at least about 36%, at least about 38%, or at least 40%, based on a reaction time of about 1 h (about 3600 s); although reasonable catalytic yield is not often characterized as being "too high," with a maximum of approximately 100% in a 1-h reaction time, it is theoretically possible for relatively high yields, such as high yields in relatively short reaction times, to detrimentally affect the ability to control the reaction product, e.g., such that a maximum reasonable yield may optionally be approximately 100% in a reaction time of about 1 minute or less, e.g., approximately about 100% in a reaction time of about 10 minutes or less, approximately 100% in a reaction time of about 30 minutes or less, approximately 100% in a reaction time of about 1 h or less, approximately about 95% in a reaction time of about 1 hour or less, or approximately 90% in a reaction time of about 1 hour or less.

In some embodiments, it can be desirable to attain both relatively low product molecular weight and relatively high product vinylidene content. However, in many metallocene reactions where a vinylidene bond is a significant unsaturation product (at least 30 mol %, relative to the total number of moles of vinyls, vinylidenes, disubstituted vinylenes, and trisubstituted vinylenes), increasing reaction temperature can cause a decrease (or at least no increase) in both molecular weight and vinylidene content. Because reaction temperature can be one of the most ubiquitous ways to control product characterization parameters for a given catalyst system, it can often be a challenge to attain a product having both relatively low molecular weight and relatively high vinylidene content in many conventional systems. Thus, in some embodiments of the present disclosure, the combination of the reaction/polymerization/oligomerization conditions with certain metallocene catalyst systems can advantageously result in both decreasing molecular weight and increasing vinylidene content with increasing reaction temperature, thereby allowing heightened control of desired parameters without having to sacrifice one too much to attain the other. In some embodiments, e.g., by carefully selecting the elements of the metallocene catalyst system, the average activity level of the catalyst system be can be further advantageously maintained at or above a sufficiently high level, so as to attain a minimum reasonable yield of oligomeric product, relative to monomeric reactant(s).

Typically, one or more metallocene compounds, one or more activators, and one or more monomers are contacted to produce polymer or oligomer. These catalysts may be supported and, as such, may be useful in the known slurry, solution, or bulk operating modes conducted in single, series, or parallel reactors. If the catalyst, activator, or co-activator is a soluble compound, the reaction can be carried out in a solution mode. Even if one of the components is not completely soluble in the reaction medium or in the feed solution, either at the beginning of the reaction or during or at later stages of the reaction, a solution or slurry type operation may still be applicable. In any instance, the catalyst system components, dissolved or suspended insolvents, such as toluene or other conveniently available aromatic solvents, or in aliphatic solvent, or in the feed alpha-olefin stream, can be fed into the reactor under inert atmosphere (usually nitrogen or argon blanketed atmosphere) to allow the polymerization or oligomerization to take place.

The polymerization or oligomerization can be run in a batch mode, where all the components are added into a reactor and allowed to react to a pre-designed degree of conversion, either to partial conversion or full conversion. Subsequently, the catalyst can be deactivated by any possible means, such as exposure to air or water, or by addition of alcohols or solvents containing deactivating agents.

The polymerization or oligomerization can additionally or alternatively be carried out in a semi-continuous operation, where feeds and catalyst system components can be continuously and/or simultaneously added to the reactor so as to maintain a constant ratio of catalyst system components to feed olefin(s). When all feeds and catalyst system components are added, the reaction may be allowed to proceed to a pre-determined stage. The reaction can then be discontinued by catalyst deactivation in the same manner as described for batch operation.

The polymerization or oligomerization can additionally or alternatively be carried out in a continuous operation, where feeds and catalyst system components can be continuously and/or simultaneously added to the reactor so to maintain a constant ratio of catalyst system and feed olefins. The reaction product can be continuously withdrawn from the reactor, as in a typical continuous stirred tank reactor (CSTR) operation. The residence times of the reactants can be controlled by a pre-determined degree of conversion. The withdrawn product can then typically be quenched in the separate reactor in a similar manner as other operation. In some embodiments, any of the processes to prepare PAOs described herein are continuous processes, which can include a) continuously introducing a feed stream comprising at least 10 mol % of the one or more $C_6$ to $C_{24}$ alpha-olefins into a reactor, b) continuously introducing the metallocene compound and the activator into the reactor, and c) continuously withdrawing the PAO from the reactor. Additionally or alternatively, the continuous process can include the step of maintaining a partial pressure of hydrogen in the reactor of about 215 psi (about 1.5 MPa) or less, based upon the total pressure of the reactor, e.g., about 175 psi (about 1.2 MPa) or less, about 115 psi (about 790 kPa) or less, about 100 psi (about 690 kPa) or less, about 65 psi (about 450 kPa) or less, about 50 psi (about 350 kPa) or less, about 40 psi (about 280 kPa) or less, about 25 psi (about 170 kPa) or less, or about 10 psi (about 69 kPa) or less. Additionally or alternatively the hydrogen, if present in the reactor, in the feed, or in both, at a concentration of about 1000 ppm or less by weight, e.g., about 750 wppm or less, about 500 wppm or less, about 250 wppm or less, about 100 wppm or less, about 50 wppm or less, about 25 wppm or less, about 10 wppm or less, or about 5 wppm or less.

Example reactors can range in size from 2 mL and up. Usually, the reactors are larger than one liter in volume for commercial production. The production facility may have one single reactor, or several reactors, arranged in series or in parallel or in both to improve productivity, product properties, and general process efficiency. The reactors and associated equipment are usually pre-treated to ensure proper reaction rates and catalyst performance. The reaction is usually conducted under inert atmosphere, where the catalyst system and teed components may be out of contact with any catalyst deactivator or poison, e.g., polar oxygen, nitrogen, sulfur, and/or acetylenic compounds.

One or more reactors in series or in parallel may be used in the present disclosure. The metallocene compound, activator and when required, co-activator, may be delivered as a solution or slurry in a solvent or in the alpha-olefin feed stream, either separately to the reactor, activated in-line just prior to the reactor, or pre-activated and pumped as an activated solution or slurry to the reactor. Polymerizations/oligomerization can be carried out in either single reactor operation, in which monomer, or several monomers, catalyst/activator/co-activator, optional scavenger, and optional modifiers may be added continuously to a single reactor or in series reactor operation, in which the above components can be added to each of two or more reactors connected in series. The catalyst system components can be added to the first reactor in the series. The catalyst system component may alternatively be added to both reactors, with one component being added to first reaction and another component to other reactors. In some embodiments, the metallocene compound can be activated in the reactor in the presence of olefin, Alternatively, the metallocene compound (such as a dichloride form of the metallocene compound) may be pre-treated with an alkylaluminum reagent, especially triisobutylaluminum, tri-n-hexylaluminum, and/or tri-n-octylaluminum, followed by charging into the reactor containing other catalyst system component and the feed olefins, or followed by pre-activation with the other catalyst system component to give the fully activated catalyst, which can then be fed into the reactor containing feed olefins. In another alternative, the pre-catalyst metallocene can be mixed with the activator and/or the co-activator, and this activated catalyst can then be charged into reactor, together with feed olefin stream containing some scavenger or co-activator.

In another alternative, the whole or part of the co-activator can be pre-mixed with the feed olefins and charged into the reactor at the same time as the other catalyst solution containing metallocene and activators and/or co-activator.

The catalyst compositions can be used individually or can be mixed with other known polymerization catalysts to prepare polymer or oligomer blends. Monomer and catalyst selection can allow polymer or oligomer blend preparation under conditions analogous to those using individual catalysts. Polymers having increased PDI are available from polymers made with mixed catalyst systems and can thus be achieved. Mixed catalyst can comprise two or more metallocene compounds and or two or more activators.

The PAOs described herein can additionally or alternatively be produced in homogeneous solution processes. Generally, this involves polymerization or oligomerization in a continuous reactor in which the polymer formed and the starting monomer and catalyst materials supplied may be agitated to reduce or avoid concentration or temperature gradients. Temperature control in the reactor can generally be obtained by balancing the heat of polymerization and with reactor cooling by reactor jackets or cooling coils or a cooled side-stream of reactant to cool the contents of the reactor, auto refrigeration, pre-chilled feeds, vaporization of liquid medium (diluent, monomers, or solvent) or a combination thereof. Adiabatic reactors with pre-chilled feeds may additionally or alternatively be used. The reactor temperature may vary with the catalyst used and the product desired. Higher temperatures can tend to give lower molecular weights, and lower temperatures can tend to give higher molecular weights; however, this is not a fixed rule. In general, the reactor temperature can vary between about 0° C. and about 300° C., e.g., from about 10° C. to about 230° C. or from about 25° C. to about 200° C. Usually, it is important to control the reaction temperature as pre-determined. In order to produce fluids with narrow polydispersity, such as to promote the highest possible shear stability, it can be useful to control the reaction temperature to obtain minimum of temperature fluctuation in the reactor or over the course of the reaction time. If multiple reactors are used in series or in parallel, it may be useful to keep the temperature constant in a pre-determined value, e.g., to minimize any broadening of molecular weight distribution. In order to produce a product with broader molecular weight distribution, one can adjust the reaction temperature swing or fluctuation, or, as in series operation, the second reactor temperature may be higher than the first reactor temperature. In parallel reactor operation, the temperatures of the two reactors may be independent. More than one type of metallocene catalyst can be used.

The pressure in any reactor used herein can vary from about 0.1 atmosphere to about 100 atmospheres (about 1.5 psia to about 1500 psia), e.g., from about 0.5 atm to about 80 atm (from about 7 psia to about 1200 psia) or from about 1.0 atm to about 50 atm (from about 15 psia to about 750 psia). The reaction can be carried out under an atmosphere of nitrogen or with some hydrogen. Sometimes a small amount of hydrogen may be added to the reactor to improve catalyst performance. When present, the amount of hydrogen can be kept at such a level to improve catalyst productivity, but not induce too much (such as any significant) hydrogenation of olefins, especially the feed alpha-olefins (the reaction of alpha-olefins into saturated paraffins can be very detrimental to the efficiency of the process). The amount of hydrogen partial pressure can be kept low, e.g., less than about 50 psi (about 350 kPa), less than about 25 psi (about 170 kPa), less than about 10 psi (about 69 kPa), or less than about 5 psi (about 35 kPa); additionally or alternatively, the concentration of hydrogen in the reactant phase, in the reactor and/or feed, can be less than about 10,000 ppm (by wt.), e.g., less than about 1000 ppm, less than about 500 ppm, less than about 100 ppm, less than about 50 ppm, less than about 25 ppm, or less than about 10 ppm.

The reaction time or reactor residence time can depend on the catalyst used, the amount of catalyst used, and the desired alpha-olefin conversion level. Different metallocene compounds typically have different activities. Usually, a higher degree of alkyl substitution on the Cp ring, or bridging can improve catalyst productivity. High amounts of catalyst loading can tend to give higher alpha-olefin conversion at shorter reaction times. However, high amount of catalyst usage can make the production process uneconomical and difficult to manage the reaction heat or to control the reaction temperature. Therefore, it can be useful to choose a catalyst with maximum catalyst productivity to minimize the amount of metallocene and activator needed. When the catalyst system is a metallocene plus methylalumoxane, the range of methylalumoxane used can be in the range of about 0.1 milligram/gram (mg/g) to about 500 mg/g of alpha-olefin feed, e.g., from about 0.05 mg/g to about 10 mg/g. Furthermore, the molar ratios of the aluminum to metallocene (Al/M molar ratio) can range from about 2 to about 4000, e.g., from about 10 to about 2000, from about 50 to about 1000, or from about 100 to about 500. When the catalyst system is a metallocene plus a Lewis Acid or an ionic promoter with NCA component, the metallocene use can be in the range of about 0.01 microgram/gram (mcg/g) to about 500 mcg/g of metallocene component relative to alpha-olefin feed, e.g., from about 0.1 mcg/g to about 100 mcg/g, and/or the molar ratio of the NCA activator to metallocene can be in the range from about 0.1 to about 10, e.g., from about 0.5 to about 5 or from about 0.5 to about 3. If a co-activator of alkylaluminum compound is used, the molar ratio of the Al to metallocene can be in the range from about 1 to about 1000, e.g., from about 2 to about 500 or from about 4 to about 400.

In some embodiments, the process can have the highest possible alpha-olefin conversion (close to 100%) of feed alpha-olefin in shortest possible reaction time. However, in CSTR operation, sometimes it can be beneficial to run the reaction at an optimum alpha-olefin conversion, which can be less than about 100% alpha-olefin conversion, but can be close to about 100%. There are also occasions, when partial alpha-olefin conversion can be more desirable, e.g., when a narrow product PDI is desirable, because partial conversion can avoid a PDI broadening effect. If the reaction is conducted to less than 100% conversion of the alpha-olefin, the unreacted starting material after separation from other product and solvents/diluents can be simply removed, or may be recycled to increase the total process efficiency. Conversion, also called alpha-olefin conversion, is determined by dividing the amount (grams) of isolated PAO recovered from the polymerization mixture (after the polymerization has been stopped) by the amount (grams) of alpha-olefin introduced into the reactor. (When reported in %, conversion=(grams isolated PAO/grams alpha-olefin used)×100). In some embodiments, the conversion for the polymerization reactions described herein is about 20% or more, alternatively about 40% or more, alternatively about 60% or more, alternatively about 70% or more, alternatively about 80% or more, alternatively about 90% or more, alternatively about 95% or more. Isolated PAO is the PAO product obtained after solvent, unreacted monomer and other volatiles (such as dimer) have been removed (such as by vacuum flash).

Example residence times for any process described herein can be from about 1 minute to about 20 hours, e.g., from about 5 minutes to about 10 hours.

Each of these processes may also be employed in single reactor, parallel or series reactor configurations. The process can be carried out in a continuous stirred tank reactor or plug flow reactor, or more than one reactor operated in series or parallel. These reactors may or may not have internal cooling and the monomer feed may or may not be refrigerated. See the general disclosure of U.S. Pat. No. 5,705,577 for general process conditions.

When a solid supported catalyst is used, a slurry polymerization/oligomerization process generally operates in the similar temperature, pressure, and residence time range as described previously. In a slurry polymerization or oligomerization, a suspension of solid catalyst, promoters, monomer and comonomers are added. The suspension including diluent is intermittently or continuously removed from the reactor. The catalyst is then separated from the product by filtration, centrifuge, or settlement. The fluid is then distilled to remove solvent, any unreacted components and light product. A portion or all of the solvent and unreacted component or light components can be recycled for reuse.

If the catalyst used is un-supported or is a solution catalyst, when the reaction is complete or when the product is withdrawn from the reactor (such as in a CSTR), the product may still contain soluble, suspended, or mixed catalyst system components. These components can be deactivated and/or removed. Any of the usual catalyst deactivation methods or aqueous wash methods can be used to remove the catalyst system component. Typically, the reaction can be deactivated by addition of stoichiometric amount or excess of air, moisture, alcohol, isopropanol, etc. The mixture can then be washed with dilute sodium hydroxide or with water to remove catalyst system components. The residual organic layer may then be subjected to distillation to remove solvent, which can optionally be recycled for reuse. The distillation can further remove any light reaction product, e.g., from $C_{18}$ and less.

Polymerization or oligomerization in absence of hydrogen may be advantageous to provide polymers or oligomers with high degree of unsaturated double bonds.

In some embodiments, in the process of the present disclosure, due to the structure features of the metallocene compound, the polymerization reaction mixture exiting the polymerization reactor can typically comprise oligomers including vinylidenes, trisubstituted vinylenes, optionally disubstituted vinylenes, and optionally vinyls, optionally residual olefin monomer feed, optionally solvents, and components derived from the catalyst system.

The polymerization reaction mixture can then be quenched, e.g., by the addition of a quenching agent such as water, CO2, methanol, ethanol, mixtures thereof, and the like. Subsequently, the polymerization reaction mixture can be separated to remove the residual monomer, which can be recycled to the polymerization reactor. Monomer removal can be carried out by means such as flashing under vacuum, distillation, or extraction. The resultant mixture can comprise a first reactor effluent including vinylidenes, trisubstituted vinylenes, optionally disubstituted vinylenes, and optionally vinyls.

Without being bound by theory, it is believed that, a non-coordinating anion with a large molecular size (e.g., dimethylanilinium tetrakisperfluoronaphthylborate) can tend to result in higher selectivity toward vinyls and a lower selectivity toward vinylidenes, as compared to non-coordinating anions with a small molecular size (e.g., dimethylanilinium tetrakisperfluorophenylborate) when used as the activator for the same metallocene compound of the present disclosure.

Optionally, hydrogen is absent or present at 1 mol % or less, preferably 0.5 mol % or less in the first polymerization reaction. Optionally no hydrogen is added into the polymerization process.

In an embodiment of the invention, little or no scavenger is used in the first polymerization to produce the polymer, i.e., scavenger (such as trialkyl aluminum, e.g. tri-n-octylaluminum) is present at zero mol %, alternately the scavenger is present at a molar ratio of scavenger metal to transition metal of less than 100:1, preferably less than 50:1, preferably less than 15:1, preferably less than 10:1. Alternately less than 100 ppm of scavenger is present in the first polymerization. Preferably less than 100 ppm of alkylaluminum, such as trialkyl aluminum, is present in the first polymerization reaction. Trialkyl aluminum is typically represented by the formula $R_3Al$, where each R is independently, a $C_1$ to $C_{40}$, preferably $C_1$ to $C_{20}$ alkyl group, such as methyl, ethyl, propyl, butyl, pentyl, hexyl, heptyl, octyl, nonyl, decyl, undecyl, docecyl, isomers thereof, and mixtures thereof.

In an embodiment, little or no alumoxane (i.e., less than 0001 wt %) is used in the first polymerization processes described herein. In an embodiment, alumoxane is present at 0.00 mol %, or the alumoxane is present at a molar ratio of aluminum to catalyst compound transition metal less than 500:1, or less than 300:1, or less than 100:1, or less than 1:1.

Alternately $C_4$ olefins (such as isobutylene, butadiene, n-butene) are substantially absent from the PAO and/or the polymerization process. Alternately $C_2$ to $C_4$ olefins are substantially absent from the PAO and or the polymerization process (first and or second polymerizations). Alternately isobutylene is substantially absent from the PAO and or the polymerization process (first and or second polymerizations). By substantially absent is meant that the monomer(s) is/are present in the PAO at 1 wt % or less, preferably at 0.5 wt or less, preferably at 0 wt %. Likewise substantially absent in relation to the polymerization process means that the monomer(s) is/are present in the monomer feed at 1 wt % or less, preferably at 0.5 wt % or less, preferably at 0 wt %.

Optionally the catalyst productivity is 50,000 grams of PAO product per gram of first catalyst (gPAO/gCat) or more, preferably 55,000 gPAO/gCat or more, preferably 60,000 gPAO/gCat or more, preferably 100,000 gPAO/gCat or more.

Optionally PAO dimer selectivity is 85% or more, preferably 90% or more, preferably 95% or more, based upon the PAO produced.

Optionally the first polymerization temperature is 100° C. or more, preferably 100° C. or more, preferably 120° C. or more.

Optionally the first polymerization residence time is 1 hour or more, preferably 2 hours or more, preferably 3 hours or more, optionally up to 5 hours.

Optionally hydrogen is absent or present at 1 mol % or less in the polymerization reaction (first and/or second), preferably 0.5 mol % or less in the first and or second polymerization reaction; little or no scavenger is used in the first and or second polymerization to produce the polymer; the catalyst productivity is 50,000 grams of PAO product per gram of catalyst (gPAO/gCat) or more, preferably 55,000 gPAO/gCat or more, preferably 60,000 gPAO/gCat or more, preferably 100,000 gPAO/gCat or more; the PAO dimer selectivity in the first polymerization is 85% or more, preferably 90% or more, preferably 95% or more, based upon the PAO produced; and the reactor temperature of the first polymerization is 100° C. or more, preferably 100° C. or more, preferably 120° C. or more.

Optionally, the PAO produced has an Mn of 350 g/mol or less and the catalyst has high conversion (e.g., at least 60%, at least 70%, at least 80%, at least 90%, based upon the weight of the monomer entering the first reactor and the PAO produced).

Optionally the catalyst loading is 0.1 gram catalyst per gram of monomer or less (gCat/gMon), preferably 0.01 gCat/gMon or less, preferably 0.005 gCat/gMon or less, preferably 0.001 gCat/gMon or less, preferably 0.0001 gCat/gMon or less.

Optionally, the PAO produced has an Mn of 350 g/mol or less and the catalyst has high conversion (e.g., at least 60%, at least 70%, at least 80%, at least 90%, based upon the weight of the monomer entering the first reactor and the PAO produced), and the catalyst loading is 0.1 gram catalyst per gram of monomer or less (gCat/gMon) in the first reactor, preferably 0.01 gCat/gMon or less, preferably 0.005 gCat/gMon or less, preferably 0.001 gCat/gMon or less, preferably 0.0001 gCat/gMon or less.

Optionally, vinylidene content of the PAO produced is 95% or more, preferably 98% or more, the Mn is 350 g/mol or less, preferably 320 g/mol or less, preferably 300 g/mol or less, the conversion is at least 60%, at least 70%, at least 80%, at least 90%, based upon the weight of the monomer entering the first reactor and the PAO produced, the PAO dimer selectivity is at least 60%, at least 70%, at least 80%, at least 90%, based upon the weight of the PAO produced in the first reactor, and the productivity of the continuous process is at least 60,000 g/hour (preferably 70,000 g/hour or more, preferably 100,000 g/hr or more) with a catalyst loading is 0.1 gram catalyst per gram of monomer or less (gCat/gMon) in the first reactor, preferably 0.01 gCat/gMon or less, preferably 0.005 gCat/gMon or less, preferably 0.001 gCat/gMon or less, preferably 0.0001 gCat/gMon or less.

V. ADDITIONAL EMBODIMENTS

The present disclosure provides, among others, the following embodiments, each of which may be considered as optionally including any alternate embodiments:

Clause 1. A process to produce a poly alpha-olefin (PAO), comprising:

introducing a first alpha-olefin and a first catalyst system comprising a metallocene compound into a continuous stirred tank reactor or a continuous tubular reactor under first reactor conditions, wherein the alpha-olefin is introduced to the reactor at a flow rate of about 100 g/hr, to form a first reactor effluent comprising PAO dimer comprising at least 96 mol % of vinylidene and 4 mol % or less of trisubstituted vinylene and disubstituted vinylene, based on total moles of vinylidene, trisubstituted vinylene, and disubstituted vinylene; and introducing the first reactor effluent, a second alpha-olefin and a second catalyst composition comprising an acid catalyst into a second reactor under second reactor conditions to form a second reactor effluent comprising PAO trimer.

Clause 2. The process of Clause 1, wherein the metallocene compound is represented by the formula:

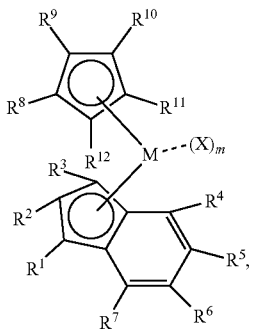

wherein:

each of $R^1$, $R^2$, and $R^3$ is independently hydrogen, a substituted or unsubstituted linear, branched linear, or cyclic $C_1$-$C_{20}$ hydrocarbyl group, wherein a first one of $R^1$, $R^2$, and $R^3$ is not hydrogen and at least one of $R^1$, $R^2$, and $R^3$ is hydrogen;

each of $R^4$, $R^5$, $R^6$, and $R^7$ is independently hydrogen, a substituted or unsubstituted linear, branched linear, or cyclic $C_1$-$C_{30}$ hydrocarbyl group, or one or more of $R^4$ and $R^5$, $R^5$ and $R^6$, or $R^6$ and $R^7$, taken together with the carbon atoms in the indenyl ring to which they are directly connected, collectively form one or more substituted or unsubstituted rings fused to the indenyl ring;

each of $R^8$, $R^9$, $R^{10}$, $R^{11}$, and $R^{12}$ is independently a substituted or unsubstituted linear, branched linear, or cyclic $C_1$-$C_{30}$ hydrocarbyl, silylcarbyl, or germanyl group;

M is a group 3, 4 or 5 transition metal;

each X is independently a halogen, a hydride, an amide, an alkoxide, a sulfide, a phosphide, a diene, an amine, a phosphine, an ether, or a $C_1$-$C_{20}$ substituted or unsubstituted linear, branched linear, or cyclic hydrocarbyl group, or optionally two or more X moieties may together form a fused ring or ring system; and m is an integer equal to 1, 2, or 3.

Clause 3. The process of Clause 1, wherein the metallocene compound is represented by the formula:

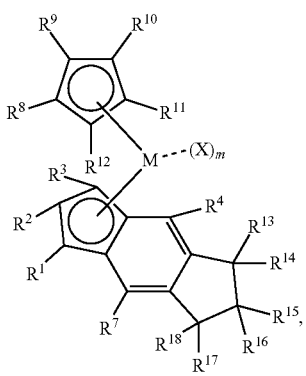

wherein:

each of $R^1$, $R^2$, and $R^3$ is independently hydrogen or a substituted or unsubstituted linear, branched linear, or cyclic $C_1$-$C_{20}$ hydrocarbyl or silylcarbyl group;

each of $R^4$ and $R^7$ is independently a substituted or unsubstituted linear, branched linear, or cyclic $C_1$-$C_{30}$ hydrocarbyl or silylcarbyl group;

each of $R^8$, $R^9$, $R^{10}$, $R^{11}$, and $R^{12}$ is independently a hydrogen, or a substituted or unsubstituted linear, branched linear, or cyclic $C_1$-$C_{20}$ hydrocarbyl, silylcarbyl, or germanyl group, or optionally at least three of $R^8$, $R^9$, $R^{10}$, $R^{11}$, and $R^{12}$ are not hydrogen;

each of $R^{13}$, $R^{14}$, $R^{15}$, $R^{16}$, $R^{17}$, and $R^{18}$ is independently hydrogen or a substituted or unsubstituted linear, branched linear, or cyclic $C_1$-$C_{20}$ hydrocarbyl or silylcarbyl group;

M is a group 3, 4 or 5 transition metal;

each X is independently a halogen, a hydride, an amide, an alkoxide, a sulfide, a phosphide, a diene, an amine, a phosphine, an ether, or a $C_1$-$C_{20}$ substituted or unsubstituted linear, branched, or cyclic hydrocarbyl group, or optionally two or more X moieties may together form a fused ring or ring system; and m is an integer equal to 1, 2, or 3.

Clause 4. The process of any one of Clauses 1-3, wherein the first alpha-olefin is a $C_6$-$C_{16}$ alpha-olefin.

Clause 5. The process of any one of Clauses 1-4, wherein the second alpha-olefin is a $C_6$-$C_{16}$ alpha-olefin.

Clause 6. The process of any one of Clauses 1-5, wherein the acid catalyst is a Lewis acid.

Clause 7. The process of any one of Clauses 1-6, wherein the second reactor conditions comprise an acid catalyst loading of from about 5 mmolCat/100 gLAO to about 15 mmolCat/100 gLAO.

Clause 8. The process of any one of Clauses 1-7, wherein the second reactor conditions comprise a temperature of from about 10° C. to about 40° C.

Clause 9. The process of any one of Clauses 1-8, wherein the acid catalyst is $BF_3$.

Clause 10. The process of any one of Clauses 1-9, wherein the amount of PAO trimer in the second reactor effluent is 75 wt % or more, based on a total weight of PAO dimer, PAO trimer, and higher oligomers, where the higher oligomers are oligomers that have degree of polymerization of 4 or more, of alpha-olefin in the second reactor effluent.

Clause 11. The process of Clause 10, wherein the second reactor effluent comprises, 75 wt % or more of PAO trimer, 9 wt % or less of PAO dimer, and 16 wt % or less of higher oligomers of alpha-olefin, based on a total weight of PAO dimer, PAO trimer, and higher oligomers of alpha-olefin in the second reactor effluent.

Clause 12. The process of any one of Clauses 1-11, wherein the amount of PAO trimer in the second reactor effluent is greater than 80 wt %, based on a total weight of PAO dimer, PAO trimer, and higher oligomers of alpha-olefin in the second reactor effluent.

Clause 13. The process of any one of Clauses 1-12, wherein the amount of vinylidene in the PAO dimer in the first reactor effluent is about 96 mol % or more, based on total moles of vinylidene, disubstituted vinylene, and trisubstituted vinyl ene in the PAO dimer in the first reactor effluent.

Clause 14. The process of Clause 13, wherein the PAO dimer in the first reactor effluent further comprises, based on the total moles (100 mol %) of vinylidene, disubstituted vinylene, and trisubstituted vinylene in the PAO dimer in the first reactor effluent:

up to 4 mol % of trisubstituted vinylene,
up to 4 mol % of disubstituted vinylene, or
up to 4 mol % of trisubstituted vinylene and disubstituted vinylene.

Clause 15. The process of any one of Clauses 1-14, wherein the PAO dirtier in the first reactor effluent comprises, based on total moles (100 mol %) of vinylidene, disubstituted vinylene, and trisubstituted vinylene in the PAO dimer in the first reactor effluent:
98 mol % or more vinylidene, and up to 2 mol % of trisubstituted vinylene, and/or disubstituted vinylene.

Clause 16. The process of any one of Clauses 1-15, wherein the PAO dimer in the first reactor effluent further comprises, based on the total moles (100 mol %) of vinylidene, disubstituted vinylene, and trisubstituted vinylene in the PAO dimer in the first reactor effluent:
98 mol % or more vinylidene, and
up to 1 mol % trisubstituted vinylene,
up to 1 mol % disubstituted vinylene, or
up to 1 mol % trisubstituted vinylene and disubstituted vinylene.

Clause 17. The process of any one of Clauses 1-16, wherein the PAO dimer in the first reactor effluent further comprises, based on the total moles (100 mol %) of vinylidene, disubstituted vinylene, and trisubstituted vinylene in the PAO dimer in the first reactor effluent:
98 mol % or more vinylidene, and
up to 0.5 mol % trisubstituted vinylene,
up to 0.5 mol % disubstituted vinylene, or
up to 0.5 mol % trisubstituted vinylene and disubstituted vinylene.

Clause 18. The process of any one of Clauses 1-17, wherein the activator comprises one or more of:
N,N-dimethylanilinium tetrakis(perfluorophenyl)borate,
N,N-dimethylanilinium tetrakis(perfluoronaphthyl)borate,
triphenylcarbonium tetrakis(perfluorophenyl)borate,
triphenylcarbonium tetrakis(perfluoronaphthyl)borate,
N,N-dimethylanilinium tetrakis(perfluorophenyl)aluminate,
N,N-dimethylanilinium tetrakis(perfluoronaphthyl)aluminate alumoxane, modified alumoxane, and aluminum alkyl.

Clause 19. The process of any one of Clauses 1-15, wherein the second catalyst composition further comprises an alcohol and an alkyl acetate.

Clause 20. The process of any one of Clauses 1-19, wherein the metallocene compound is selected from the group consisting of:

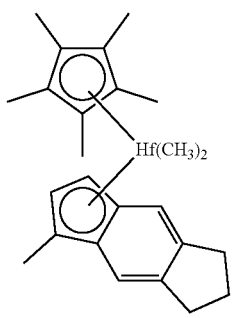, 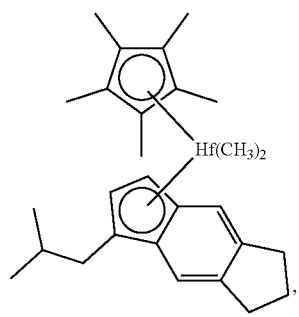,

-continued

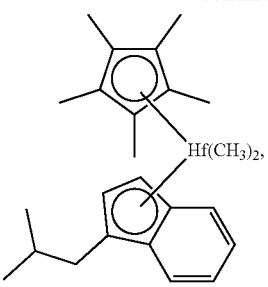

or a combination thereof.

Clause 21. The process of any one of Clauses 1-20, wherein the second reactor conditions include a second reactor temperature of less than 60° C. and an acid catalyst composition loading of less than 30 mmol per 100 g of second alpha-olefin.

Clause 22. The process of any one of Clauses 1-21, wherein the PAO trimer has a number average molecular weight (Mn) of 300 or less, in accordance with $^1$H nuclear magnetic resonance spectroscopy.

Clause 23. The process of any of Clauses 1 to 22, further comprising functionalizing the PAO trimer with a reactant to form a functionalized PAO product.

Clause 24. The process of any of Clauses 1 to 23, further comprising hydrogenating the product, PAO trimer, or functionalized PAO product to form a hydrogenated PAO product.

Clause 25. A lubricant comprising the PAO dimer, PAO trimer, functionalized PAO product, or hydrogenated PAO product produced in any of Clauses 1 to 24.

Clause 26. A fuel comprising the PAO dimer, PAO trimer, functionalized PAO product, or hydrogenated PAO product produced in any of Clauses 1 to 24.

Clause 27. A driveline or electric vehicle fluid comprising the PAO dimer, PAO trimer, functionalized PAO product, or hydrogenated PAO product produced in any of Clauses 1 to 24.

Clause 28. An engine oil comprising the PAO dimer, PAO trimer, functionalized PAO product, or hydrogenated PAO product produced in any of Clauses 1 to 24.

Clause 29. A gear oil comprising the PAO dimer, PAO trimer, functionalized PAO product, or hydrogenated PAO product produced in any of Clauses 1 to 24.

Clause 30. A compressor oil comprising the PAO dimer, PAO trimer, functionalized PAO product, or hydrogenated PAO product produced in any of Clauses 1 to 24.

Clause 31. The process of Clauses 1 to 24 wherein the process has a conversion of at least 60%, based upon the weight of the monomer entering the reactor and the PAO produced and a selectivity for dimer of at least 85 wt %, based upon the PM) produced; and the metallocene compound is represented by formula (Z):

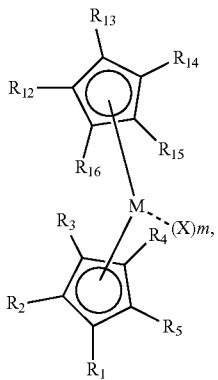

(Z)

wherein:

each $R^1$, $R^2$, and $R^3$ is, independently, hydrogen or a substituted or unsubstituted linear, branched (such as branched linear), or cyclic $C_1$-$C_{20}$, preferably $C_1$-$C_8$, hydrocarbyl group, wherein one of $R^1$, $R^2$, and $R^3$ is a substituted or unsubstituted linear, branched (such as branched linear), or cyclic $C_1$-$C_{20}$, preferably $C_1$-$C_8$, hydrocarbyl group, and either (i) two of $R^1$, $R^2$, and $R^3$ are each a hydrogen, or (ii) one of $R^1$, $R^2$, and $R^3$ is a hydrogen or a substituted or unsubstituted linear, branched (such as branched linear), or cyclic $C_1$-$C_{20}$, preferably $C_1$-$C_8$, hydrocarbyl group, and one of $R^1$, $R^2$, and $R^3$, taken together with $R^{16}$, is a bridging group connecting the first and second cyclopentadienyl rings;

$R^4$ and $R^5$ are each independently a substituted or unsubstituted linear, branched (such as branched linear), or cyclic $C_1$-$C_{30}$ hydrocarbyl group, or $R^4$ and $R^5$, taken together with the carbon atoms in the first cyclopentadienyl ring to which they are directly connected, collectively form one or more substituted or unsubstituted rings annotated to the first cyclopentadienyl ring;

$R^{12}$, $R^{13}$, $R^{14}$, and $R^{15}$ are each independently a hydrogen, or a substituted or unsubstituted linear, branched (such as branched linear), or cyclic $C_1$-$C_{20}$, preferably $C_1$-$C_8$, hydrocarbyl group; and $R^{16}$ is a hydrogen, a substituted or unsubstituted linear, branched (such as branched linear), or cyclic $C_1$-$C_{20}$, preferably $C_1$-$C_8$, hydrocarbyl group, substituted silyl or substituted germanyl group, or, taken together with one of $R^1$, $R^2$, and $R^3$, is a bridging group connecting the first and second cyclopentadienyl rings, optionally at least three of $R^{12}$, $R^{13}$, $R^{14}$, $R^{15}$, and $R^{16}$ are not hydrogen, optionally two or more of $R^{12}$, $R^{13}$, $R^{14}$, $R^{15}$ and $R^{16}$ moieties may together form a fused ring or ring system, provided that the fused ring or ring system is not unsaturated when $R^1$ is bridged to $R^{16}$, and where $R^2$ is not Me when $R^1$ or $R^3$ is bridged to $R^{16}$;

M is a transition metal having an integer valency of v;

each X is independently a halogen, a hydride, an amide, an alkoxide, a sulfide, a phosphide, a diene, an amine, a phosphine, an ether, or a $C_1$-$C_{20}$ substituted or unsubstituted linear, branched, or cyclic hydrocarbyl group, or optionally two or more X moieties may together form a fused ring or ring system; and m is an integer equal to v-2.

Clause 32. The process of Clause 31, wherein one of $R^1$, $R^2$, and $R^3$ is a substituted or unsubstituted linear, branched (such as branched linear), or cyclic $C_1$-$C_6$ hydrocarbyl group, and two of $R^1$, $R^2$, and $R^3$ are each a hydrogen.

Clause 33. The process of Clause 31, wherein one of $R^1$ and $R^3$ is a substituted or unsubstituted linear, branched (such as branched linear), or cyclic $C_1$-$C_6$ hydrocarbyl group, $R^2$ is a hydrogen, and one of $R^1$ and $R^3$ is a substituted or unsubstituted linear, branched (such as branched linear), or cyclic $C_1$-$C_6$ hydrocarbyl group, or, taken together with $R^{16}$, is a bridging group connecting the first and second cyclopentadienyl rings.

Clause 34. The process of Clause 33, wherein the bridging group comprises:

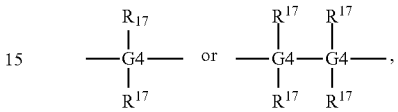

where each G4, the same or different at each occurrence, is independently carbon, silicon, or germanium, and $R^{17}$, the same or different at each occurrence, is each independently a $C_1$-$C_{20}$, preferably $C_1$-$C_8$, substituted or unsubstituted linear, branched, or cyclic hydrocarbyl group.

Clause 35. The process of any one of the preceding Clauses 31 to 34, wherein each X is independently a halogen or a substituted or unsubstituted linear, branched, or cyclic $C_1$-$C_6$ hydrocarbyl group; M comprises Zr or Hf and m is 2.

Clauses 36. The process of any one of the preceding Clauses 31 to 35, wherein M is Zr, m is 2 and each X is independently a methyl, an ethyl, a propyl, a butyl, a phenyl, a benzyl, a chloride, a bromide, or an iodide.

Clauses 37. The process of Clause 31 wherein the a polymerization reactor is a continuous stirred tank reactor or a continuous tubular reactor, the alpha-olefin is introduced to the reactor at a flow rate of at least 100,000 g/hr, the polymerization residence time is from 2 to 5 hours, and the polymerization temperature is 120° C. or more.

Clause 38. The process of Clause 37 where the vinylidene content of the PAO produced is 95% or more based on total moles of vinylidene, disubstituted vinylene, and trisubstituted vinylene in the PAO product, the Mn of the PAO product is 350 g/mol or less, the conversion is at least 60%, at least 70%, at least 80%, at least 90%, based upon the weight of the monomer entering the reactor and the PAO produced, the PAO dimer selectivity is at least 60%, based upon the weight of the PAO produced, and the productivity of the continuous process is at least 60,000 g/hour with a catalyst loading of 0.1 gram catalyst per gram of monomer or less.

VI. CHARACTERIZATION

For the characterization, proton NMR ($^1$H-NMR) was used to determine the mol % of the unsaturated species. Specifically, an NMR instrument of 500 MHz is run under the following conditions: a 30° flip angle RF pulse, 8 scans, with a relaxation delay of ~5 s between pulses; sample (60-100 mg) dissolved in $CDCl_3$ (deuterated chloroform) in a 5 mm NMR tube; and signal collection temperature at about 25° C. The following approach is taken in determining the concentrations of the various olefins among all of the olefins from an NMR spectrum. First, peaks corresponding to different types of hydrogen atoms in vinyls (T1), vinylidenes (T2), di-substituted vinylenes (T3), and trisubstituted vinylenes (T4) are identified at the peak regions in Table A. Second, areas of each of the above peaks (A1, A2, A3, and A4, respectively) are then integrated. Third, quantities of each type of olefins (Q1, Q2, Q3, and Q4, respectively) in moles are calculated (as A1/2, A2/2, A3/2, and A4, respectively). Fourth, the total quantity of all olefins (Qt) in moles is calculated as the sum total of all four types (Qt=Q1+Q2+Q3+Q4). Finally, the molar concentrations ($C_1$, $C_2$, $C_3$, and $C_4$, respectively, in mol %) of each type of olefin, on the basis of the total molar quantity of all of the olefins, is then calculated (in each case, Ci=100*Qi/Qt).

TABLE A

| Type No. | Olefin Structure | Hydrogen Atoms Peak Region (ppm) | Peak Area | Number of Hydrogen Atoms | Quantity of Olefin (mol) | Concentration of Olefin (mol %) |
|---|---|---|---|---|---|---|
| T1 | $CH_2$=CH—$R^1$ | 4.95-5.10 | A1 | 2 | Q1 = A1/2 | C1 |
| T2 | $CH_2$=$CR^1R^2$ | 4.65-4.84 | A2 | 2 | Q2 = A2/2 | C2 |
| T3 | $CHR^1$=$CHR^2$ | 5.31-5.55 | A3 | 2 | Q3 = A3/2 | C3 |
| T4 | $CR^1R^2$=$CHR^3$ | 5.11-5.30 | A4 | 1 | Q4 = A4 | C4 |

Gas chromatography (GC) was used to determine the composition of the synthesized oligomers by molecular weight. The gas chromatograph is a HP model equipped with a 15 meter dimethyl siloxane and flame ionization detector. A ~0.04 g sample was diluted in methylene chloride solvent, a nonane internal standard was added, and the mixture injected into the column. The starting temperature was about 40° C., held for about 1 minute, program-heated at about 15° C. per minute to about 250° C. and held for about 2 minutes. The sample was then heated at a rate of about 25° C. per minute to about 360° C. and held for about 17.3 minutes. The conversion, olefin isomerization, and oligomer distribution can be determined by the GC method.

VII. EXAMPLES

VII. A. Examples—Metallocene Dimer Selective Process

All catalyst syntheses were carried out in an $N_2$ purged thy box using standard air sensitive procedures. Celite (Sigma-Aldrich) and 3 Å molecular sieves (Sigma-Aldrich or Acres) were dried in a vacuum oven at 250° C. for 3 days. Solvents were purged with $N^2$ and dried and stored over 3 Å molecular sieves. NMR solvents were dried and stored over 3 Å molecular sieves. MeMgI (3 M in $Et_2O$, Sigma-Aldrich), $CH_3I$ (Sigma-Aldrich), isoButyl bromide (Sigma-Aldrich), nhexyl bromide (Sigma-Aldrich), nbutyl bromide (Sigma-Aldrich), 1,2,3,5-tetrahydro-s-indacene (GLSyntech) were used as received. Pentamethylcyclopentadienylhafnium trichloride ($Me_5CpHfCl_3$) was either purchased from Strem Chemicals or synthesized in a manner analogous to that described in *Journal of Organometallic Chemistry*, 1988, v. 340, 37-40.

Pentamethylcyclopentadienyl(1-methyl-1,5,6,7-tetrahydro-s-indacenyl)HfMe$_2$ (Catalyst I.A)

1-Methyl-1,5,6,7-tetrahydro-s-indacenyl Lithium: 1,5,6,7-tetrahydro-s-indacenyl lithium was synthesized in a manner analogous to that described in U.S. Ser. No. 16/270,085.

MeI (6.74 g, 47.5 mmol) was slowly added to 1,5,6,7-tetrahydro-s-indacenyl Lithium (7.0 g, 43.2 mmol) in $Et_2O$ (100 ml) and THF (20 ml). The reaction stirred for 4 hours. All solvents were then removed by a stream of nitrogen and the crude product was reslurried into pentane for 15 minutes. The solid was removed by filtration on celite. The solid was washed by pentane. All solvents were then removed in vacuo and 1-methyl-1,5,6,7-tetrahydro-s-indacene was isolated as a clear oil (6.95 g, 41.0 mmol), which was then dissolved into $Et_2O$ (100 ml), nBuLi (3.7 ml, 11M) was then slowly added and stirred for 1 hour. Then all $Et_2O$ was removed in vacuo and then pentane was added to the solution and the mixture was stirred for additional 10 minutes and then filtered to collect the product as a white solid (6.97 g).

1-methyl (1,5,6,7-tetrahydro-s-indacenyl) lithium (0.3 g, 1.6 mmol) was mixed with $CpMe_5HfCl_3$ (0.7 g, 1.1 mmol) in $Et_2O$ (15 ml) and stir it overnight. $Et_2O$ was then removed by a stream of nitrogen and the crude product was re-slurried into pentane for 15 minutes and was cooled under −35° C. The product was isolated by filtration as a mixture of LiCl and was used for the next step with no further purification. The crude hafnium dichloride (0.78 g, 1.4 mmol) was slurried into toluene (20 ml) and MeMgI (0.94 ml, 3 M in $Et_2O$) was then added and the reaction was stirred at 70° C. for 16 hours. The reaction was cooled to room temperature and 1,4-dioxane was added. The mixture was stirred for 15 minutes, and the solids were removed by filtration on CELITE and washed by $Et_2O$. Volatiles were then removed under vacuo. Final product ($C_{25}H_{34}Hf$) was isolated as a solid (0.4 g), which was analyzed by $^1H$ NMR ($CD_2Cl_2$, 400 MHz): δ 7.45-7.33 (m, 1H), 7.02-6.92 (m, 1H), 5.32 (dd, J=2.9, 0.9 Hz, 1H), 5.27 (dd, J=2.8, 0.6 Hz, 1H), 2.99-2.86 (m, 4H), 2.19 (s, 3H), 2.11-1.99 (m, 2H), 1.88 (s, 15H), −1.08 (s, 3H), −2.12 (s, 3H).

Pentamethylcyclopentadienyl(1-isobutyl-1,5,6,7-tetrahydro-s-indacenyl)HfMe$_2$ (Catalyst I.B)

1-isoButyl-1,5,6,7-tetrahydro-s-indacenyl Lithium: isoButyl bromide (1.69 g, 12 mmol) was added to 1,5,6,7-tetrahydro-s-indacenyl Lithium (2.0 g, 12 mmol) in THF (100 ml). The reaction stirred for 16 hours. THF was then removed by a stream of nitrogen, and the crude product was reslurried into pentane for 15 minutes. The solid was removed by filtration on celite. The solid was washed by pentane. All solvents were then removed in vacuo and 1-isoButyl-1,5,6,7-tetrahydro-s-indacene was isolated as a clear oil (2.54 g, 12 mmol), which was dissolved into $Et_2O$ (50 ml). nBuLi (1.1 ml, 11M) was then slowly added and stirred for 1 hour. Then all $Et_2O$ was removed in vacuo and then pentane was added to the solution and stirred for additional 10 minutes and filtered to collect the product as a white solid (2.5 g).

1-isobutyl-1,5,6,7-tetrahydro-s-indacenyl lithium (0.27 g, 1.2 mmol) was mixed with $CpMe_5HfCl_3$ (0.52 g, 1.2 mmol) in $Et_2O$ (20 ml) and stirred overnight. $Et_2O$ was then removed by a stream of nitrogen and the crude product was reslurried into pentane for 15 minutes. The mixture was cooled at −35° C. for 1 hour. The product was isolated by filtration as a mixture of LiCl and was used for the next step with no further purification. The crude hafnium dichloride (0.68 g, 1.1 mmol) was slurried into toluene (20 ml) and MeMgI (0.71 ml, 3 M in $Et_2O$) was then added and the reaction was stirred at 70° C. for 16 hours. The reaction was cooled to room temperature and 1,4-dioxane (0.38 ml) was added. The mixture was stirred for 15 minutes and solids were removed by filtration on CELITE and washed by $Et_2O$. Volatiles were then removed under vacuo. The product slowly became a solid, to which was added 0.5 ml of pentane. This was swirled and cooled at −35° C. for 3 hours, and pentane was pipetted away. Final product ($C_{28}H_{40}Hf$) was isolated as a solid (0.4 g), which was analyzed by 1H NMR (CD2Cl2, 400 MHz): δ 7.38 (s, 1H), 6.97 (d, J=1.4 Hz, 1H), 5.34 (dd, J=2.9, 0.8 Hz, 1H), 5.27 (d, J=2.9 Hz, 1H), 2.99-2.88 (m, 4H), 2.80 (dd, J=13.5, 5.8 Hz, 1H), 2.04 (p, J=7.3 Hz, 2H), 1.93-1.79 (m, 17H), 0.93 (d, J=6.5 Hz, 3H), 0.85 (d, J=6.4 Hz, 3H), −1.08 (s, 2H), −2.14 (s, 3H).

Dimethylsilyl(tetramethylcyclopentadienyl)(1-isobutylindenyl)Hafnium dimethyl (Catalyst I.C)

Indenyl Lithium: To a solution of indene (10 g, 86.1 mmol) was slowly added 11M nBuLi (7.9 ml, 86.9 mmol) and stirred for 1 hour. Then all $Et_2O$ was removed under vacuo and then add pentane into the solution and let it stir for additional 10 minutes then filter to collect the product as a white solid (10.0 g).

Indenyl lithium (6.55 g, 54 mmol) was mixed with isobutyl Bromide (7.35, 54 mmol) in THF (30 ml)/$Et_2O$ (100 ml) and stirred at room temperature for 16 hours. All solvents were removed under vacuo, and the crude product was reslurried into pentane. All solids were removed by filtration on Celite. Then all solvents were removed by a stream of nitrogen. The crude product was isolated as a clear oil. To the solution of the oil (7.9 g, 46 mmol) in $Et_2O$ (50 ml) was slowly added 11M nBuLi (4.17 ml). The reaction stirred at room temperature for 30 minutes. Most $Et_2O$ was removed by a stream of nitrogen. Then pentane was added and the mixture was stirred for 10 minutes. The lithiated product was collected by filtration as a solid (7.85 g) and was used with no further purification. 5.9 g of the solid was then mixed with $CpMe_5HfCl_3$ (13.07 g, 33 mmol) in $Et_2O$ (100 ml) and was stirred overnight. Most $Et_2O$ was then removed by a stream of nitrogen and pentane was added, then filtered to collect the crude product, which was used for the next step with no further purification. The crude Hafnium dichloride (14.65 g, 25.5 mmol) was slurried into toluene (50 ml) and MeMgI (16.3 ml, 3 M in $Et_2O$) was then added and the reaction was stirred at 70° C. for 16 hours. The reaction was cooled to room temperature and 1,4-dioxane was added. The mixture was stirred for 15 minutes and solids were removed by filtration on Celite and was washed by $Et_2O$. All volatiles were then removed under vacuo. 3 ml of pentane was added to help the product solidify. Pure product ($C_{25}H_{36}Hf$) was isolated as a solid (11.0 g), which was analyzed by $^1H$ NMR ($CDCl_3$, 400 MHz): δ 7.63-7.57 (m, 1H), 7.21-7.10 (m, 3H), 5.43 (d, J=2.9, 1H), 5.36 (d, J=2.9 Hz, 1H), 2.85 (dd, J=13.8, 6.0 Hz, 1H), 2.11-1.80 (m, 17H), 0.94 (d, J=6.5 Hz, 3H), 0.87 (d, J=6.5 Hz, 3H), −1.03 (s, 3H), −2.09 (s, 3H).

Synthesis of (Pentamethylcyclopentadienyl)(1-nHexylindenyl)Hafnium dimethyl (21)

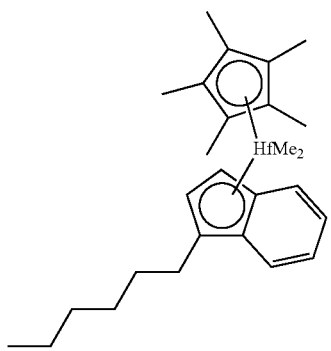

Indenyl lithium (0.90 g, 7 mmol) was mixed with n-hexyl bromide (1.32 g, 7 mmol) in THF (20 ml) and stirred at room temperature for 16 hours. All solvents were removed in vacuo, and the crude product was reslurried into pentane. All solids were removed by filtration on Celite. Then all solvents were removed by a stream of nitrogen. The crude product was isolated as a clear oil. To the solution of the oil (1.52 g, 7 mmol) in $Et_2O$ (20 ml) was slowly added 11M nBuLi (0.65 ml). The reaction stirred at room temperature for 30 minutes. All $Et_2O$ was removed by a stream of nitrogen. Then pentane was added and the mixture was stirred for 10 minutes and then placed under −35° C. for 30 minutes. The lithiated product was collected by filtration as a solid (1.12 g), which was then mixed with $CpMe_5HfCl_3$ (2.11 g, 5 mmol) in $Et_2O$ (15 ml) and was stirred overnight. Most $Et_2O$ was then removed by a stream of nitrogen and pentane was added and then filtered to collect the crude product, which was used for the next step with no further purification. The crude Hafnium dichloride (2.15 g, 3 mmol) was slurried into toluene (20 ml) and MeMgI (2.3 ml, 3 M in $Et_2O$) was then added and the reaction was stirred at 70° C. for 16 hours. The reaction was cooled to room temperature and 1,4-dioxane was added. The mixture was stirred for 15 minutes and solids were removed by filtration on Celite and was washed by $Et_2O$. All volatiles were then removed in vacuo. 1 ml of pentane was added to help the product solidify. Pure product ($C_{27}H_{40}Hf$) was isolated as a solid (1.6 g), which was analyzed by $^1H$ NMR ($CD_2Cl_2$, 400 MHz): δ 7.66-7.59 (m, 1H), 7.24-7.11 (m, 3H), 5.48 (dd, J=2.9, 0.8 Hz, 1H), 5.44 (d, J=2.9 Hz, 1H), 2.91 (ddd, J=14.8, 9.3, 5.6 Hz, 1H), 2.33 (ddd, J=14.5, 9.6, 6.0 Hz, 1H), 1.92 (s, 15H), 1.77-1.59 (m, 1H), 1.57-1.15 (m, 7H), 1.00-0.80 (m, 3H), −1.03 (s, 3H), −2.11 (s, 3H).

Synthesis of (Pentamethylcyclopentadienyl)(1-nButylindenyl)Hafnium dimethyl (22)

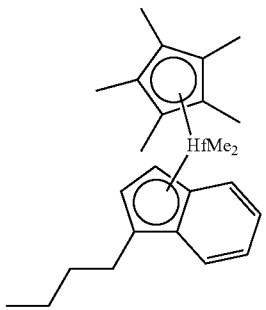

Indenyl lithium (0.80 g, 7 mmol) was mixed with n-butyl bromide (0.90 g, 7 mmol) in THF (20 ml) and stir at room temperature for 16 hours. All solvents were removed under vacuo, and the crude product was reslurried into pentane. All solids were removed by filtration on Celite. Then all solvents were removed by a stream of nitrogen. The crude product was isolated as a clear oil. To the solution of the oil (1.04 g, 6 mmol) in $Et_2O$ (20 ml) was slowly added 11M nBuLi (0.55 ml). Let the reaction stir at room temperature for 30 minutes. All $Et_2O$ was removed by a stream of nitrogen. Then pentane was added and the mixture was stirred for 10 minutes. The lithiated product was collected by filtration as a solid (1.04 g). 0.5 g of the solid was then mixed with $CpMe_5HfCl_3$ (1.16 g, 3 mmol) in $Et_2O$ (15 ml) and was stirred overnight. Most $Et_2O$ was then removed by a stream of nitrogen and pentane was added. Filter to collect the crude product, which was used for the next step with no further purification. The crude Hafnium dichloride (0.88 g, 1 mmol) was slurried into toluene (20 ml) and MeMgI (1 ml, 3 M in Et2O) was then added and the reaction was stirred at 70° C. for 16 hours. The reaction was cooled to room temperature and 1,4 dioxane was added. The mixture was stirred for 15 minutes and solids were removed by filtration on Celite and was washed by Et$_2$O. All volatiles were then removed under vacuo. 1 ml of pentane was added to help the product solidify. Pure product (C$_{25}$H$_{36}$Hf) was isolated as a solid (0.7 g), which was analyzed by $^1$H NMR (CD$_2$Cl$_2$, 400 MHz): δ 7.64-7.56 (m, 1H), 7.22-7.09 (m, 3H), 5.45 (dd, J=2.9, 0.8 Hz, 1H), 5.41 (d, J=2.9 Hz, 1H), 2.95-2.82 (m, 1H), 2.37-2.24 (m, 1H), 1.89 (s, 15H), 1.72-1.56 (m, 1H), 1.53-1.25 (m, 3H), 0.93 (t, J=7.3 Hz, 3H), −1.06 (s, 3H), −2.14 (s, 3H).

Example I.1 (using Catalyst I.A). An about 97% pure 1-decene was fed through an adsorbent column filled with alumina adsorbent to a stainless steel Parr vessel where it was sparged with nitrogen for 1 hour to obtain a purified feed. The catalyst was Catalyst I.A. A catalyst solution including purified toluene, TNOA, and N,N-dimethylanilinium tetrakis(pentafluorophenyl)borate (hereinafter referred to as "Activator 1") was prepared per the following recipe based on 1 gram of Catalyst I.A: Catalyst I.A (1 g), purified toluene (394 g), TNOA (1 g), Activator 1 (1.6 g). The olefin feedstream was added at a rate of about 2,080 grams per hour to a 2. gallon stainless steel Parr reactor held at about 120° C. for oligomerization. The 1-decene and catalyst solution were fed into the reactor at a ratio of about 64,200 grams of LAO per gram of catalyst. The residence time in the reactor was about 2.9 hours. The reactor was run at liquid full conditions, with no addition of any gas. When the system reached steady-state, a reactor effluent was collected and quenched by addition of deionized water. BH-40 was slurried into the reactor effluent at 0.2 wt % and the material taken through a vacuum filtration. The conversion, oligomer distribution, and LAO isomerization was determined by GC. The dimer was then isolated by vacuum distillation. The mole percentage of each type of olefin in the distilled intermediate PAO dimer was determined by proton NMR.

Example I.2 (using Catalyst I.A). Similar to Example I.1 except about 0.66 grams of TNOA was added to the catalyst solution, the oligomerization temperature used was about 140° C., and Catalyst I.A was used at a ratio of about 68,100 g LAO/gCat.

Example I.3 (using Catalyst I.A). Similar to Example I.1 except the oligomerization temperature used was about 130° C., and Catalyst I.A was used at a ratio of about 65,200 g LAO/gCat.

Example I.4 (using Catalyst I.A). Similar to Example I.1 except about 0.75 gram of TNOA was added to the catalyst solution, the oligomerization temperature used was about 140° C., and Catalyst I.A was used at a ratio of about 72,500 g LAO/gCat.

Example I.5 (using Catalyst I.A). Similar to Example I.1 except no TNOA was added to the catalyst solution, the oligomerization temperature used was about 140° C., and Catalyst I.A was used at a ratio of about 74,200 g LAO/gCat.

Example I.6 (using Catalyst I.B). Similar to Example I.1 except 0.75 g of TNOA was added to the catalyst solution, 1.5 g of Activator I was added to the catalyst solution recipe, the oligomerization temperature used was about 135° C., and Catalyst I.A was used at a ratio of about 71,400 g LAO/gCat.

Example I.7 (using Catalyst I.B). Similar to Example I.1 except about 0.75 grams of TNOA was added to the catalyst solution, the oligomerization temperature used was about 140° C., about 1.5 grams of Activator 1 was added to the catalyst solution recipe, and Catalyst I.B was used at a ratio of about 72,100 g LAO/gCat.

Example I.8 (using Catalyst I.B). Similar to Example I.1 except no TNOA was added to the catalyst solution, the oligomerization temperature used was about 140° C., about 1.5 grams of Activator 1 was added to the catalyst solution recipe, and Catalyst 1,B was used at a ratio of about 80,300 g LAO/gCat.

Example I.9 (using Catalyst I.B). Similar to Example I.1 except the oligomerization temperature used was about 148.5° C., about 1.5 grams of Activator 1 was added to the catalyst solution recipe, and Catalyst I.B was used at a ratio of about 67,700 g LAO/gCat.

Example I.10 (using Catalyst I.B). Similar to Example I.1 except 50 ppmw of TNOA was additionally added in-line with the 1-decene prior to addition to the oligomerization reactor, the oligomerization temperature used was about 130° C., about 1.5 grams of Activator 1 was added to the catalyst solution recipe, and Catalyst I.B was used at a ratio of about 82,300 g LAO/gCat.

Example I.11 (using Catalyst I.B). Similar to Example I.1 except 50 ppmw of TNOA was additionally added in-line with the 1-decene prior to addition to the oligomerization reactor, the oligomerization temperature used was about 105° C., about 1,5 grams of Activator 1 was added to the catalyst solution recipe, and Catalyst I.B was used at a ratio of about 82,600 g LAO/gCat.

Example I.12 (using Catalyst I.B). Similar to Example I.1 except the oligomerization temperature used was about 148° C., about 1.5 grams of Activator 1 was added to the catalyst solution recipe, and Catalyst I.B was used at a ratio of about 70,000 g LAO/gCat.

Example I.13 (using Catalyst I.C). Similar to Example I.1 except 0.87 g of TNOA was added to the catalyst solution, 1.8 grams of Activator 1 was added to the catalyst solution recipe, and Catalyst I.C was used at a ratio of about 87,200 g LAO/gCat.

Example I.14 (using Catalyst I.C). Similar to Example I.1, except the temperature used was 110° C., 0.87 g of TNOA was added to the catalyst solution, 1.8 grams of Activator 1 was added to the catalyst solution recipe, and Catalyst I.C was used at a ratio of about 87,200 g LAO/gCat.

Example C.Ex.I.1 (using Catalyst C.Cat. A). Similar to Example I.1 except that about the 1-decene flowrate was 3,000 g/hr so that the reactor residence time was about 2 hours, 250 ppmw of TNOA was additionally added in-line with the 1-decene prior to addition to the oligomerization reactor, about 6 grams of TNOA was added to the catalyst batch recipe, about L9 grams of Activator I was added to the catalyst solution recipe, and Catalyst C.Cat. A was added at a ratio of about 33,500 g LAO/gCat.

Three of the Hf-based metallocene catalysts that demonstrate the dimer selective process to produce olefins having very high vinylidene content and very low vinylene content are shown in Scheme 1. The comparative catalyst, C.Cat. A, is also shown in Scheme 1:

Scheme 1

(I-A)

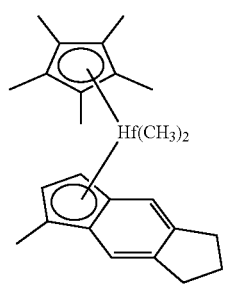

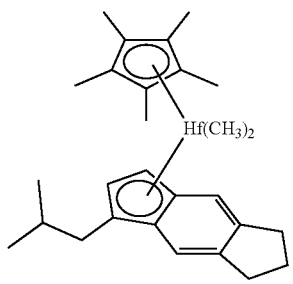

(I-B)

Figure 3:
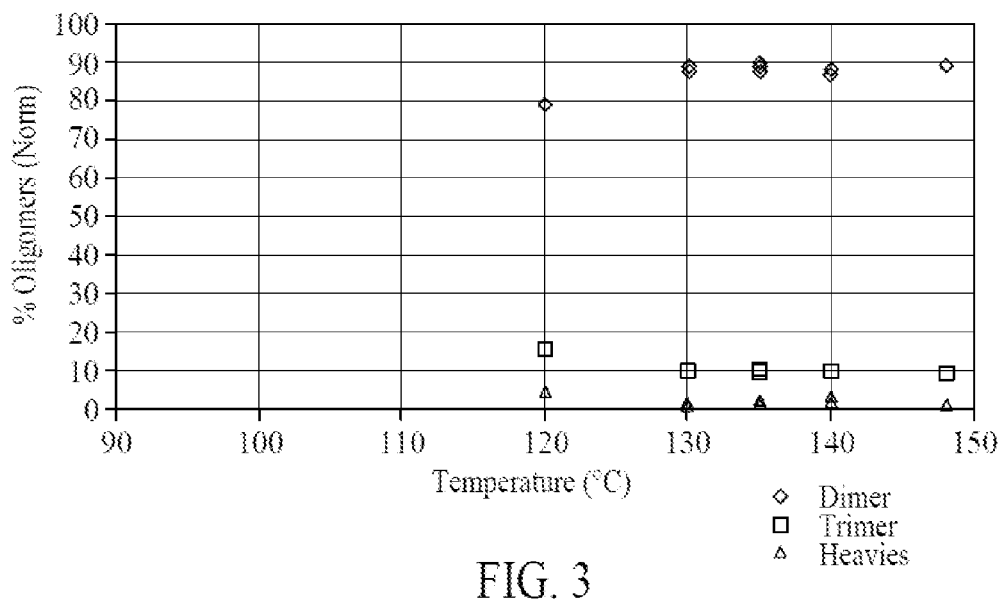
FIG. 3 is a plot of oligomer distribution at various temperatures according to at least one embodiment.
Figure 4:
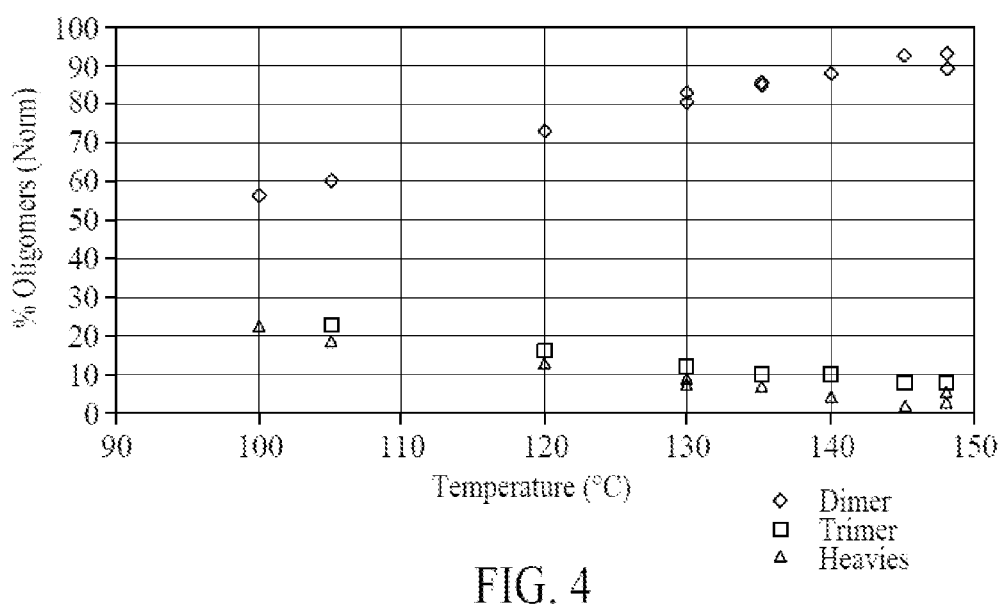
FIG. 4 is a plot of oligomer distribution at various temperatures according to at least one embodiment.
Figure 5:
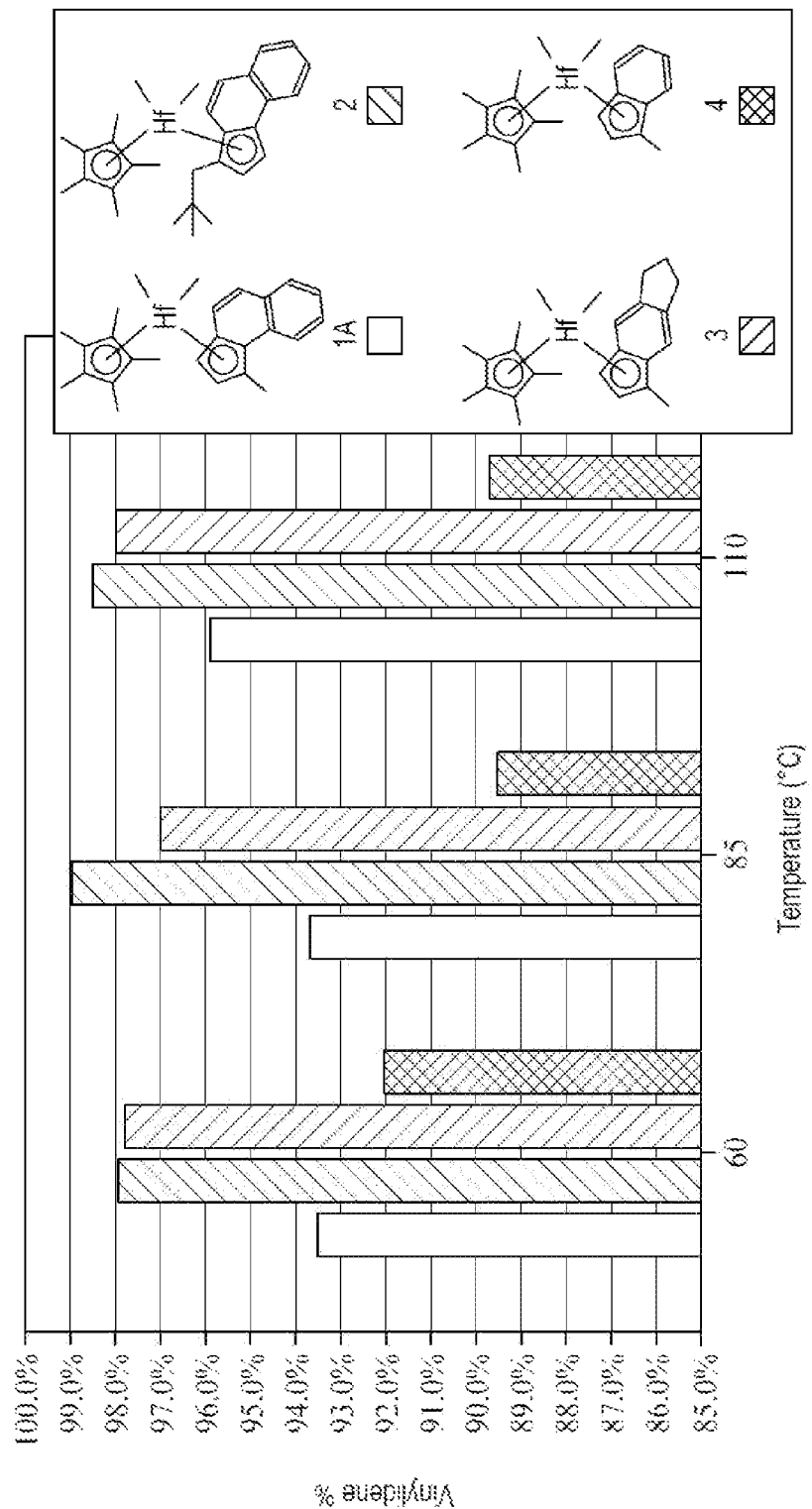
FIG. 5 is a bar graph comparing mole percent vinylidene according to the polymerization temperature of catalysts according to at least one embodiment.
Figure 6:
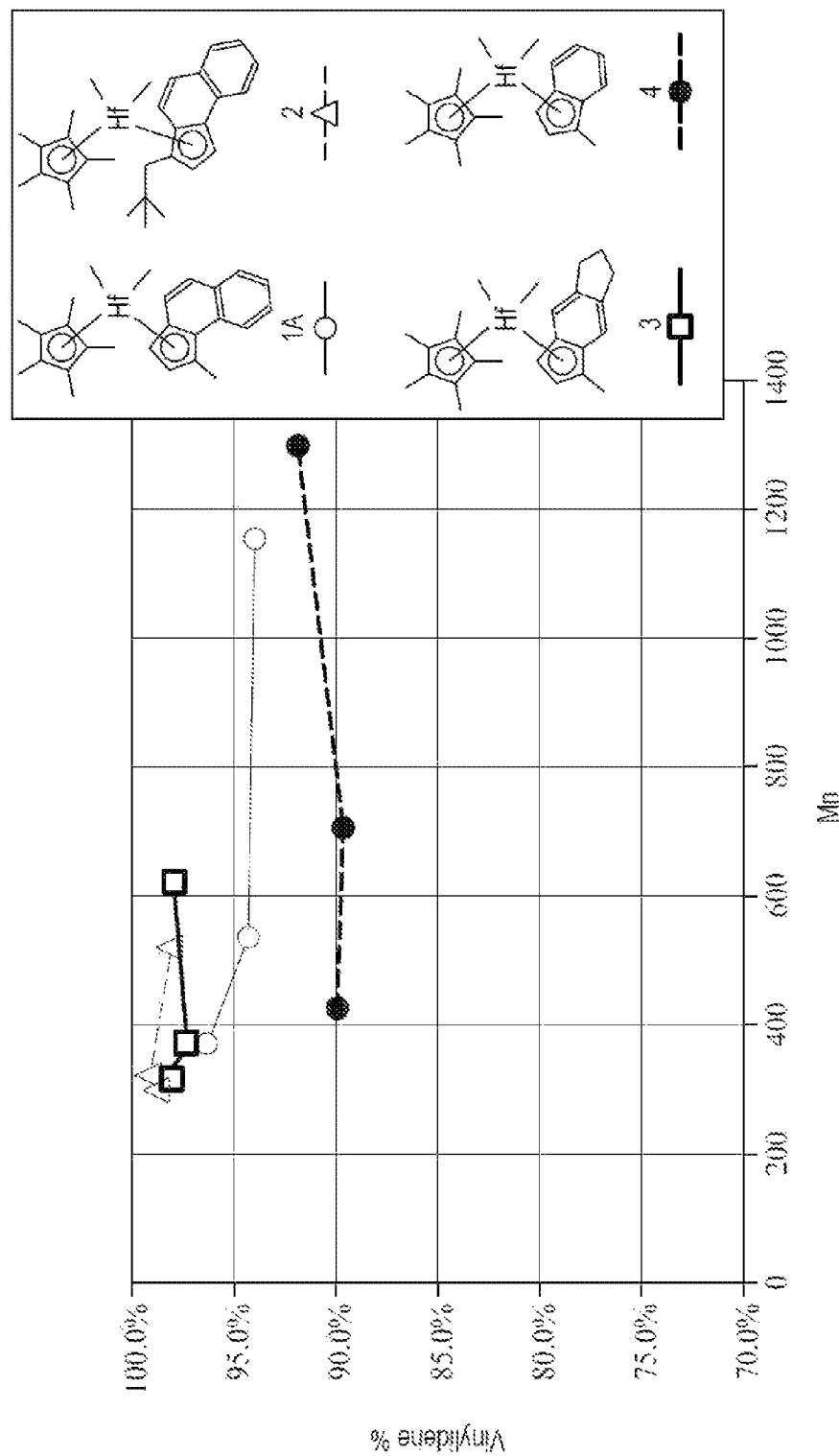
FIG. 6 is a graph comparing mole percent vinylidene versus $M_n$ of 1-decene oligomers produced using catalysts and methods according to at least one embodiment.

FIG. 3 (Catalyst I.A) and FIG. 4 (Catalyst I.B) are plots of the oligomer distributions (dimer, trimer, and heavies) produced by the metallocene dimer selective process at various temperatures. Both Catalyst I.A and Catalyst I.B produce dimer ($C_{20}$) selectivity of about 87% or more with very low trimer and heavies content (higher oligomers of alpha olefin).

Tables 2 and 3 show various characteristics of the oligomerization for inventive Examples such as Dimer Selectivity, distributions of the olefins in terms of mole percentages of each type as determined by $^1$H NMR, the catalyst productivity, the catalyst activity, the LAO conversion, and LAO isomerization.

TABLE 2

| Sample | Cat. | Dimer Selectivity | Vinylidene (mol %) | Trisubstituted Vinylene (mol %) | Vinylene (mol %) | Cat. Productivity (gPAO/gCat) | Cat Activity (gPAO/sec mol cat) | LAO Conversion (wt %) | LAO Isomerization (wt %) |
|---|---|---|---|---|---|---|---|---|---|
| Ex. I.1 | I.A | 78.9 | 96.4 | 3.3 | 0.3 | 52,300 | 2,480 | 81 | 1.8 |
| Ex. I.2 | I.A | 90.1 | 94.9 | 4.8 | 0.3 | 58,500 | 2,780 | 86 | 2.6 |
| Ex. I.3 | I.A | 88.7 | N/D | N/D | N/D | 58,500 | 2,780 | 90 | 1.9 |
| Ex. I.4 | I.A | 89.6 | N/D | N/D | N/D | 60,100 | 2,860 | 83 | 2.2 |
| Ex. I.5 | I.A | 85.8 | N/D | N/D | N/D | 49,200 | 2,140 | 66 | 2.0 |
| Ex. I.6 | I.B | 91.2 | 97.9 | 2.0 | 0.1 | 60,700 | 3,000 | 85 | 12 |
| Ex. I.7 | I.B | 92.6 | N/D | N/D | N/D | 62,500 | 3,090 | 87 | 2.5 |
| Ex. I.8 | I.B | 81.7 | N/D | N/D | N/D | 23,800 | 1,170 | 30 | 1.6 |
| Ex. I.9 | I.B | 93.3 | N/D | N/D | N/D | 55,700 | 2,750 | 82 | 2.5 |
| Ex. I.10 | I.B | 79.7 | 97.8 | 2.0 | 0.2 | 61,000 | 3,010 | 74 | 1.9 |
| Ex. I.11 | I.B | 59.3 | N/D | N/D | N/D | 52,700 | 2,600 | 64 | 1.5 |
| Ex. I.12 | I.B | 92.2 | N/D | N/D | N/D | 57,100 | 2,820 | 82 | 2.6 |
| Ex. I.13 | I.C | 91.9 | 96.8 | 3.0 | 0.2 | 68,200 | 2,980 | 78 | 2.6 |
| Ex. I.14 | I.C | 88.1 | N/D | N/D | N/D | 73,500 | 3,200 | 84 | 2.4 |
| C.Ex. I.1 | C.Cat A | 43.6 | 48.8 | 41.1 | 10.0 | 31,800 | 1,830 | 95 | 2.7 |

-continued (I-C)

TABLE 3

| Sample | Cat. | Cat. Productivity (gPAO/gCat) | Cat Activity (g PAO/sec mol cat) | LAO Conversion (wt %) | LAO Isomerization (wt %) |
|---|---|---|---|---|---|
| Ex. I.1 | I.A | 52,300 | 2,480 | 81 | 1.8 |
| Ex. I.2 | I.A | 58,500 | 2,780 | 86 | 2.6 |
| Ex. I.3 | I.A | 58,500 | 2,780 | 90 | 1.9 |
| Ex. I.4 | I.A | 60,100 | 2,860 | 83 | 2.2 |
| Ex. I.5 | I.A | 49,200 | 2,340 | 66 | 2.0 |
| Ex. I.6 | I.B | 60,700 | 3,000 | 85 | 2.2 |
| Ex. I.7 | I.B | 62,500 | 3,090 | 87 | 2.5 |
| Ex. I.8 | I.B | 23,800 | 1,170 | 30 | 1.6 |
| Ex. I.9 | I.B | 55,700 | 2,750 | 82 | 2.5 |
| Ex. I.10 | I.B | 61,000 | 3,010 | 74 | 1.9 |
| Ex. I.11 | I.B | 52,700 | 2,600 | 64 | 1.5 |
| Ex. I.12 | I.B | 57,100 | 2,820 | 82 | 2.6 |
| Ex. I.13 | I.C | 68,200 | 2,980 | 78 | 2.6 |
| C.Ex. I.1 | C.C at A | 31,800 | 1,830 | 95 | 2.7 |

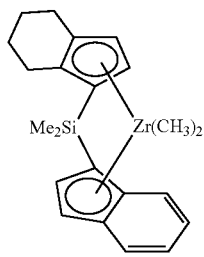

(C.Cat. A)

With reference to Tables 2 and 3, the inventive catalysts show much higher dimer selectivities than the control catalyst (C.Cat. A). The unsaturations present within the dimer species produced by Catalyst I.A, Catalyst I.B, and Catalyst I.C in comparison to the conventional catalyst C.Cat. A are also shown. The dimers produced by Catalyst I.A, Catalyst I.B, and Catalyst I.C contain less than about 0.5 mol % vinylenes, about 3 mol % trisubstituted vinylenes, and greater than about 96 mol % vinylidene. In contrast, the conventional catalyst produces a very high amount of vinylenes at about 8 mol % and a relatively minimal amount of vinylidene at about 49 mol %. The inventive catalysts also show a much higher catalyst productivity than the conventional catalyst. The catalyst productivity almost doubles that of the conventional catalyst.

Overall, the metallocene catalysts described herein can selectively dimerize alpha-olefins to a product having very high vinylidene content and very low vinylene content. In terms of processing, the catalyst productivity is significantly higher than conventional catalysts. Moreover, the catalysts show a much higher conversion to PAO dimer and less unreacted alpha-olefin monomer relative to conventional catalysts. Further the novel metallocene catalysts show a much lower conversion to PAO trimer, PAO tetramer, and higher oligomers of alpha-olefin relative to conventional catalysts.

VII. B Examples—Process for Producing PAO Trimers from PAO Dimers

Metallocene dimer samples were prepared by oligomerizing a $C_{10}$ LAO using an example metallocene catalyst (Catalyst I.A or Catalyst I.B) or a comparative catalyst (C.Cat. A), followed by a distillation. Their yield to the desired hybrid trimer product can be compared.

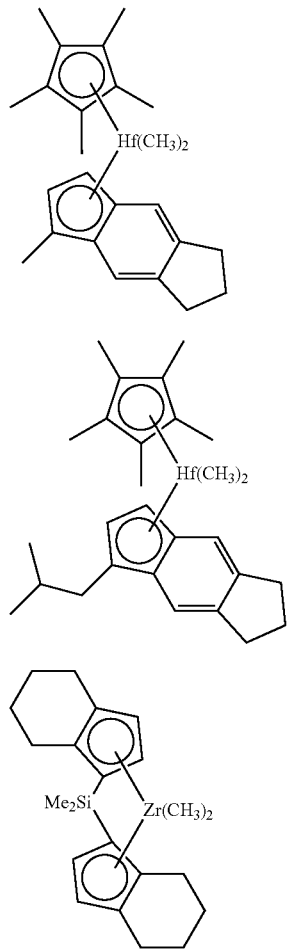

Example Procedure for the $BF_3$-Catalyzed Reaction Using a Batch Reactor

Sample Ex. II.1: Example dimer was produced using the following procedure: An about 97% pure 1-decene was fed through an adsorbent column filled with alumina to a stainless steel Parr vessel where it was sparged with nitrogen for 1 hour to obtain a purified feed. A catalyst solution including purified toluene, TNOA, and N,N-dimethylanilinium tetrakis(pentafluorophenyl)borate (hereinafter referred to as "Activator 1") was prepared per the following recipe based on 1 gram of Catalyst I.A: Catalyst I.A (1 g), purified toluene (394 g), TNOA (1 g), Activator 1 (1.6 g), 200 g of 1-decene was pre-charged into a 2 gallon stainless steel Parr reactor and heated to 85° C. Then, additional 1-decene was fed at 1040 g/hr co-currently with catalyst solution, which was fed at 0.19 mL/min. The reactor was filled over a period of 2 hours at which point the feeds were stopped. The reactor was pressured up to 25 psi under a nitrogen atmosphere and held for 3 hours at a constant 85° C. After 3 hours, the reactor effluent was discharged, quenched by addition of water, and the reactor effluent collected in a product can. 0.2% cellulose was slurried into the reactor effluent and vacuum filtered. Then, dimer was isolated by vacuum batch distillation. Using 1H NMR, the approximate unsaturation distribution was 97 mol % vinylidene, 3 mol % trisubstituted vinylene, and ~0 mol % disubstituted vinylene.

The Example Dimer produced from the above procedure was mixed with 1-octene in a composition of about 50 mol % metallocene PAO dimer and about 50 mol % 1-octene and degassed by pulling a light vacuum in a Parr reactor. The catalyst system used was butanol/butyl acetate in a molar ratio of about 1:1, saturated with $BF_3$. About 496 grams of the degassed olefin mixture was added along with the catalyst component (fed at a ratio of about 15 mmol/100 g olefin) and fed into a 2 L stainless steel Parr reactor over the span of about 1 hour. The reactor temperature was about 21° C. and pressure held at about 140 kPa (about 20 psia) under a $BF_3$ atmosphere. After about 1 hour, the reaction continued to react for about 4 hours before the reactor effluent was discharged into a vessel filled with 10% caustic. The resultant sample was water washed and the oil phase analyzed by GC.

Sample C.Ex. II.1: For the comparative example, the same procedure as above for Sample Ex. II.1 was used except the metallocene PAO dimer is Comparative Dimer made per the procedure described in C.Ex. I.1.

Example Procedure for the $BF_3$-Catalyzed Reaction Using a CSTR

Sample Ex. II.2: Example dimer was collected as a composite from the procedures described in Ex. I.1 and Ex. I.11. The unsaturated distribution of this composite was approximated at roughly 97 mol % vinylidene, 3 mol % trisubstituted vinylene, and ~0 mol % disubstituted vinylene.

A composite of the Example Dimer from the sections above was taken and mixed with 1-decene in a composition of about 50 mol % metallocene dimer and 50 mol % 1-decene and degassed by pulling a light vacuum in a Parr reactor. The catalyst system used was butanol/butyl acetate in a molar ratio of about 1:1, saturated with $BF_3$. The olefin mixture was added along with the catalyst component (fed at a ratio of about 15 mmol/100 g olefin) and into a series of two 2 L stainless steel Parr reactor. The reactor temperature for both reactors was about 21° C. and held under about 140 kPa (about 20 psia) of $BF_3$ atmosphere. The residence time of the first reactor was about 1.6 hours and the residence time of the second reactor was about 0.8 hours. The product was collected in a vessel filled with 10% caustic, water washed, and a sample of the oil phase was taken by GC.

Sample C.Ex. II.2: For the comparative example, the same procedure as above for Sample Ex. II.2 was used except the metallocene PAO dimer is Comparative Dimer as described in C.Ex. I.1.

TABLE 4

| Sample | PAO Dimer | Product Mixture from Second Oligomerization-Batch Reactor | | |
|---|---|---|---|---|
| | | Dimer, wt % | Trimer, wt % | Tetramer+, wt % |
| Ex. II.1 | Example Dimer | 9.0 | 82.9 | 8.1 |
| C.Ex. II.1 | Comparative Dimer | 25.9 | 63.7 | 10.4 |

| Sample | PAO Dimer | Product Mixture from Second Oligomerization-CSTR | | |
|---|---|---|---|---|
| | | Dimer, wt % | Trimer, wt % | Tetramer+, wt % |
| Ex. II. | Example Dimer | 4.0 | 82.7 | 13.3 |
| C.Ex. II.2 | Comparative Dimer | 8.6 | 75.7 | 15.7 |

Table 4 shows that use of the Example Dimer in the second oligomerization process provides significant yield advantages for the desired PAO trimer product. The yield advantage over the Comparative Dimer in the second oligomerization is likely due to the quality of the dimer entering the second oligomerization process because the disubstituted and trisubstituted vinylenes do not react in the second oligomerization process. For example, the desired trimer product is formed at a very high yield of about 83 wt % from the Example Dimer, which has a much higher percentage of vinylidene (about 97 mol %) with little to no disubstituted vinylene (about 0 mol %) and very low amounts of trisubstituted vinylene (about 3 mol %). This is an improvement over the conventional dimer for the second oligomerization process by about 20 wt % In addition, the conversion is much better for the example dimer. For example, there is much less dimer in the example product mixture (less than about 9 wt %) relative to the comparative product mixture (about 26 wt %). With respect to the CSTR conditions, use of the example dimer generates significantly higher yields of the desired PAO trimer product, even when using identical reactor conditions in a single continuous run. As shown in Table 4, there is an improvement in yield of more than about 7 wt %.

The "trimer region" (25 to 27.5 minutes) of the GC spectra from Ex. II.2 was assessed to identify different trimer isomers. Peak regions 1, 2, and 3 illustrate isomerized trimer species. Peak 4 (at about 27 minutes) is the "hybrid trimer" peak. An integration of the peak area shows the following composition: Peak 1—2.3 wt %; Peak 2—3.5 wt %; Peak 3—9.5 wt %; Peak 4—84.6 wt %.

The "trimer region" (25 to 27.5 minutes) of the GC spectra from C.Ex. 112 was assessed to identify different trimer isomers. Peak regions 1, 2, and 3 illustrate isomerized trimer species. Peak 4 (at about 27 minutes) is the "hybrid trimer" peak. An integration of the peak area shows the following composition: Peak 1—2.1 wt %, Peak 2—5.9 wt %; Peak 3—11.4 wt %; Peak 4—80.6 wt %.

Within the trimer region, peak 4 is present at 84.6 wt % in Ex.II.2 and 80.6 wt % in C.Ex.II.2. So in addition to Ex. II.2 creating a greater quantity of trimer, of the types of trimer species being formed, Ex. II.2 provided a higher concentration of hybrid trimer species as a result of the improved processing conditions, which can provide improved product properties.

Moreover, the second oligomerization process according to the present disclosure uses significantly less catalyst than conventional processes. Conventional processes use about 30 mmol of catalyst per 100 g LAO. The second oligomerization process described herein can be performed using from about 0.5 mmol to about 15 mmol of catalyst per 100 g LAO, such as from about 5 to about 15 mmol of catalyst per 100 g LAO. Furthermore, the second oligomerization process according to the present disclosure can be performed at temperatures below 32° C., whereas conventional processes are performed at 32° C.

The second oligomerization process described herein shows that a lower amount of disubstituted vinylene in the PAO dimer of the intermediate PAO can be more important than a higher amount of vinylidene in the PAO dimer of the intermediate PAO. A higher quality dimer is a dimer having a low amount of disubstituted vinylene and, optionally, a lower amount of trisubstituted vinylene. The data shows a large increase in the yield of the trimer can be effected by making a higher quality dimer. In addition, the selectivity towards the trimer over the undesired tetramer and heavies can be tuned by making a higher quality PAO dimer feedstock. Reducing the amount of disubstituted vinylene in the PAO dimer feedstock makes the feedstock more reactive for the second oligomerization process.

Conventional methods of forming hybrid trimers involve reaction of a PAO dimer feedstock that contains a significant amount of disubstituted vinylene. The disubstituted vinylene, however, is not highly reactive when added to a $BF_3$ catalyzed conventional reactor, and the reaction kinetics are very slow. In addition, the unreacted dimer in the stream going into the $BF_3$ catalyzed conventional reactor contaminates the stream produced from the $BF_3$ process and reduces the value of that by-product.

The methods described herein can overcome the problems with conventional methods by, at least, reducing (or eliminating) the amount of disubstituted vinylene in the PAO dirtier feedstock.

VII. C Examples—Apparatus for Producing PAOs

In this example, PAO trimer produced from the metallocene reactor and hybrid trimer produced from the hybrid reactor are both collectively included in the term Trimer. Similarly, tetramer+ produced from the metallocene reactor and tetramer+ produced from the hybrid reactor are both collectively included in the term tetramer+.

Table 5 shows a comparison of the product distribution produced by a conventional apparatus and an example apparatus in conjunction with a comparative catalyst and an inventive catalyst. The conventional apparatus can have the configuration in FIG. 1 and can utilize either the conventional, non-dimer selective catalyst C.Cat. A or the inventive catalyst.

The example apparatus can have the same configuration as shown in FIG. 2 and can utilize either the conventional, non-dimer selective catalyst C.Cat. A or the inventive catalyst.

Using the inventive catalyst increases the yield of trimer from 66 kTa to 83 kTa when using the conventional apparatus. This is a result of the high dimer selectivity afforded with use of the inventive catalyst.

Using the inventive apparatus in conjunction with the comparative catalyst decreases the trimer yield from 66 kTa to 46 kTa. However, with the use of the inventive catalyst, the trimer yield can actually increase from 66 kTa to 75 kTa using this inventive and simplified apparatus.

TABLE 5

| Apparatus | Amounts (kTa) | | | | | |
|---|---|---|---|---|---|---|
| | LAO Feed 1 | LAO Feed 2 | Monomer/Catalyst Component Purge | Dimer | Trimer | Tetramer+ |
| Conventional (C. Cat. A) | 91 | 9 | 1 | 4 | 66 | 30 |
| Example III.1 (Catalyst I.B) | 88 | 12 | 1 | 4 | 83 | 13 |
| Example III.2 (C. Cat. A) | 100 | — | 1 | 3 | 46 | 50 |
| Example III.3 (with Catalyst I.B) | 100 | — | 1 | 7 | 75 | 17 |

Values are shown in kilotons per annum (kTa), and are approximate values.

Conventional Metallocene PAO reactor effluent was generated with the same procedure as C. Ex. I. The expected yields using the conventional apparatus was estimated had the mPAO dimer been reacted in the second oligomerization as described in C.Ex. II.2.

Example III.1. Metallocene PAO reactor effluent was generated by the procedure described in Ex. I.12. The expected yields using the conventional apparatus were estimated had the mPAO dimer been reacted in the second oligomerization as described in Ex II.2.

Example III.2. Metallocene PAO reactor effluent was generated with the same procedure as C. Ex. I. The expected yields using the inventive apparatus after the second oligomerization step as described in C.Ex II.2 were estimated.

Example III.3. Metallocene PAO reactor effluent was generated in the same manner as described as Ex. I.12. The expected yields using the inventive apparatus were determined with use of the following procedure:

The metallocene PAO reactor effluent was mixed with additional 1-decene at a ratio of about 90% metallocene PAO reactor effluent, about 10% additional 1-decene. This mixture was sent to a degas vessel held at a light vacuum. The catalyst system used was butanol/butyl acetate in a molar ratio of about 1:1, saturated with $BF_3$. The olefin mixture was added along with the catalyst component (fed at a ratio of about 15 mmol/100 g olefin) and into a series of two 2 L stainless steel Parr reactor. The reactor temperature for both reactors was about 21° C. and held under about 140 kPa (about 20 psia) of $BF_3$ atmosphere. The residence time of the first reactor was about 0.7 hours and the residence time of the second reactor was about 1.6 hours. The product was collected in a vessel, quenched with caustic, water washed, and a sample of the oil phase was taken by GC.

Table 6 shows the product distribution from the second oligomerization step.

TABLE 6

| Second Oligomerization Effluent | Example III.3 (wt %) |
|---|---|
| Monomer & other lights | 1 |
| Dimer | 7 |
| Trimer | 75 |
| Tetramer+ & other heavies | 17 |

The novel metallocene catalyst enables the production of a desirable metallocene reactor product distribution having very low amounts of trimers, tetramers, and higher oligomers. The novel metallocene dimer also enables the production of a desirable PAO dimer composition having very low amounts of vinylenes. Because the product distribution of the metallocene reactor product has such low amounts of undesired products, the metallocene reactor product can be fed directly to the second oligomerization reactor and without the use of a separation stage. The novel design allows the reduction of costs and the simplification of operation, while significantly improving the desired product yield.

In another variant, an amount of trimer can be blended with the tetramer+ as a stream in order to reduce the viscosity of the bottom product. In one example, the bottom stream will have 20% trimer in its composition in order to reduce the viscosity of the bottoms product stream to around a kinematic viscosity at 100° C. of 6 cSt. This can be beneficial to create a high-valued co-product. The resulting products to be produced would be as follows:

TABLE 7

| Apparatus | Amounts (kTa) | | | | | |
|---|---|---|---|---|---|---|
| | LAO Feed 1 | LAO Feed 2 | Monomer/Catalyst Component Purge | Dimer | Trimer | 20% trimer and 80% Tetramer+ |
| Conventional (C. Cat A) | 91 | 9 | 1 | 4 | 59 | 36 |
| Conventional (Catalyst I.B) | 88 | 12 | 1 | 4 | 79 | 17 |
| Example III.1 (C. Cat. A) | 100 | — | 1 | 3 | 33 | 63 |
| Example III.2 (with Catalyst I.B) | 100 | — | 1 | 7 | 71 | 71 |

Values are shown in kilotons per annum (kTa), and are approximate values.

As shown in Table 7, the novel catalyst still shows improved yields of the preferred total trimer product even when a portion of it is used to lower the viscosity of the bottoms stream in order to maximize its value.

VII. D Examples—Functionalization of LAO Dimers and Trimers

Example 5 Alkylated Naphthalene from $C_{20}$ mPAO dimer

Overview: A chemical product usable as a lubricant basestock was prepared by alkylating naphthalene with C20=umPAO (dimer of C10=LAO produced using one of the inventive metallocene catalysts described in the present disclosure) with an acid catalyst.

Procedure: A Parr reactor was charged with naphthalene (1.51 mol), a USY-H zeolite catalyst (2.0 wt. %), and an inert hydrocarbon solvent (2.0 wt. %). The mixture was heated to 200° C. with stirring. C20=umPAO olefin (1.35 mol) was added to the reactor over a period of 60 minutes.

The reactor temperature was increased to 210° C. for 90 minutes. Heating was discontinued and the reactor contents filtered through Celite to remove catalyst. The filtrate was subjected to vacuum distillation to remove unreacted naphthalene and unreacted C20=umPAO olefin. The distillation pot bottoms contained a mixture of monoalkylated and dialkylated naphthalene. This mixture was collected as the lubricant basestock product.

The properties of the Alkylated Naphthalene derived from the $C_{20}$ mPAO dimer are shown below in Table 8:

TABLE 8

| Property | Units | Method | Value |
|---|---|---|---|
| Wt. % total alkylate after 90 minutes at 210° C. | Wt % | GC | 90.36 |
| Wt. % monoalkylate (of total alkylate) | Wt % | GC | 90.5 |
| Wt. % dialkylate (of total alkylate) | Wt % | GC | 9.5 |

TABLE 8-continued

| Property | Units | Method | Value |
|---|---|---|---|
| Kinematic Viscosity @ 100° C. | cSt | D445 | 6.95 |
| Kinematic Viscosity @ 40° C. | cSt | D445 | 54.1 |
| Viscosity Index | | D2270 | 79 |
| Pour Point | ° C. | D5950 | −51 |
| Noack Volatility | % | D5800 | 5.5 |
| RPVOT | Min | D2272 | 164 |

Example 5.1 Alkylated Naphthalene Testing in Driveline or Electric Vehicle Fluids The Alkylated Naphthalene material isolated in Example 5 was then used to formulate a driveline or electric vehicle fluid.

The table below (Table 9) shows the treat rate of the individual materials. Comparative examples are shown in Blends 2, 3, and 4, which use base stocks that are used widely in the industry today.

TABLE 9

| Driveline/EV blend | |
|---|---|
| Component/Blend # | Blend 1 |
| PAO 4 | 74.50% |
| Yubase 4 | 0.00% |
| mPAO 150 | 0.50% |
| Synnestic 5 | |
| Esterex A32 | |
| Inventive C20 Alkylated Naphthalene (Example 5) | 15.00% |
| HiTec 3491LV | 10.00% |

| Property | | Base on Method | Properties |
|---|---|---|---|
| Kinematic Viscosity @ 100° C. | cSt | ASTM D445 | 5.328 |
| Kinematic Viscosity @ 40° C. | cSt | ASTM D445 | 25.76 |
| Viscosity Index | No-unit | ASTM D2270 | 146 |
| Pour Point | ° C. | ASTM D5950 | |
| Brookfield Viscosity @ −40° C. | cP | ASTM D2983 | 5,010 |
| RPVOT | min | D2272 | 783 |
| Specific Gravity @ 15.6° C. | No-unit | ASTM D4052 | 0.839 |

| Driveline/EV blend | | | |
|---|---|---|---|
| Component/Blend # | Blend 2 | Blend 3 | Blend 4 |
| PAO 4 | 75.40% | 72.80% | |
| Yubase 4 | | | 89.00% |
| mPAO 150 | 4.60% | 2.20% | 1.00% |
| Synnestic 5 | | 15.00% | |
| Esterex A32 | 10.00% | | |
| Inventive C20 Alkylated Naphthalene (Example 5) | | | |
| HiTec 3491LV | 10.00% | 10.00% | 10.00% |

| Property | | Base on Method | Properties | | |
|---|---|---|---|---|---|
| Kinematic Viscosity @ 100° C. | cSt | ASTM D445 | 5.662 | 5.634 | 5.493 |
| Kinematic Viscosity @ 40° C. | cSt | ASTM D445 | 26.04 | 27.50 | 26.33 |
| Viscosity Index | No-unit | ASTM D2270 | 167 | 150 | 152 |
| Pour Point | ° C. | ASTM D5950 | | | |
| Brookfield Viscosity @ −40° C. | cP | ASTM D2983 | 4,470 | 8,060 | 12,380 |

TABLE 9-continued

| RPVOT | min | D2272 | 1461 | 904 | |
|---|---|---|---|---|---|
| Specific Gravity @ 15.6° C. | No-unit | ASTM D4052 | 0.839 | 0.841 | 0.843 |

The inventive $C_{20}$ alkylated naphthalene formulation has much higher viscosity index compared to the commercial example, while maintaining other critical properties such as low temperature performance and good specific gravity (high specific can contribute to higher energy/torque transfer and improved heat transfer).

Example 5.2 Alkylated Naphthalene Testing in Industrial Oils

The Alkylated Naphthalene material isolated in Example 5 was then used to formulate an industrial gear oil.

The table below (Table 10) shows the treat rate of the individual materials. A comparative example is shown in the first and second column using commercial materials available in the market today.

TABLE 10

| | Product | Blend 1 | Blend 2 | Blend 3 |
|---|---|---|---|---|
| | mPAO 150 | 65.00% | 65.00% | 65.00% |
| | PAO 6 | 20.35% | 20.35% | 20.35% |
| | Inventive C20 Alkylated Naphthalene (Example 5) | | | 12.00% |
| | Synnestic 5 | | 12.00% | |
| | Esterex A51 | 12.00% | | |
| | HiTec 307 | 2.65% | 2.65% | 2.65% |
| Totals | | | | |
| 100° C. Kinematic Viscosity, cSt | ASTM D445 | 43.5 | 43.89 | 41.01 |
| 40° C. Kinematic Viscosity, cSt | ASTM D445 | 338.3 | 350.4 | 331.3 |
| Viscosity index | ASTM D2270 | 185.9 | 182.7 | 177.9 |
| Brookfield Viscosity @ −40° C., cP | ASTM D2983 | 353,200 | 465,600 | 366,000 |
| Pour point, ° C. | ASTM D5950 | −51 | −51 | −51 |
| RPVOT, min | D2272 | 187 | 191 | 72 |

In the above example, the gear oil formulated with the inventive example had directionally poorer viscosity index and oxidative stability, with similar Brookfield viscosity to commercial formulations.

Example 5.3 Alkylated Naphthalene Testing in Compressor or Hydraulic Oils

The Alkylated Naphthalene material isolated in Example 5 was then used to formulate a compressor or hydraulic oil.

The table below (Table 11) shows the treat rate of the individual materials. A comparative example is shown in the first column using commercial materials available in the market today.

TABLE 11

| ISO 32 | | |
|---|---|---|
| Product | Blend 1 | Blend 2 |
| SpectraSyn 4 | | 44.13% |
| SpectraSyn 6 | 20.00% | |

TABLE 11-continued

| ISO 32 | | |
|---|---|---|
| Product | Blend 1 | Blend 2 |
| SpectraSyn 8 | 24.13% | |
| Inventive C20 Alkylated Naphthalene (Example 5) | | 55.00% |
| Synnestic 5 | 55.00% | |
| HiTec 521 | 0.87% | 0.87% |
| Properties | | |
| 100° C. Kinematic Viscosity, cSt | ASTM D445 | 5.464 | 5.311 |
| 40° C. Kinematic Viscosity, cSt | ASTM D445 | 30.66 | 30.71 |
| Viscosity index | ASTM D2270 | 115 | 105 |
| Pour Point, ° C. | ASTM D97 | −45 | −63 |
| Flash Point, ° C. | ASTM D93 | >200 | >200 |
| RPVOT, min | ASTM D2272 | 462 | 360 |

In the above example, the compressor or hydraulic fluid formulated with the inventive example had directionally poorer viscosity index and oxidative stability, but with an improved pour point.

Example 6 Alkylated Anisole from $C_{20}$ mPAO Dimer

Overview: A chemical product usable as a lubricant basestock was prepared by alkylating anisole with C20=umPAO (dimer of C10=LAO using one of the inventive metallocene catalysts described in the present disclosure) with an acid catalyst.

Procedure: A reactor was charged with anisole (3.50 mol) and a USY-H zeolite catalyst (2.0 wt %). The mixture was heated to 150° C. with stirring. C20=umPAO olefin (3.12 mol) was added to the reactor over a period of 60 minutes. The reaction continued for an additional 90 minutes. Heating was discontinued and the reactor contents filtered through celite to remove catalyst. The filtrate was subjected to vacuum distillation to remove unreacted anisole and unreacted C20=umPAO olefin. The distillation pot bottoms contained primarily monoalkylated anisole with only trace amounts of dialkylated anisole. This mixture was collected as the lubricant basestock product. The properties of the Alkylated Anisole derived from the C20 mPAO dimer are shown below (Table 12).

TABLE 12

| Test | Units | Method | Value |
|---|---|---|---|
| Wt. % total alkylate 90 minutes after olefin addition at 150° C. | Wt % | GC | 76.2 |
| Wt. % monoalkylate (of total alkylate) | Wt % | GC | >99% |
| Wt. % dialkylate (of total alkylate) | Wt % | GC | <1% |
| Kinematic Viscosity @ 100° C. | cSt | D445 | 4.6 |

TABLE 12-continued

| Test | Units | Method | Value |
|---|---|---|---|
| Kinematic Viscosity @ 40° C. | cSt | D445 | 26.8 |
| Viscosity Index | | D2270 | 72 |
| Pour Point | ° C. | D5950 | −63 |
| Noack Volatility | % | D5800 | 13.0 |
| RPVOT | Min | D2272 | 395 |

Example 6.1 Alkylated Anisole Testing in Driveline or Electric Vehicle Fluids

The Alkylated Anisole material isolated in Example 6 was then used to formulate a driveline or electric vehicle fluid.

The table below (Table 13) shows the treat rate of the individual materials. Comparative examples are shown in Blends 2, 3, and 4, which use base stocks that are used widely in the industry today.

TABLE 13

| Driveline/EV blend | | | | |
|---|---|---|---|---|
| Component/Blend # | | | Blend 1 | Blend 2 |
| PAO 4 | | | 72.80% | 75.40% |
| Yubase 4 | | | 0.00% | 0.00% |
| mPAO 150 | | | 2.20% | 4.60% |
| Synnestic 5 | | | | |
| Esterex A32 | | | | 10.00% |
| Inventive C20 Alkylated Anisole (Example 6) | | | 15.00% | |
| HiTec 3491LV | | | 10.00% | 10.00% |
| Property | | Base on Method | Property | |
| Kinematic Viscosity @ 100° C. | cSt | ASTM D445 | 5.959 | 5.662 |
| Kinematic Viscosity @ 40° C. | cSt | ASTM D445 | 30.10 | 26.04 |
| Viscosity Index | No-unit | ASTM D2270 | 148 | 167 |
| Pour Point | ° C. | ASTM D5950 | −69 | loaded |
| Brookfield Viscosity @ −40° C. | cP | ASTM D2983 | 6,860 | 4,470 |
| RPVOT | min | D2272 | 1073 | 1461 |
| Specific Gravity @ 15.6° C. | No-unit | ASTM D4052 | 0.841 | 0.839 |

| Driveline/EV blend | | | | |
|---|---|---|---|---|
| Component/Blend # | | | Blend 3 | Blend 4 |
| PAO 4 | | | 72.80% | |
| Yubase 4 | | | 0.00% | 89.00% |
| mPAO 150 | | | 2.20% | 1.00% |
| Synnestic 5 | | | 15.00% | |
| Esterex A32 | | | | |
| Inventive C20 Alkylated Anisole (Example 6) | | | | |
| HiTec 3491LV | | | 10.00% | 10.00% |
| Property | | Base on Method | Property | |
| Kinematic Viscosity @ 100° C. | cSt | ASTM D445 | 5.634 | 5.493 |
| Kinematic Viscosity @ 40° C. | cSt | ASTM D445 | 27.50 | 26.330 |
| Viscosity Index | No-unit | ASTM D2270 | 150 | 152 |
| Pour Point | ° C. | ASTM D5950 | | |
| Brookfield Viscosity @ −40° C. | cP | ASTM D2983 | 8,060 | 12,380 |
| RPVOT | min | D2272 | 904 | |
| Specific Gravity @ 15.6° C. | No-unit | ASTM D4052 | 0.841 | 0.843 |

The formulation containing the inventive alkylated anisole had excellent low temperature properties, and excellent oxidative stability (indicated by RPVOT results). The inventive-containing formulation also has higher specific gravity than Blend 2, and comparable specific gravity to Blend 3 and 4. High specific gravity formulations can contribute to higher energy/torque transfer and improved heat transfer.

Example 6.2 Alkylated Anisole Testing in Industrial Oils

The Alkylated Anisole material isolated in Example 6 was then used to formulate an industrial gear oil.

The table below (Table 14) shows the treat rate of the individual materials. A comparative example is shown in the first and second column using commercial materials available in the market today.

TABLE 14

| Product | | Blend 1 | Blend 2 | Blend 3 |
|---|---|---|---|---|
| mPAO 150 | | 65.00% | 65.00% | 65.00% |
| PAO 6 | | 20.35% | 20.35% | 20.35% |
| Inventive C20 Alkylated Anisole (Example 6) | | | | 12.00% |
| Synnestic 5 | | | 12.00% | |
| Esterex A51 | | 12.00% | | |
| HiTec 307 | | 2.65% | 2.65% | 2.65% |
| Totals | | | | |
| 100° C. Kinematic Viscosity, cSt | ASTM D445 | 43.5 | 43.89 | 43.9 |
| 40° C. Kinematic Viscosity, cSt | ASTM D445 | 338.3 | 350.4 | 353.3 |
| Viscosity index | ASTM D2270 | 185.9 | 182.7 | 181.6 |
| Brookfield Viscosity @ −40° C., cP | ASTM D2983 | 353,200 | 465,600 | 360,000 |
| Pour point, ° C. | ASTM D5950 | −51 | −51 | −54 |
| RPVOT, min | D2272 | 187 | 191 | 91 |

In the above example, the gear oil formulated with the inventive example had directionally poorer viscosity index and oxidative stability, with similar Brookfield viscosity to commercial formulations.

Example 6.3 Alkylated Anisole Testing in Compressor or Hydraulic Oils

The Alkylated Anisole material isolated in Example 6 was then used to formulate a compressor or hydraulic oil.

The table below (Table 15) shows the treat rate of the individual materials. A comparative example is shown in the first column using commercial materials available in the market today.

TABLE 15

| | ISO 32 | |
|---|---|---|
| Product | Blend 1 | Blend 2 |
| SpectraSyn 4 | | |
| SpectraSyn 6 | 20.00% | 15.00% |
| SpectraSyn 8 | 24.13% | 29.13% |
| C20-Alkyl Anisole | | 55.00% |
| Synnestic 5 | 55.00% | |
| HiTec 521 | 0.87% | 0.87% |
| Properties | | |
| 100° C. Kinematic Viscosity, cSt | ASTM D445 | 5.464 | 5.501 |

TABLE 15-continued

| | ISO 32 | | |
|---|---|---|---|
| | Product | Blend 1 | Blend 2 |
| 40° C. Kinematic Viscosity, cSt | ASTM D445 | 30.66 | 31.33 |
| Viscosity index | ASTM D2270 | 115 | 112 |
| Pour Point, ° C. | ASTM D97 | −45 | −66 |
| Flash Point, ° C. | ASTM D93 | >200 | >200 |
| RPVOT, min | ASTM D2272 | 462 | 371 |

In the above example, the compressor or hydraulic fluid formulated with the inventive example had directionally poorer viscosity index and oxidative stability, but with an improved pour point.

VII. E Examples—First Oligomerization

Synthesis of catalysts I.C and 21-22 was described in earlier section.

Synthesis of the following catalysts and characterization thereof, as well as polymerizations using the catalysts can be found in U.S. Ser. No. 16/270,085, filed Feb. 7, 2019.

TABLE 16

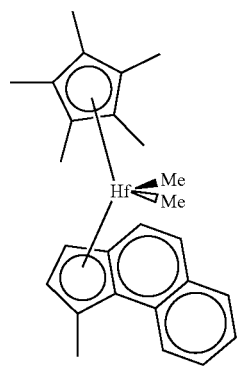

1A

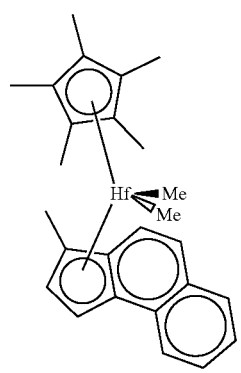

B

TABLE 16-continued
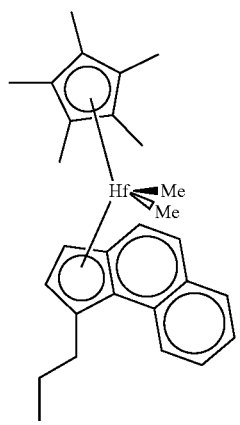
C
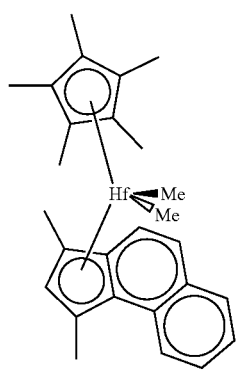
D
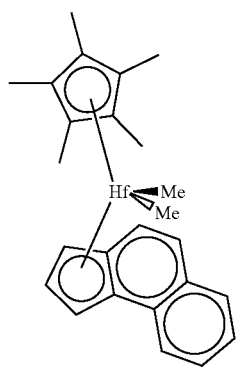
E
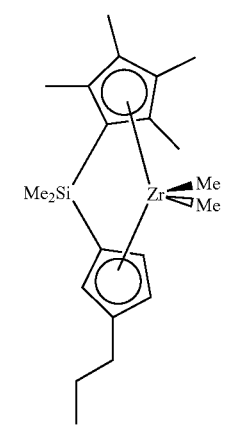
F (comparative)
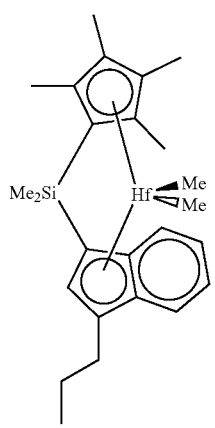
G (comparative)
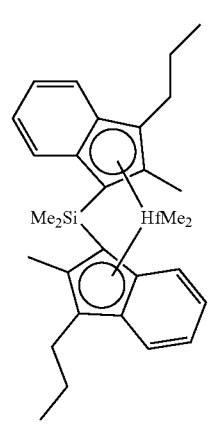
H (comparative)
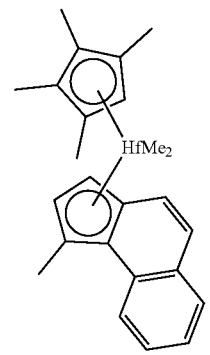
J
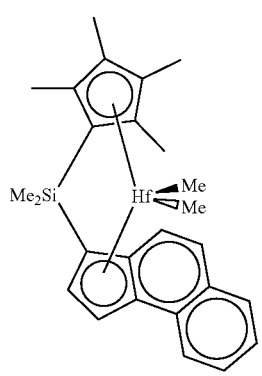
K (comparative)

TABLE 16-continued
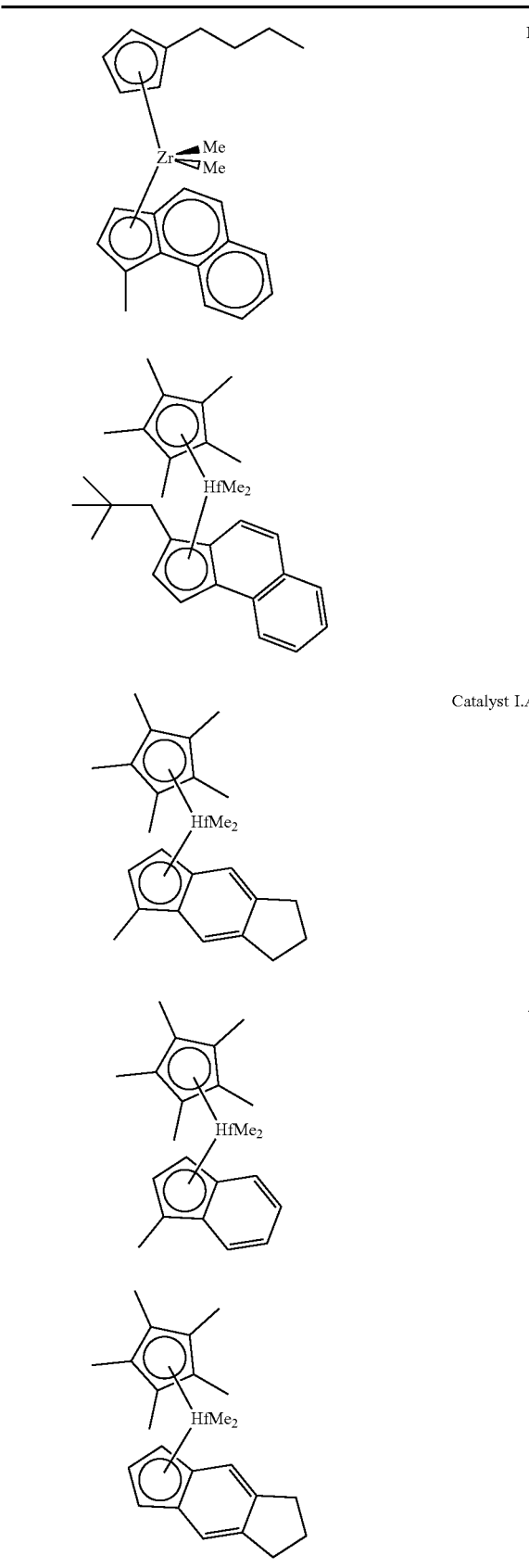
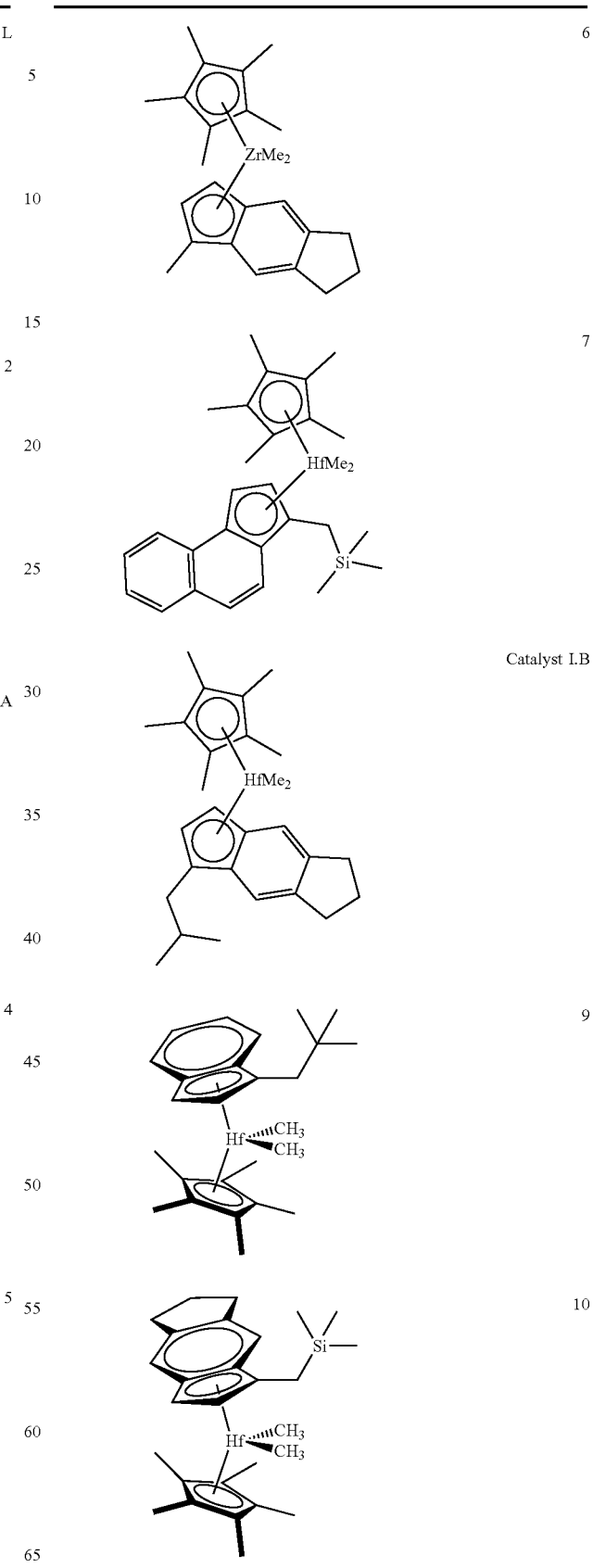

TABLE 16-continued
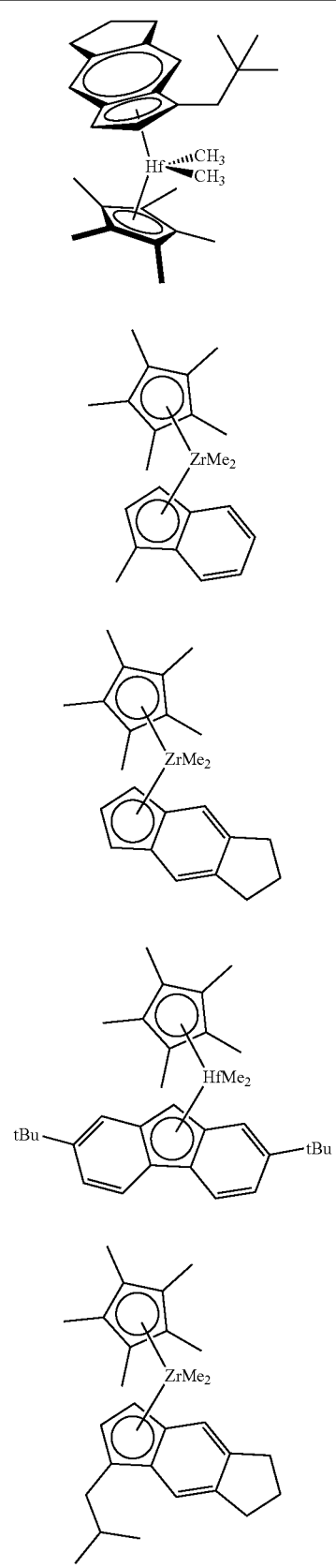
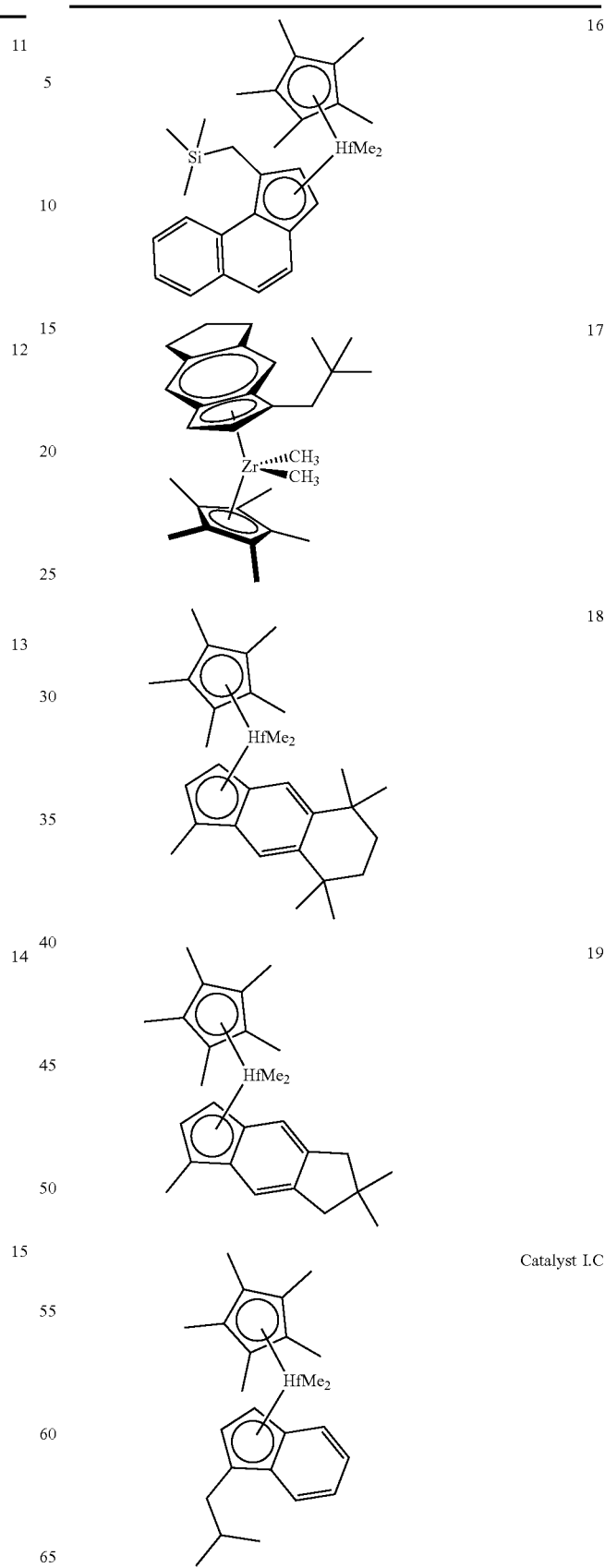

TABLE 16-continued

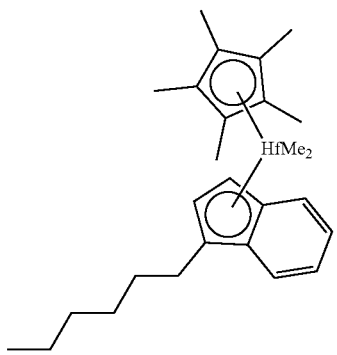

21

TABLE 16-continued

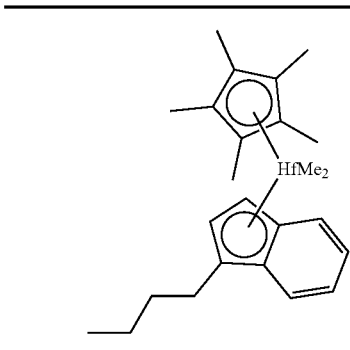

22

TABLE 16

Catalyst 0.08 (0.4 mmol/l in toluene) (MC), with 0.08 μmol N,N-Dimethylanilinium Tetrakisperfluorophenylborate (Activator 1) activator (0.4 mmol/l in toluene), about 0.6 μmol of TNOA (0.01 mol/l in isohexane), 2mL 1-Decene, isohexane solvent, 1 h.

| Ex. # | | MC | Conditions Temp (° C.) | Activity (g/ s · mol) | Olefins Distribution (%) Di | Vi | Tri | Vd | Yield (g) | Mn* (g/ mol) | Conv. %** | % Vinyl-idene (avg) | Mn* (avg) (g/mol) |
|---|---|---|---|---|---|---|---|---|---|---|---|---|---|
| 1 | a | 1A | 60 | 1370 | 0.7 | 3.6 | 2.6 | 93.1 | 0.394 | 1166 | 26.6 | 93.5 | 1153 |
|   | b |    | 60 | 1420 | 0.5 | 3.4 | 2.3 | 93.8 | 0.409 | 1140 | 27.6 |      |      |
| 2 | a | 1A | 85 | 2320 | 0.3 | 3.3 | 2.6 | 93.7 | 0.669 | 555  | 45.1 | 93.8 | 538  |
|   | b |    | 85 | 2050 | 0.4 | 3.1 | 2.7 | 93.8 | 0.589 | 520  | 39.7 |      |      |
| 3 | a | 1A | 110 | 2810 | 0.2 | 1.0 | 2.9 | 96.0 | 0.809 | 371 | 54.6 | 95.9 | 372 |
|   | b |    | 110 | 2810 | 0.2 | 1.2 | 2.8 | 95.8 | 0.809 | 372 | 54.6 |      |     |
| 4 | a | B  | 60 | 721 | 0.3 | 4.5 | 3.8 | 91.4 | 0.208 | 1282 | 14.0 | 91.4 | 1285 |
|   | b |    | 60 | 745 | 0.0 | 4.6 | 4.1 | 91.3 | 0.215 | 1287 | 14.5 |      |      |
| 5 | a | B  | 85 | 1460 | 0.3 | 5.1 | 4.3 | 90.3 | 0.421 | 632 | 28.4 | 89.8 | 636 |
|   | b |    | 85 | 1470 | 0.4 | 5.5 | 4.8 | 89.3 | 0.424 | 640 | 28.6 |      |     |
| 6 | a | B  | 110 | 2170 | 0.2 | 3.3 | 5.3 | 91.2 | 0.625 | 413 | 42.2 | 91.2 | 415 |
|   | b |    | 110 | 2250 | 0.2 | 3.4 | 5.4 | 91.1 | 0.649 | 417 | 43.8 |      |     |
| 7 | a | 1A/B | 60 | 1090 | 0.5 | 3.8 | 2.8 | 92.9 | 0.314 | 1203 | 21.2 | 92.6 | 1191 |
|   | b | (1:1) | 60 | 1100 | 0.7 | 3.8 | 3.2 | 92.3 | 0.318 | 1178 | 21.5 |     |      |
| 8 | a | 1A/B | 85 | 1940 | 0.7 | 4.3 | 4.3 | 90.6 | 0.558 | 572 | 37.7 | 91.4 | 581 |
|   | b | (1:1) | 85 | 1900 | 0.4 | 4.2 | 3.3 | 92.1 | 0.547 | 589 | 36.9 |     |     |
| 9 | a | IA/B | 110 | 2280 | 0.3 | 3.1 | 4.0 | 92.6 | 0.658 | 402 | 44.4 | 93.1 | 405 |
|   | b | (1:1) | 110 | 2680 | 0.2 | 2.5 | 3.8 | 93.5 | 0.772 | 408 | 52.1 |     |     |
| 10 | a | C | 60 | 555 | — | 2.7 | 2.5 | 94.7 | 0.160 | 967 | 10.8 | 94.5 | 982 |
|    | b |   | 60 | 651 | — | 3.1 | 2.7 | 94.2 | 0.188 | 996 | 12.7 |      |     |
| 11 | a | C | 85 | 1440 | — | 3.9 | 3.4 | 92.8 | 0.416 | 535 | 28.1 | 93.5 | 541 |
|    | b |   | 85 | 1220 | — | 3.1 | 2.7 | 94.2 | 0.351 | 546 | 23.7 |      |     |
| 12 | a | C | 110 | 2980 | — | 1.6 | 3.0 | 95.5 | 0.860 | 361 | 58.0 | 95.5 | 361 |
|    | b |   | 110 | 3290 | — | 1.4 | 3.2 | 95.4 | 0.947 | 361 | 63.9 |      |     |
| 13 | a | D | 60 | 3820 | 0.9 | 23.0 | 3.4 | 72.6 | 1.10 | 3004 | 74.2 | 72.9 | 3039 |
|    | b |   | 60 | 3830 | 0.9 | 22.9 | 3.0 | 73.2 | 1.10 | 3074 | 74.2 |      |      |
| 14 | a | D | 85 | 4340 | 1.2 | 12.0 | 4.3 | 82.5 | 1.25 | 987 | 84.3 | 83.3 | 1012 |
|    | b |   | 85 | 4360 | 0.5 | 12.2 | 3.2 | 84.1 | 1.26 | 1036 | 85.0 |     |      |
| 15 | a | D | 110 | 4130 | 0.5 | 5.9 | 3.4 | 90.2 | 1.19 | 578 | 80.3 | 90.0 | 577 |
|    | b |   | 110 | 4140 | 0.5 | 6.5 | 3.2 | 89.8 | 1.19 | 576 | 80.3 |     |     |
| 16 | a | E | 60 | 4240 | 3.7 | 6.4 | 3.8 | 86.1 | 1.22 | 4550 | 82.3 | 85.3 | 4445 |
|    | b |   | 60 | 4270 | 3.9 | 6.1 | 5.5 | 84.5 | 1.23 | 4339 | 83.0 |      |      |
| 17 | a | E | 85 | 4540 | 2.3 | 2.1 | 6.8 | 88.8 | 1.31 | 1285 | 88.4 | 88.8 | 1288 |
|    | b |   | 85 | 4600 | 2.3 | 1.9 | 7.1 | 88.7 | 1.32 | 1291 | 89.1 |     |      |
| 18 | a | E | 110 | 4050 | 1.4 | 4.1 | 6.1 | 88.4 | 1.17 | 729 | 78.9 | 87.7 | 723 |
|    | b |   | 110 | 4050 | 1.8 | 4.3 | 7.0 | 86.9 | 1.17 | 717 | 78.9 |     |     |
| 19 | a | F[c] | 60 | 4370 | 3.3 | — | 7.3 | 89.4 | 1.26 | 1048 | 85.0 | 89.2 | 1044 |
|    | b |      | 60 | 4350 | 3.4 | — | 7.5 | 89.0 | 1.25 | 1040 | 84.3 |      |      |
| 20 | a | F[c] | 85 | 4380 | 4.1 | — | 11.6 | 84.3 | 1.26 | 551 | 85.0 | 84.3 | 551 |
|    | b |      | 85 | 4450 | 4.1 | — | 11.6 | 84.2 | 1.28 | 550 | 86.4 |     |     |
| 21 | a | F[c] | 110 | 4230 | 5.7 | — | 16.5 | 77.8 | 1.22 | 402 | 82.3 | 77.8 | 409 |
|    | b |      | 110 | 4240 | 5.6 | — | 16.8 | 77.7 | 1.22 | 415 | 82.3 |     |     |
| 22 | a | G[c] | 60 | 1600 | 0.8 | 6.0 | 9.8 | 83.3 | 0.462 | 3519 | 31.2 | 83.4 | 3612 |
|    | b |      | 60 | 1540 | 0.9 | 6.0 | 9.8 | 83.4 | 0.443 | 3704 | 29.9 |      |      |
| 23 | a | G[c] | 85 | 2120 | 1.2 | 8.3 | 12.9 | 77.5 | 0.610 | 1311 | 41.2 | 78.9 | 1321 |
|    | b |      | 85 | 1990 | 0.5 | 7.6 | 11.6 | 80.2 | 0.572 | 1330 | 38.6 |      |      |

TABLE 16-continued

Catalyst 0.08 (0.4 mmol/l in toluene) (MC), with 0.08 μmol N,N-Dimethylanilinium Tetrakisperfluorophenylborate (Activator 1) activator (0.4 mmol/l in toluene), about 0.6 μmol of TNOA (0.01 mol/l in isohexane), 2mL 1-Decene, isohexane solvent, 1 h.

| Ex. # | | MC | Conditions Temp (° C.) | Activity (g/ s · mol) | Olefins Distribution (%) Di | Vi | Tri | Vd | Yield (g) | Mn* (g/ mol) | Conv. %** | % Vinyl- idene (avg) | Mn* (avg) (g/mol) |
|---|---|---|---|---|---|---|---|---|---|---|---|---|---|
| 24 | a | G<sup>c</sup> | 110 | 1740 | 1.0 | 8.7 | 15.8 | 74.6 | 0.502 | 702 | 33.9 | 74.9 | 702 |
| | b | | 110 | 1520 | 0.9 | 8.6 | 15.4 | 75.1 | 0.438 | 701 | 29.6 | | |
| 25 | a | H<sup>c</sup> | 60 | 2480 | — | 33.4 | 19.4 | 47.2 | 0.713 | 6554 | 48.1 | 49.2 | 6863 |
| | b | | 60 | 2590 | — | 33.4 | 15.4 | 51.2 | 0.745 | 7172 | 50.3 | | |
| 26 | a | H<sup>c</sup> | 85 | 3050 | 0.7 | 37.5 | 17.2 | 44.6 | 0.880 | 2167 | 59.4 | 44.6 | 2212 |
| | b | | 85 | 2600 | 0.9 | 37.4 | 17.2 | 44.5 | 0.748 | 2256 | 50.5 | | |
| 27 | a | H<sup>c</sup> | 110 | 1660 | 0.7 | 30.8 | 17.6 | 50.9 | 0.478 | 953 | 32.3 | 51.3 | 892 |
| | b | | 110 | 2280 | 0.9 | 28.6 | 18.9 | 51.7 | 0.658 | 830 | 44.4 | | |
| 28 | a | J | 60 | 1730 | 1.2 | 1.6 | 12.3 | 84.9 | 0.499 | 2386 | 33.7 | 84.3 | 2372 |
| | b | | 60 | 1740 | 1.4 | 1.9 | 12.9 | 83.7 | 0.502 | 2358 | 33.9 | | |
| 29 | a | J | 85 | 2730 | 1.4 | 2.1 | 16.8 | 79.7 | 0.787 | 867 | 53.1 | 79.9 | 878 |
| | b | | 85 | 2870 | 1.3 | 2.0 | 16.6 | 80.0 | 0.826 | 888 | 55.7 | | |
| 30 | a | J | 110 | 2910 | 1.4 | 1.6 | 20.8 | 76.2 | 0.838 | 509 | 56.5 | 76.3 | 511 |
| | b | | 110 | 2890 | 1.3 | 1.5 | 20.9 | 76.3 | 0.832 | 513 | 56.1 | | |
| 31 | a | K<sup>c</sup> | 60 | 4120 | 12.3 | 0.0 | 16.0 | 71.6 | 1.19 | 12368 | 80.3 | 67.6 | 12286 |
| | b | | 60 | 3970 | 15.9 | 0.0 | 20.6 | 63.5 | 1.14 | 12203 | 76.9 | | |
| 32 | a | K<sup>c</sup> | 85 | 4570 | 5.5 | 4.3 | 18.2 | 72.1 | 1.32 | 4740 | 89.1 | 72.0 | 4902 |
| | b | | 85 | 4610 | 5.5 | 4.4 | 18.2 | 71.9 | 1.33 | 5064 | 89.7 | | |
| 32 | a | K<sup>c</sup> | 110 | 3830 | 4.3 | 11.3 | 17.3 | 67.1 | 1.10 | 3020 | 74.2 | 66.5 | 3007 |
| | b | | 110 | 3710 | 4.4 | 11.4 | 18.4 | 65.8 | 1.07 | 2993 | 72.2 | | |
| 33 | a | K<sup>c</sup> | 60 | 485 | 9.6 | — | 12.5 | 77.9 | 0.140 | 1930 | 9.4 | 78.2 | 1959 |
| | b | | 60 | 486 | 9.8 | — | 11.8 | 78.4 | 0.140 | 1988 | 9.4 | | |
| 35 | a | L | 85 | 815 | 8.1 | 0.4 | 12.1 | 79.4 | 0.235 | 864 | 15.9 | 79.1 | 863 |
| | b | | 85 | 887 | 8.3 | 0.6 | 12.4 | 78.7 | 0.256 | 861 | 17.3 | | |
| 36 | a | L | 110 | 1330 | 8.9 | 0.4 | 14.2 | 76.5 | 0.383 | 534 | 25.8 | 75.8 | 525 |
| | b | | 110 | 1310 | 9.4 | 0.5 | 15.0 | 75.1 | 0.377 | 515 | 25.4 | | |

*Mn estimated by <sup>1</sup>H NMR;
**Conv. % calculated from isolated yield and it is the minimum conversion due to volatility of the dimer product;
<sup>c</sup>Comparative catalysts and polymerization examples.

TABLE 17

Catalyst 0.08 μmol (0.4 mmol/l in toluene) (MC), with 0.08 μmol N,N-Dimethylanilinium tetrakisperfluoronaphthylborate activator (0.4 mmol/l in toluene), about 0.6 μmol of TNOA (0.01 mol/l in isohexane), 2 mL 1-Decene, isohexane solvent, 1 h.

| Ex. # | | MC | Conditions Temp (° C.) | Activity (g/ s · mol) | Olefins Distribution (%) Di | Vi | Tri | Vd | Yield (g) | Mn* (g/ mol) | Conv. %** |
|---|---|---|---|---|---|---|---|---|---|---|---|
| 37 | a | 1A | 60 | 696 | 1.2 | 7.3 | 8.8 | 82.7 | 0.200 | 1885 | 13.5 |
| | b | | 60 | 663 | 1.1 | 7.2 | 8.6 | 83.2 | 0.191 | 2009 | 12.9 |
| 38 | a | 1A | 85 | 1350 | 0.9 | 7.6 | 7.6 | 83.8 | 0.388 | 772 | 26.2 |
| | b | | 85 | 1280 | 0.6 | 7.4 | 7.4 | 84.6 | 0.369 | 796 | 24.9 |
| 39 | a | 1A | 110 | 2050 | 0.4 | 5.5 | 6.6 | 87.5 | 0.590 | 456 | 39.8 |
| | b | | 110 | 7340 | 0.4 | 5.2 | 6.7 | 87.7 | 0.674 | 460 | 45.5 |
| 40 | a | D | 60 | 2600 | 1.0 | 34.7 | 8.7 | 55.6 | 0.750 | 4353 | 50.6 |
| | b | | 60 | 2500 | 1.7 | 33.2 | 10.3 | 54.8 | 0.719 | 4353 | 48.5 |
| 41 | a | D | 85 | 3280 | 1.0 | 31.9 | 6.4 | 60.7 | 0.946 | 1405 | 63.8 |
| | b | | 85 | 3480 | 0.9 | 30.8 | 7.4 | 60.9 | 1.00 | 1349 | 67.5 |
| 42 | a | D | 110 | 3850 | 1.0 | 19.3 | 5.8 | 73.9 | 1.11 | 657 | 74.9 |
| | b | | 110 | 3690 | 0.7 | 21.8 | 6.6 | 71.0 | 1.06 | 669 | 71.5 |

*Mn estimated by <sup>1</sup>H NMR.
**Conv. % calculated from isolated yield and it is the minimum conversion due to volatility of the dimer product.

TABLE 18

Catalyst 0.08 µmol (0.4 mmol/l in toluene) (MC), with 0.08 µmol N,N-Dimethylanilinium Tetrakisperfluorophenylborate (Activator 1) activator (0.4 mmol/l in toluene), about 0.6 µmol of TNOA (0.01 mol/l in isohexane), 2 mL, 1-Decene, isohexane solvent, 1 h.

| Ex. # | T (° C.) | MC | Isolated Yield (g) | % Vinyl-ene | % Tri-sub | % Vinyl | % Vinyl-idene | Mn* g/mol | % Vinyl-idene (avg) | Mn* (avg) (g/mol) | Conv. %** |
|---|---|---|---|---|---|---|---|---|---|---|---|
| 43A | 60 | 1A | 0.3942 | 0.7 | 2.6 | 3.6 | 93.1 | 1166 | 93.5 | 1153 | 26.6 |
| 43B | 60 | 1A | 0.4087 | 0.5 | 2.3 | 3.4 | 93.8 | 1140 | | | 27.6 |
| 44A | 85 | 1A | 0.6694 | 0.3 | 2.6 | 3.3 | 93.7 | 555 | 93.8 | 537 | 45.2 |
| 44B | 85 | 1A | 0.5894 | 0.4 | 2.7 | 3.1 | 93.8 | 520 | | | 39.8 |
| 45A | 110 | 1A | 0.8086 | 0.2 | 2.9 | 1.0 | 95.9 | 371 | 95.9 | 372 | 54.6 |
| 45B | 110 | 1A | 0.8092 | 0.2 | 2.8 | 1.2 | 95.8 | 372 | | | 54.6 |
| 46A | 60 | 2 | 0.1097 | 0.4 | 1.1 | 0.8 | 97.8 | 504 | 97.9 | 519 | 7.4 |
| 46B | 60 | 2 | 0.1064 | 0.4 | 1.0 | 0.7 | 97.9 | 533 | | | 7.2 |
| 47A | 85 | 2 | 0.194 | 0.1 | 0.8 | 0.1 | 99.0 | 324 | 99.0 | 325 | 13.1 |
| 47B | 85 | 2 | 0.1762 | 0.1 | 0.8 | 0.2 | 98.9 | 327 | | | 11.9 |
| 48A | 110 | 2 | 0.3025 | 0.2 | 1.3 | 0.2 | 98.3 | 303 | 98.5 | 303 | 20.4 |
| 48B | 110 | 2 | 0.2614 | 0.1 | 1.1 | 0.1 | 98.7 | 303 | | | 17.6 |
| 49A | 60 | Cat. I.A | 0.1548 | 0.3 | 0.7 | 0.9 | 98.1 | 622 | 97.7 | 620 | 10.4 |
| 49B | 60 | Cat. I.A | 0.1594 | 0.4 | 1.1 | 1.3 | 97.2 | 618 | | | 10.8 |
| 50A | 85 | Cat. I.A | 0.4458 | 0.8 | 2.1 | 1.2 | 95.9 | 367 | 97.0 | 373 | 30.1 |
| 50B | 85 | Cat. I.A | 0.4442 | 0.2 | 0.9 | 0.7 | 98.2 | 379 | | | 30.0 |
| 51A | 110 | Cat. I.A | 0.8584 | 0.1 | 1.3 | 0.2 | 98.4 | 320 | 98.1 | 317 | 57.9 |
| 51B | 110 | Cat. I.A | 0.8568 | 0.3 | 1.6 | 0.4 | 97.7 | 315 | | | 57.8 |
| 52A | 60 | 4 | 0.1827 | 0.3 | 3.1 | 4.7 | 91.9 | 1313 | 91.9 | 1298 | 12.3 |
| 52B | 60 | 4 | 0.1844 | 0.3 | 3.2 | 4.6 | 91.9 | 1284 | | | 12.4 |
| 53A | 85 | 4 | 0.7312 | 0.1 | 3.5 | 6.7 | 89.8 | 722 | 89.5 | 710 | 49.3 |
| 53B | 85 | 4 | 0.5846 | 0.2 | 4.0 | 6.6 | 89.2 | 699 | | | 39.4 |
| 54A | 110 | 4 | 0.8993 | 0.3 | 4.7 | 5.8 | 89.2 | 426 | 89.8 | 430 | 60.7 |
| 54B | 110 | 4 | 0.9406 | 0.2 | 4.0 | 5.4 | 90.4 | 435 | | | 63.5 |

*Mn estimated by $^1$H NMR;
**Conv % calculated from isolated yield and it is the minimum conversion due to volatility of the dimer product.

TABLE 19

Catalyst 0.08 µmol (0.4 mmol/l in toluene) (MC), with 0.08 µmol N,N-Dimethylanilinium Tetrakisperfluorophenylborate (Activator 1) activator (0.4 mmol/l in toluene), about 0.6 µmol of TNOA (0.01 mol/l in isohexane), 2 mL 1-Decene, isohexane solvent, 1 h.

| Ex. # | T (° C.) | MC | Isolated Yield (g) | % Vinyl-ene | % Tri-sub | % Vinyl | % Vinyl-idene | Mn* g/mol | % Vinyl-idene (avg) | Mn* (avg) (g/mol) | Conv. %** |
|---|---|---|---|---|---|---|---|---|---|---|---|
| 55A | 60 | 5 | 1.2137 | 1.5 | 5.7 | 2.4 | 90.4 | 7552 | 90.4 | 2592 | 81.9 |
| 55B | 60 | 5 | 1.1997 | 1.5 | 5.7 | 2.4 | 90.4 | 7632 | | | 81.0 |
| 56A | 85 | 5 | 1.2801 | 1.2 | 8.9 | 1.2 | 88.8 | 914 | 88.7 | 917 | 86.4 |
| 56B | 85 | 5 | 1.2557 | 1.2 | 9.1 | 1.1 | 88.6 | 921 | | | 84.7 |
| 57A | 110 | 5 | 1.1828 | 1.1 | 11.4 | 1.0 | 86.5 | 534 | 86.1 | 536 | 79.8 |
| 57B | 110 | 5 | 1.2055 | 1.2 | 12.1 | 1.0 | 85.7 | 538 | | | 81.3 |
| 58A | 60 | 6 | 0.0278 | 0.6 | 0.6 | 0.3 | 98.5 | 552 | 98.1 | 551 | 1.9 |
| 58B | 60 | 6 | 0.0285 | 0.6 | 1.1 | 0.6 | 97.6 | 549 | | | 1.9 |
| 59A | 85 | 6 | 0.1436 | 0.4 | 1.0 | 0.4 | 98.2 | 356 | 98.1 | 353 | 9.7 |
| 59B | 85 | 6 | 0.1477 | 0.4 | 1.1 | 0.4 | 98.1 | 351 | | | 10.0 |
| 60A | 110 | 6 | 0.3657 | 0.5 | 1.5 | 0.3 | 97.8 | 313 | 98.1 | 314 | 24.7 |
| 60B | 110 | 6 | 0.3488 | 0.2 | 1.1 | 0.2 | 98.4 | 315 | | | 23.5 |
| 61A | 60 | 7 | 0.1337 | 0.6 | 4.0 | 7.2 | 88.2 | 1919 | 87.2 | 1913 | 9.0 |
| 61B | 60 | 7 | 0.1306 | 0.6 | 5.2 | 7.8 | 86.3 | 1907 | | | 8.8 |
| 62A | 85 | 7 | 0.1532 | 0.5 | 5.4 | 9.3 | 84.8 | 872 | 85.4 | 874 | 10.3 |
| 62B | 85 | 7 | 0.1626 | 0.5 | 4.6 | 8.9 | 86.0 | 876 | | | 11.0 |
| 63A | 110 | 7 | 0.1944 | 0.4 | 4.9 | 8.8 | 85.9 | 507 | 86.2 | 520 | 13.1 |
| 63B | 110 | 7 | 0.2602 | 0.3 | 4.7 | 8.5 | 86.4 | 532 | | | 17.6 |
| 64A | 60 | Cat. I.B | 01246 | 0.5 | 1.2 | 1.0 | 97.3 | 583 | 96.6 | 588 | 8.4 |
| 64B | 60 | Cat. I.B | 0.1245 | 0.5 | 1.9 | 1.8 | 96.0 | 593 | | | 8.4 |
| 65A | 85 | Cat. I.B | 0.4319 | 0.2 | 1.2 | 0.8 | 97.8 | 369 | 97.8 | 368 | 29.1 |

TABLE 19-continued

Catalyst 0.08 µmol (0.4 mmol/l in toluene) (MC), with 0.08 µmol N,N-Dimethylanilinium Tetrakisperfluorophenylborate (Activator 1) activator (0.4 mmol/l in toluene), about 0.6 µmol of TNOA (0.01 mol/l in isohexane), 2 mL 1-Decene, isohexane solvent, 1 h.

| Ex. # | T (° C.) | MC | Isolated Yield (g) | % Vinyl-ene | % Tri-sub | % Vinyl | % Vinyl-idene | Mn* g/mol | % Vinyl-idene (avg) | Mn* (avg) (g/mol) | Conv. %** |
|---|---|---|---|---|---|---|---|---|---|---|---|
| 65B | 85 | Cat. I.B | 0.4452 | 0.2 | 1.2 | 0.7 | 97.9 | 367 | | | 30.0 |
| 66A | 110 | Cat. I.B | 0.8973 | 0.0 | 1.1 | 0.2 | 98.6 | 317 | 98.4 | 317 | 60.5 |
| 66B | 110 | Cat. I.B | 0.9322 | 0.1 | 1.4 | 0.3 | 98.2 | 317 | | | 62.9 |
| 67A | 60 | 9 | 0.0323 | 0.0 | 3.3 | 1.3 | 95.4 | 507 | 95.3 | 513 | 2.2 |
| 67B | 60 | 9 | 0.0326 | 0.0 | 3.3 | 1.6 | 95.1 | 518 | | | 2.2 |
| 68A | 85 | 9 | 0.1665 | 0.0 | 3.2 | 0.7 | 96.1 | 330 | 96.4 | 327 | 11.2 |
| 68B | 85 | 9 | 0.1832 | 0.0 | 3.0 | 0.4 | 96.6 | 325 | | | 12.4 |
| 69A | 110 | 9 | 0.1824 | 0.0 | 2.3 | 0.3 | 97.4 | 309 | 97.3 | 307 | 12.3 |
| 69B | 110 | 9 | 0.226 | 0.0 | 2.5 | 0.4 | 97.1 | 306 | | | 15.2 |
| 70A | 60 | 10 | 0.0695 | 0.5 | 1.3 | 1.3 | 96.8 | 794 | 97.5 | 794 | 4.7 |
| 70B | 60 | 10 | 0.0622 | 0.4 | 1.2 | 0.1 | 98.2 | 794 | | | 4.2 |
| 71A | 85 | 10 | 0.0821 | 0.3 | 1.3 | 2.0 | 96.4 | 490 | 96.7 | 489 | 5.5 |
| 71B | 85 | 10 | 0.0913 | 0.3 | 1.1 | 1.7 | 97.0 | 488 | | | 6.2 |
| 72A | 110 | 10 | 0.1419 | 0.1 | 1.2 | 1.2 | 97.4 | 362 | 97.3 | 361 | 9.6 |
| 72B | 110 | 10 | 0.1801 | 0.2 | 1.3 | 1.3 | 97.2 | 360 | | | 12.2 |
| 73A | 60 | 11 | 0.0917 | 0.3 | 0.8 | 1.0 | 97.9 | 636 | 97.3 | 630 | 6.2 |
| 73B | 60 | 11 | 0.092 | 0.4 | 1.4 | 1.5 | 96.7 | 625 | | | 6.2 |
| 74A | 85 | 11 | 0.2414 | 0.1 | 0.9 | 1.1 | 98.0 | 406 | 98.0 | 399 | 16.3 |
| 74B | 85 | 11 | 0.2651 | 0.1 | 0.9 | 1.0 | 98.0 | 393 | | | 17.9 |
| 75A | 110 | 11 | 0.6764 | 0.0 | 1.2 | 0.5 | 98.3 | 317 | 98.3 | 317 | 45.6 |
| 75B | 110 | 11 | 0.6827 | 0.0 | 1.1 | 0.5 | 98.4 | 317 | | | 46.1 |
| 76A | 60 | 12 | 0.039 | — | — | — | — | — | — | — | 2.6 |
| 76B | 60 | 12 | 0.0351 | — | — | — | — | — | | | 2.4 |
| 77A | 85 | 12 | 0.1596 | 0.3 | 1.5 | 0.2 | 98.0 | 344 | 97.8 | 345 | 10.8 |
| 77B | 85 | 12 | 0.1621 | 0.3 | 1.7 | 0.4 | 97.6 | 346 | | | 10.9 |
| 78A | 110 | 12 | 0.2002 | 0.8 | 2.7 | 0.0 | 96.4 | 311 | 97.2 | 313 | 13.5 |
| 78B | 110 | 12 | 0.2236 | 0.3 | 1.7 | 0.0 | 98.0 | 315 | | | 15.1 |
| 79A | 60 | 13 | 0.5464 | 3.4 | 5.3 | 2.3 | 89.0 | 1191 | 91.0 | 1246 | 36.9 |
| 79B | 60 | 13 | 0.5493 | 2.6 | 3.4 | 1.0 | 93.0 | 1301 | | | 37.1 |
| 80A | 85 | 13 | 0.8176 | 1.6 | 4.5 | 0.6 | 93.4 | 550 | 93.3 | 553 | 55.2 |
| 80B | 85 | 13 | 0.8451 | 1.6 | 4.6 | 0.6 | 93.2 | 557 | | | 57.0 |
| 81A | 110 | 13 | 0.9876 | 1.3 | 6.8 | 0.1 | 91.8 | 382 | 91.9 | 383 | 66.6 |
| 81B | 110 | 13 | 0.9961 | 1.2 | 6.7 | 0.1 | 91.9 | 385 | | | 67.2 |
| 82A | 60 | 14 | 0.0467 | — | — | — | — | — | — | — | 3.2 |
| 82B | 60 | 14 | 0.0462 | — | — | — | — | — | | | 3.1 |
| 83A | 85 | 14 | 0.1268 | 4.0 | 3.7 | 1.8 | 90.5 | 854 | 90.4 | 847 | 8.6 |
| 83B | 85 | 14 | 0.1369 | 3.9 | 3.8 | 1.9 | 90.3 | 839 | | | 9.2 |
| 84A | 110 | 14 | 0.0899 | 2.0 | 5.1 | 2.6 | 90.4 | 593 | 90.6 | 585 | 6.1 |
| 84B | 110 | 14 | 0.0912 | 1.6 | 5.0 | 2.4 | 90.9 | 577 | | | 6.2 |
| 85A | 60 | 15 | 0.0207 | — | — | — | — | — | — | — | 1.4 |
| 85B | 60 | 15 | 0.0209 | — | — | — | — | — | | | 1.4 |
| 86A | 85 | 15 | 0.0974 | 0.3 | 1.4 | 0.9 | 97.4 | 365 | 97.6 | 361 | 6.6 |
| 86B | 85 | 15 | 0.1094 | 0.4 | 1.3 | 0.6 | 97.7 | 358 | | | 7.4 |
| 87A | 110 | 15 | 0.2949 | 1.2 | 2.7 | 0.7 | 96.0 | 298 | 97.2 | 305 | 19.9 |
| 87B | 110 | 15 | 0.3415 | 0.3 | 1.2 | 0.1 | 98.4 | 312 | | | 23.0 |
| 88A | 60 | 16 | 0.1052 | 0.5 | 4.2 | 6.8 | 88.6 | 1780 | 89.3 | 1770 | 7.1 |
| 88B | 60 | 16 | 0.1152 | 0.4 | 3.3 | 6.2 | 90.1 | 1760 | | | 7.8 |
| 89A | 85 | 16 | 0.1241 | 0.6 | 4.9 | 8.9 | 85.6 | 857 | 83.9 | 815 | 8.4 |
| 89B | 85 | 16 | 0.1415 | 1.4 | 7.7 | 8.8 | 82.2 | 773 | | | 9.5 |
| 90A | 110 | 16 | 0.1986 | 0.3 | 5.5 | 10.4 | 83.8 | 661 | 85.3 | 586 | 13.4 |
| 90B | 110 | 16 | 0.2248 | 0.4 | 4.6 | 8.2 | 86.8 | 511 | | | 15.2 |
| 91A | 60 | 17 | 0.0195 | — | — | — | — | — | — | — | 1.3 |
| 91B | 60 | 17 | 0.0189 | — | — | — | — | — | | | 1.3 |
| 92A | 85 | 17 | 0.0735 | — | — | — | — | — | — | — | 5.0 |
| 92B | 85 | 17 | 0.0929 | — | — | — | — | — | | | 6.3 |
| 93A | 110 | 17 | 0.2384 | 0.2 | 1.3 | 0.4 | 98.1 | 314 | 97.1 | 310 | 16.1 |
| 93B | 110 | 17 | 0.2354 | 0.9 | 2.4 | 0.6 | 96.1 | 305 | | | 15.9 |

*Mn estimated by $^1$H NMR;
**Conv % calculated from isolated yield and it is the minimum conversion due to volatility of the dimer product.
"—" indicates insufficient material for analysis or data not available.

TABLE 20

Catalyst 0.04 μmol (0.8 mmol/l in toluene) (MC), with 0.04 μmol N,N-dimethylanilinium tetrakis(perfluoronaphthyl)borate as activator (0.8 mmol/l in toluene), about 0.6 μmol of TNOA (0.01 mol/l in isohexane), 2 mL 1-decene isohexane solvent, 1 h.

| Ex. # | T (° C.) | MC | Isolated Yield (g) | % Vinyl-ene | % Tri-sub | % Vinyl | % Vinyl-idene | Mn* g/mol | % Vinyl-idene (avg) | Mn* (avg) (g/mol) | Conv. %** |
|---|---|---|---|---|---|---|---|---|---|---|---|
| 94A | 85 | 18 | 0.0594 | 0.5% | 6.3 | 5.1 | 88.2 | 521 | 87.6 | 533 | 4.0 |
| 94B | 85 | 18 | 0.0539 | 0.6% | 7.2 | 5.2 | 87.0 | 546 | | | 3.6 |
| 95A | 85 | 19 | 0.1231 | 0.7% | 4.3 | 3.8 | 91.3 | 492 | 91.5 | 496 | 8.3 |
| 95B | 85 | 19 | 0.1287 | 0.6% | 4.2 | 3.5 | 91.7 | 501 | | | 8.7 |

*Mn estimated by $^1$H NMR.
**Conv % calculated from isolated yield and it is the minimum conversion due to volatility of the dimer product.

TABLE 21

Catalyst 0.08 μmol (0.4 mmol/l in toluene) (MC), with 0.08 μmol N,N-Dimethylanilinium Tetrakisperfluorophenylborate (Activator 1) activator (0.4 mmol/l in toluene), about 0.6 μmol of TNOA (0.01 mol/l in isohexane), 2 mL 1-Decene, isohexane solvent, 1 h. Polymerization procedure and characterization method were analogous to that described in USSN 16/270,085.

| Ex. # | T (° C.) | MC | Isolated Yield (g) | % Vinyl-ene | % Tri-sub | % Vinyl | % Vinyl-idene | Mn* g/mol | % Vinyl-idene (avg) | Mn* (avg) (g/mol) | Conv. %** |
|---|---|---|---|---|---|---|---|---|---|---|---|
| 96A | 60 | 4 | 0.2356 | 0.3 | 1.1 | 0.6 | 98.0 | 459 | 98.4 | 455 | 15.9 |
| 96B | 60 | 4 | 0.2440 | 0.2 | 0.8 | 0.4 | 98.6 | 457 | | | 16.5 |
| 97A | 85 | 4 | 0.7848 | 0.1 | 1.0 | 0.3 | 98.6 | 320 | 98.5 | 320 | 53.0 |
| 97B | 85 | 4 | 0.8154 | 0.2 | 1.1 | 0.2 | 98.4 | 319 | | | 55.0 |
| 98A | 110 | 4 | 0.9963 | 0.1 | 1.2 | 0.2 | 98.6 | 303 | 98.3 | 302 | 67.2 |
| 98B | 110 | 4 | 1.0326 | 0.2 | 1.2 | 0.2 | 98.5 | 303 | | | 69.7 |
| 96C | 60 | 4 | 0.2439 | 0.3 | 0.9 | 0.5 | 98.4 | 453 | | | 16.5 |
| 96D | 60 | 4 | 0.2524 | 0.2 | 0.8 | 0.5 | 98.5 | 452 | | | 17.0 |
| 97C | 85 | 4 | 0.7783 | 0.2 | 1.1 | 0.3 | 98.5 | 321 | | | 52.5 |
| 97D | 85 | 4 | 0.8072 | 0.2 | 1.1 | 0.2 | 98.6 | 319 | | | 54.5 |
| 98C | 110 | 4 | 1.0651 | 0.1 | 1.1 | 0.1 | 98.7 | 303 | | | 71.9 |
| 98D | 110 | 4 | 1.0187 | 0.5 | 1.7 | 0.3 | 97.5 | 297 | | | 68.7 |
| 99A | 60 | Cat. I.C | 0.1845 | 0.2 | 1.2 | 0.3 | 98.3 | 418 | 98.3 | 419 | 12.4 |
| 99B | 60 | Cat. I.C | 0.1800 | 0.2 | 1.3 | 0.3 | 98.1 | 414 | | | 12.1 |
| 100A | 85 | Cat. I.C | 0.7116 | 0.2 | 1.7 | 0.2 | 98.0 | 317 | 98.1 | 318 | 48.0 |
| 100B | 85 | Cat. I.C | 0.7393 | 0.1 | 1.5 | 0.2 | 98.2 | 318 | | | 49.9 |
| 101A | 110 | Cat. I.C | 0.9879 | 0.2 | 1.7 | 0.1 | 98.1 | 300 | 98.2 | 301 | 66.7 |
| 101B | 110 | Cat. I.C | 1.0074 | 0.1 | 1.6 | 0.1 | 98.1 | 301 | | | 68.0 |
| 99C | 60 | Cat. I.C | 0.1728 | 0.2 | 1.4 | 0.3 | 98.1 | 420 | | | 11.7 |
| 99D | 60 | Cat. I.C | 0.1675 | 0.1 | 1.1 | 0.3 | 98.5 | 424 | | | 11.3 |
| 100C | 85 | Cat. I.C | 0.7074 | 0.1 | 1.6 | 0.2 | 98.1 | 318 | | | 47.7 |
| 100D | 85 | Cat. I.C | 0.7492 | 0.1 | 1.5 | 0.2 | 98.2 | 318 | | | 50.6 |
| 101C | 110 | Cat. I.C | 0.9942 | 0.1 | 1.5 | 0.1 | 98.3 | 302 | | | 67.1 |
| 101D | 110 | Cat. I.C | 0.9777 | 0.0 | 1.5 | 0.1 | 98.3 | 302 | | | 66.0 |
| 102A | 60 | 21 | 0.3051 | 0.1 | 0.5 | 0.2 | 99.3 | 362 | 99.1 | 360 | 20.6 |
| 102B | 60 | 21 | 0.3027 | 0.2 | 0.6 | 0.2 | 99.0 | 359 | | | 20.4 |
| 103A | 85 | 21 | 0.8871 | 0.1 | 0.7 | 0.1 | 99.1 | 308 | 99.1 | 308 | 59.9 |
| 103B | 85 | 21 | 0.9261 | 0.1 | 0.7 | 0.1 | 99.1 | 308 | | | 62.5 |
| 104A | 110 | 21 | 1.0198 | 0.1 | 0.8 | 0.1 | 99.0 | 299 | 98.9 | 298 | 68.8 |
| 104B | 110 | 21 | 1.0143 | 0.1 | 0.8 | 0.1 | 98.9 | 298 | | | 68.4 |
| 102C | 60 | 21 | 0.2995 | 0.1 | 0.6 | 0.1 | 99.1 | 361 | | | 20.2 |
| 102D | 60 | 21 | 0.3067 | 0.2 | 0.6 | 0.1 | 99.1 | 359 | | | 20.7 |
| 103C | 85 | 21 | 0.8404 | 0.1 | 0.7 | 0.1 | 99.1 | 308 | | | 56.7 |
| 103D | 85 | 21 | 0.9171 | 0.1 | 0.7 | 0.1 | 99.1 | 307 | | | 61.9 |
| 104C | 110 | 21 | 1.0324 | 0.2 | 0.9 | 0.1 | 98.8 | 297 | | | 69.7 |
| 104D | 110 | 21 | 1.0181 | 0.1 | 0.8 | 0.1 | 99.0 | 298 | | | 68.7 |
| 105A | 60 | 22 | 0.1025 | 0.2 | 0.7 | 0.2 | 98.8 | 395 | 98.9 | 397 | 6.9 |

TABLE 21-continued

Catalyst 0.08 μmol (0.4 mmol/l in toluene) (MC), with 0.08 μmol N,N-Dimethylanilinium Tetrakisperfluorophenylborate (Activator 1) activator (0.4 mmol/l in toluene), about 0.6 μmol of TNOA (0.01 mol/l in isohexane), 2 mL 1-Decene, isohexane solvent, 1 h. Polymerization procedure and characterization method were analogous to that described in USSN 16/270,085.

| Ex. # | T (° C.) | MC | Isolated Yield (g) | % Vinyl-ene | % Tri-sub | % Vinyl | % Vinyl-idene | Mn* g/mol | % Vinyl-idene (avg) | Mn* (avg) (g/mol) | Conv. %** |
|---|---|---|---|---|---|---|---|---|---|---|---|
| 105B | 60 | 22 | 0.0976 | 0.2 | 0.7 | 0.2 | 99.0 | 400 | | | 6.6 |
| 106A | 85 | 22 | 0.6733 | 0.1 | 1.0 | 0.1 | 98.7 | 309 | 98.6 | 310 | 45.4 |
| 106B | 85 | 22 | 0.6777 | 0.1 | 1.1 | 0.1 | 98.7 | 310 | | | 45.7 |
| 107A | 110 | 22 | 0.9701 | 0.1 | 1.3 | 0.1 | 98.5 | 297 | 98.3 | 296 | 65.5 |
| 107B | 110 | 22 | 0.9234 | 0.1 | 1.1 | 0.1 | 98.7 | 297 | | | 62.3 |
| 105C | 60 | 22 | 0.1059 | 0.1 | 0.7 | 0.2 | 99.0 | 396 | | | 7.1 |
| 105D | 60 | 22 | 0.0988 | 0.2 | 0.8 | 0.4 | 98.7 | 399 | | | 6.7 |
| 106C | 85 | 22 | 0.6181 | 0.1 | 1.0 | 0.1 | 98.8 | 311 | | | 41.7 |
| 106D | 85 | 22 | 0.6426 | 0.3 | 1.4 | 0.3 | 98.1 | 309 | | | 43.4 |
| 107C | 110 | 22 | 0.9484 | 0.2 | 1.2 | 0.1 | 98.5 | 297 | | | 64.0 |
| 107D | 110 | 22 | 0.8789 | 0.4 | 1.6 | 0.3 | 97.7 | 294 | | | 59.3 |

*Mn in this table estimated by $^1$H NMR using methods described in U.S.S.N. 16/270,085;
**Conv % calculated from isolated yield and it is the minimum conversion due to volatility of the dimer product.

Note that runs in Ex. 52A-54B appear to be outliers as re-runs with metallocene 4 in Ex. 96A-98D all appear to give lower Mn and higher vinylidene % at similar conditions.

VII. F. End Use Examples

Example 1: Isolating $C_{10}$ Dimer+$C_{10}$ LAO ($C_{30}$) Using Inventive Two-Step Process The catalyst batch includes based metallocene catalysts shown in the examples and those mentioned in U.S. Ser. No. 16/270,085, a Lewis acid activator, scavenger and a solvent.

A feed comprising $C_{10}$ alpha-olefin was contacted with the catalyst system described above in a polymerization reactor using the procedure described in Ex. II.2.

The $C_{30}$ material was hydrogenated to a Bromine number less than 1 in a stainless steel Parr reactor at 232° C. and 2413 kPa (350 psi) of hydrogen for 2 hours using 0.5 wt % Nickel catalyst in a slurry reactor. The $C_{30}$ material was vacuum filtered to remove residual catalyst.

The $C_{30}$ material was then analyzed and properties are shown below (Table 22A):

TABLE 22A

| Property | Based on Method | UNIT | Property |
|---|---|---|---|
| Kinematic Viscosity @ 100° C. | ASTM D445 | cSt | 3.516 |
| Kinematic Viscosity @ 40° C. | ASTM D445 | cSt | 14.21 |

TABLE 22A-continued

| Property | Based on Method | UNIT | Property |
|---|---|---|---|
| Viscosity Index | ASTM D2270 | No-unit | 130 |
| Pour Point, ° C. | ASTM D5950 | ° C. | −78 |
| Brookfield @-40° C. | ASTM D2983 | cP | 1,488 |
| Noack Volatility, evaporation loss % | ASTM D5800, Procedure B | wt % | 12.31 |
| RPVOT | ASTM D2272 | minutes | 102 |
| CCS Apparent Viscosity @ −25° C. | ASTM D5293 | cP | 362 |
| CCS Apparent Viscosity @ −30° C. | ASTM D5293 | cP | 571 |
| CCS Apparent Viscosity @ −35° C. | ASTM D5293 | cP | 903 |
| HTHS Apparent Viscosity @ 150° C. | ASTM D5481 | cP | 1.377 |
| MRV Apparent Viscosity @ −40° C. | SWRI/ASTM D4684 | cP | 1,300 |
| Flash point (COC)- open cup | SWRI/ASTM D92 | ° C. | 223 |

The results above indicate that the Co3 material isolated above has excellent low viscosity with exceptional volatility and low-temperature properties. Additionally the oxidative stability (RPVOT) is improved above conventional low vis PAOs produced strictly from Lewis-Acid processing steps.

Example 1.1 $C_{30}$ Testing in Engine Oils

The $C_{30}$ material isolated in the inventive two-step process described in Example 1 was then used to formulate an engine oil.

TABLE 22B

| Engine Oil Component(KV100° C.)/Blend# | Blend 1 0W-20 | Blend 2 0W-20 |
|---|---|---|
| Inventive C30 PAO (Example 1) | 13.00% | 29.20% |
| Gr II 4 cSt | 67.00% | 0.00% |
| Gr II 5 cSt | 0.00% | 50.80% |
| AN 5 | 5.00% | 5.00% |
| Infineum SV203 | 5.00% | 5.00% |

TABLE 22B-continued

| | | | | |
|---|---|---|---|---|
| | | Infineum P6003 ™ | 10.00% | 10.00% |
| | | Total | 100.00% | 100.00% |
| Property | UNIT | Based on Method | | |
| Kinematic Viscosity @ 100° C. | cSt | ASTM D445 | 8.923 | 9.473 |
| Kinematic Viscosity @ 40° C. | cSt | ASTM D445 | 53.89 | 52.59 |
| Viscosity Index | No-unit | ASTM D2270 | 145 | 166 |
| Pour Point | ° C. | ASTM D5950 | −30 | −33 |
| CCS Apparent Viscosity @−25° C. | cP | ASTM D5293 | 2,042 | 2,044 |
| CCS Apparent Viscosity @−30° C. | cP | ASTM D5293 | 3,513 | 3,466 |
| CCS Apparent Viscosiy @−35° C. | cP | ASTM D5293 | 6,493 | 6,193 |
| MRV Apparent Viscosity @−40° C. | cP | SWRI/ASTM D4684 | 44,300 | 28,500 |
| HTHS Apparent Viscosity @ 150° C. | cP | ASTM D5481 | 2.947 | 2.952 |
| Noack Volatility, evaporation loss | wt % | ASTM D5800, Procedure B | 12.02 | 11.18 |

The results above indicate that the $C_{30}$ inventive material provides the engine oil with excellent low temperature properties, even when blended with high concentrations of low-quality Gr II base stocks. The volatility of the blend was also very low, thanks to the low volatility of the $C_{30}$ material.

Example 1.2 $C_{30}$ Testing in Driveline or Electric Vehicle Fluids

The $C_{30}$ material isolated in the inventive two-step process described in Example 1 was then used to formulate a driveline or electric vehicle fluid.

The table below (Table 22C) shows the treat rate of the individual materials. A comparative example is shown in the first column using conventional PAO material, which are derived from standard $BF_3$-catalyst processes.

TABLE 22C

Figure 7:
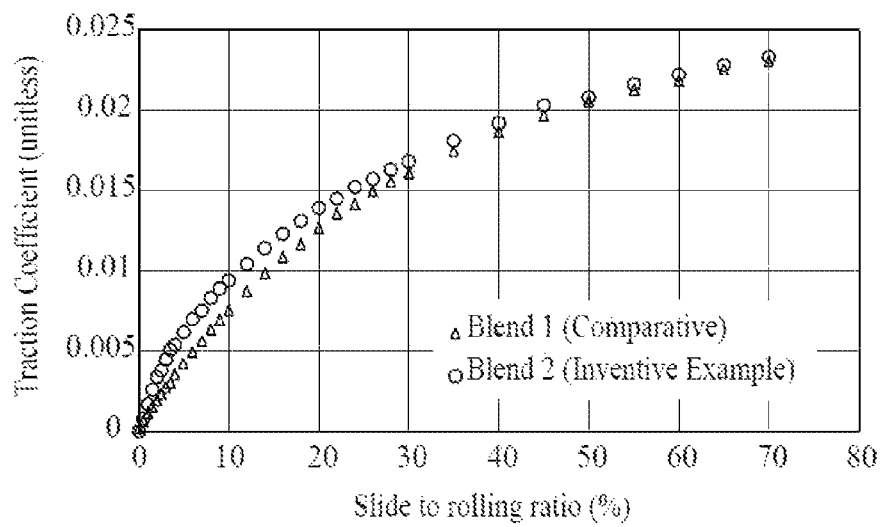
FIG. 7 is a graph illustrating traction coefficient versus slide to rolling ratio (%), according to at least one embodiment.

| | Driveline/EV fluids | | |
|---|---|---|---|
| Component/Blend# | | Blend 1 | Blend 2 |
| Inventive C30 PAO (Example 1) | | | 88.00% |
| PAO 2 | | 15.20% | |
| PAO 4 | | 72.80% | |
| HiTEC 3419D | | 12.00% | 12.00% |
| Property | Base on Method | Data | |
| Kinematic Viscosity @ 100° C. | cSt ASTM D445 | 4.106 | 4.156 |
| Kinematic Viscosity @ 40° C. | cSt ASTM D445 | 18.27 | 17.91 |
| Viscosity Index | No-unit ASTM D2270 | 128 | 139 |
| Pour Point | ° C. ASTM D5950 | −75 | −75 |
| Brookfield Viscosity @−40° C. | cP ASTM D2983 | 2,550 | 2,340 |
| Oxidation Stability, RPVOT | min ASTM D2272 | 686 | 658 |
| Noack Volatility, evaporation loss (200 C.) | % run at 200 C. | 7.118 | 1.69 |
| MTM Traction (80° C.) | | FIG. 7 | |

The viscosity index of the inventive example was much better than standard PAO blend. The volatility was also much lower, since the formulation does not require use of high volatility molecules such as PAO 2. This is an example of how uniquely tailored molecules have advantages over commercial molecules. While the comparative blend has similar viscosity, the inventive example achieves higher viscosity index and drastically lower volatility, which are both highly desirable properties for driveline and electric vehicle fluids.

Example 1.3 $C_{30}$ Testing in Industrial Oils

The $C_{30}$ material isolated in the inventive two-step process described in Example 1 was then used to formulate an industrial gear oil. The benefits exhibited in this example can also be applied to automotive gear oils which have similar formulations approaches.

The table below (Table 23) shows the treat rate of the individual materials. A comparative example is shown in the first column using PAO 4 material, which is a PAO produced from a $BF_3$ catalyzed process and is widely used in the industry.

TABLE 23

Figure 8:
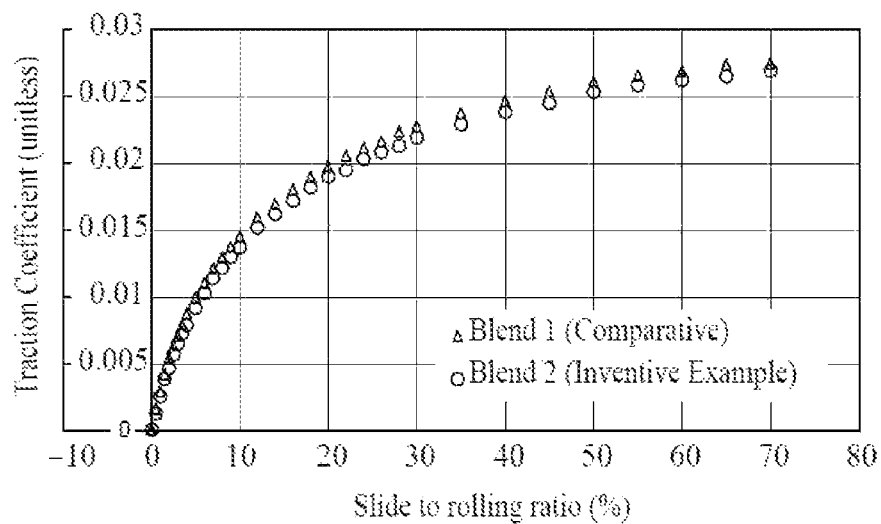
FIG. 8 is a graph illustrating traction coefficient versus slide to rolling ratio (%), according to at least one embodiment.

| | | ISO 320 | |
|---|---|---|---|
| | Product | Blend 1 | Blend 2 |
| | mPAO 150 | 66.35% | 67.61% |
| | SpectraSyn 4 | 19.00% | |
| | Inventive C30 PAO (Example 1) | | 17.74% |
| | Esterex A51 | 12.00% | 12.00% |
| | HiTec 307 | 2.65% | 2.65% |
| 100° C. Kinematic Viscosity, cSt | ASTM D445 | 42.36 | 42.76 |
| 40° C. Kinematic Viscosity, cSt | ASTM D445 | 320.6 | 320.3 |
| Viscosity index | ASTM D2270 | 188 | 190 |
| Brookfield Viscosity @−40° C., cP | ASTM D2983 | 300,600 | 268,200 |
| Pour point, ° C. | ASTM D5950 | −54 | −54 |
| RPVOT (min) | D2272 | 53 | 55 |
| MTM(80° C.) | Standard method | FIG. 8 | |

The inventive material provides, inter alia, two advantages:
- The inventive lower viscosity material allows for wider bi-modal blend of the two primary base stocks (i.e. the viscosity difference is wider between the two PAO base stocks used in each blend), which provides improved viscosity index, and lower traction coefficient compared to the commercial example
- The low-temperature performance of the inventive fluid is better than commercial materials Example 1.4 $C_{30}$ Testing in Compressor or Hydraulic Oils The $C_{30}$ material isolated in the inventive two-step process described in Example 1 was then used to formulate a compressor or hydraulic fluid.

The table below (Table 24) shows the treat rate of the individual materials. A comparative example is shown in the first column using PAO 4 and PAO 8 material, which is a PAO produced from a $BF_3$ catalyzed process and is widely used in the industry.

TABLE 24

|  |  | ISO 32 | |
| --- | --- | --- | --- |
| Product |  | Blend 1 | Blend 2 |
| SpectraSyn 4 |  | 31.50% |  |
| Inventive C30 PAO (Example 1) |  |  | 23.76% |
| SpectraSyn 8 |  | 47.63% | 55.37% |
| Synnestic 5 |  | 20.00% | 20.00% |
| HiTec 521 |  | 0.87% | 0.87% |
| Product Property |  |  |  |
| 100° C. Kinematic Viscosity, cSt | ASTM D445 | 5.669 | 5.702 |
| 40° C. Kinematic Viscosity, cSt | ASTM D445 | 30.14 | 30.00 |
| Viscosity index | ASTM D2270 | 131 | 134 |
| Pour Point, ° C. | ASTM D97 | −54 | −51 |
| Flash Point, ° C. | ASTM D93 | >200 | >200 |
| RPVOT, min | ASTM D2272 | 326 | 321 |
| MTM(80° C.) | Standard method | FIG. 9 | |

When comparing the two blends, the inventive material's lower viscosity material allows for wider bimodal blend of the two primary base stocks (i.e. the viscosity difference is wider between the two PAO base stocks used in each blend), which provides improved viscosity index, and lower traction coefficient compared to the commercial example.

Example 2: Isolating $C_6$ Dimer+$C_6$ LAO ($C_{18}$) Using Inventive Two-Step Process The catalyst batch includes based metallocene catalysts shown in the examples and those mentioned in U.S. Ser. No. 16/270,085, a Lewis acid activator, scavenger and a solvent.

A feed comprising of $C_6$ alpha-olefin was contacted with the catalyst system described above in a polymerization reactor under the following polymerization conditions.

A 1-hexene stream was fed through an adsorbent column filled with alumina adsorbent to a stainless steel Parr vessel where it was sparged with nitrogen for 1 hour to obtain a purified feed. The catalyst was Catalyst I.A. A catalyst solution including purified toluene, TNOA, and N,N-dimethylanilinium tetrakis(pentafluorophenyl)borate (hereinafter referred to as "Activator 1") was prepared per the following recipe based on 1 gram of Catalyst I.A: Catalyst I.A (1 g), purified toluene (394 g), TNOA (0.67 g), Activator 1 (1.6 g). The olefin feedstream was added at a rate of about 1,040 grams per hour to a 1 gallon stainless steel Parr reactor held at about 140° C. for oligomerization. The 1-hexene and catalyst solution were fed into the reactor at a ratio of about 55,700 grams of LAO per gram of catalyst. The residence time in the reactor was about 2.9 hours. The reactor was run at liquid full conditions, with no addition of any gas. When the system reached steady-state, a reactor effluent was collected and quenched by addition of deionized water. Cellulose was slurried into the reactor effluent at 0.2 wt % and the material taken through a vacuum filtration. The conversion and oligomer distribution was determined by GC. The dimer was then isolated by vacuum distillation.

The resulting distribution of oligomers is shown below (Table 25):

TABLE 25

|  | Distribution from metallocene reaction |
| --- | --- |
| $C_6$ Monomer & other lights (wt %) | 20.3 |
| $C_{12}$ Dimer (wt %) | 67.1 |
| $C_{18}$ Trimer (wt %) | 8.3 |
| $C_{24}$+ Heavies (wt %) | 4.3 |

The dimer portion was then isolated through distillation. The dimer portion was then fed to an acid catalyst reaction ($BF_3$), along with a 1:1 molar ratio of $C_6$ alpha olefin under the following reaction conditions:

i) The dimer from above was added to 1-hexene in a composition of about 50 mol % metallocene PAO and 50 mol % 1-hexene and degassed by pulling a light vacuum in a Parr reactor. The catalyst system used was butanol/butyl acetate in a molar ratio of about 1:1, saturated with $BF_3$. Catalyst was added co-currently with the catalyst system components at a ratio of 15 mmol catalyst/100 g LAO and fed into a 2 L stainless steel Parr reactor over the span of about 2 hours. The reactor temperature was about 21° C. and pressure held at about 140 kPa (about 20 psia) under a $BF_3$ atmosphere. After the 2 hour addition period, the reaction continued to react for about 4 hour before the reactor effluent was discharged into a vessel filled with 10% caustic. The resultant sample was water washed and the oil phase analyzed by GC.

The resulting distribution of oligomers is shown below (Table 26).

TABLE 26

|  | Distribution from $BF_3$ reaction |
| --- | --- |
| $C_6$ Monomer & other lights (wt %) | ~0 |
| $C_{12}$ Dimer (wt %) | 2.2 |
| $C_{18}$ Trimer (wt %) | 42.2 |
| $C_{24}$+ Heavies (wt %) | 55.6 |

An overall yield of $C_{18}$ material can be calculated based on a mass balance, and is shown below (Table 27):

TABLE 27

|  | Yield of $C_{18}$ material |
| --- | --- |
| Inventive example using HD catalyst | 28.3 |

The $C_{18}$ material was hydrogenated to a Bromine number less than 1 in a stainless steel Parr reactor at 232° C. and 2413 kPa (350 psi) of hydrogen for 2 hours using 0.5 wt % Nickel catalyst in a slurry reactor. The $C_{18}$ material was vacuum filtered to remove residual catalyst.

The $C_{18}$ material was then analyzed and properties are shown below (Table 28):

TABLE 28

Figure 10:
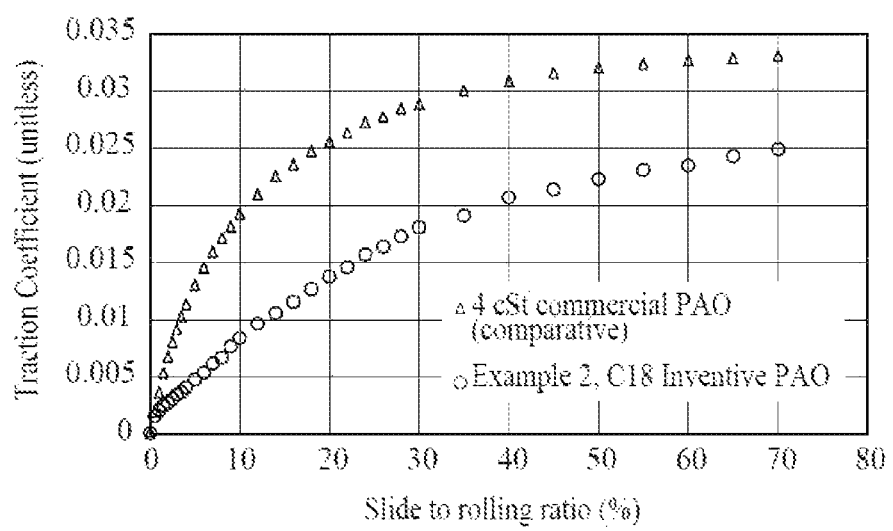
FIG. 10 is a graph illustrating traction coefficient versus slide to rolling ratio (%), according to at least one embodiment.

| Property | Based on Method | UNIT | Result |
| --- | --- | --- | --- |
| Kinematic Viscosity @ 100° C. | ASTM D445 | cSt | 1.341 |
| Kinematic Viscosity @ 40° C. | ASTM D445 | cSt | 3.688 |
| Viscosity Index | ASTM D2270 | No-unit | 78 |
| Pour Point, ° C. | ASTM D5950 | ° C. | −96 |
| CCS Apparent Viscosity @−35° C. | ASTM D5293 | cP | 306 |
| MTM traction @ 80 C. | Standard MTM | | FIG. 10 |

The inventive example provides a very unique balance having very-low viscosity with excellent cold-temperature properties. The PAO would be ideal for use in cooling, driveline, and electric vehicle fluids.

Figure 9:
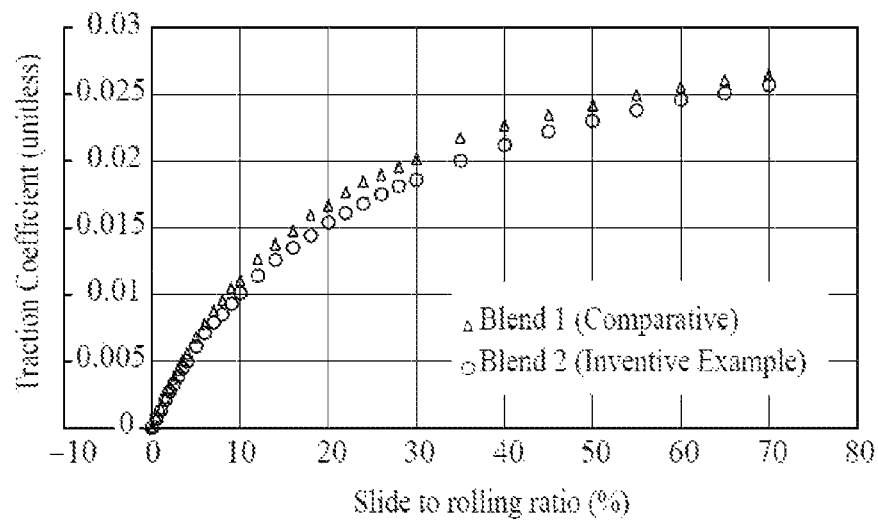
FIG. 9 is a graph illustrating traction coefficient versus slide to rolling ratio (%), according to at least one embodiment.

In FIG. 9, the MTM traction is compared against a commercial 4 cSt PAO produced from $BF_3$ catalyst processes widely used in the industry. The inventive example provides exceptionally low traction.

Example 3: Isolating $C_{12}$ Dimer+C8 LAO (C32) Using Inventive Two-Step Process The catalyst batch includes based metallocene catalysts shown in the examples and those mentioned in U.S. Ser. No. 16/270,085, a Lewis acid activator, scavenger and a solvent.

A feed comprising $C_{12}$ alpha-olefin was contacted with the catalyst system described above in a polymerization reactor under the following polymerization conditions.

A 1-dodecene stream was fed through an adsorbent column filled with alumina adsorbent to a stainless steel Parr vessel where it was sparged with nitrogen for 1 hour to obtain a purified feed. The catalyst was Catalyst I.A. A catalyst solution including purified toluene, TNOA, and N,N-dimethylanilinium tetrakis(pentafluorophenyl)borate (hereinafter referred to as "Activator 1") was prepared per the following recipe based on 1 gram of Catalyst I.A: Catalyst I.A (1 g), purified toluene (394 g), TNOA (0.67 g), Activator 1 (1.6 g). The olefin feedstream was added at a rate of about 1,040 grams per hour to a 1 gallon stainless steel Parr reactor held at about 140° C. for oligomerization. The 1-dodecene and catalyst solution were fed into the reactor at a ratio of about 59,600 grams of LAO per gram of catalyst. The residence time in the reactor was about 2.9 hours. The reactor was run at liquid full conditions, with no addition of any gas. When the system reached steady-state, a reactor effluent was collected and quenched by addition of deionized water. Cellulose was slurried into the reactor effluent at 0.2 wt % and the material taken through a vacuum filtration. The conversion and oligomer distribution was determined by GC. The dimer was then isolated by vacuum distillation.

The resulting distribution of oligomers is shown below (Table 29):

TABLE 29

| | Distribution from metallocene reaction |
| --- | --- |
| $C_{12}$ Monomer & other lights (wt %) | 19.3 |
| $C_{24}$ Dimer (wt %) | 73.8 |

TABLE 29-continued

| | Distribution from metallocene reaction |
| --- | --- |
| $C_{36}$ Trimer (wt %) | 5.5 |
| $C_{48+}$ Heavies (wt %) | 1.4 |

The dimer portion was then isolated through distillation. The dimer portion was then fed to an acid catalyst reaction ($BF_3$), along with a 1:1 molar ratio of $C_8$ alpha olefin under the following reaction conditions:

The dimer from above was added to 1-octene in a composition of about 50 mol % metallocene dimer and 50% 1-octene and degassed by pulling a light vacuum in a Parr reactor. The catalyst system used was butanol/butyl acetate in a molar ratio of about 1:1, saturated with $BF_3$. Catalyst was added co-currently with the catalyst system components at a ratio of 15 mmol catalyst/100 g LAO and fed into a 2 L stainless steel Parr reactor over the span of about 2 hours. The reactor temperature was about 21° C. and pressure held at about 140 kPa (about 20 psia) under a $BF_3$ atmosphere. After the 2 hour addition period, the reaction continued to react for about 4 hours before the reactor effluent was discharged into a vessel filled with 10% caustic. The resultant sample was water washed and the oil phase analyzed by GC.

The resulting distribution of oligomers is shown below (Table 30).

TABLE 30

| | Distribution from $BF_3$ reaction |
| --- | --- |
| $C_8$ & other lights (wt %) | 2.7 |
| $C_{16}$-$C_{24}$ (wt %) | 13.8 |
| $C_{32}$ (desired) (wt %) | 71.5 |
| $C_{36+}$ Heavies (wt %) | 12.0 |

An overall yield of $C_{32}$ material (desired product) can be calculated based on a mass balance, and is shown below (Table 31):

TABLE 31

| | Yield of $C_{32}$ material (desired product) |
| --- | --- |
| Inventive example using HD catalyst | 52.8 |

The $C_{32}$ material was hydrogenated to a Bromine number less than 1 in a stainless steel Parr reactor at 232° C. and 2413 kPa (350 psi) of hydrogen for 2 hours using 0.5 wt % Nickel catalyst in a slurry reactor. The $C_{32}$ material was vacuum filtered to remove residual catalyst.

The $C_{32}$ material was then analyzed and properties are shown below (Table 32) and FIG. 10:

TABLE 32

| Property | Based on Method | UNIT | Property |
| --- | --- | --- | --- |
| Kinematic Viscosity @ 100° C. | ASTM D445 | cSt | 4.004 |
| Kinematic Viscosity @ 40° C. | ASTM D445 | cSt | 16.9 |

TABLE 32-continued

| Property | Based on Method | UNIT | Property |
|---|---|---|---|
| Viscosity Index | ASTM D2270 | No-unit | 138 |
| Pour Point, ° C. | ASTM D5950 | ° C. | −57 |
| Noack Volatility, evaporation loss % | ASTM D5800, Procedure B | wt % | 7.89 |
| Brookfield @-40° C. | ASTM D2983 | cP | 2034 |
| CCS Apparent Viscosity @-35° C. | ASTM D5293 | cP | 1180 |

The inventive $C_{32}$ PAO has a similar viscosity to commercial 4 cSt PAOs produced from $BF_3$ processes widely used in the industry. The inventive example has an exceptionally low volatility and excellent low temperature properties.

Figure 11:
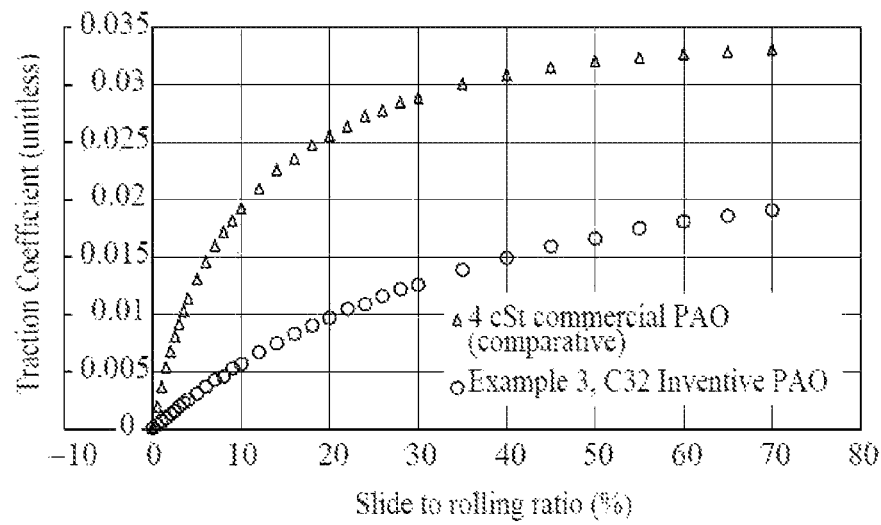
FIG. 11 is a graph illustrating traction coefficient versus slide to rolling ratio (%), according to at least one embodiment.

In FIG. 11, the MTM traction is compared against a commercial 4 cSt PAO produced from $BF_3$ catalyst processes widely used in the industry. The inventive example provides exceptionally low traction compared to the commercial material.

Example 4: Isolating $C_{12}$ Dimer+$C_6$ LAO ($C_{30}$) Using Inventive Two-Step Process The catalyst batch includes Hf based metallocene catalysts shown in the examples and those mentioned in U.S. Ser. No. 16/270,085, a Lewis acid activator, scavenger and a solvent.

A feed comprising of $C_{12}$ alpha-olefin was contacted with the catalyst system described above in a polymerization reactor under the following polymerization conditions.

A 1-dodecene stream was fed through an adsorbent column filled with alumina adsorbent to a stainless steel Parr vessel where it was sparged with nitrogen for 1 hour to obtain a purified feed. The catalyst was Catalyst I.A. A catalyst solution including purified toluene, TNOA, and N,N-dimethylanilinium tetrakis(pentafluorophenyl)borate (hereinafter referred to as "Activator 1") was prepared per the following recipe based on 1 gram of Catalyst I.A: Catalyst I.A (1 g), purified toluene (394 g), TNOA (0.67 g), Activator 1 (1.6 g). The olefin feedstream was added at a rate of about 1,040 grams per hour to a 1 gallon stainless steel Parr reactor held at about 140° C. for oligomerization. The 1-dodecene and catalyst solution were fed into the reactor at a ratio of about 59,600 grams of LAO per gram of catalyst. The residence time in the reactor was about 2.9 hours. The reactor was run at liquid full conditions, with no addition of any gas. When the system reached steady-state, a reactor effluent was collected and quenched by addition of deionized water. Cellulose was slurried into the reactor effluent at 0.2 wt % and the material taken through a vacuum filtration. The conversion and oligomer distribution was determined by GC. The dimer was then isolated by vacuum distillation.

The resulting distribution of oligomers is shown below (Table 33):

TABLE 33

| | Distribution from metallocene reaction |
|---|---|
| $C_{12}$ Monomer & other lights (wt %) | 19.3 |
| $C_{24}$ Dimer (wt %) | 73.8 |
| $C_{36}$ Trimer (wt %) | 5.5 |
| $C_{48+}$ Heavies (wt %) | 1.4 |

The dimer portion was then isolated through distillation. The dimer portion was then fed to an acid catalyst reaction ($BF_3$), along with a 1:1 molar ratio of $C_6$ alpha olefin under the following reaction conditions:

a) The dimer from above was added to 1-hexene in a composition of about 50 mol % metallocene dimer and 50 mol % 1-hexene and degassed by pulling a light vacuum in a Parr reactor. The catalyst system used was butanol/butyl acetate in a molar ratio of about 1:1, saturated with $BF_3$. Catalyst was added co-currently with the catalyst system components at a ratio of 15 mmol catalyst/100 g LAO and fed into a 2 L stainless steel Parr reactor over the span of about 2 hours. The reactor temperature was about 21° C. and pressure held at about 140 kPa (about 20 psia) under a $BF_3$ atmosphere. After the 2 hour addition period, the reaction continued to react for about 4 hours before the reactor effluent was discharged into a vessel filled with 10% caustic. The resultant sample was water washed and the oil phase analyzed by GC.

The resulting distribution of oligomers is shown below (Table 34).

TABLE 34

| | Distribution from $BF_3$ reaction |
|---|---|
| $C_6$ & other lights (wt %) | <0.1 |
| $C_{12}$-$C_{24}$ (wt %) | 17.4 |
| $C_{30}$ (desired) (wt %) | 65.7 |
| $C_{36+}$ Heavies (wt %) | 17.0 |

An overall yield of $C_{30}$ material (desired product) can be calculated based on a mass balance, and is shown below (Table 35):

TABLE 35

| | Yield of $C_{30}$ material (desired product) |
|---|---|
| Inventive example using HD catalyst | 48.9 |

The $C_{30}$ material was hydrogenated to a Bromine number less than 1 in a stainless steel Parr reactor at 232° C. and 2413 kPa (350 psi) of hydrogen for 2 hours using 0.5 wt % Nickel Oxide catalyst in a slurry reactor. The $C_{30}$ material was vacuum filtered to remove residual catalyst.

The $C_{30}$ material was then analyzed and properties are shown below (Table 36) and FIG. 11:

TABLE 36

| Property | Based on Method | UNIT | Property |
|---|---|---|---|
| Kinematic Viscosity @ 100° C. | ASTM D445 | cSt | 3.74 |
| Kinematic Viscosity @ 40° C. | ASTM D445 | cSt | 15.58 |
| Viscosity Index | ASTM D2270 | No-unit | 138 |
| Pour Point, ° C. | ASTM D5950 | ° C. | −54 |
| Noack Volatility, evaporation loss % | ASTM D5800, Procedure B | wt % | 11.75 |
| Brookfield @-40° C. | ASTM D2983 | cP | 1902 |
| CCS Apparent Viscosity @-35° C. | ASTM D5293 | cP | 1071 |

The results indicate that the $C_{30}$ material isolated above has excellent low viscosity with exceptional volatility and low-temperature properties.

Figure 12:
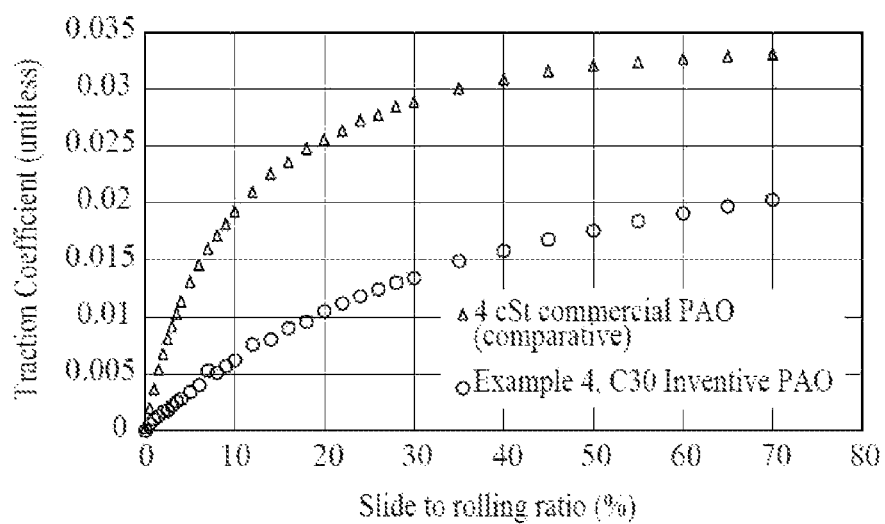
FIG. 12 is a graph illustrating traction coefficient versus slide to rolling ratio (%), according to at least one embodiment.

In FIG. 12, the MTM traction is compared against a commercial 4 cSt PAO produced from $BF_3$ catalyst processes widely used in the industry. The inventive example provides exceptionally low traction compared to the commercial material.

The results from this experiment are remarkably similar to the results shown in Example 1, where a $C_{30}$ material was Obtained using the two-step process with 1-decene. When comparing Example 1 and Example 5, it is evident that the two-step process with dimer-selective catalyst allows significant feed flexibility not achievable with current technology. For example, Example 5 provides a product remarkably similar to Example 1 (similar properties and same carbon number), but with a completely different set of LAO feeds. This type of feed-flexibility is highly desirable to base stock manufacturers in order to ensure reliable feed supply and to improve economics with lower cost feeds. The inventive catalyst of the present disclosure provides commercial application of that feed flexibility.

All documents described herein are incorporated by reference herein, including any priority documents and/or testing procedures to the extent they are not inconsistent with this text. As is apparent from the foregoing general description and the specific embodiments, while forms of the present disclosure have been illustrated and described, various modifications can be made without departing from the spirit and scope of the present disclosure. Accordingly, it is not intended that the present disclosure be limited thereby. Likewise, the term "comprising" is considered synonymous with the term "including." Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

What is claimed is:

1. A process to produce a poly alpha-olefin (PAO), comprising:
    introducing a first group of one or more alpha-olefins and a first catalyst system comprising a metallocene compound into a continuous stirred tank reactor or a continuous tubular reactor under first reactor conditions, wherein the alpha-olefin is introduced to the reactor at a flow rate of about 100 g/hr or more, to form a first reactor effluent comprising PAO dimer comprising at least 96 mol % of vinylidene and 4 mol % or less of trisubstituted vinylene and disubstituted vinylene, based on total moles of vinylidene, trisubstituted vinylene, and disubstituted vinylene; and
    introducing the first reactor effluent, a second group of one or more alpha-olefins and a second catalyst composition comprising an acid catalyst into a second reactor under second reactor conditions to form a second reactor effluent comprising PAO trimer.

* * * * *